US007927791B2

(12) United States Patent
Welch et al.

(10) Patent No.: US 7,927,791 B2
(45) Date of Patent: Apr. 19, 2011

(54) METHODS FOR IDENTIFYING SMALL MOLECULES THAT MODULATE PREMATURE TRANSLATION TERMINATION AND NONSENSE MEDIATED MRNA DECAY

(75) Inventors: Ellen M. Welch, Califon, NJ (US); Neil Gregory Almstead, Princeton, NJ (US); Robert F. Rando, Annandale, NJ (US); Mathew C. Pellegrini, Bedminster, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 1310 days.

(21) Appl. No.: 10/521,775

(22) PCT Filed: Jul. 24, 2003

(86) PCT No.: PCT/US03/23075
§ 371 (c)(1),
(2), (4) Date: Nov. 23, 2005

(87) PCT Pub. No.: WO2004/010106
PCT Pub. Date: Jan. 29, 2004

(65) Prior Publication Data
US 2006/0257866 A1 Nov. 16, 2006

Related U.S. Application Data

(60) Provisional application No. 60/398,344, filed on Jul. 24, 2002, provisional application No. 60/398,332, filed on Jul. 24, 2002.

(51) Int. Cl.
C12Q 1/68 (2006.01)
C07H 21/02 (2006.01)

(52) U.S. Cl. .......................... 435/6; 536/23.1

(58) Field of Classification Search .................. None
See application file for complete search history.

(56) References Cited

U.S. PATENT DOCUMENTS

| 4,668,625 A | 5/1987 | Cambiaghi et al. |
| 5,015,570 A | 5/1991 | Scangos et al. |
| 5,510,240 A | 4/1996 | Lam et al. |
| 5,593,835 A | 1/1997 | Rando et al. |
| 5,641,627 A | 6/1997 | Moehle |
| 5,650,316 A | 7/1997 | Aggarwal et al. |
| 5,663,317 A | 9/1997 | Falkow et al. |
| 5,666,341 A | 9/1997 | Horibe et al. |
| 5,667,975 A | 9/1997 | Dykstra et al. |
| 5,679,566 A | 10/1997 | He et al. |
| 5,712,096 A | 1/1998 | Stern et al. |
| 5,716,825 A | 2/1998 | Hancock et al. |
| 5,721,099 A | 2/1998 | Still et al. |
| 5,804,563 A | 9/1998 | Still et al. |
| 5,807,682 A | 9/1998 | Grossman et al. |
| 5,837,449 A | 11/1998 | Ecker et al. |
| 5,840,702 A | 11/1998 | Bedwell |
| 5,866,341 A | 2/1999 | Spinella et al. |
| 5,871,923 A | 2/1999 | Moehle |
| 6,004,749 A | 12/1999 | Giordano et al. |
| 6,060,240 A | 5/2000 | Kamb et al. |
| 6,071,700 A | 6/2000 | He et al. |
| 6,090,912 A | 7/2000 | Lebl et al. |
| 6,107,029 A | 8/2000 | Giordano |
| 6,147,344 A | 11/2000 | Annis et al. |
| 6,207,391 B1 | 3/2001 | Wu et al. |
| 6,211,477 B1 | 4/2001 | Cardott et al. |
| 6,232,075 B1 | 5/2001 | Williams |
| 6,320,040 B1 | 11/2001 | Cook et al. |
| 6,329,146 B1 | 12/2001 | Crooke et al. |
| 6,355,428 B1 | 3/2002 | Schroth et al. |
| 6,391,542 B1 | 5/2002 | Anderson et al. |
| 6,458,538 B1 | 10/2002 | Beckman et al. |
| 6,503,713 B1 * | 1/2003 | Rana ................................. 435/6 |
| 6,503,721 B2 | 1/2003 | Arenas et al. |
| 6,596,481 B1 | 7/2003 | Rothschild et al. |
| 6,875,736 B2 | 4/2005 | Rana et al. |
| 6,992,096 B2 | 1/2006 | Karp et al. |
| 7,026,122 B2 | 4/2006 | Beckmann et al. |
| 7,291,461 B2 | 11/2007 | Welch et al. |
| 7,354,709 B2 * | 4/2008 | Yang et al. ........................ 435/6 |

(Continued)

FOREIGN PATENT DOCUMENTS

EP 1 218 544 4/2001

(Continued)

OTHER PUBLICATIONS

Shiroki et al., Methods in Molecular Biology, 118, 449-458, 1999.*
Gorski et al.(J. Mol. Evol., 1987, 24:236-251).*
Aboul-Ela et al., "The structure of the human immunodeficiency virus type-1 TAR RNA reveals principles of RNA recognition by Tat protein." *J. Mol. Biol.* 1995; 253:313-332.
Aggarwal et al., "Triple helix-forming oligodeoxyribonucleotides targeted to the human tumor necrosis factor, TNF, gene inhibit TNF production and block the TNF-dependent growth of human glioblastoma tumor cells." *Cancer Res.* 1996; 56:5156-5164.

(Continued)

*Primary Examiner* — Nancy Vogel
(74) *Attorney, Agent, or Firm* — Jones Day

(57) ABSTRACT

The present invention relates to a method for screening and identifying compounds that modulate premature translation termination and/or nonsense-mediated messenger ribonucleic acid ("mRNA") by interacting with a preselected target ribonucleic acid ("RNA"). In particular, the present invention relates to identifying compounds that bind to regions of the 28S ribosomal RNA ("rRNA") and analogs thereof. Direct, noncompetitive binding assays are advantageously used to screen libraries of compounds for those that selectively bind to a preselected target RNA. Binding of target RNA molecules to a particular compound is detected using any physical method that measures the altered physical property of the target RNA bound to a compound. The structure of the compound attached to the labeled RNA is also determined. The methods used will depend, in part, on the nature of the library screened. The methods of the present invention provide a simple, sensitive assay for high-throughput screening of libraries of compounds to identify pharmaceutical leads.

32 Claims, 11 Drawing Sheets

U.S. PATENT DOCUMENTS

Figure 1:
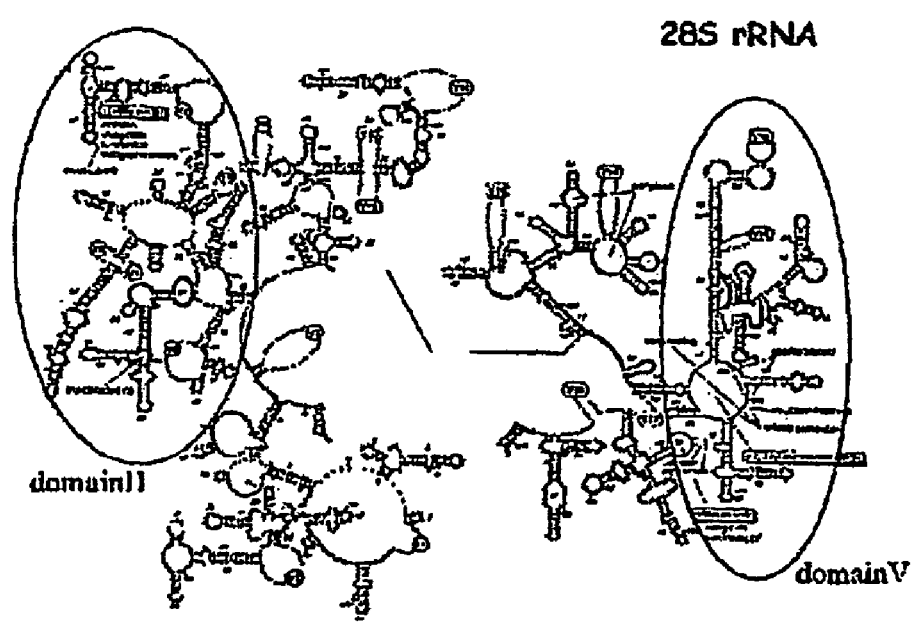

| | | | |
|---|---|---|---|
| 2003/0232360 | A1 | 12/2003 | Wilusz et al. |
| 2004/0067900 | A1 | 4/2004 | Wilde et al. |
| 2004/0162345 | A1* | 8/2004 | Berger et al. .......... 514/553 |
| 2004/0219545 | A1 | 11/2004 | Rando et al. |
| 2005/0142545 | A1 | 6/2005 | Conn et al. |
| 2005/0221368 | A1 | 10/2005 | Rana et al. |
| 2006/0134681 | A1 | 6/2006 | Beckmann et al. |
| 2006/0166926 | A1 | 7/2006 | Wilde et al. |
| 2006/0167065 | A1 | 7/2006 | Wilde et al. |
| 2006/0167263 | A1 | 7/2006 | Wilde et al. |
| 2006/0194234 | A1 | 8/2006 | Conn et al. |
| 2006/0228730 | A1 | 10/2006 | Rando et al. |

FOREIGN PATENT DOCUMENTS

| | | |
|---|---|---|
| EP | 1 238 110 B1 | 6/2001 |
| EP | 1 377 684 | 10/2002 |
| EP | 1 543 157 A2 | 6/2005 |
| EP | 2 036 991 | 3/2009 |
| WO | WO 95/05389 | 2/1995 |
| WO | WO 96/22301 | 7/1996 |
| WO | WO 97/09342 | 3/1997 |
| WO | WO 99/20797 | 4/1999 |
| WO | WO 99/24595 | 5/1999 |
| WO | WO 99/45150 | 9/1999 |
| WO | WO 00/03240 | 1/2000 |
| WO | WO 00/09464 | 2/2000 |
| WO | WO 01/25486 | 4/2001 |
| WO | WO 01/44516 | 6/2001 |
| WO | WO 02/083837 | 10/2002 |
| WO | WO 02/083953 | 10/2002 |
| WO | WO 2004/010106 | 1/2004 |
| WO | WO 2004/091502 | 10/2004 |
| WO | WO 2005/086768 | 9/2005 |
| WO | WO 2006/044456 | 4/2006 |

OTHER PUBLICATIONS

Andreutti-Zaugg, C. et al., "Inhibition of nonsense-mediated messenger RNA decay in clinical samples facilitates detection of human MSH2 mutations with an in vivo fusion protein assay and conventional techniques," *Cancer Research* 1997; 57(15): 3288-3293.

Bakheet et al., "ARED: human AU-rich element-containing mRNA database reveals an unexpectedly diverse functional repertoire of encoded proteins." *Nucleic Acids Res.* 2001; 29:246-254.

Barton-Davis et al., "Animoglycoside antibiotics restore dystrophin function to skeletal muscles of *mdx* mice" *Journal of Clinical Investigation* Aug. 1999; 104(4): 375-381.

Bateman J.F. et al., "Reliable and sensitive detection of premature termination mutations using a protein truncation test designed to overcome problems of nonsense-mediated mRNA instability." *Human Mutation* 1999; 13(4): 311-317.

Bayer, "Towards the Chemical Synthesis of Proteins." *Angew. Chem.* 1991; 30:113-129.

Beal & Dervan, "Second structural motif for recognition of DNA by oligonucleotide-directed triple-helix formation." *Science* 1991; 251(4999):1360-1363.

Bedwell et al., "Suppression of a CFTR premature stop mutation in a bronchial epithelial cell line." *Nature Medicine* Nov. 1997; 3(11): 1280-1284.

Blackwell et al., "A one-bead, one-stock solution approach to chemical genetics: part 1." *Chem & Bio.* 2001; 8:1167-1182.

Burbaum J.J. & Siga, N.H. et al., "New technologies for high-throughput screening," *Curr. Opin. in Chem. Bio.*; 72-78.

Buzina, A. & Shulman, M.J., "Infrequent Translation of a Nonsense Codon is sufficient to decrease mRNA Level." *Molecular Biology of the Cell* Mar. 1999; 10: 515-524.

Carter et al., "A Regulatory mechanism that detects premature nonsense codons in T-cell receptor transcripts in vivo is reversed by protein synthesis inhibitors in vitro" *J. Biol. Chem.* 1996; 270(48): 28995-29003.

Carter et al., "A splicing-dependent regulatory mechanism that detects translation signals." *The EMBO Journal* 1996; 15(21): 5965-5975.

Chastain & Tinoco, "Structural elements in RNA." *Prog. Nucleic Acid Res. Mol. Bio.* 1991; 41:131-177.

Chow & Bogdan, "A structural basis for RNA-ligand interactions." *Chem. Rev.* 1997; 97:1489-1514.

Churcher et al., "High affinity binding of TAR RNA by the human immunodeficiency virus type-1 tat protein requires base-pairs in the RNA stem and amino acid residues flanking the basic region" *J. Mol. Biol.* 1993; 230:90-110.

Clemons et al., "A one-bead, one-stock solution approach to chemical genetics: part 2." *Chem & Bio.* 2001; 8:1183-1195.

Cordingley et al., "Sequence-Specific Interaction of Tat Protein and Tat Peptides with the Transactivation-Responsive Sequence Element of Human Immunodeficiency Virus Type 1 in vitro." *Proc. Natl. Acad. Sci. USA* 1990; 87:8985-8989.

Culbertson, M.R., "Unforeseen consequences for gene expression, inherited genetic disorder and cancer." *TIG Nature Medicine* Feb. 1999; 15(2): 74-80.

Cundliffe et al., "How antibiotic-producing organisms avoid suicide." *Ann. Rev. Microbiol.* 1989; 43:207-233.

Cundliffe et al., "The Ribosome: Structure, Function, & Evolution." Schlessinger et al., eds. American Society for Microbiology, Washington D.C. 1990; pp. 409-417.

Darling, T. N. et al., "Cycloheximide facilitates the identification of aberrant transcripts resulting from a novel splice-site mutation in COL17A1 in a patient with generalized atrophic benign epidermolysis bullosa." *J. of Invest. Dermatol.* Feb. 1998; 110(2): 165-169.

Darling, T.N. et al, Premature Termination Codons are present on both alleles of the Bullous Pemphigoid Antigen 2/Type XVIII Collagen Gene in Five Austrian Families with Generallized Atrophic Benign Epidermolysis Bullosa. *J. Invest. Dermatol.* Apr. 1997; 108(4): 463-468.

Dinman, J.D. et al., "Translating old drugs into new treatments: ribosomal frameshifting as a target for antiviral agents." *Tibtech* (reviews) Apr. 1998; 16:190-196.

Felber & Pavlakis, "A quantitative bioassay for HIV-1 based on trans-activation." *Science* 1988; 239:184-187.

Fernandes, "Technological advances in high-throughput screening." *Curr Opin Chem Biol.* 1998; 2:597-603.

Frankel A. D. & Pabo, "Cellular uptake of the tat protein from human immunodeficiency virus." *Cell* 1998; 55:1189-1194.

Garvin, A.M., "A complete protein truncation test for BRCA1 and BRCA2." *European Journal of Human Genetics.* May 1998; 6(3): 226-234.

Gottesfeld et al. Regulation of gene expression by small molecules. *Nature* 1997; 387(6629):202-205.

Gottesfeld et al., "Chemical Approaches to Control Gene Expression." *Gene Expr* 2000; 9:77-91.

Hamy et al., "A new class of HIV-1 Tat antagonist acting through Tat-TAR inhibition." *Biochem* 1998; 37(15):5086-5095.

Hamy et al., "An inhibitor of the Tat/TAR RNA interaction that effectively suppresses HIV-1 replication." *Proc. Natl. Acad. Sci. USA* 94:3548-3553.

Harnden et al., "Thiazolinone Analogues of Indomycin with antiviral and antibacterial activity." *J. of Med. Chem.* 1978; 21:82-87.

Helene et al., "Control of gene expression by triple helix-forming oligonucleotides. The antigene strategy." *Ann N Y Acad Sci* 1992; 660:27-36.

Hentze, M.W. & Kulozik, A.E. "A Perfect Message: RNA Surveillance and Nonsense-Mediated Decay" *Cell* Feb. 1999; 96: 307-310.

Ho et al., "Specific inhibition of formation of transcription complexes by a calicheamicin oligosaccharide: a paradigm for the development of transcriptional antagonists." *Proc Natl Acad Sci USA* 1994; 91(20):9203-9207.

Howard et al., "Aminoglycoside antibiotics restore CFTR function by overcoming premature stop mutations." *Nature Medicine* Apr. 1996; 2(4): 467-46.

Huq et al., "Controlling human immunodeficiency virus type 1 gene expression by unnatural peptides." *Biochem.* 1999; 38:5172-5177.

Hutchin et al., "A molecular basis for human hypersensitivity to aminoglycoside antibiotics" *Nucl. Acids Res* 1993; 21(18):4174-4179.

Hwang et al., "Inhibition of gene expression in human cells through small molecule-RNA interactions." *Proc. Natl. Acad. Sci. USA* 1999; 96(23):12977-13002.

Jackson, R.J. & Hunt, T. "Preparation and Use of Nuclease-Treated Rabbit Reticulocyte Lysates for the Translation of Eukaryotic Messenger RNA." *Methods in Enzymology* 1983; 96: 50-75.

Jakobovits et al., "A discrete element 3' of human immunodeficiency virus 1 (HIV-1) and HIV-2 mRNA initiation sites mediates transcriptional activation by an HIV trans activator." *Mol. Cell. Bio.* 1988; 8:2555-2561.

Jhaveri et al., "In Vitro Selection of RNA Aptamers to a Protein Target by Filter Immobilization" Curr. Prot. in Molec. Bio. 2000; 24.3.1-24.3.25.

Jones & Peterlin, "Control of RNA initiation and elongation at the HIV-1 promoter." *Annu Rev Biochem* 1994; 63:717-743.

Kuruvilla et al., "Dissecting glucose signalling with diversity-oriented synthesis and small-molecule microarrays." *Nature* 2002; 416:653-657.

Li, S. & Wilkinson, F., "Nonsense Surveillance in Lymphocytes?" *Immunity* Feb. 1998; 8: 135-141.

Liu et al., "Sequence-selective carbohydrate-DNA interaction: Dimeric and monomeric forms of the calicheamicin oligosaccharide interfere with transcription factor function." *Proc Natl Acad Sci USA* 1996; 93(2):940-944.

Maher et al., "Oligonucleotide-directed DNA triple-helix formation: an approach to artificial repressors?" *Antisense Res Dev* 1991; 1(3):277-281.

Mazumder et al., "Inhibition of the Human Immunodeficiency Virus Type 1 Integrase by Guanosine Quartet Structures." *Biochem.* 1996; 35:13762-13771.

Mei et al., "Inhibitors of protein-RNA complexation that target the RNA: specific recognition of human immunodeficiency virus type 1 TAR RNA by small organic molecules." *Biochem.* 1998; 37(40):14204-14212.

Mei et al., "Discovery of selective, small-molecule inhibitors of RNA complexes—I. The Tat protein/TAR RNA complexes required for HIV-1 transcription." *Bioorg. Med. Chem.* 1997; 5:1173-1184.

Miller, "Development of antisense and antigene oligonucleotide analogs." *Prog. Nucleic Acid Res. Mol. Bio.* 1996; 52:261-291.

Milligan et al., "Oligoribonucleotide synthesis using T7 RNA polymerase and synthetic DNA templates." *Nucleic Acids Res.* 1987;15:8783-8798.

Misiura et al., "Biotinyl and phosphotyrosinyl phosphoramidite derivatives useful in the incorporation of multiple reporter groups on synthetic oligonucleotides." *Nucleic Acids Res.* 1990; 18:4345-4354.

Muller et al., "Interaction of fluorescently labeled dideoxyncleotides with HIV-1 reverse transcriptase." *Biochem.* 1991; 30:3709-3715.

Needels et al., "Generation and screening of an oligonucleotide-encoded synthetic peptide library", *Proc. Natl. Acad. Sci. USA* 1993; 90:10700-10704.

Neenhold & Rana, "Major groove opening at the HIV-1 Tat binding site of TAR RNA evidenced by a rhodium probe." *Biochem.* 1995; 34:6303-6309.

Nielsen, "Applications of peptide nucleic acids." *Curr. Opin. Biotechnol.* 1999; 10(1):71-75.

Nordeen, "Luciferase reporter gene vectors for analysis of promoters and enhancers." *Bio Techniques* 1998; 6:454-457.

Ohlmeyer et al., "Complex synthetic chemical libraries indexed with molecular tags." *Proc. Natl. Acad. Sci. USA* 1993; 90(23):10922-10926.

Ojwang et al., "Achieving antisense inhibition by oligodeoxynucleotides containing N7 modified 2'-deoxyguanosine using tumor necrosis factor receptor type 1." *METHODS: A Companion to Methods in Enzymology* 1999; 18:244-251.

Ping et al., "Dynamics of RNA-protein interactions in the HIV-1 Rev-RRE complex visualized by 6-thioguanosine-mediated photocrosslinking" *RNA* 1997; 3:850-860.

Puglisi et al., "Conformation of the TAR RNA-arginine complex by NMR spectroscopy." *Science* 1992; 257:76-80.

Purohit et al., "Interactions of a small RNA with antibiotic and RNA ligands of the 30S subunit" *Nature* 1994; 370(6491):659-662.

Rando et al., "Biologic activity of guanosine quartet forming oligonucleotides" in "Applied Antisense Oligonucleotide Technology" Stein and Krieg, eds, John Wiley and Sons, New York, 1998; pp. 335-352.

Ruiz-Echevarria et al., "Making sense of nonsense in yeast" *TIBS* Nov. 1996; 21: 433-438.

Scaringe et al., Chemical synthesis of biologically active oligoribonucleotides using beta-cyanoethyl protected ribonucleoside phosphoramidites. *Nucleic Acids Res* 1990; 18:5433-5441.

Shah et al., "Incorporation of an artificial protease and nuclease at the HIV-1 Tat binding site of trans-activation responsive RNA." *Bioconjugate Chem.*1996; 7:283-289.

Shah et al., "Synthesis of uridine phosphoramidite analogs: reagents for site-specific incorporation of photoreactive sites into RNA sequences." *Bioconjugate Chem.* 1994; 5:508-512.

Stage et al., "Inhibition of the hammerhead ribozyme by neomycin" *RNA* 1995; 1(1):95-101.

Sternson et al., "Split-Pool Synthesis of 1,3-Dioxanes Leading to Arrayed Stock Solutions of Single Compounds Sufficient for Multiple Phenotypic and Protein-Binding Assays." *J. Am. Chem. Soc.* 2001; 123:1740-1747.

Still, "Discovery of sequence-selective peptide binding by synthetic receptors using encoded combinatorial libraries." *Accounts of Chem. Res.* 1996; 29:(3) 155-163.

Von Ahsen et al., "Antibiotic inhibition of group I ribozyme function." *Nature* (London) 1991; 353(6342):368-370.

Wang & Rana, "RNA conformation in the Tat-TAR complex determined by site-specific photo-cross-linking." *Biochem* 1996; 35:6491-6499.

Weeks & Crothers, "Major groove accessibility of RNA." *Science* 1993; 261(5128):1574-1577.

White et al., "Recognition of the four Watson-Crick base pairs in the DNA minor groove by synthetic ligands." *Nature* 1998; 391(6666):468-471.

Woodcock et al., "Interaction of antibiotics with A- and P-site-specific bases in 16S ribosomal RNA" *EMBO J.* 1991; 10:3099-3103.

Xavier et al., "RNA as a drug target: methods for biophysical characterization and screening." *Trends Biotechnol* 2001; 18:349-356.

Xian et al., "DNA-protein binding assays from single sea urchin egg: a high sensitivity capillary electrophoresis method." Proc. Natl. Acad Sci. 1996; 93:86-90.

Zapp et al. "Small molecules that selectively block RNA binding of HIV-1 Rev protein inhibit Rev function and viral production" *Cell* 1993; 74(6):969-978.

Iordanov et al., Ribotoxic stress response: activation of the stress-activated protein kinase JNK 1 by inhibitors of the peptidyl transferase reaction and by sequence-specific RNA damage to the alpha-sarcin/ricin loop in the 28S rRNA.Mol Cell Biol. Jun. 1997; 17(6):3373-81.

Shimizu et al., Interaction among silkworm ribosomal proteins P1, P2 and P0 required for functional protein binding to the GTPase-associated domain of 28S rRNA.Nucleic Acids Res. Jun. 15, 2002;30(12):2620-7.

Contreras et al. 1982, "Simple, efficient in vitro synthesis of capped RNA useful for direct expression of cloned eukaryotic genes." *Nucl. Acids. Res* 10:6353.

Dignam et al., "Preparation of extracts from higher eukaryotes." *Methods Enzymol.*, 1990, 182: 194-203.

European Search Report, dated Feb. 17, 2009, of EP 1 377 684 published on Oct. 24, 2002.

European Search Report, dated Feb. 18, 2004, of EP 1 218 544 published on Apr. 12, 2001.

International Preliminary Examination Report, dated Aug. 30, 2002, of PCT/US2000/027389, now published as WO 01/25486 on Apr. 12, 2001.

International Preliminary Examination Report, dated Jun. 23, 2005, of PCT/US2003/019670, now published as WO 04/001010 on Dec. 21, 2003.

International Preliminary Examination Report, dated Oct. 11, 2003, of PCT/US2002/011757, now published as WO 02/083953 on Oct. 24, 2002.

International Preliminary Examination Report, dated Oct. 11, 2003, of PCT/US2002/011758, now published as WO 02/083837 on Oct. 24, 2002.

International Search Report, dated Apr. 12, 2001 of PCT/US2000/027389, now published as WO 01/25486 on Apr. 12, 2001.

International Search Report, dated Mar. 4, 2004 of PCT/US2003/019670, now published as WO 04/001010 on Dec. 21, 2003.
International Search Report, dated Oct. 24, 2002 of PCT/US2002/011757, now published as WO 02/083953 on Oct. 24, 2002.
International Search Report, dated Oct. 24, 2002 of PCT/US2002/011758, now published as WO 02/083837 on Oct. 24, 2002.
Krieg & Melton, "Formation of the 3' end of histone mRNA by post-transcriptional processing." Nature, 1984, 308:203.
Notice of Allowance dated Aug. 17, 2002 of U.S. Appl. No. 09/679,451, filed Oct. 4, 2000.
Notice of Allowance dated Jun. 21, 2002 of U.S. Appl. No. 09/461,508, filed Dec. 14, 1999.
Notice of Allowance, dated Aug. 25, 2005, of U.S. Appl. No. 10/226,803, filed Aug. 21, 2002.
Notice of Allowance, dated Jul. 11, 2007, of U.S. Appl. No. 10/519,243, filed Mar. 23, 2005.
Office Action, dated Feb. 5, 2001, of U.S. Appl. No. 09/679,451, filed Oct. 4, 2000.
Office Action, dated Jun. 14, 2001, of U.S. Appl. No. 09/679,451, filed Oct. 4, 2000.
Office Action, dated Jan. 8, 2002, of U.S. Appl. No. 09/679,451, filed Oct. 4, 2000.
Office Action, dated Jun. 13, 2002, of U.S. Appl. No. 09/679,451, filed Oct. 4, 2000.
Office Action, dated Jun. 27, 2005, of U.S. Appl. No. 10/475,024, filed Feb. 3, 2004.
Office Action, dated Oct. 19, 2005, of U.S. Appl. No. 10/475,026, filed Jun. 27, 2004.
Office Action, dated Nov. 19, 2003, of U.S. Appl. No. 10/295,761, filed Nov. 15, 2002.
Office Action, dated Jul. 22, 2004, of U.S. Appl. No. 10/295,761, filed Nov. 15, 2002.
Office Action, dated Jul. 6, 2001, of U.S. Appl. No. 09/461,508, filed Dec. 14, 1999.
Office Action, dated Mar. 20, 2001, of U.S. Appl. No. 09/461,508, filed Dec. 14, 1999.
Office Action, dated Feb. 25, 2003, of U.S. Appl. No. 10/226,803, filed Aug. 21, 2002.
Office Action, dated Sep. 10, 2003, of U.S. Appl. No. 10/226,803, filed Aug. 21, 2002.
Office Action, dated Apr. 7, 2004, of U.S. Appl. No. 10/226,803, filed Aug. 21, 2002.
Office Action, dated Jan. 24, 2005, of U.S. Appl. No. 10/226,803, filed Aug. 21, 2002.
Office Action, dated Nov. 8, 2004, of U.S. Appl. No. 10/226,803, filed Aug. 21, 2002.
Office Action, dated Feb. 26, 2007, of U.S. Appl. No. 10/519,243, filed Mar. 23, 2005.
Office Action, dated Oct. 1, 2007 of U.S. Appl. No. 11/098,946, filed Apr. 4, 2005.
Office Action, dated Jun. 12, 2007, of U.S. Appl. No. 11/098,946, filed Apr. 4, 2005.
Office Action, dated Jul. 20, 2008, of U.S. Appl. No. 11/098,946, filed Apr. 4, 2005.
Office Action, dated Feb. 7, 2008, of U.S. Appl. No. 11/347,748, filed Feb. 3, 2006.
Office Action, dated Nov. 12, 2008, of U.S. Appl. No. 11/347,748, filed Feb. 3, 2006.
Office Action, dated Jan. 14, 2009, of U.S. Appl. No. 11/359,729, filed Feb. 21, 2006.
Response to Office Action, dated Apr. 5, 2001, of U.S. Appl. No. 09/679,451, filed Oct. 4, 2000.
Response to Office Action, dated Nov. 14, 2001, of U.S. Appl. No. 09/679,451, filed Oct. 4, 2000.
Response to Office Action, dated Aug. 29, 2005, of U.S. Appl. No. 10/475,024, filed Feb. 3, 2004.
Response to Office Action, dated Feb. 19, 2004, of U.S. Appl. No. 10/295,761, filed Nov. 15, 2002.
Response to Office Action, dated Jun. 7, 2004, of U.S. Appl. No. 10/295,761, filed Nov. 15, 2002.
Response to Office Action, dated Oct. 22, 2004, of U.S. Appl. No. 10/295,761, filed Nov. 15, 2002.
Response to Office Action, dated Apr. 16, 2001, of U.S. Appl. No. 09/461,508, filed Dec. 14, 1999.
Response to Office Action, dated Jan. 7, 2002, of U.S. Appl. No. 09/461,508, filed Dec. 14, 1999.
Response to Office Action, dated Jun. 25, 2003, of U.S. Appl. No. 10/226,803, filed Aug. 21, 2002.
Response to Office Action, dated Jan. 12, 2004 of U.S. Appl. No. 10/226,803, filed Aug. 21, 2002.
Response to Office Action, dated Jul. 7, 2004, of U.S. Appl. No. 10/226,803, filed Aug. 21, 2002.
Response to Office Action, dated Nov. 11, 2004, of U.S. Appl. No. 10/226,803, filed Aug. 21, 2002.
Response to Office Action, dated May 24, 2005, of U.S. Appl. No. 10/226,803, filed Aug. 21, 2002.
Response to Office Action, dated May 24, 2007, of U.S. Appl. No. 10/519,243, filed Mar. 23, 2005.
Response to Office Action, dated Jul. 12, 2007 of U.S. Appl. No. 11/098,946, filed Apr. 4, 2005.
Response to Office Action, dated Mar. 3, 2008 of U.S. Appl. No. 11/098,946, filed Apr. 4, 2005.
Response to Office Action, dated Aug. 7, 2008, of U.S. Appl. No. 11/347,748, filed Feb. 3, 2006.
Response to Notice of Allowability, dated Nov. 23, 2005, of U.S. Appl. No. 10/226,803, filed Aug. 21, 2002.
Ainsworth. 2005, "Running the red light," Nature 438(7069):726-728.
Burke et al., 1985, "Suppression of a nonsense mutation in mammalian cells in vivo by the aminoglycoside antibiotics G-418 and paromycin," Nucleic Acids Research, 13(17):6265-6272.
Connolly, 2005, "Neurodegeneration caused by the translation of nonsense: Does macromolecular misfolding impair the synchrony of gene expression?" Medical Hypothesis, 64(5): 968-972.
Coulson et al., 1997, "Down-regulation of the Amyloid Protein Precurson of Alzheimer's disease by Antisense Oligonucleotides Reduces Neuronal Adhesion to Specific Substrate." Brain Research,770:72-80.
Denman et al., 1997, "Facilitated reduction of beta-amyloid peptide precursor by synthetic oligonucleotides in COS-7 cells expressing a hammerhead ribozyme" Archives of Biochem & Biophys, 348(I):82-90.
Huq et al., 1997, "Specific recognition of HIV-1 TAR RNA by a D-tat peptide", Nature Structural Biology, 4(II): 881-882.
Kulyte et al., 2005, "Gene selective suppression of nonsense termination using antisense agents." Biochimica et Biophysica Acta, 1730(3), 165-172.
Maquat, 1995, "When cells stop making sense: Effects of nonsense codons on RNA metabolism in vertebrate cells", RNA, 1:453-465.
Sagesser et al., 1997, "Detection and Isolation of RNA-Binding Proteins by RNA-Ligand Screening of a cDNA Expression Library", Nucl Acids Res., 25: 3816-3822.
Weng et al., 1996, "Identification and characterization of mutations in the UPFI gene that affect nonsense suppression and the formation of the Upf protein complex but not mRNA turnover", Mol Cell Biol., 16(10):5491-506.
European Search Report, dated Feb. 11, 2009 of EP 2 036 991 published Mar. 18, 2009.
International Preliminary Examination Report, dated Jul. 4, 2002 of PCT/US00/34232 filed Dec. 13, 2000, now WO 01/44516.
International Search Report, dated Mar. 28, 2002 of PCT/US00/34232 filed Dec. 13, 2000, now WO 01/44516.
Office Action, dated Aug. 11, 2004, of U.S. Appl. No. 10/226,803, filed Aug. 21, 2002.
Notice of Allowance, dated Aug. 17, 2002, of U.S. Appl. No. 09/679,451, filed Oct. 4, 2000.
Office Action, dated Nov. 4, 2005, of U.S. Appl. No. 10/475,024, filed Feb. 3, 2004.
Notice of Allowance, dated Nov. 9, 2004, of U.S. Appl. No. 10/295,761, filed Nov. 15, 2002.
Response to Office Action, dated May 11, 2009, of U.S. Appl. No. 11/347,748, filed Feb. 3, 2006.
Office Action, dated Aug. 27, 2009, of U.S. Appl. No. 11/347,748, filed Feb. 3, 2006.

Notice of Abandonment, dated Mar. 18, 2010, of U.S. Appl. No. 11/347,748, filed Feb. 3, 2006.
Office Action, dated Jan. 14, 2009, of U.S. Appl. No. 11/359,721, filed Feb. 21, 2006.
Notice of Abandonment, dated Sep. 9, 2009, of U.S. Appl. No. 11/359,721, filed Feb. 21, 2006.
Office Action, dated Dec. 11, 2007, of U.S. Appl. No. 11/318,940, filed Dec. 22, 2005.
Response to Office Action, dated Jun. 11, 2008, of U.S. Appl. No. 11/318,940, filed Dec. 22, 2005.
Office Action, dated Oct. 28, 2008, of U.S. Appl. No. 11/318,940, filed Dec. 22, 2005.
Response to Office Action, dated Apr. 23, 2009, of U.S. Appl. No. 11/318,940, filed Dec. 22, 2005.
Office Action, dated Jun. 8, 2009, of U.S. Appl. No. 11/318,940, filed Dec. 22, 2005.
Response to Office Action, dated Nov. 9, 2009 of U.S. Appl. No. 11/318,940, filed on Dec. 22, 2005.
Office Action, dated Feb. 1, 2010, of U.S. Appl. No. 11/318,940, filed Dec. 22, 2005.
Notice of Abandonment, dated Aug. 18, 2010, of U.S. Appl. No. 11/318,940, filed Dec. 22, 2005.
Notice of Abandonment, dated Mar. 19, 2009, of U.S. Appl. No. 11/098,946, filed Apr. 4, 2005.

* cited by examiner

7. DMSO
8. Paromomycin
9. Compound A (A, B, E, F, G, H)
10. Compound B (A, B, E, F, G, H)
11. Compound C (C, D)
12. Compound D (A, B, E, F, G, H)

7. DMSO
8. paromomycin
9. Compound E (J)
10. Compound F (J)
11. Compound G (I)
12. Compound H (J)

METHODS FOR IDENTIFYING SMALL MOLECULES THAT MODULATE PREMATURE TRANSLATION TERMINATION AND NONSENSE MEDIATED MRNA DECAY

This application is entitled to and claims priority benefit to U.S. Provisional Patent Application No. 60/398,344, filed Jul. 24, 2002 and U.S. Provisional Patent Application No. 60/398, 332, filed Jul. 24, 2002, both of which are incorporated herein by reference in their entirety.

1. INTRODUCTION

The present invention relates to a method for screening and identifying compounds that modulate premature translation termination and/or nonsense-mediated messenger ribonucleic acid ("mRNA") decay by interacting with a preselected target ribonucleic acid ("RNA"). In particular, the present invention relates to methods of identifying compounds that bind to regions of the 28S ribosomal RNA ("rRNA") and analogs thereof Direct, non-competitive binding assays are advantageously used to screen libraries of compounds for those that selectively bind to a preselected target RNA. Binding of target RNA molecules to a particular compound is detected using any physical method that measures the altered physical property of the target RNA bound to a compound. The methods of the present invention provide a simple, sensitive assay for high-throughput screening of libraries of compounds to identify pharmaceutical leads.

2. BACKGROUND OF THE INVENTION

Protein synthesis encompasses the processes of translation initiation, elongation, and termination, each of which has evolved to occur with great accuracy and has the capacity to be a regulated step in the pathway of gene expression. Recent studies, including those suggesting that events at termination may regulate the ability of ribosomes to recycle to the start site of the same mRNA, have underscored the potential of termination to regulate other aspects of translation. The RNA triplets UAA, UAG, and UGA are non-coding and promote translational termination. Termination starts when one of the three termination codons enters the A site of the ribosome, thereby signaling the polypeptide chain release factors to bind and recognize the termination signal. Subsequently, the ester bond between the 3' nucleotide of the transfer RNA ("tRNA") located in the ribosome's P site and the nascent polypeptide chain is hydrolyzed, the completed polypeptide chain is released, and the ribosome subunits are recycled for another round of translation.

Nonsense-mediated mRNA decay is a surveillance mechanism that minimizes the translation and regulates the stability of RNAs that contain chain termination nonsense mutations (see, e.g., Hentze & Kulozik, 1999, Cell 96:307-310; Culbertson, 1999, Trends in Genetics 15:74-80; Li & Wilkinson, 1998, Immunity 8:135-141; and Ruiz-Echevarria et al., 1996, Trends in Biological Sciences, 21:433-438). Chain termination nonsense mutations are caused when a base substitution or frameshift mutation changes a codon into a termination codon, i.e., a premature stop codon that causes translational termination. In nonsense-mediated mRNA decay, mRNAs with premature stop codons are frequently subjected to degradation. A truncated protein is produced as a result of the translation apparatus prematurely terminating at the stop codon.

Nonsense mutations cause approximately 10 to 30 percent of the individual cases of virtually all inherited diseases. Although nonsense mutations inhibit the synthesis of a full-length protein to one percent or less of wild-type levels, minimally boosting the expression levels of the full-length protein to between five and fifteen percent of normal levels can eliminate or greatly reduce the severity of disease. Nonsense suppression causes the read-through of a termination codon and the generation of full-length protein. Certain aminoglycosides have been found to promote nonsense suppression (see, e.g. Bedwell et al., 1997, Nat. Med. 3:1280-1284 and Howard et al., 1996, Nat. Med. 2:467-469). Clinical approaches that target the translation termination event to promote nonsense suppression have recently been described for model systems of cystic fibrosis and muscular dystrophy; gentamicin is an aminoglycoside antibiotic that causes translational misreading and allows the insertion of an amino acid at the site of the nonsense codon in models of cystic fibrosis, Hurlers Syndrome, and muscular dystrophy (see, e.g., Barton-Davis et al., 1999, J. Clin. Invest. 104:375-381). These results strongly suggest that drugs that promote nonsense suppression by altering translation termination efficiency of a premature termination codon can be therapeutically valuable in the treatment of diseases caused by nonsense mutations.

Certain classes of known antibiotics have been characterized and found to interact with RNA. For example, the antibiotic thiostrepton binds tightly to a 60-mer from ribosomal RNA (Cundliffe et al., 1990, in The Ribosome: Structure, Function & Evolution (Schlessinger et al., eds.) American Society for Microbiology, Washington, D.C. pp. 479-490), and bacterial resistance to various antibiotics often involves methylation at specific rRNA sites (Cundliffe, 1989, Ann. Rev. Microbiol. 43:207-233). In addition, certain aminoglycosides and other protein synthesis inhibitors have been found to interact with specific bases in 16S rRNA (Woodcock et al., 1991, EMBO J. 10:3099-3103); moreover, an oligonucleotide analog of the 16S rRNA has been shown to interact with certain aminoglycosides (Purohit et al., 1994, Nature 370:659-662). Aminoglycosidic aminocyclitol (aminoglycoside) antibiotics and peptide antibiotics are known to inhibit group I intron splicing by binding to specific regions of the RNA (von Ahsen et al., 1991, Nature (London) 353:368-370). Some of these same aminoglycosides have also been found to inhibit hammerhead ribozyme function (Stage et al., 1995, RNA 1:95-101). A molecular basis for hypersensitivity to aminoglycosides has been found to be located in a single base change in mitochondrial rRNA (Hutchin et al., 1993, Nucleic Acids Res. 21:4174-4179). Aminoglycosides have also been shown to inhibit the interaction between specific structural RNA motifs and the corresponding RNA binding protein. Zapp et al. (Cell, 1993, 74:969-978) has demonstrated that the aminoglycosides neomycin B, lividomycin A, and tobramycin can block the binding of Rev, a viral regulatory protein required for viral gene expression, to its viral recognition element in the IIB (or RRE) region of HIV RNA. This blockage appears to be the result of competitive binding of the antibiotics directly to the RRE RNA structural motif.

Citation or identification of any reference in Section 2 of this application is not an admission that such reference is available as prior art to the present invention.

3. SUMMARY OF THE INVENTION

The present invention provides methods for identifying compounds that modulate translation termination and/or nonsense-mediated mRNA decay by identifying compounds that bind to preselected target elements of nucleic acids including, but not limited to, specific RNA sequences, RNA structural motifs, and/or RNA structural elements. In particular, the present invention provides methods of identifying compounds that bind to regions of the 28S rRNA and analogs thereof The specific target RNA sequences, RNA structural motifs, and/or RNA structural elements (i.e., regions or fragments of the 28S rRNA and analogs thereof) are used as targets for screening small molecules and identifying those that directly bind these specific sequences, motifs, and/or structural elements. For example, methods are described in which a preselected target RNA having a detectable label or method of detection is used to screen a library of compounds, preferably under physiologic conditions; and any complexes formed between the target RNA and a member of the library are identified using physical methods that detect the labeled or altered physical property of the target RNA bound to a compound Further, methods are described in which a preselected target RNA is used to screen a library of compounds, with each compound in the library having a detectable label or method of detection, preferably under physiologic conditions; and any complexes formed between the target RNA and a member of the library are identified using physical methods that detect the labeled or altered physical property of the compound bound to target RNA.

The present invention provides methods for identifying compounds that bind to a target RNA (e.g., regions or fragments of 28S rRNA, or RNA containing a premature stop codon), said methods comprising contacting a target RNA having a detectable label with a library of compounds free in solution, in, e.g., labeled tubes or microtiter plate, and detecting the formation of a target RNA:compound complex. In particular, the present invention provides methods for identifying compounds that bind to a target RNA (e.g., regions or fragments of the 28S rRNA, or RNA containing a premature stop codon), said methods comprising contacting a target RNA having a detectable label with a library of compounds free in solution, in, e.g., labeled tubes or a microtiter plate, and detecting the formation of a target RNA:compound complex. Compounds in the library that bind to the labeled target RNA will form a detectably labeled complex. The detectably labeled complex can then be identified and removed from the uncomplexed, unlabeled complex, and from uncomplexed, labeled target RNA, by a variety of methods, including, but not limited to, methods that differentiate changes in the electrophoretic, chromatographic, or thermostable properties of the complexed target RNA. Such methods include, but are not limited to, electrophoresis, fluorescence spectroscopy, surface plasmon resonance, mass spectrometry, scintillation proximity assay, structure-activity relationships ("SARS") by NMR spectroscopy, size exclusion chromatography, affinity chromatography, and nanoparticle aggregation.

The present invention provides methods for identifying compounds that bind to a target RNA (e.g., regions of 28S rRNA or RNA containing a premature stop codon), said methods comprising contacting a target RNA having a detectable label with a library of compounds bound, wherein each compound in the library is attached to a solid support, and detecting the formation of a target RNA:compound complex. In particular, the present invention provides methods for identifying compounds that bind to a target RNA (e.g., regions or fragments of 28S rRNA, or RNA containing a premature stop codon), said methods comprising contacting a target RNA having a detectable label with a library of compounds wherein each compound is attached to a solid support, (e.g., a bead-based library of compounds or a microarray of compounds), and detecting the formation of a target RNA:compound complex. Compounds in the library that bind to the labeled target RNA will form a detectably labeled complex. Compounds in the library that bind to the labeled target RNA will form a solid support detectably labeled complex (e.g., a bead-based-detectably labeles complex), which can be separated from the unbound solid support, (e.g., beads) and unbound target RNA in the liquid phase by a number of physical means, including, but not limited to, flow cytometry, affinity chromatography, manual batch mode separation, suspension of beads in electric fields, and microwave of the bead-based detectably labeled complex.

The present invention provides methods for identifying compounds that bind to a target RNA (e.g., regions or fragments of 28S rRNA or RNA containing a premature stop codon), said methods comprising contacting a target RNA with a library of compounds, wherein each compound in the library is detectably labeled, and detecting the formation of a target RNA:compound complex. In particular, the present invention provides methods for identifying compounds that bind to a target RNA (e.g. regions or fragments of 28S rRNA, or RNA containing a premature stop codon), said methods comprising contacting a target RNA with a library of compounds free in solution, in, e.g., labeled tubes or a microtiter plate, wherein each compound in the library is detectably labeled, and detecting the formation of a target RNA:compound complex. Compounds in the library that bind to the labeled target RNA will form a detectably labeled complex. The detectably labeled complex can then be identified and removed from the uncomplexed, unlabeled complex, and from uncomplexed, target RNA, by a variety of methods, including, but not limited to, methods that differentiate changes in the electrophoretic, chromatographic, or thermostable properties of the complexed target RNA. Such methods include, but are not limited to, electrophoresis, fluorescence spectroscopy, surface plasmon resonance, mass spectrometry, scintillation proximity assay, structure-activity relationships ("SARS") by NMR spectroscopy, size exclusion chromatography, affinity chromatography, and nanoparticle aggregation.

The present invention provides methods for identifying compounds that bind to a target RNA (e.g., regions or fragments of 28S rRNA or RNA containing a premature stop codon), said methods comprising contacting a target RNA attached or conjugated to a solid support with a library of compounds, wherein each compound in the library is detectably labeled, and detecting the formation of a target RNA:compound complex. Target RNA molecules that bind to labeled compounds will form a detectable labeled complex. Target RNA molecules that bind to labeled compounds will form solid support-detectably labeled complex, which can be separated from unbound solid support-target RNA and unbound labeled compounds in the liquid phase by a number of means, including, but not limited to, flow cytometry, affinity chromatography, manual batch mode separation, suspension of beads in electric fields, and microwave of the bead-based detectably labeled complex.

In a specific embodiment, the invention provides a method for identifying a compound that binds to a target RNA, said method comprising: (a) contacting a detectably labeled target RNA molecule with a library of compounds under conditions that permit direct binding of the labeled target RNA to a member of the library of compounds and the formation of a detectably labeled target RNA:compound complex, wherein the target RNA is a region or fragment of 28S rRNA, or contains a premature stop codon; and (b) detecting the formation of a labeled target RNA:compound complex. In another embodiment, the invention provides a method for identifying a compound that binds to a target RNA, said method comprising detecting the formation of a detectably labeled target RNA:compound complex formed from contacting a detectably labeled RNA with a member of a library of compounds under conditions that permit direct binding of the labeled target RNA to a member of the library of compounds and the formation of a labeled target RNA:compound complex, wherein the target RNA is a region or fragment of 28S rRNA, or contains a premature stop codon. In accordance with these embodiments, each compound in the library may be attached to a solid support. Non-limiting examples of solid supports include a silica gel, a resin, a derivatized plastic film, a glass bead, cotton, a plastic bead, a polystyrene bead, an aluminum gel, a glass slide or a polysaccharide.

In another specific embodiment, the invention provides a method for identifying a compound that binds to a target RNA, said method comprising: (a) contacting a target RNA molecule with a library of detectably labeled compounds under conditions that permit direct binding of the target RNA to a member of the library of labeled compounds and the formation of a detectable target RNA:compound complex, wherein the target RNA is a region or fragment of 28S rRNA, or contains a premature stop codon; and (b) detecting the formation of a target RNA:compound complex. In another embodiment, the invention provides a method for identifying a compound that binds to a target RNA, said method comprising detecting the formation of a target RNA:compound complex formed from contacting a RNA with a member of a library of detectably labeled compounds under conditions that permit direct binding of the target RNA to a member of the library of labeled compounds and the formation of a target RNA:compound complex, wherein the target RNA is a region or fragment of 28S rRNA, or contains a premature stop codon. In accordance with these embodiments, the target RNA may be attached to a solid support. Non-limiting examples of solid supports include a silica gel, a resin, a derivatized plastic film, a glass bead, cotton, a plastic bead, a polystyrene bead, an aluminum gel, a glass slide or a polysaccharide.

In another specific embodiment, the invention provides a method for identifying a compound that binds to a target RNA, said method comprising: (a) contacting a detectably labeled target RNA molecule with a library of detectably labeled compounds under conditions that permit direct binding of the labeled target RNA to a member of the library of labeled and the formation of a detectable target RNA:compound complex, wherein the target RNA is a region or fragment of 28S rRNA, or contains a premature stop codon; and (b) detecting the formation of a target RNA:compound complex. In another embodiment, the invention provides a method for identifying a compound that binds to a target RNA, said method comprising detecting the formation of a target RNA:compound complex formed from contacting a labeled RNA with a member of a library of detectably labeled compounds under conditions that permit direct binding of the labeled target RNA to a member of the library of labeled compounds and the formation of a target RNA:compound complex, wherein the target RNA is a region or fragment of 28S rRNA or contains a premature stop codon. In accordance with these embodiments, the target RNA may be attached to a solid support. Non-limiting examples of solid supports are provided infra. A number of techniques can be used to detect the interaction between target RNA and the compounds of the invention. In a specific embodiment, fluorescence resonance energy transfer (FRET) is used to detect the interaction between the target RNA and the compound of the invention. Examples of FRET assays are known in the art and are also provided herein (see, e.g., Section 5.6.2).

The methods described herein for the identification of compounds that directly bind to 28S rRNA or a RNA containing a premature stop codon are well suited for high-throughput screening. The direct binding method of the invention offers advantages over drug screening systems for competitors that inhibit the formation of naturally-occurring RNA binding protein:target RNA complexes; i.e., competitive assays. The direct binding method of the invention is rapid and can be set up to be readily performed, e.g., by a technician, making it amenable to high-throughput screening. The methods of the invention also eliminate the bias inherent in the competitive drug screening systems, which require the use of a preselected host cell factor that may not have physiological relevance to the activity of the target RNA. Instead, the methods of the invention are used to identify any compound that can directly bind to a target RNA, (e.g. 28S rRNA or a RNA containing a premature stop codon), preferably under physiologic conditions. As a result, the compounds so identified can inhibit the interaction of the target RNA with any one or more of the native host cell factors (whether known or unknown) required for activity of the RNA in vivo.

The compounds utilized in the assays described herein may be members of a library of compounds. In specific embodiment, the compound is selected from a combinatorial library of compounds comprising peptides; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small organic molecule libraries. In a preferred embodiment, the small organic molecule libraries are libraries of benzodiazepines, isoprenoids, thiazolidinones, metathiazanones, pyrrolidines, morpholino compounds, or diazepindiones.

In certain embodiments, the compounds are screened in pools. Once a positive pool has been identified, the individual compounds of that pool are tested separately. In certain embodiments, the pool size is at least 2, at least 5, at least 10, at least 25, at least 50, at least 75, at least 100, at least 150, at least 200, at least 250, or at least 500 compounds.

Once a compound is identified in accordance with the invention, the structure of the compound may be determined utilizing well-known techniques or by referring to a predetermined code. The methods used will depend, in part, on the nature of the library screened. For example, assays of microarrays of compounds, each having an address or identifier, may be deconvoluted, e.g., by cross-referencing the positive sample to original compound list that was applied to the individual test assays. Another method for identifying compounds includes de novo structure determination of the compounds using, for example, mass spectrometry or nuclear magnetic resonance ("NMR"). The compounds identified are useful for any purpose to which a binding reaction may be put, for example in assay methods, diagnostic procedures, cell sorting, as inhibitors of target molecule function, as probes, as sequestering agents and the like. In addition, small organic molecules which interact specifically with target RNA molecules may be useful as lead compounds for the development of therapeutic agents.

A compound identified in accordance with the methods of the invention may bind to a premature stop codon. A compound identified in accordance with the methods of invention may also disrupt an interaction between a premature stop codon and the mRNA translation machinery. In a preferred embodiment, a compound identified in accordance with the methods of the invention binds to RNA and suppresses premature translation termination and/or nonsense-mediated mRNA decay of a gene encoding a protein, polypeptide or peptide whose expression is beneficial to a subject. In another preferred embodiment, a compound identified in accordance with the methods of the invention binds to RNA and increases premature translation termination and/or nonsense-mediated mRNA decay of a gene encoding a protein, polypeptide or peptide whose expression is detrimental to a subject. In a specific embodiment, a compound identified in accordance with the methods of the invention preferentially or differentially modulates premature translation termination and/or nonsense-mediated mRNA decay of a specific nucleotide sequence of interest relative to another nucleotide sequence.

In certain embodiments of the invention, the compound identified using the assays described herein is a small molecule. In a preferred embodiment, the compound identified using the assays described herein is not known to affect premature translation termination and/or nonsense-mediated mRNA decay of a nucleic acid sequence, in particular a nucleic acid sequence of interest. In another preferred embodiment, the compound identified using the assays described herein has not been used as or suggested to be used in the prevention, treatment, management and/or amelioration of a disorder associated with, characterized by or caused by a premature stop codon. In another preferred embodiment, the compound identified using the assays described herein has not been used as or suggested to be used in the prevention, treatment, management and/or amelioration of a particular disorder described herein.

A compound identified in accordance with the methods of the invention may be tested in ill vitro and/or in vivo assays well-known to one of skill in the art or described herein to determine the prophylactic or therapeutic effect of a particular compound for a particular disorder. In particular, a compound identified utilizing the assays described herein may be tested in an animal model to determine the efficacy of the compound in the prevention, treatment or amelioration of a disorder associated with, characterized by or caused by a premature stop codon, or a disorder described herein, or a symptom thereof. In addition, a compound identified utilizing the assays described herein may be tested for its toxicity in in vitro and/or in vivo assays well-known to one of skill in the art. Further, a compound identified as binding to a target RNA utilizing assays described herein or those well-known in the art may be tested for its ability to modulate premature translation and/or nonsense mediated mRNA decay.

In a specific embodiment, the invention provides a method for identifying a compound to test for its ability to modulate premature translation termination or nonsense-mediated mRNA decay, said method comprising: (a) contacting a detectably labeled target RNA molecule with a library of compounds under conditions that permit direct binding of the labeled target RNA to a member of the library of compounds and the formation of a detectably labeled target RNA:compound complex, wherein the target RNA is a region or fragment of 28S rRNA or contains a premature stop codon; and (b) detecting a detectably labeled target RNA:compound complex formed in step(a), so that if a target RNA:compound complex is detected then the compound identified is tested for its ability to modulate premature translation or nonsense-mediated mRNA decay.

In a specific embodiment, the invention provides a method for identifying a compound to test for its ability to modulate premature translation termination or nonsense-mediated mRNA decay, said method comprising: (a) contacting a target RNA molecule with a library of detectably labeled compounds under conditions that permit direct binding of the target RNA to a member of the library of labeled compounds and the formation of a detectably labeled target RNA:compound complex, wherein the target RNA is a region or fragment of 28S rRNA or contains a premature stop codon; and (b) detecting a detectably labeled target RNA:compound complex formed in step(a), so that if a target RNA:compound complex is detected then the compound identified is tested for its ability to modulate premature translation or nonsense-mediated mRNA decay.

The invention provides cell-based and cell-free assays to test the ability of a compound identified in accordance with the methods of the invention to modulate premature translation termination and/or nonsense-mediated mRNA decay. In particular, the invention provides cell-based and cell-free reporter assays for the identification of a compound that modulates premature translation termination and/or nonsense-mediated mRNA decay. In general, the level of expression and/or activity of a reporter gene product in the reporter gene based-assays described herein is indicative of the effect of the compound on premature translation termination and/or nonsense-mediated mRNA decay. The reporter gene-based assays described herein for the identification of compounds that modulate premature translation termination and/or nonsense-mediated mRNA decay are well suited for high-throughput screening.

The reporter gene cell-based assays may be conducted by contacting a compound with a cell containing a nucleic acid sequence comprising a reporter gene, wherein the reporter gene contains a premature stop codon or nonsense mutation, and measuring the expression of the reporter gene. The reporter gene cell-free assays may be conducted by contacting a compound with a cell-free extract and a nucleic acid sequence comprising a reporter gene, wherein the reporter gene contains a premature stop codon or nonsense mutation, and measuring the expression of the reporter gene. In the cell-based and cell-free reporter gene assays described herein, the alteration in reporter gene expression or activity relative to a previously determined reference range, or to the expression or activity of the reporter gene in the absence of the compound or the presence of an appropriate control (e.g., a negative control) indicates that a particular compound modulates premature translation termination and/or nonsense-mediated mRNA decay. In particular, an increase in reporter gene expression or activity relative to a previously determined reference range, or to the expression in the absence of the compound or the presence of an appropriate control (e.g., a negative control) may, depending upon the parameters of the reporter gene assay, indicate that a particular compound reduces or suppresses premature translation termination and/or nonsense-mediated mRNA decay (i.e., increases nonsense suppression). In contrast, a decrease in reporter gene expression or activity relative to a previously determined reference range, or to the expression in the absence of the compound or the presence of an appropriate control (e.g., a negative control) may, depending upon the parameters of the reporter gene-based assay, indicate that a particular compound enhances premature translation termination and/or nonsense-mediated mRNA decay (i.e., decreases nonsense suppression).

In a specific embodiment, the invention provides a method of identifying a compound that modulates premature translation termination or nonsense-mediated mRNA decay, said method comprising: (a) contacting a detectably labeled target RNA molecule with a library of compounds under conditions that permit direct binding of the labeled target RNA to a member of the library of compounds and the formation of a detectably labeled target RNA:compound complex, wherein the target RNA is a region of 28S rRNA or contains a premature stop codon; (b) detecting a labeled target RNA:compound complex formed in step(a); so that if a target RNA:

compound complex is detected, then (c) contacting the compound with a cell-free translation mixture and a nucleic acid sequence comprising a regulatory element operably linked to a reporter gene, wherein the reporter gene contains a premature stop codon; and (d) detecting the expression of the reporter gene, wherein a compound that modulates premature translation termination or nonsense-mediated mRNA decay is identified if the expression of the reporter gene in the presence of the compound is altered relative to the expression of the reporter gene in the absence of the compound or the presence of a negative control. In accordance with this embodiment, each compound in the library may be attached to a solid support.

In another embodiment, the invention provides a method of identifying a compound that modulates premature translation termination or nonsense-mediated mRNA decay, said method comprising: (a) contacting a detectably labeled target RNA molecule with a library of compounds under conditions that permit direct binding of the labeled target RNA to a member of the library of compounds and the formation of a detectably labeled target RNA:compound complex, wherein the target RNA is a region of 28S rRNA or contains a premature stop codon; (b) detecting a labeled target RNA:compound complex formed in step(a); so that if a target RNA compound complex is detected, then (c) contacting the compound with a cell containing a nucleic acid sequence comprising a regulatory element operably linked to a reporter gene, wherein the reporter gene contains a premature stop codon; and (d) detecting the expression of the reporter gene, wherein a compound that modulates premature translation termination or nonsense-mediated mRNA decay is identified if the expression of the reporter gene in the presence of the compound is altered relative to the expression of the reporter gene in the absence of the compound or the presence of a negative control. In accordance with this embodiment, each compound in the library may be attached to a solid support.

In a specific embodiment, the invention provides a method of identifying a compound that modulates premature translation termination or nonsense-mediated mRNA decay, said method comprising: (a) contacting a detectably labeled target RNA molecule with a library of compounds under conditions that permit direct binding of the labeled target RNA to a member of the library of compounds and the formation of a detectably labeled target RNA:compound complex, wherein the target RNA is a region of 28S rRNA or contains a premature stop codon; (b) detecting a labeled target RNA:compound complex formed in step(a); then (c) contacting the compound with a cell-free translation mixture and a nucleic acid sequence comprising a regulatory element operably linked to a reporter gene, wherein the reporter gene contains a premature stop codon; and (d) detecting the expression of the reporter gene, wherein a compound that modulates premature translation termination or nonsense-mediated mRNA decay is identified if the expression of the reporter gene in the presence of the compound is altered relative to the expression of the reporter gene in the absence of the compound or the presence of a negative control. In accordance with this embodiment, each compound in the library may be attached to a solid support.

In another embodiment, the invention provides a method of identifying a compound that modulates premature translation termination or nonsense-mediated mRNA decay, said method comprising: (a) contacting a detectably labeled target RNA molecule with a library of compounds under conditions that permit direct binding of the labeled target RNA to a member of the library of compounds and the formation of a detectably labeled target RNA:compound complex, wherein the target RNA is a region of 28S rRNA or contains a premature stop codon; (b) detecting a labeled target RNA:compound complex formed in step(a); then (c) contacting the compound with a cell containing a nucleic acid sequence comprising a regulatory element operably linked to a reporter gene, wherein the reporter gene contains a premature stop codon; and (d) detecting the expression of the reporter gene, wherein a compound that modulates premature translation termination or nonsense-mediated mRNA decay is identified if the expression of the reporter gene in the presence of the compound is altered relative to the expression of the reporter gene in the absence of the compound or the presence of a negative control. In accordance with this embodiment, each compound in the library may be attached to a solid support.

In a specific embodiment, the invention provides a method of identifying a compound that modulates premature translation termination or nonsense-mediated mRNA decay, said method comprising: (a) contacting a target RNA molecule with a library of detectably labeled compounds under conditions that permit direct binding of the target RNA to a member of the library of labeled compounds and the formation of a detectably labeled target RNA:compound complex, wherein the target RNA is a region of 28S rRNA or contains a premature stop codon; (b) detecting a labeled target RNA:compound complex formed in step(a); then (c) contacting the compound with a cell-free translation mixture and a nucleic acid sequence comprising a regulatory element operably linked to a reporter gene, wherein the reporter gene contains a premature stop codon; and (d) detecting the expression of the reporter gene, wherein a compound that modulates premature translation termination or nonsense-mediated mRNA decay is identified if the expression of the reporter gene in the presence of the compound is altered relative to the expression of the reporter gene in the absence of the compound or the presence of a negative control. In accordance with this embodiment, the target RNA may be attached or conjugated to a solid support, or detectably labeled.

In another embodiment, the invention provides a method of identifying a compound that modulates premature translation termination or nonsense-mediated mRNA decay, said method comprising: (a) contacting a target RNA molecule with a library of detectably labeled compounds under conditions that permit direct binding of the target RNA to a member of the library of labeled compounds and the formation of a detectably labeled target RNA:compound complex, wherein the target RNA is a region of 28S rRNA or contains a premature stop codon; (b) detecting a labeled target RNA:compound complex formed in step(a); then (c) contacting the compound with a cell containing a nucleic acid sequence comprising a regulatory element operably linked to a reporter gene, wherein the reporter gene contains a premature stop codon; and (d) detecting the expression of the reporter gene, wherein a compound that modulates premature translation termination or nonsense-mediated mRNA decay is identified if the expression of the reporter gene in the presence of the compound is altered relative to the expression of the reporter gene in the absence of the compound or the presence of a negative control. In accordance with this embodiment, the target RNA may be attached or conjugated to a solid support, or detectably labeled.

In a specific embodiment, the invention provides a method of identifying a compound that modulates premature translation termination or nonsense-mediated mRNA decay, said method comprising: (a) contacting a target RNA molecule with a library of detectably labeled compounds under conditions that permit direct binding of the target RNA to a member of the library of labeled compounds and the formation of a detectably labeled target RNA:compound complex, wherein the target RNA is a region of 28S rRNA or contains a premature stop codon; (b) detecting a labeled target RNA:compound complex formed in step(a); so that if a target RNA:compound complex is detected, then (c) contacting the compound with a cell-free translation mixture and a nucleic acid sequence comprising a regulatory element operably linked to a reporter gene, wherein the reporter gene contains a premature stop codon; and (d) detecting the expression of the reporter gene, wherein a compound that modulates premature translation termination or nonsense-mediated mRNA decay is identified if the expression of the reporter gene in the presence of the compound is altered relative to the expression of the reporter gene in the absence of the compound or the presence of a negative control. In accordance with this embodiment, the target RNA may be attached or conjugated to a solid support, or detectably labeled.

In another embodiment, the invention provides a method of identifying a compound that modulates premature translation termination or nonsense-mediated mRNA decay, said method comprising: (a) contacting a target RNA molecule with a library of detectably labeled compounds under conditions that permit direct binding of the target RNA to a member of the library of labeled compounds and the formation of a detectably labeled target RNA:compound complex, wherein the target RNA is a region of 28S rRNA or contains a premature stop codon; (b) detecting a labeled target RNA:compound complex formed in step(a); so that if a target RNA:compound complex is detected, then (c) contacting the compound with a cell containing a nucleic acid sequence comprising a regulatory element operably linked to a reporter gene, wherein the reporter gene contains a premature stop codon; and (d) detecting the expression of the reporter gene, wherein a compound that modulates premature translation termination or nonsense-mediated mRNA decay is identified if the expression of the reporter gene in the presence of the compound is altered relative to the expression of the reporter gene in the absence of the compound or the presence of a negative control. In accordance with this embodiment, the target RNA may be attached or conjugated to a solid support, or detectably labeled.

The invention provides methods for preventing, treating, managing or ameliorating a disorder associated with, characterized by or caused by a premature translation termination and/or nonsense-mediated mRNA decay or a symptom thereof, said method comprising administering to a subject in need thereof a therapeutically or prophylactically effective amount of a compound, or a pharmaceutically acceptable salt thereof, identified according to the methods described herein.

The present invention may be understood more fully by reference to the detailed description and examples, which are intended to illustrate non-limiting embodiments of the invention.

3.1 Terminology

As used herein, the term "compound" refers to any agent or complex that is being tested for its ability to interact with a target nucleic acid (in particular, a target RNA) or has been identified as interacting with a target nucleic acid (in particular, a target RNA).

As used herein, the terms "disorder" and "disease" are to refer to a condition in a subject.

As used herein, a "dye" refers to a molecule that, when exposed to radiation, emits radiation at a level that is detectable visually or via conventional spectroscopic means. As used herein, a "visible dye" refers to a molecule having a chromophore that absorbs radiation in the visible region of the spectrum (i.e., having a wavelength of between about 400 nm and about 700 nm) such that the transmitted radiation is in the visible region and can be detected either visually or by conventional spectroscopic means. As used herein, an "ultraviolet dye" refers to a molecule having a chromophore that absorbs radiation in the ultraviolet region of the spectrum (i.e., having a wavelength of between about 30 nm and about 400 nm). As used herein, an "infrared dye" refers to a molecule having a chromophore that absorbs radiation in the infrared region of the spectrum (i.e., having a wavelength between about 700 nm and about 3,000 nm). A "chromophore" is the network of atoms of the dye that, when exposed to radiation, emits radiation at a level that is detectable visually or via conventional spectroscopic means. One of skill in the art will readily appreciate that although a dye absorbs radiation in one region of the spectrum, it may emit radiation in another region of the spectrum. For example, an ultraviolet dye may emit radiation in the visible region of the spectrum. One of skill in the art will also readily appreciate that a dye can transmit radiation or can emit radiation via fluorescence or phosphorescence.

As used herein, the term "effective amount" refers to the amount of a compound which is sufficient to (i) reduce or ameliorate the progression, severity and/or duration of a disorder (e.g., a disorder associated with, characterized by or caused by premature translation termination and/or nonsense-mediated mRNA decay), or one or more symptoms thereof, (ii) prevent the development, recurrence or onset of a disorder (e.g., a disorder associated with, characterized by or caused by premature translation termination and/or nonsense-mediated mRNA decay), or one or more symptoms thereof, (iii) prevent the advancement of a disorder (e.g., a disorder associated with, characterized by or caused by premature translation termination and/or nonsense-mediated mRNA decay), or one or more symptoms thereof, or (iv) enhance or improve the therapeutic effect(s) of another therapy.

As used herein, the term "fragment", in the context of a protein or polypeptide refers to a peptide sequence of at least 5 contiguous residues, at least 10 contiguous residues, at least 15 contiguous residues, at least 20 contiguous residues, at least 25 contiguous residues, at least 40 contiguous residues, at least 50 contiguous residues, at least 60 contiguous residues, at least 70 contiguous residues, at least 80 contiguous residues, at least 90 contiguous residues, at least 100 contiguous residues, at least 125 contiguous residues, at least 150 contiguous residues, at least 175 contiguous residues, at least 200 contiguous residues, or at least 250 contiguous residues of the sequence of another protein or polypeptide. In a specific embodiment, a fragment of a protein or polypeptide retains at least one function of the protein or polypeptide.

As used herein, the term "fragment", in the context of a nucleic acid sequence refers to a nucleotide sequence of at least 5 contiguous bases, at least 10 contiguous bases, at least 15 contiguous bases, at least 20 contiguous bases, at least 25 contiguous bases, at least 40 contiguous bases, at least 50 contiguous bases, at least 60 contiguous bases, at least 70 contiguous bases, at least 80 contiguous bases, at least 90 contiguous bases, at least 100 contiguous bases, at least 125 contiguous bases, at least 150 contiguous bases, at least 175 contiguous bases, at least 200 contiguous bases, or at least 250 contiguous bases of the sequence of another nucleic acid sequence. In a specific embodiment, a fragment of a nucleic acid sequence retains at least one domain of the nucleic acid sequence.

As used herein, the term "in combination" refers to the use of more than one therapy (e.g., prophylactic and/or therapeutic agents). The use of the term "in combination" does not restrict the order in which therapies (e.g., prophylactic and/or therapeutic agents) are administered to a subject with a disorder (e.g., a disorder associated with, characterized by or caused by premature translation termination and/or nonsense-mediated mRNA decay). A first therapy (e.g., a prophylactic or therapeutic agent such as a compound identified in accordance with the methods of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as a chemotherapeutic agent or a TNF-α antagonist) to a subject with a disorder (e.g., a disorder associated with, characterized by or caused by premature translation termination and/or nonsense-mediated mRNA decay).

As used herein, a "label" or "detectable label" is a composition that is detectable, either directly or indirectly, by spectroscopic, photochemical, biochemical, immunochemical, or chemical means. For example, useful labels include radioactive isotopes (e.g., $^{32}P$, $^{35}S$, and $^{3}H$), dyes, fluorescent dyes, electron-dense reagents, enzymes and their substrates (e.g., as commonly used in enzyme-linked immunoassays, e.g. alkaline phosphatase and horse radish peroxidase), biotin, streptavidin, digoxigenin, or haptens and proteins for which antisera or monoclonal antibodies are available. Moreover, a label or detectable moiety can include an "affinity tag" that, when coupled with the target nucleic acid and incubated with a compound or compound library, allows for the affinity capture of the target nucleic acid along with molecules bound to the target nucleic acid. One skilled in the art will appreciate that an affinity tag bound to the target nucleic acids has, by definition, a complimentary ligand coupled to a solid support that allows for its capture. For example, useful affinity tags and complimentary ligands or partners include, but are not limited to, biotin-streptavidin, complimentary nucleic acid fragments (e.g., oligo dT-oligo dA, oligo T-oligo A, oligo dG-oligo dC, oligo G-oligo C), aptamer complexes, aptamers, or haptens and proteins for which antisera or monoclonal antibodies are available. The label or detectable moiety is typically bound, either covalently, through a linker or chemical bound, or through ionic, van der Waals or hydrogen bonds to the molecule to be detected.

As used herein, a "library" in the context of compounds refers to a plurality of compounds with which a target nucleic acid molecule is contacted. A library can be a combinatorial library, e.g., a collection of compounds synthesized using combinatorial chemistry techniques, or a collection of unique chemicals of low molecular weight (less than 1000 daltons) that each occupy a unique three-dimensional space.

As used herein, the terms "manage", "managing" and "management" refer to the beneficial effects that a subject derives from a therapy (e.g., a prophylactic or therapeutic agent) which does not result in a cure of the disorder, (e.g., a disorder associated with, characterized by or caused by premature translation termination and/or nonsense-mediated mRNA decay). In certain embodiments, a subject is administered one or more therapies to "manage" a disease or disorder so as to prevent the progression or worsening of the disease or disorder.

As used herein, the phrase "modulation of premature translation termination and/or nonsense-mediated mRNA decay" refers to the regulation of gene expression by altering the level of nonsense suppression. For example, if it is desirable to increase production of a defective protein encoded by a gene with a premature stop codon, i.e., to permit read through of the premature stop codon of the disease gene so translation of the gene can occur, then modulation of premature translation termination and/or nonsense-mediated mRNA decay entails up-regulation of nonsense suppression. Conversely, if it is desirable to promote the degradation of an mRNA with a premature stop codon, then modulation of premature translation termination and/or nonsense-mediated mRNA decays entails down-regulation of nonsense suppression.

As used herein, the terms "non-responsive" and "refractory" describe patients treated with a currently available therapy (e.g., prophylactic or therapeutic agent) for a disorder (e.g., a disorder associated with, characterized by or caused by premature translation termination and/or nonsense-mediated mRNA decay such as, e.g., cancer), which is not clinically adequate to relieve one or more symptoms associated with such disorder. Typically, such patients suffer from severe, persistently active disease and require additional therapy to ameliorate the symptoms associated with their disorder.

As used herein, "nonsense-mediated mRNA decay" refers to any mechanism that mediates the decay of mRNAs containing a premature translation termination codon.

As used herein, a "nonsense mutation" is a point mutation changing a codon corresponding to an amino acid to a stop codon.

As used herein, "nonsense suppression" refers to the inhibition or suppression of premature translation termination and/or nonsense-mediated mRNA decay.

As used herein, the phrase "pharmaceutically acceptable salt(s)" includes but is not limited to salts of acidic or basic groups that may be present in compounds identified using the methods of the present invention. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety may form pharmaceutically or cosmetically acceptable salts with various amino acids, in addition to the acids mentioned above. Compounds that are acidic in nature are capable of forming base salts with various pharmacologically or cosmetically acceptable cations. Examples of such salts include alkali metal or alkaline earth metal salts and, particularly, calcium, magnesium, sodium lithium, zinc, potassium, and iron salts.

As used herein, the term "previously determined reference range" refers to a reference range for the readout of a particular assay. Each laboratory will establish its own reference range for each particular assay. In a preferred embodiment, at least one positive control and at least one negative control are included in each batch of compounds analyzed.

As used herein, a "premature termination codon" or "premature stop codon" refers to the occurrence of a stop codon instead of a codon corresponding to an amino acid.

As used herein, "premature translation termination" refers to the result of a mutation that changes a codon corresponding to an amino acid to a stop codon.

As used herein, the terms "prevent", "preventing" and "prevention" refer to the prevention of the development, recurrence or onset of a disorder (e.g., a disorder associated with, characterized by or caused by premature translation termination and/or nonsense-mediated mRNA decay) or one or more symptoms thereof resulting from the administration of one or more compounds identified in accordance the methods of the invention or the administration of a combination of such a compound and a known therapy for such a disorder.

As used herein, the terms "prophylactic agent" and "prophylactic agents" refer to any agent(s) which can be used in the prevention of a disorder (e.g., a disorder associated with, characterized by or caused by premature translation termination and/or nonsense-mediated mRNA decay). In certain embodiments, the term "prophylactic agent" refers to a compound identified in the screening assays described herein. In certain other embodiments, the term "prophylactic agent" refers to an agent other than a compound identified in the screening assays described herein which is known to be useful for, or has been or is currently being used to prevent or impede the onset, development and/or progression of a disorder (e.g., a disorder associated with, characterized by or caused by premature translation termination and/or nonsense-mediated mRNA decay) or one or more symptoms thereof.

As used herein, the phrase "prophylactically effective amount" refers to the amount of a therapy (e.g., a prophylactic agent) which is sufficient to result in the prevention of the development, recurrence or onset of one or more symptoms associated with a disorder (e.g., a disorder associated with, characterized by or caused by premature translation termination and/or nonsense-mediated mRNA decay).

As used herein, the term "purified," in the context of a compound, e.g. a compound identified in accordance with the method of the invention, refers to a compound that is substantially free of chemical precursors or other chemicals when chemically synthesized. In a specific embodiment, the compound is 60%, preferably 65%, 70%, 75%, 80%, 85%, 90%, or 99% free of other, different compounds. In a preferred embodiment, a compound identified in accordance with the methods of the invention is purified.

As used herein, the term "reporter gene" refers to a nucleotide sequence encoding a protein, polypeptide or peptide that is readily detectable either by its presence or activity. Any reporter gene well-known to one of skill in the art may be used in reporter gene constructs to ascertain the effect of a compound on premature translation termination.

As used herein, the term "small molecule" and analogous terms include, but are not limited to, peptides, peptidomimetics, amino acids, amino acid analogs, polynucleotides, polynucleotide analogs, nucleotides, nucleotide analogs, organic or inorganic compounds (i.e., including heterorganic and/or ganometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, the terms "subject" and "patient" are used interchangeably herein. The terms "subject" and "subjects" refer to an animal, preferably a mammal including a non-primate (e.g., a cow, pig, horse, cat, dog, rat, and mouse) and a primate (e.g., a chimpanzee, a monkey such as a cynomolgous monkey and a human), and more preferably a human. In one embodiment, the subject is refractory or non-responsive to current therapies for a disorder (e.g., a disorder associated with, characterized by or caused by premature translation termination and/or nonsense-mediated mRNA decay). In another embodiment, the subject is a farm animal (e.g., a horse, a cow, a pig, etc.) or a pet (e.g., a dog or a cat). In a preferred embodiment, the subject is a human.

As used herein, the term "synergistic" refers to a combination of a compound identified using one of the methods described herein, and another therapy (e.g., a prophylactic or therapeutic agent), which combination is more effective than the additive effects of the therapies. A synergistic effect of a combination of therapies (e.g., prophylactic or therapeutic agents) permits the use of lower dosages of one or more of the therapies and/or less frequent administration of said therapies to a subject with disorder (e.g., a disorder associated with, characterized by or caused by premature translation termination and/or nonsense-mediated mRNA decay). The ability to utilize lower dosages of a therapy (e.g., a prophylactic or therapeutic agent) and/or to administer said therapy less frequently reduces the toxicity associated with the administration of said therapy to a subject without reducing the efficacy of said therapies in the prevention, treatment, management or amelioration of a disorder (e.g., a disorder associated with, characterized by or caused by premature translation termination and/or nonsense-mediated mRNA decay). In addition, a synergistic effect can result in improved efficacy of therapies (e.g., prophylactic or therapeutic agents) in the prevention, treatment, management or amelioration of a disorder (e.g., a disorder associated with, characterized by or caused by premature translation termination and/or nonsense-mediated mRNA decay). Finally, a synergistic effect of a combination of therapies (e.g., prophylactic or therapeutic agents) may avoid or reduce adverse or unwanted side effects associated with the use of either therapy alone.

As used herein, the term "substantially one type of compound" means that the assay can be performed in such a fashion that at some point, only one compound need be used in each reaction so that, if the result is indicative of a binding event occurring between the target RNA molecule and the compound, the compound can be easily identified.

As used herein, a "target nucleic acid" refers to RNA, DNA, or a chemically modified variant thereof. In a preferred embodiment, the target nucleic acid is RNA. A target nucleic acid also refers to tertiary structures of the nucleic acids, such as, but not limited to loops, bulges, pseudoknots, guanosine quartets and turns. A target nucleic acid also refers to RNA elements such as, but not limited to, 28S rRNA and structural analogs thereof, which are described in Sections 5.1 and 5.2. Non-limiting examples of target nucleic acids are presented in Sections 5.1 and 5.2.

As used herein, a "target RNA" refers to RNA or a chemically modified variant thereof. A target RNA also refers to tertiary structures of RNA, such as, but not limited to loops, bulges, pseudoknots, guanosine quartets and turns. A target RNA also refers to RNA elements such as, but not limited to, 28S rRNA and structural analogs thereof, which are described in Sections 5.1 and 5.2. Non-limiting examples of target RNAs are presented in Sections 5.1 and 5.2. In a specific embodiment, a target RNA is at least 25 nucleotides, preferably at least 30 nucleotides, at least 35 nucleotides, at least 40 nucleotides, at least 45 nucleotides, at least 50 nucleotides, at least 55 nucleotides, at least 60 nucleotides, at least 65 nucleotides, at least 70 nucleotides, at least 75 nucleotides, at least 80 nucleotides, at least 85 nucleotides, at least 90 nucleotides, at least 95 nucleotides, at least 100 nucleotides, at least 125 nucleotides, at least 150 nucleotides, at least 175 nucleotides or at least 200 nucleotides in length.

As used herein, the terms "therapeutic agent" and "therapeutic agents" refer to any agent(s) which can be used in the prevention, treatment, management or amelioration of one or more symptoms of a disorder (e.g., a disorder associated with, characterized by or caused by premature translation termination and/or nonsense-mediated mRNA decay). In certain embodiments, the term "therapeutic agent" refers to a compound identified in the screening assays described herein. In other embodiments, the term "therapeutic agent" refers to an agent other than a compound identified in the screening assays described herein which is known to be useful for, or has been or is currently being used to prevent, treat, manage or ameliorate a disorder (e.g., a disorder associated with, characterized by or caused by premature translation termination and/or nonsense-mediated mRNA decay) or one or more symptoms thereof.

As used herein, the term "therapeutically effective amount" refers to that amount of a therapy (e.g., a therapeutic agent) sufficient to result in (i) the amelioration of one or more symptoms of a disorder (e.g., a disorder associated with, characterized by or caused by premature translation termination and/or nonsense-mediated mRNA decay), (ii) prevent advancement of a disorder (e.g., a disorder associated with, characterized by or caused by premature translation termination and/or nonsense-mediated mRNA decay), (iii) cause regression of a disorder (e.g., a disorder associated with, characterized by or caused by premature translation termination and/or nonsense-mediated mRNA decay), or (iv) to enhance or improve the therapeutic effect(s) of another therapy (e.g., therapeutic agent).

As used herein, the terms "treat", "treatment" and "treating" refer to the reduction or amelioration of the progression, severity and/or duration of a disorder (e.g., a disorder associated with, characterized by or caused by premature translation termination and/or nonsense-mediated mRNA decay) or one or more symptoms thereof resulting from the administration of one or more compounds identified in accordance the methods of the invention, or a combination of one or more compounds identified in accordance with the invention and another therapy.

As used herein, the terms "therapy" and "therapies" refer to any method, protocol and/or agent that can be used in the prevention, treatment, management or amelioration of a disesase or disorder or one or more symptoms thereof. In certain embodiments, such terms refer to chemotherapy, radiation therapy, surgery, supportive therapy and/or other therapies useful in the prevention, treatment, management or amelioration of a disease or disorder or one or more symptoms thereof known to skilled medical personnel.

4. DESCRIPTION OF DRAWINGS

FIG. 1. The human 28S rRNA. Domains II and V are circled.

Figure 2:
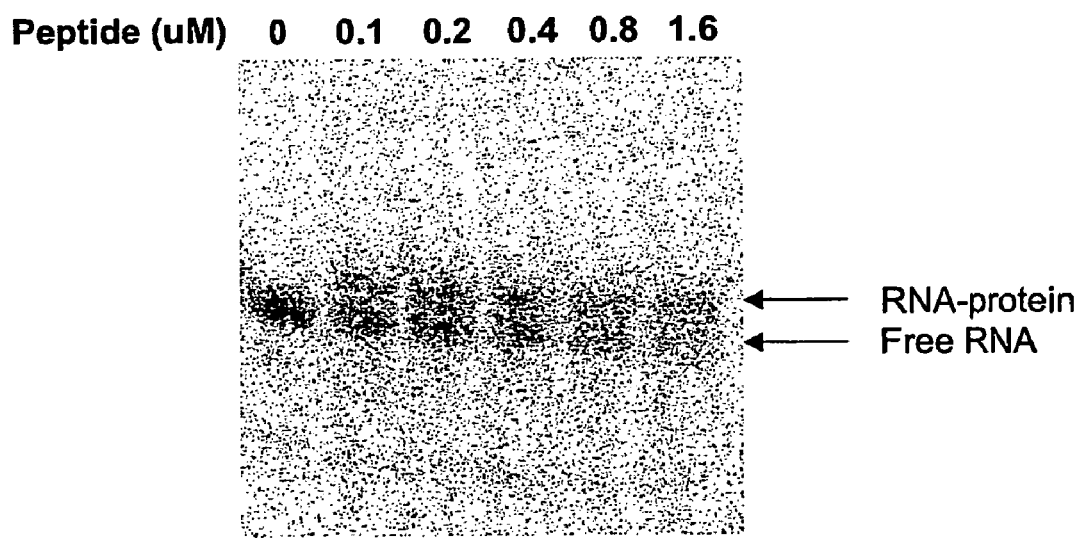

FIG. 2. Gel retardation analysis to detect peptide-RNA interactions. In 20 µl reactions containing 50 pmole end-labeled TAR RNA oligonucleotide, increasing concentrations of Tat$_{47-58}$ peptide (0.1 uM, 0.2 uM, 0.4 uM, 0.8 uM, 1.6 uM) was added in TK buffer. The reaction mixture was then heated at 90° C for 2 min and allowed to cool slowly to 24° C. 10 µl of 30% glycerol was added to each sample and applied to a 12% non-denaturing polyacrylamide gel. The gel was electrophoresed using 1200 volt-hours at 4° C. in TBE Buffer. Following electrophoresis, the gel was dried and the radioactivity was quantitated with a phosphorimager. The concentration of peptide added is indicated above each lane.

Figure 3:
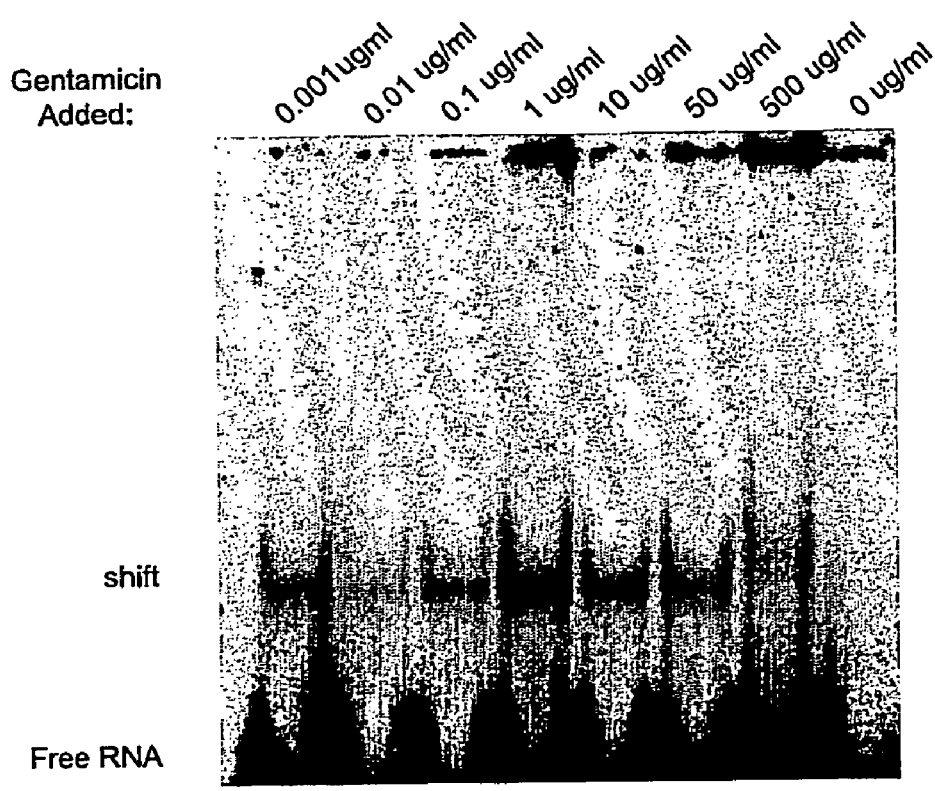

FIG. 3. Gentamicin interacts with an oligonucleotide corresponding to the 16S rRNA. 20 µl reactions containing increasing concentrations of gentamicin (1 ng/ml, 10 ng/ml, 100 ng/ml, 1 µg/ml, 10 µg/ml, 50 µg/ml, 500 µg/ml) were added to 50 pmole end-labeled RNA oligonucleotide in TKM buffer, heated at 90° C. for 2 min and allowed to cool slowly to 24° C. 10 µl of 30% glycerol was added to each sample and the samples were applied to a 13.5% non-denaturing polyacrylamide gel. The gel was electrophoresed using 1200 volt-hours at 4° C. in TBE Buffer. Following electrophoresis, the gel was dried and the radioactivity was quantitated using a phosphorimager. The concentration of gentamicin added is indicated above each lane.

Figure 4:
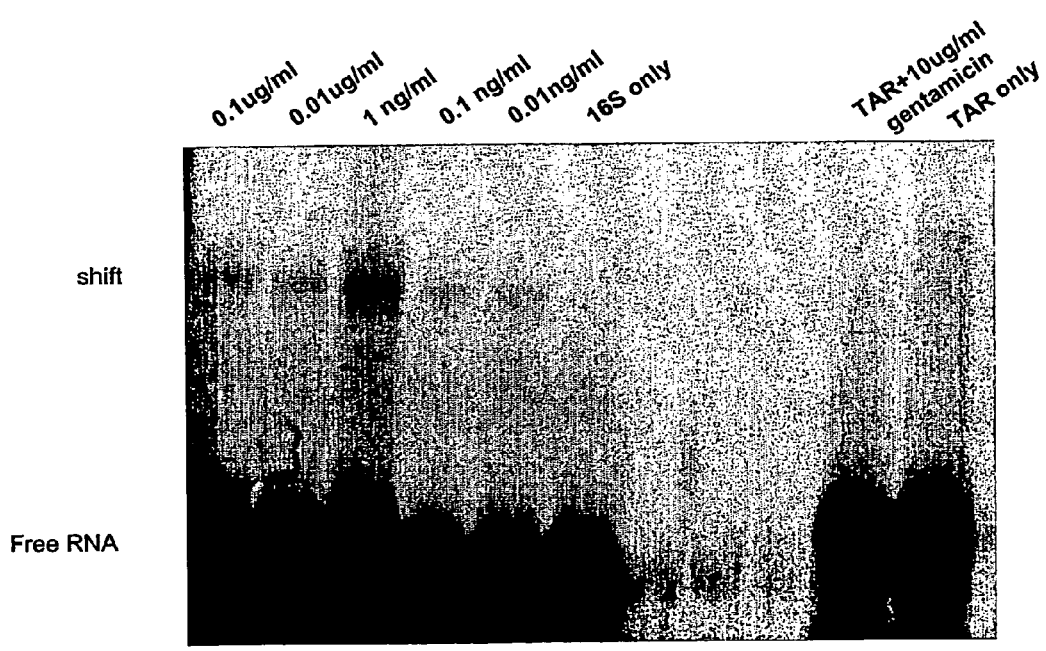

FIG. 4. The presence of 10 pg/ml gentamicin produces a gel mobility shift in the presence of the 16S rRNA oligonucleotide. 20 µl reactions containing increasing concentrations of gentamicin (100 ng/ml, 10 ng/ml, 1 ng/ml, 100 pg/ml, and 10 pg/ml) were added to 50 pmole end-labeled RNA oligonucleotide in TKM buffer were treated as described for FIG. 3.

Figure 5:
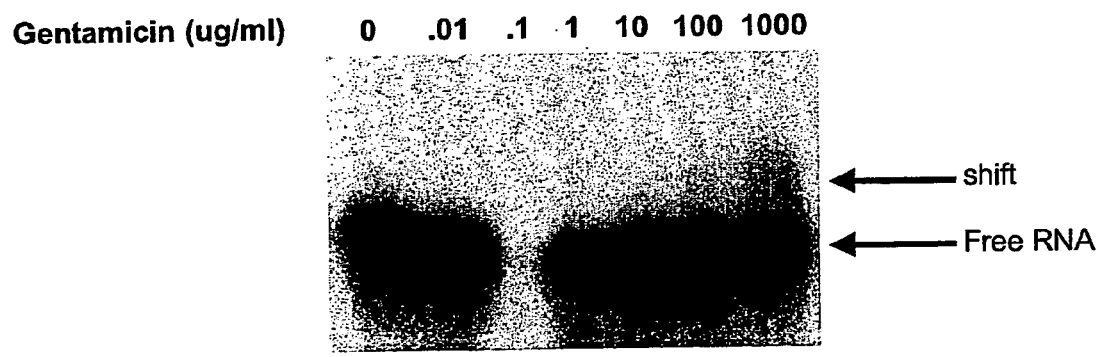

FIG. 5. Gentamicin binding to the 16S rRNA oligonucleotide is weak in the absence of $MgCl_2$. Reaction mixtures containing gentamicin (1 µg/ml, 100 µg/ml, 10 µg/ml, 1 µg/ml, 0.1 µg/ml, and 10 ng/ml) were treated as described in FIG. 3 except that the TKM buffer does not contain $MgCl_2$.

Figure 6:
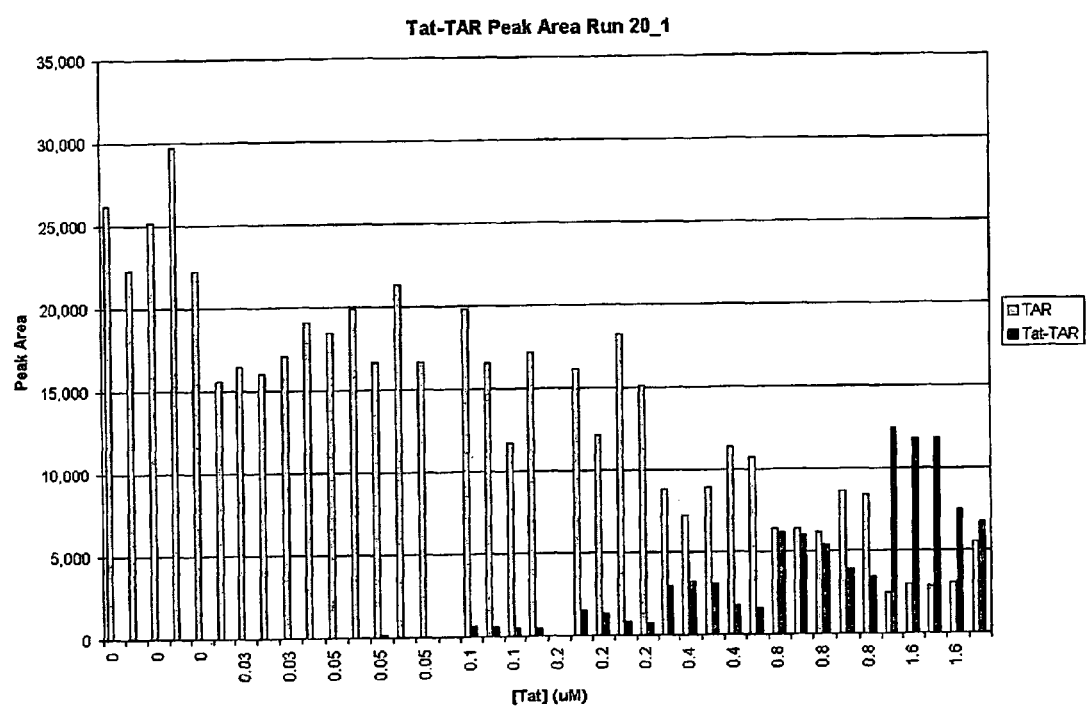

FIG. 6. Gel retardation analysis to detect peptide-RNA interactions. In reactions containing increasing concentrations of Tat$_{47-58}$ peptide (0.1 mM, 0.2 mM, 0.4 mM, 0.8 mM, 1.6 mM) 50 pmole TAR RNA oligonucleotide was added in TK buffer. The reaction mixture was then heated at 90° C. for 2 min and allowed to cool slowly to 24° C. The reactions were loaded onto a SCE9610 automated capillary electrophoresis apparatus (SpectruMedix; State College, Pennsylvania). The peaks correspond to the amount of free TAR RNA ("TAR") or the Tat-TAR complex ("Tat-TAR"). The concentration of peptide added is indicated below each lane.

Figure 7:
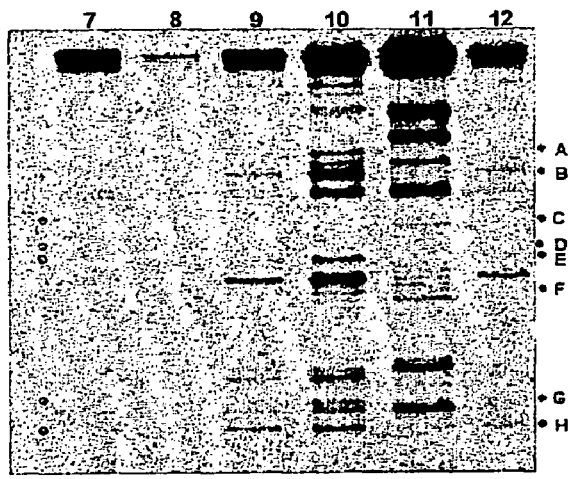
Figure 7:
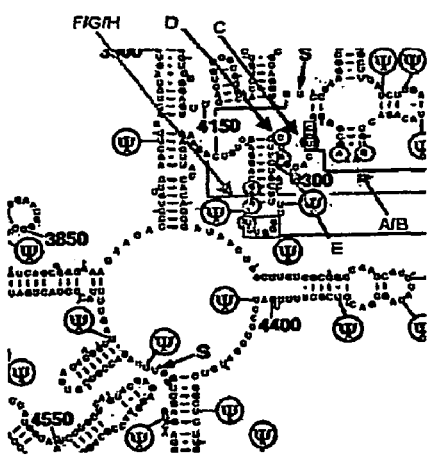

FIG. 7. Small molecules involved in nonsense suppression alter the chemical footprinting pattern in Domain V of the 28S rRNA. 100 pmol of ribosomes were incubated with 100 µM compound, followed by treatment with the chemical modifying agents kethoxal (KE) and dimethyl sulfate (DMS, not shown). Following chemical modification, rRNA was prepared and analyzed in primer extension reactions using end-labeled oligonucleotides hybridizing to rRNA A sequencing reaction was run in parallel as a marker.

Figure 8:
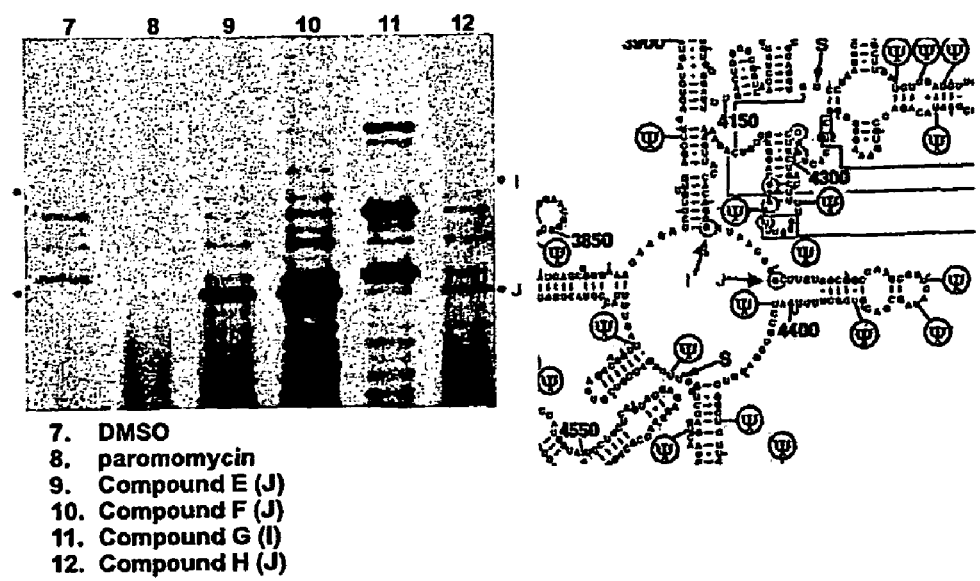

FIG. 8. Small molecules involved in nonsense suppression alter the chemical footprinting pattern in Domain V of the 28S rRNA. 100 pmol of ribosomes were incubated with 100 µM compound, followed by treatment with the chemical modifying agents kethoxal (KE) and dimethyl sulfate (DMS, not shown). Following chemical modification, rRNA was prepared and analyzed in primer extension reactions using end-labeled oligonucleotides hybridizing to rRNA. A sequencing reaction was run in parallel as a marker.

Figure 9:
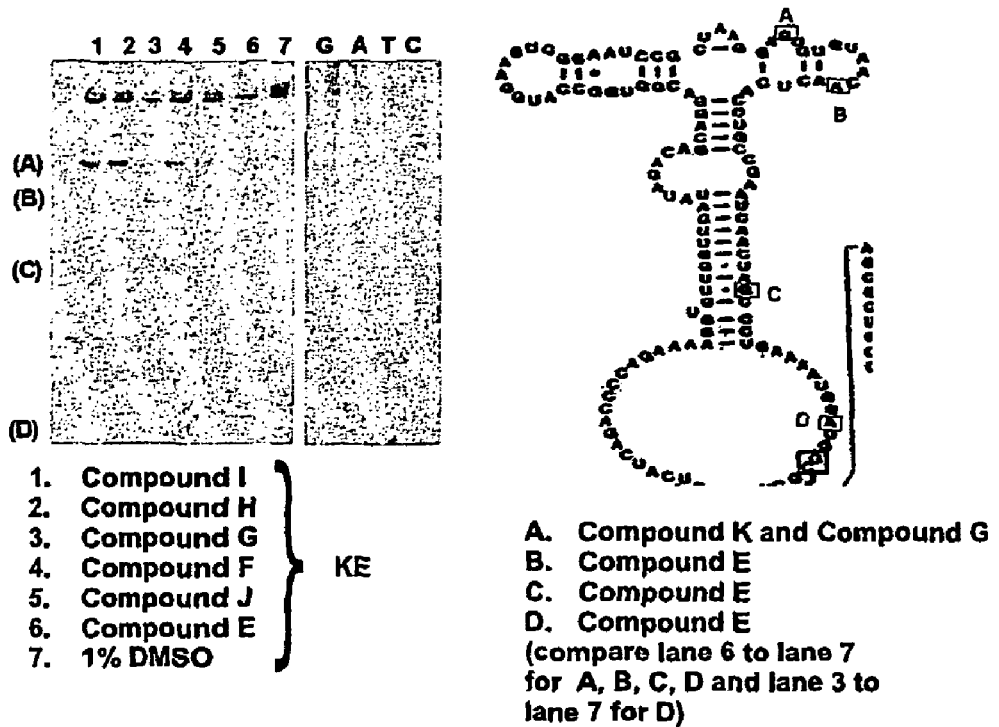

FIG. 9. Small molecules involved in nonsense suppression alter the chemical footprinting pattern in Domain II (GTPase Center) of the 28S rRNA. 100 pmol of ribosomes were incubated with 100 µM compound, followed by treatment with the chemical modifying agents kethoxal (KE) and dimethyl sulfate (DMS, not shown). Following chemical modification, rRNA was prepared and analyzed in primer extension reactions using end-labeled oligonucleotides hybridizing to rRNA. A sequencing reaction was run in parallel as a marker.

Figure 10:
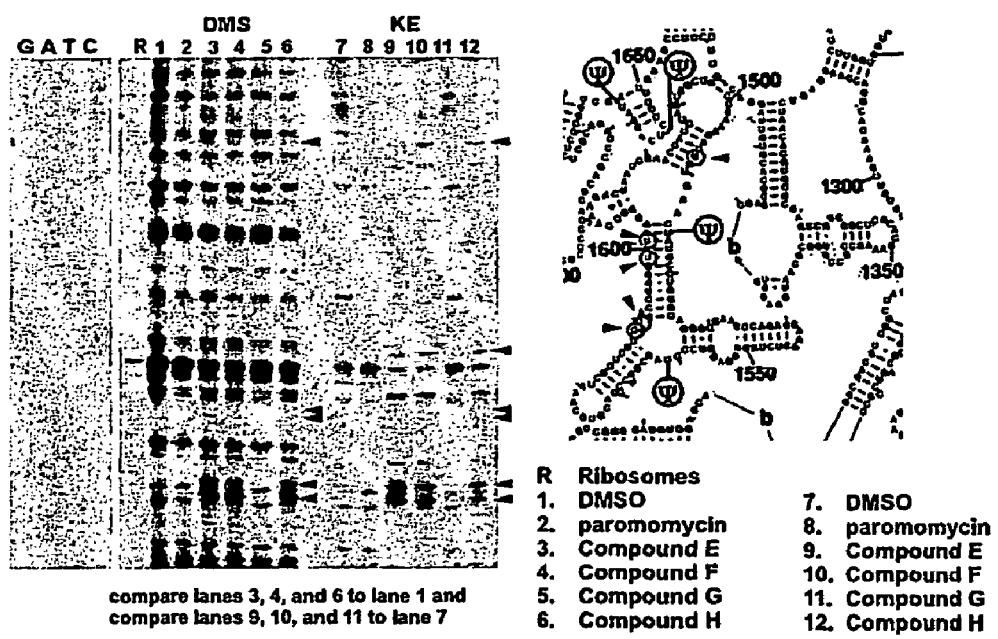

FIG. 10. Small molecules involved in nonsense suppression alter the chemical footprinting pattern of domain II of the 28S rRNA. 100 pmol of ribosomes were incubated with 100 µM compound, followed by treatment with chemical modifying agents dimethyl sulfate (DMS) and kethoxal (KE). Following chemical modification, rRNA was prepared and analyzed in primer extension reactions using end-labeled oligonucleotides hybridizing to rRNA. A sequencing reaction was run in parallel as a marker.

Figure 11:
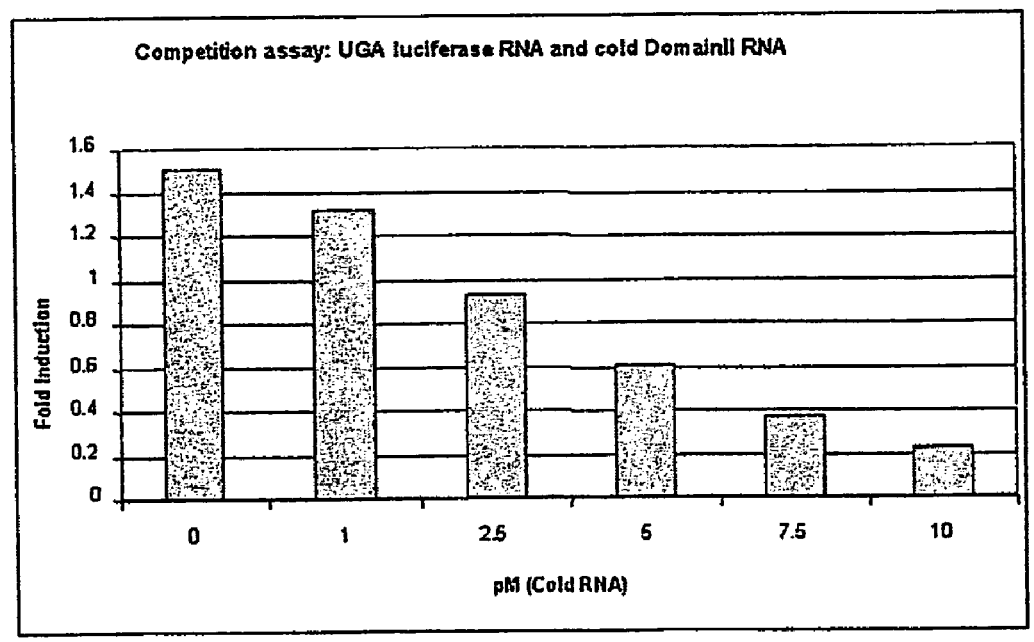

FIG. 11. A specific region of Domain II can compete for compound binding and prevents nonsense suppression in vitro. The in vitro nonsense suppression assay was performed using a luciferase construct with a UGA nonsense mutation. 0.1 mM compound was present in the reaction to induce nonsense suppression. Competitor RNA corresponding to Domain II was added at the indicated concentrations (0, 1, 2.5, 5, 7.5, 10 pM) to titrate the small molecule and prevent nonsense suppression.

5. DETAILED DESCRIPTION OF THE INVENTION

The present invention provides methods for identifying compounds that modulate translation termination and/or nonsense-mediated mRNA decay by identifying compounds that bind to preselected target elements of nucleic acids including, but not limited to, specific RNA sequences, RNA structural motifs, and/or RNA structural elements. In particular, the present invention provides methods of identifying compounds that bind to regions of the 28S rRNA and analogs thereof. The specific target RNA sequences, RNA structural motifs, and/or RNA structural elements (i.e., regions of the 28S rRNA and analogs thereof) are used as targets for screening small molecules and identifying those that directly bind these specific sequences, motifs, and/or structural elements. For example, methods are described in which a preselected target RNA having a detectable label or method of detection is used to screen a library of compounds, preferably under physiologic conditions; and any complexes formed between the target RNA and a member of the library are identified using physical methods that detect the labeled or altered physical property of the target RNA bound to a compound. Further, methods are described in which a preselected target RNA is used to screen a library of compounds, with each compound in the library having a detectable label or method of detection, preferably under physiologic conditions; and any complexes formed between the target RNA and a member of the library are identified using physical methods that detect the labeled or altered physical property of the compound bound to target RNA.

The present invention provides methods for identifying compounds that bind to a target RNA (e.g., regions or fragments of 28S rRNA or RNA containing a premature stop codon), said methods comprising contacting a target RNA having a detectable label with a library of compounds free in solution, and detecting the formation of a target RNA:compound complex. In particular, the present invention provides methods for identifying compounds that bind to a target RNA (e.g., regions or fragments of 28S rRNA or RNA containing a premature stop codon), said methods comprising contacting a target RNA having a detectable label with a library of compounds free in solution, in, e.g., labeled tubes or a microtiter plate, and detecting the formation of a target RNA:compound complex. Compounds in the library that bind to the labeled target RNA will form a detectably labeled complex. The detectably labled complex can then be identified and removed from the uncomplexed, unlabeled complex, and from uncomplexed, labeled target RNA, by a variety of methods, including, but not limited to, methods that differentiate changes in the electrophoretic, chromatographic, or thermostable properties of the complexed target RNA. Such methods include, but are not limited to, electrophoresis, fluorescence spectroscopy, surface plasmon resonance, mass spectrometry, scintillation proximity assay, structure-activity relationships ("SARS") by NMR spectroscopy, size exclusion chromatography, affinity chromatography, and nanoparticle aggregation.

The present invention provides methods for identifying compounds that bind to a target RNA (e.g., regions or fragments of 28S rRNA or RNA containing a premature stop codon), said methods comprising contacting a target RNA with a library of compounds, wherein each compound in the library is detectably labeled, and detecting the formation of a target RNA:compound complex. In particular, the present invention provides methods for identifying compounds that bind to a target RNA (e.g., regions or fragments of 28S rRNA, or RNA containing a premature stop codon), said methods comprising contacting a target RNA with a library of compounds free in solution, in, e.g., labeled tubes or a microtiter plate, wherein each compound in the library is detectably labeled, and detecting the formation of a target RNA:compound complex. Compounds in the library that bind to the labeled target RNA will form a detectably labeled complex. The detectably labled complex can then be identified and removed from the uncomplexed, unlabeled complex, and from uncomplexed, target RNA, by a variety of methods, including, but not limited to, methods that differentiate changes in the electrophoretic, chromatographic, or thermostable properties of the complexed target RNA. Such methods include, but are not limited to, electrophoresis, fluorescence spectroscopy, surface plasmon resonance, mass spectrometry, scintillation proximity assay, structure-activity relationships ("SARS") by NMR spectroscopy, size exclusion chromatography, affinity chromatography, and nanoparticle aggregation.

The present invention provides methods for identifying compounds that bind to a target RNA (e.g., regions or fragments of 28S rRNA or RNA containing a premature stop codon), said methods comprising contacting a target RNA having a detectable label with a library of compounds bound, wherein each compound in the library is attached to a solid support; and detecting the formation of a target RNA:compound complex. In particular, the present invention provides methods for identifying compounds that bind to a target RNA (in particular, regions of 28S rRNA or RNA containing a premature stop codon), said method comprising contacting a target RNA having a detectable label with a library of compounds, wherein each compound is attached to a solid support (e.g., a bead-based library of compounds or a microarray of compounds), and detecting the formation of a target RNA:compound complex. Compounds in the library that bind to the labeled target RNA will form a detectably labeled complex. Compounds in the library that bind to the labeled target RNA will form a solid support (e.g., a bead-based) detectably labeled complex, which can be separated from the unbound beads and unbound target RNA in the liquid phase by a number of physical means, including, but not limited to, flow cytometry, affinity chromatography, manual batch mode separation, suspension of beads in electric fields, and microwave of the bead-based detectably labeled complex.

The present invention provides methods for identifying compounds that bind to a target RNA (e.g., regions of 28S rRNA or RNA containing a premature stop codon), said methods comprising contacting a target RNA attached or conjugated to a solid support with a library of compounds, wherein each compound in the library is detectably labeled, and detecting the formation of a target RNA:compound complex. Target RNA molecules that bind to labeled compounds will form a detectable labeled complex. Target RNA molecules that bind to labeled compounds will form a solid support-based detectably labeled complex, which can be separated from the unbound solid support-target RNA and unbound compounds in the liquid phase by a number of means, including, but not limited to, flow cytometry, affinity chromatography, manual batch mode separation, suspension of beads in electric fields, and microwave of the bead-based detectably labeled complex.

Thus, the methods of the present invention provide a simple, sensitive assay for high-throughput screening of libraries of compounds, in which the compounds of the library that specifically bind a preselected target nucleic acid are easily distinguished from non-binding members of the library. In one embodiment, the structures of the binding molecules are deciphered from the input library by methods depending on the type of library that is used. In another embodiment, the structures of the binding molecules are ascertained by de novo structure determination of the compounds using, for example, mass spectrometry or nuclear magnetic resonance ("NMR"). The compounds so identified are useful for any purpose to which a binding reaction may be put, for example in assay methods, diagnostic procedures, cell sorting, as inhibitors of target molecule function, as probes, as sequestering agents and lead compounds for development of therapeutics, and the like. Small organic compounds that are identified to interact specifically with the target RNA molecules are particularly attractive candidates as lead compounds for the development of therapeutic agents.

The assays of the invention reduce bias introduced by competitive binding assays which require the identification and use of a host cell factor (presumably essential for modulating RNA function) as a binding partner for the target RNA. The assays of the present invention are designed to detect any compound or agent that binds to 28S rRNA, preferably under physiologic conditions. Such agents can then be tested for biological activity, without establishing or guessing which host cell factor or factors is required for modulating the function and/or activity of 28S rRNA.

5.1 28S rRNA and Analogs Thereof

The ribosome is a 2.5-MDa ribonucleoprotein complex involved in the decoding of genetic material from mRNA to proteins. A combination of biophysical and biochemical analysis have provided three dimensional models of the ribosome as well as detailed analyses into the mechanism of the individual steps in translation (see, e.g., Green & Noller, 1997, Annu. Rev. Biochem. 66:679-716; Cate et al., 1999, Science 285(5436):2095-2104; and Ban et al., 2000, Science.289(5481): 905-920.).

The 28S rRNA is one of the ribosomal RNA components of the 60S subunit of eukaryotic ribosomes. The 28S rRNA sequences are conserved when expressed as mature rRNAs, although the 28S rRNA contains variable sequence tracts that are interspersed among conserved core sequences and lacking in the counterpart bacterial 23S rRNA (see, e.g., Hancock & Dover, 1988, Mol. Biol. Evol. 5:377-391). A diagram of the 28S rRNA is presented in FIG. 1, with domains II and V circled. As indicated in FIG. 1, a GTPase center has been mapped to domain II and the peptidyl transferase center has been mapped to domain V.

Compounds that interact in these regions or modulate local changes within these domains of the ribosome (e.g., alter base pairing interactions, base modification or modulate binding of trans-acting factors that bind to these regions) have the potential to modulate translation termination. These regions, i.e., domains II and V are conserved from prokaryotes to eukaryotes, but the role of these regions in modulating translation termination has not been realized in eukaryotes. In bacteria, when a short RNA fragment, complementary to the E. coli 23S rRNA segment comprising nucleotides 735 to 766 (in domain II), is expressed in vivo, suppression of UGA nonsense mutations, but not UAA or UAG, results (Chernyaeva et al., 1999, J Bacteriol 181:5257-5262). Other regions of the 23S rRNA in E. coli have been implicated in nonsense suppression including the GTPase center in domain II (nt 10341120; Jemiolo et al., 1995, Proc. Nat. Acad. Sci. 92:12309-12313).

Genetic mutations in bacteria have also identified rRNA mutations that either increase the level of frameshifting in the trpE or the suppression of a nonsense mutations in the trpA gene (reviewed in Green & Noller, 1997, Annu. Rev. Biochem. 66:679-716). The frameshifting mutations mapped to domains IV and V of the 23S rRNA. Disruption of the interaction of the CCA end of the tRNA with the peptidyl transferase center of the ribosome has been demonstrated to result in an increased translational error frequency (reviewed in Green & Noller, 1997, Annu. Rev. Biochem. 66:679-716).

Regions of the 28S rRNA involved in frameshifting, nonsense mutation suppression, GTPase activity, or peptidyl transferase are attractive target RNAs to identify compounds that modulate premature translation termination and/or nonsense mediated decay. The interference of a compound with one or more of these functions could potentially mediate translation termination by interfering with premature translation termination. Without being bound by theory, a compound could potentially mediate translation termination by causing read through of a premature translation codon, therefore allowing the synthesis of the full-length protein.

In a preferred embodiment, the target RNA comprises a region of 28S rRNA corresponding to domain II (see, e.g., nucleotides 1310 to 2333 of accession number M11167) or domain V of 28S rRNA (see, e.g., nucleotides 3859 to 4425 of accession number M11167) or an analog thereof It will become apparent to one of skill in the art that an analog of the 28S rRNA has an analogous structure and function to native 28S rRNA. For example, an analog of human 28S rRNA includes, but is not limited to, a human 28S rRNA retropseudogene (see, e.g., Wang et al., 1997, Gene 196:105-111, Accession Number L20636). Regions corresponding to domain II or domain V of the 28S rRNA pseudogene could be used as target RNAs in the present invention. In a preferred embodiment, the 28S rRNA is a human 28S rRNA, although the teachings of the present invention are applicable to mammals.

Synthesis of the target RNAs, i.e., regions of 28S rRNA, can be performed by methods known to one of skill in the art (see, e.g., Sambrook et al., 1989, Molecular Cloning, A Laboratory Manual, 2d Ed., Cold Spring Harbor Laboratory Press, Cold Spring Harbor, New York and Glover, D. M. (ed.), 1985, DNA Cloning: A Practical Approach, MRL Press, Ltd., Oxford, U.K. Vol. I, II). In a preferred embodiment, the target RNAs are cloned as DNAs downstream of a promoter, such as but not limited to T7, T3, or Sp6 promoters, and in vitro transcribed with the corresponding polymerase. A detectable label can be incorporated into the in vitro transcribed RNA or alternatively, the target RNA is end-labeled (see Section 5.3 infra). Alternatively, the target RNA can be amplified by polymerase chain reaction with a primer containing an RNA promoter and subsequently in vitro transcribed, as described in U.S. Pat. No.6,271,002, which is incorporated by reference in its entirety.

5.2 Stop Codon Containing Target RNA

The present invention provides for methods for screening and identifying compounds that modulate premature translation termination and/or nonsense-mediated mRNA decay. A target RNA may be engineered to contain a premature stop codon or, alternatively, a target RNA may naturally contain a premature stop codon. The premature stop codon may any one of the stop codons known in the art including UAG, UAA and UGA.

The stop codons are UAG, UAA, and UGA, i.e., signals to the ribosome to terminate protein synthesis, presumably through protein release factors. Even though the use of these stop codons is widespread, they are not universal. For example, UGA specifies tryptophan in the mitochondria of mammals, yeast, Neurospora crassa, Drosophila, protozoa, and plants (see, e.g., Breitenberger & RajBhandary, 1985, Trends Biochem Sci 10:481). Other examples include the use of UGA for tryptophan in Mycoplasma and, in ciliated protozoa, the use of UAA and UAG for glutamine (see, e.g., Jukes et al., 1987, Cold Spring Harb Symp Quant Biol. 52:769-776), the use of UGA for cysteine in the ciliate Euplotes aediculatus (see, e.g., Kervestin et al., 2001, EMBO Rep August 2001 ;2(8):680-684), the use of UGA for tryptophan in Blepharisma americanum and the use of UAR for glutamine in Tetrahymena, and three spirotrichs, Stylonychia lemnae, S. mytilus, and Oxytricha trifallax (see, e.g., Lozupone et al., 2001, Curr Biol 11(2):65-74). It has been proposed that the ancestral mitochondrion was bearing the universal genetic code and subsequently reassigned the UGA codon to tryptophan independently, at least in the lineage of ciliates, kinetoplastids, rhodophytes, prymnesiophytes, and fungi (see, e.g., Inagaki et al., 1998, J Mol Evol 47(4):378-384).

The readthrough of stop codons also occurs in positive-sense ssRNA viruses by a variety of naturally occurring suppressor tRNAs. Such naturally-occurring suppressor tRNAs include, but are not limited to, cytoplasmic tRNATyr, which reads through the UAG stop codon; cytoplasmic tRNAsGln, which read through UAG and UAA; cytoplasmic tRNAsLeu, which read through UAG; chloroplast and cytoplasmic tRNAsTrp, which read through UGA; chloroplast and cytoplasmic tRNAsCys, which read through UGA; cytoplasmic tRNAsArg, which read through UGA (see, e.g. Beier & Grimm, 2001, Nucl Acids Res 29(23):4767-4782 for a review); and the use of selenocysteine to suppress UGA in E. coli (see, e.g., Baron & Böck, 1995, The selenocysteine inserting tRNA species: structure and function In SöllD. and RajBhandary, U.L. (eds), tRNA: Structure, Biosynthesis and Function, ASM Press, Washington, D.C., pp.529 544). The mechanism is thought to involve unconventional base interactions and/or codon context effects.

As described above, the stop codons are not necessarily universal, with considerable variation amongst organelles (e.g., mitochondria and chloroplasts), viruses (e.g., single strand viruses), and protozoa (e.g., ciliated protozoa) as to whether the codons UAG, UAA, and UGA signal translation termination or encode amino acids. Even though a single release factor most probably recognizes all of the stop codons in eukaryotes, it appears that all of the stop codons are not suppressed in a similar matter. For example, in the yeast Saccharomyces pombe, nonsense suppression has to be strictly codon specific (see, e.g., Hottinger et al., 1984, EMBO J 3:423-428). In another example, significant differences were found in the degree of suppression amongst three UAG codons and two UAA codons in different mRNA contexts in Escherichia coli and in human 293 cells, although data suggested that the context effects of nonsense suppression operated differently in E. coli and human cells (see, e.g., Martin et al., 1989, Mol Gen Genet 217(2 3):411 8). Since unconventional base interactions and/or codon context effects have been implicated in nonsense suppression, it is conceivable that compounds involved in nonsense suppression of one stop codon may not necessarily be involved in nonsense suppression of another stop codon. In other words, compounds involved in suppressing UAG codons may not necessarily be involved in suppressing UGA codons.

In a specific embodiment, a target RNA contains or is engineered to contain the premature stop codon UAG. In another embodiment, a target RNA contains or is engineered to contain the premature stop codon UGA.

In a particular embodiment, a target RNA contains or is engineered to contain two or more stop codons. In accordance with this embodiment, the stop codons are preferably at least 10 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, at least 75 nucleotides or at least 100 nucleotides apart from each other. Further, in accordance with this embodiment, at least one of the stop codons is preferably UAG or UGA.

In a specific embodiment, a target RNA contains or is engineered to contain a premature stop codon at least 15 nucleotides, preferably at least 20 nucleotides, at least 25 nucleotides, at least 30 nucleotides, at least 35 nucleotides, at least 40 nucleotides, at least 45 nucleotides, at least 50 nucleotides or at least 75 nucleotides from the start codon in the coding sequence. In another embodiment, a target RNA contains or is engineered to contain a premature stop codon at least 15 nucleotides, preferably at least 25 nucleotides, at least 50 nucleotides, at least 75 nucleotides, at least 100 nucleotides, at least 125 nucleotides, at least 150, at least 175 nucleotides or at least 200 nucleotides from the native stop codon in the coding sequence of the full-length protein, polypeptide or peptide. In another embodiment, a target RNA contains or is engineered to contain a premature stop codon at least 15 nucleotides (preferably at least 20 nucleotides, at least 25 nucleotides, at least 30 nucleotides, at least 35 nucleotides, at least 40 nucleotides, at least 45 nucleotides, at least 50 nucleotides or at least 75 nucleotides) from the start codon in the coding sequence and at least 15 nucleotides (preferably at least 25 nucleotides, at least 50 nucleotides, at least 75 nucleotides, at least 100 nucleotides, at least 125 nucleotides, at least 150, at least 175 nucleotides or at least 200 nucleotides) from the native stop codon in the coding sequence of the full-length protein, polypeptide or peptide. In accordance with these embodiments, the premature stop codon is preferably UAG or UGA.

The premature translation stop codon can be produced by in vitro mutagenesis techniques such as, but not limited to, polymerase chain reaction ("PCR"), linker insertion, oligonucleotide-mediated mutagenesis, and random chemical mutagenesis.

5.3 Target RNAs (Detectably Labeled or Attached to a Solid Support)

Target nucleic acids, including but not limited to RNA and DNA, useful in the methods of the present invention have a label that is detectable via conventional spectroscopic means or radiographic means. Preferably, target nucleic acids are labeled with a covalently attached dye molecule. Useful dye-molecule labels include, but are not limited to, fluorescent dyes, phosphorescent dyes, ultraviolet dyes, infrared dyes, and visible dyes. Preferably, the dye is a visible dye.

Useful labels in the present invention can include, but are not limited to, spectroscopic labels such as fluorescent dyes (e.g., fluorescein and derivatives such as fluorescein isothiocyanate (FITC) and Oregon Green™, rhodamine and derivatives (e.g., Texas red, tetramethylrhodimine isothiocynate (TRITC), bora-3a,4a-diaza-s-indacene (BODIPY®) and derivatives, etc.), digoxigenin, biotin, phycoerythrin, AMCA, CyDye™, and the like), radiolabels (e.g., $^3$H, $^{125}$I, $^{35}$S, $^{14}$C, $^{32}$P, $^{33}$P, etc.), enzymes (e.g., horse radish peroxidase, alkaline phosphatase etc.), spectroscopic colorimetric labels such as colloidal gold or colored glass or plastic (e.g. polystyrene, polypropylene, latex, etc.) beads, or nanoparticles—nanoclusters of inorganic ions with defined dimension from 0.1 to 1000 nm. Useful affinity tags and complimentary partners include, but are not limited to, biotin-streptavidin, complimentary nucleic acid fragments (e.g., oligo dT-oligo dA, oligo T-oligo A, oligo dG-oligo dC, oligo G-oligo C), aptamer-streptavidin, or haptens and proteins for which antisera or monoclonal antibodies are available. The label may be coupled directly or indirectly to a component of the detection assay (e.g., the detection reagent) according to methods well known in the art. A wide variety of labels may be used, with the choice of label depending on sensitivity required, ease of conjugation with the compound, stability requirements, available instrumentation, and disposal provisions.

In one embodiment, nucleic acids that are labeled at one or more specific locations are chemically synthesized using phosphoramidite or other solution or solid-phase methods. Detailed descriptions of the chemistry used to form polynucleotides by the phosphoramidite method are well known (see, e.g., Caruthers et al., U.S. Pat. Nos. 4,458,066 and 4,415,732; Caruthers et al., 1982, Genetic Engineering 4:1-17; Users Manual Model 392 and 394 Polynucleotide Synthesizers, 1990, pages 6-1 through 6-22, Applied Biosystems, Part No. 901237; Ojwang, et al., 1997, Biochemistry, 36:6033-6045). The phosphoramidite method of polynucleotide synthesis is the preferred method because of its efficient and rapid coupling and the stability of the starting materials. The synthesis is performed with the growing polynucleotide chain attached to a solid support, such that excess reagents, which are generally in the liquid phase, can be easily removed by washing, decanting, and/or filtration, thereby eliminating the need for purification steps between synthesis cycles.

The following briefly describes illustrative steps of a typical polynucleotide synthesis cycle using the phosphoramidite method. First, a solid support to which is attached a protected nucleoside monomer at its 3' terminus is treated with acid, e.g., trichloroacetic acid, to remove the 5'-hydroxyl protecting group, freeing the hydroxyl group for a subsequent coupling reaction. After the coupling reaction is completed an activated intermediate is formed by contacting the support-bound nucleoside with a protected nucleoside phosphoramidite monomer and a weak acid, e.g., tetrazole. The weak acid protonates the nitrogen atom of the phosphoramidite forming a reactive intermediate. Nucleoside addition is generally complete within 30 seconds. Next, a capping step is performed, which terminates any polynucleotide chains that did not undergo nucleoside addition. Capping is preferably performed using acetic anhydride and 1-methylimidazole. The phosphite group of the internucleotide linkage is then converted to the more stable phosphotriester by oxidation using iodine as the preferred oxidizing agent and water as the oxygen donor. After oxidation, the hydroxyl protecting group of the newly added nucleoside is removed with a protic acid, e.g., trichloroacetic acid or dichloroacetic acid, and the cycle is repeated one or more times until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases and any protecting groups on the dyes are removed by treating the polynucleotide solution in base at an elevated temperature, e.g., at about 55° C. Preferably the various protecting groups are removed using ammonium hydroxide or t-butyl amine.

Any of the nucleoside phosphoramidite monomers can be labeled using standard phosphoramidite chemistry methods (Hwang et al., 1999, Proc. Natl. Acad. Sci. USA 96(23): 12997-13002; Ojwang et al., 1997, Biochemistry. 36:6033-6045 and references cited therein). Dye molecules useful for covalently coupling to phosphoramidites preferably comprise a primary hydroxyl group that is not part of the dye's chromophore. Illustrative dye molecules include, but are not limited to, disperse dye CAS 4439-31-0, disperse dye CAS 6054-58-6, disperse dye CAS 4392-69-2 (Sigma-Aldrich, St. Louis, Mo.), disperse red, and 1-pyrenebutanol (Molecular Probes, Eugene, Oreg.). Other dyes useful for coupling to phosphoramidites will be apparent to those of skill in the art, such as fluoroscein, cy3, and cy5 fluorescent dyes, and may be purchased from, e.g., Sigma-Aldrich, St. Louis, Mo. or Molecular Probes, Inc., Eugene, Oreg.

In another embodiment, dye-labeled target molecules are synthesized enzymatically using in? vitro transcription (Hwang et al., 1999, Proc. Natl. Acad. Sci. USA 96(23): 12997-13002 and references cited therein). In this embodiment, a mixture of ribonucleoside-5'-triphosphates capable of supporting template-directed enzymatic extension (e.g., a mixture including GTP, ATP, CTP, and UTP, including one or more dye-labeled ribonucleotides; Sigma-Aldrich, St. Louis, Mo.) is added to a promoter-containing DNA template. Next, a polymerase enzyme is added to the mixture under conditions where the polymerase enzyme is active, which are well-known to those skilled in the art. A labeled polynucleotide is formed by the incorporation of the labeled ribonucleotides during polymerase-mediated strand synthesis.

In yet another embodiment of the invention, nucleic acid molecules are end-labeled after their synthesis. Methods for labeling the 5'-end of an oligonucleotide include but are by no means limited to: (i) periodate oxidation of a 5'-to-5'-coupled ribonucleotide, followed by reaction with an amine-reactive label (Heller & Morisson, 1985, in Rapid Detection and Identification of Infectious Agents, D. T. Kingsbury and S. Falkow, eds., pp. 245-256, Academic Press); (ii) condensation of ethylenediamine with 5'-phosphorylated polynucleotide, followed by reaction with an amine reactive label (Morrison, European Patent Application 232 967); (iii) introduction of an aliphatic amine substituent using an aminohexyl phosphite reagent in solid-phase DNA synthesis, followed by reaction with an amine reactive label (Cardullo et al., 1988, Proc. Natl. Acad. Sci. USA 85:8790-8794); and (iv) introduction of a thiophosphate group on the 5'-end of the nucleic acid, using phosphatase treatment followed by end-labeling with ATP-?S and kinase, which reacts specifically and efficiently with maleimide-labeled fluorescent dyes (Czworkowski et al., 1991, Biochem. 30:4821-4830).

A detectable label should not be incorporated into a target nucleic acid at the specific binding site at which compounds are likely to bind, since the presence of a covalently attached label might interfere sterically or chemically with the binding of the compounds at this site. Accordingly, if the region of the target nucleic acid that binds to a host cell factor is known, a detectable label is preferably incorporated into the nucleic acid molecule at one or more positions that are spatially or sequentially remote from the binding region.

After synthesis, the labeled target nucleic acid can be purified using standard techniques known to those skilled in the art (see Hwang et al., 1999, Proc. Natl. Acad. Sci. USA 96(23):12997-13002 and references cited therein). Depending on the length of the target nucleic acid and the method of its synthesis, such purification techniques include, but are not limited to, reverse-phase high-performance liquid chromatography ("reverse-phase HPLC"), fast performance liquid chromatography ("FPLC"), and gel purification. After purification, the target RNA is refolded into its native conformation, preferably by heating to approximately 85-95° C. and slowly cooling to room temperature in a buffer, e.g., a buffer comprising about 50 mM Tris-HCl, pH 8 and 100 mM NaCl.

In another embodiment, the target nucleic acid can also be radiolabeled. A radiolabel, such as, but not limited to, an isotope of phosphorus, sulfur, or hydrogen, may be incorporated into a nucleotide, which is added either after or during the synthesis of the target nucleic acid. Methods for the synthesis and purification of radiolabeled nucleic acids are well known to one of skill in the art. See, e.g., Sambrook et al., 1989, in *Molecular Cloning: A Laboratory Manual*, pp 10.2-10.70, Cold Spring Harbor Laboratory Press, and the references cited therein, which are hereby incorporated by reference in their entireties.

In another embodiment, the target nucleic acid can be attached to an inorganic nanoparticle. A nanoparticle is a cluster of ions with controlled size from 0.1 to 1000 nm comprised of metals, metal oxides, or semiconductors including, but not limited to $Ag_2S$, $ZnS$, $CdS$, $CdTe$, $Au$, or $TiO_2$. Nanoparticles have unique optical, electronic and catalytic properties relative to bulk materials which can be adjusted according to the size of the particle. Methods for the attachment of nucleic acids are well known to one of skill in the art (see, e.g., Niemeyer, 2001, Angew. Chem. Int. Ed. 40: 4129-4158, International Patent Publication WO/0218643, and the references cited therein, the disclosures of which are hereby incorporated by reference in their entireties).

In yet another embodiment of the invention, target nucleic acids can be attached or conjugated to a solid support for use in the assays of the invention. There are a number of methods, known in the art, that can be used to immobilize nucleic acids on a solid support. For example, modified DNA has been covalently immobilized to a variety of surfaces using amino acids (see, e.g., Running, J. A., and Urdea, M. S. (1990) Biotechniques, 8, 276-277), (Newton, C. R., et al., (1993) Nucl. Acids. Res., 21 1155-1162.), (Nikiforov, T. T., and Rogers, Y. H. (1995) Anal. Biochem., 227, 201-209). Alternatively, carboxyl groups, (Zhang, Y., et al., (1991) Nucl. Acids Res., 19, 3929-3933), epoxy groups (Lamture, J. B., et al., (1994) Nucl. Acids Res. 22, 2121-2125), (Eggers, M. D., et al., (1994) BioTechniques, 17, 516-524) or amino groups (Rasmussen, S. R,. et al., (1991) Anal. Biochem., 198, 138-142), can be used to attach nucleic acids to solid surfaces. Such embodiments would be useful in, e.g., high throughput assays intended to screen a library of compounds in order to identify molecules that bind to target nucleic acids that have been attached to a solid support. In a particular embodiment, target RNA molecules are attached or conjugated to a solid support, e.g., a slide or a bead, using an appropriate molecule that does not interfere with its binding to compounds of the invention and then subsequently screened with a library of compounds. Members of a library of compounds are preferably detectably labeled so that compounds that bind to target RNAs can be identified. Suitable detectable labels that can be used to label compounds are known in the art and also described herein. In a more preferred embodiment, target RNA molecules are immobilized on a surface suitable for preforming microarray assays. Any technique known in the art can be used to immobilize nucleic acid molecules on a solid support surface. The nucleic acid is preferably, for example, covalently attached to the solid support.

5.4 Libraries of Small Molecules

Libraries screened using the methods of the present invention can comprise a variety of types of compounds. In one embodiment, the libraries screened using the methods of the present invention can comprise a variety of types of compounds on solid supports. In other embodiments described below, the libraries can be synthesized on solid supports or the compounds of the library can be attached to solid supports by linkers. In some embodiments, the compounds are nucleic acid or peptide molecules. In a non-limiting example, peptide molecules can exist in a phage display library. In other embodiments, types of compounds include, but are not limited to, peptide analogs including peptides comprising non-naturally occurring amino acids, e.g., D-amino acids, phosphorous analogs of amino acids, such as α-amino phosphoric acids and α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used.

In a preferred embodiment, the combinatorial libraries are small organic molecule libraries, such as, but not limited to, benzodiazepines, isoprenoids, thiazolidinones, metathiazanones, pyrrolidines, morpholino compounds, and diazepindiones. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., Advanced ChemTech Europe Ltd., Cambridgeshire, UK; ASINEX Moscow Russia; BioFocus plc, Sittingbourne, UK; Bionet Research (A division of Key Organics Limited), Camelford, UK; ChemBridge Corporation, San Diego, Calif.; ChemDiv Inc, San Diego, Calif.; ChemRx Advanced Technologies, South San Francisco, Calif.; ComGenex Inc., Budapest, Hungary; Evotec OAI Ltd, Abingdon, UK; IF LAB Ltd., Kiev, Ukraine; Maybridge plc, Cornwall, UK; PharmaCore, Inc., North Carolina; SIDDCO Inc, Tucson, Ariz.; TimTec Inc., Newark, Del.; Tripos Receptor Research Ltd, Bude, UK; Toslab, Ekaterinburg, Russia). In a specific embodiment, the combinatorial libaries are small molecules.

In another embodiment, combinatorial libraries, useful in the present -invention are combinatorial libraries of labeled compounds with each compound in the library having a label that is detectable via conventional spectroscopic means or radiographic means. Preferably, compounds are labeled with a covalently attached and detectable isotope. Other useful labels in the present invention include, but are not limited to, fluorescent tags or dye molecules. Useful dye molecules, include, for example. fluorescent dyes, phosphorescent dyes, ultraviolet dyes, infrared dyes, and visible dyes. Useful fluorescent tags, include, for example, fluoresein and derivatives such as fluorescein isothiocyanate (FITC) and Oregon Green™, rhodamine and derivatives (e.g., Texas red, tetramethylrhodimine isothiocynate (TRITC), bora-3a,4a-diaza-s-indacene (BODIPY®) and derivatives, etc.), digoxigenin, biotin, phycoerythrin, AMCA, CyDye™, and the like), radiolabels (e.g., $^3H$, $^{125}I$, $^{35}S$, $^{14}C$, $^{32}P$, $^{33}P$, etc.), enzymes (e.g., horse radish peroxidase, alkaline phosphatase etc.), spectroscopic colorimetric labels such as colloidal gold or colored glass or plastic (e.g. polystyrene, polypropylene, latex, etc.) beads, or nanoparticles—nanoclusters of inorganic ions with defined dimension from 0.1 to 1000 nm. The label may be coupled directly or indirectly to a component of the detection assay (e.g. the detection reagent) according to methods well known in the art. A wide variety of labels may be used, with the choice of label depending on sensitivity required, ease of conjugation with the compound, stability requirements, available instrumentation, and disposal provisions.

In one embodiment, the combinatorial compound library for the methods of the present invention may be synthesized. There is a great interest in synthetic methods directed toward the creation of large collections of small organic compounds, or libraries, which could be screened for pharmacological, biological or other activity (Dolle, 2001, J. Comb. Chem. 3:477-517; Hall et al., 2001, J. Comb. Chem. 3:125-150; Dolle, 2000, J. Comb. Chem. 2:383A433; Dolle, 1999, J. Comb. Chem. 1:235-282). The synthetic methods applied to create vast combinatorial libraries are performed in solution or in the solid phase, i.e., on a solid support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry. Methods and strategies for the synthesis of combinatorial libraries can be found in *A Practical Guide to Combinatorial Chemistry*, A. W. Czarnik and S. H. Dewitt, eds., American Chemical Society, 1997; *The Combinatorial Index*, B. A. Bunin, Academic Press, 1998; *Organic Synthesis on Solid Phase*, F. Z. Dörwald, Wiley-VCH, 2000; and *Solid-Phase Organic Syntheses*, Vol. 1, A. W. Czarnik, ed., Wiley Interscience, 2001.

Combinatorial compound libraries of the present invention may be synthesized using apparatuses described in U.S. Pat. No. 6,358,479 to Frisina et al., U.S. Pat. No. 6,190,619 to Kilcoin et al., U.S. Pat. No. 6,132,686 to Gallup et al., U.S. Pat. No. 6,126,904 to Zuellig et al., U.S. Pat. No. 6,074,613 to Harness et al., U.S. Pat. No. 6,054,100 to Stanchfield et al., and U.S. Pat. No. 5,746,982 to Saneii et al. which are hereby incorporated by reference in their entirety. These patents describe synthesis apparatuses capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will preferably be small organic molecules. Some compounds in the library may mimic the effects of non-peptides or peptides. In contrast to solid-phase synthesis of combinatorial compound libraries, liquid-phase synthesis does not require the use of specialized protocols for monitoring the individual steps of a multi-step solid-phase synthesis (Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun Mass Spect. 8:77; Chu et al., 1995, J. Am. Chem. Soc. 117:5419; Brummel et al., 1994, Science 264:399; Stevanovic et al., 1993, Bioorg. Med. Chem. Lett. 3:431).

Combinatorial compound libraries useful for the methods of the present invention can be synthesized on solid supports. In one embodiment, a split synthesis method, a protocol of separating and mixing solid supports during the synthesis, is used to synthesize a library of compounds on solid supports (see Lam et al., 1997, Chem. Rev. 97:41-448; Ohlmeyer et al., 1993, Proc. Natl. Acad. Sci. USA 90:10922-10926 and references cited therein). Each solid support in the final library has substantially one type of compound attached to its surface. Other methods for synthesizing combinatorial libraries on solid supports, wherein one product is attached to each support, will be known to those of skill in the art (see, e.g., Nefzi et al., 1997, Chem. Rev. 97:449-472 and U.S. Pat. No. 6,087,186 to Cargill et al. which are hereby incorporated by reference in their entirety).

As used herein, the term "solid support" is not limited to a specific type of solid support. Rather a large number of supports are available and are known to one skilled in the art. Solid supports that can be used in the assays of the invention include, for example, any surface to which compounds, either natively or via a linker, can be attached. Solid supports include silica gels, resins, derivatized plastic films, glass beads, glass slides (e.g., Hergenrother et al., 2000, J. Am. Chem. Soc. 122:7849-7850 and Kuruvilla et al., 2002, Nature 416:653-657) and cotton, plastic beads, polystyrene beads, doped polystyrene beads (as described by Fenniri et al., 2000, J. Am. Chem. Soc. 123:8151-8152), polystyrene macrobeads (as described by Blackwell et al., 2001, Chemistry & Biology 8:1167-1182), alumina gels, and polysaccharides. In a specific embodiment, the solid support is a glass slide. In a more specific embodiment, the solid support is a glass microscope slide.

A suitable solid support may be selected on the basis of desired end use and suitability for various synthetic protocols. For example, for peptide synthesis, a solid support can be a resin such as p-methylbenzhydrylamine (pMBHA) resin (Peptides International, Louisville, Ky.), polystyrenes (e.g., PAM-resin obtained from Bachem Inc., Peninsula Laboratories, etc.), including chloromethylpolystyrene, hydroxymethylpolystyrene and aminomethylpolystyrene, poly (dimethylacrylamide)-grafted styrene co-divinyl-benzene (e.g., POLYHIPE resin, obtained from Aminotech, Canada), polyamide resin (obtained from Peninsula Laboratories), polystyrene resin grafted with polyethylene glycol (e.g., TENTAGEL or ARGOGEL, Bayer, Tubingen, Germany) polydimethylacrylamide resin (obtained from Milligen/Biosearch, California), or Sepharose (Pharmacia, Sweden). In another embodiment, the solid support can be a magnetic bead coated with streptavidin, such as Dynabeads Streptavidin (Dynal Biotech, Oslo, Norway).

In one embodiment, the solid phase support is suitable for ill vivo use, i.e., it can serve as a carrier or support for administration of the compound to a patient (e.g., TENTAGEL, Bayer, Tubingen, Germany). In a particular embodiment, the solid support is palatable and/or orally ingestable.

Any technique known to one of skill in the art can be used attach compounds to a solid support for use in the assays of the invention. In some embodiments of the present invention, compounds can be attached to solid supports via linkers. Linkers can be integral and part of the solid support, or they may be nonintegral that are either synthesized on the solid support or attached thereto after synthesis. Linkers are useful not only for providing points of compound attachment to the solid support, but also for allowing different groups of molecules to be cleaved from the solid support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions.

In some embodiments of the present invention, each compound contains a common functional group that mediates covalent attachment to a solid support. In a specific embodiment of the invention, the functional group that mediates covalent attachment to a solid support varies between the compounds. Compounds can be attached on a solid support in any orientation and distribution that is suitable for the assays of the invention. In a further embodiment, compounds are attached or spotted on a solid support such as, e.g., a glass slide, with high spatial density and uniform distance between each spot so that an array is formed. Each surface is subsequently probed with a compound of interest.

In one embodiment, compounds are applied directly to a surface, such as, e.g., a glass slide, using a manual transfer technique. In a particular embodiment, the compounds are transferred or spotted on a surface from a microtiter plate using a robotic arrayer. In another embodiment, the compounds are attached to beads that are subsequently transferred to wells in a microtiter plate where the compounds are released before being arrayed on a surface using any of the means described above. Any type and size of bead can be used to attach compounds of the invention. One skilled in the art would be familiar with the bead properties necessary for a specific purpose. In a particular embodiment, the bead material is polystyrene.

In another embodiment, the combinatorial compound libraries can be assembled in situ using dynamic combinatorial chemistry as described in European Patent Application 1,118,359 A1 to Lehn; Huc & Nguyen, 2001, Comb. Chem. High Throughput. Screen. 4:53-74; Lehn and Eliseev, 2001, Science 291:2331-2332; Cousins et al. 2000, Curr. Opin. Chem. Biol. 4: 270-279; and Karan & Miller, 2000, Drug. Disc. Today 5:67-75 which are incorporated by reference in their entirety.

Dynamic combinatorial chemistry uses non-covalent interaction with a target biomolecule, including but not limited to a protein, RNA, or DNA, to favor assembly of the most tightly binding molecule that is a combination of constituent subunits present as a mixture in the presence of the biomolecule. According to the laws of thermodynamics, when a collection of molecules is able to combine and recombine at equilibrium through reversible chemical reactions in solution, molecules, preferably one molecule, that bind most tightly to a templating biomolecule will be present in greater amount than all other possible combinations. The reversible chemical reactions include, but are not limited to, imine, acyl-hydrazone, amide, acetal, or ester formation between carbonyl-containing compounds and amines, hydrazines, or alcohols; thiol exchange between disulfides; alcohol exchange in borate esters; Diels-Alder reactions; thermal- or photoinduced sigmatropic or electrocyclic rearrangements; or Michael reactions.

In the preferred embodiment of this technique, the constituent components of the dynamic combinatorial compound library are allowed to combine and reach equilibrium in the absence of the target RNA and then incubated in the presence of the target RNA, preferably at physiological conditions, until a second equilibrium is reached. The second, perturbed, equilibrium (the so-called "templated mixture") can, but need not necessarily, be fixed by a further chemical transformation, including but not limited to reduction, oxidation, hydrolysis, acidification, or basification, to prevent restoration of the original equilibrium when the dynamical combinatorial compound library is separated from the target RNA.

In the preferred embodiment of this technique, the predominant product or products of the templated dynamic combinatorial library can separated from the minor products and directly identified. In another embodiment, the identity of the predominant product or products can be identified by a deconvolution strategy involving preparation of derivative dynamic combinatorial libraries, as described in European Patent Application 1,118,359 A1, which is incorporated by reference in its entirety, whereby each component of the mixture is, preferably one-by-one but possibly group-wise, left out of the mixture and the ability of the derivative library mixture at chemical equilibrium to bind the target RNA is measured. The components whose removal most greatly reduces the ability of the derivative dynamic combinatorial library to bind the target RNA are likely the components of the predominant product or products in the original dynamic combinatorial library.

5.5 Library Screening

After a target nucleic acid, such as but not limited to RNA or DNA, is labeled and a compound library is synthesized or purchased or both, the labeled target nucleic acid is used to screen the library to identify compounds that bind to the nucleic acid. Screening comprises contacting a labeled target nucleic acid with an individual, or small group, of the compounds of the compound library. Preferably, the contacting occurs in an aqueous solution, and most preferably, under physiologic conditions. The aqueous solution preferably stabilizes the labeled target nucleic acid and prevents denaturation or degradation of the nucleic acid without interfering with binding of the compounds. The aqueous solution can be similar to the solution in which a complex between the target RNA and its corresponding host cell factor (if known) is formed in vitro. For example, TK buffer, which is commonly used to form Tat protein-TAR RNA complexes in vitro, can be used in the methods of the invention as an aqueous solution to screen a library of compounds for RNA binding compounds.

Alternatively, compounds are labeled and target RNA molecules are used to screen the library of labeled compounds. After compounds are labeled, target nucleic acids are used to screen the library of labeled compounds to identify those nucleic acids that bind to the labeled compounds. Screening comprises contacting a target nucleic acid with an individual, or small group, of the compounds of the labeled compound library. Preferably, the contacting occurs in an aqueous solution, and most preferably under physiologic conditions. The aqueous solution preferably stabilizes the target nucleic acid and prevents denaturation or degradation of the nucleic acid without interfering with binding of the compounds. The aqueous solution can be similar to the solution in which a complex between the target RNA and its corresponding host cell factor (if known) is formed in vitro. For example, TK buffer, which is commonly used to form Tat protein-TAR RNA complexes in vitro, can be used in the methods of the invention as an aqueous solution to screen a library of compounds for RNA binding compounds.

The methods of the present invention for screening a library of compounds preferably comprise contacting a compound with a target nucleic acid in the presence of an aqueous solution, the aqueous solution comprising a buffer and a combination of salts, preferably approximating or mimicking physiologic conditions. The aqueous solution optionally further comprises non-specific nucleic acids, such as, but not limited to, DNA; yeast tRNA; salmon sperm DNA; homoribopolymers such as, but not limited to, poly IC, polyA, polyU, and polyC; and non-specific RNA. The non-specific RNA may be an unlabeled target nucleic acid having a mutation at the binding site, which renders the unlabeled nucleic acid incapable of interacting with a compound at that site. For example, if dye-labeled TAR RNA is used to screen a library, unlabeled TAR RNA having a mutation in the uracil 23/cytosine 24 bulge region may also be present in the aqueous solution. Without being bound by any theory, the addition of unlabeled RNA that is essentially identical to the dye-labeled target RNA except for a mutation at the binding site might minimize interactions of other regions of the dye-labeled target RNA with compounds or with the solid support and prevent false positive results.

The solution further comprises a buffer, a combination of salts, and optionally, a detergent or a surfactant. The pH of the aqueous solution typically ranges from about 5 to about 8, preferably from about 6 to about 8, most preferably from about 6.5 to about 8. A variety of buffers may be used to achieve the desired pH. Suitable buffers include, but are not limited to, Tris, Mes, Bis-Tris, Ada, Aces, Pipes, Mopso, Bis-Tris propane, Bes, Mops, Tes, Hepes, Dipso, Mobs, Tapso, Trizma, Heppso, Popso, TEA, Epps, Tricine, Gly-Gly, Bicine, and sodium-potassium phosphate. The buffering agent comprises from about 10 mM to about 100 mM, preferably from about 25 mM to about 75 mM, most preferably from about 40 mM to about 60 mM buffering agent. The pH of the aqeuous solution can be optimized for different screening reactions, depending on the target RNA used and the types of compounds in the library, and therefore, the type and amount of the buffer used in the solution can vary from screen to screen. In a preferred embodiment, the aqueous solution has a pH of about 7.4, which can be achieved using about 50 mM Tris buffer.

In addition to an appropriate buffer, the aqueous solution further comprises a combination of salts, from about 0 mM to about 100 mM KCl, from about 0 mM to about 1 M NaCl, and from about 0 mM to about 200 mM $MgCl_2$. In a preferred embodiment, the combination of salts is about 100 mM KCl, 500 mM NaCl, and 10 mM $MgCl_2$. Without being bound by any theory, Applicant has found that a combination of KCl, NaCl, and $MgCl_2$ stabilizes the target RNA such that most of the RNA is not denatured or digested over the course of the screening reaction. The optional concentration of each salt used in the aqueous solution is dependent on the particular target RNA used and can be determined using routine experimentation.

The solution optionally comprises from about 0.01% to about 0.5% (w/v) of a detergent or a surfactant. Without being bound by any theory, a small amount of detergent or surfactant in the solution might reduce non-specific binding of the target RNA to the solid support and control aggregation and increase stability of target RNA molecules. Typical detergents useful in the methods of the present invention include, but are not limited to, anionic detergents, such as salts of deoxycholic acid, 1-heptanesulfonic acid, N-laurylsarcosine, lauryl sulfate, 1-octane sulfonic acid and taurocholic acid; cationic detergents such as benzalkonium chloride, cetylpyridinium, methylbenzethonium chloride, and decamethonium bromide; zwitterionic detergents such as CHAPS, CHAPSO, alkyl betaines, alkyl amidoalkyl betaines, N-dodecyl-N,N-dimethyl-3-ammonio-1-propanesulfonate, and phosphatidylcholine; and non-ionic detergents such as n-decyl a-D-glucopyranoside, n-decyl β-D-maltopyranoside, n-dodecyl β-D-maltoside, n-octyl β-D-glucopyranoside, sorbitan esters, n-tetradecyl β-D-maltoside, octylphenoxy polyethoxyethanol (Nonidet P-40), nonylphenoxypolyethoxyethanol (NP-40), and tritons. Preferably, the detergent, if present, is a nonionic detergent. Typical surfactants useful in the methods of the present invention include, but are not limited to, ammonium lauryl sulfate, polyethylene glycols, butyl glucoside, decyl glucoside, Polysorbate 80, lauric acid, myristic acid, palmitic acid, potassium palmitate, undecanoic acid, lauryl betaine, and lauryl alcohol. More preferably, the detergent, if present, is Triton X-100 and present in an amount of about 0.1% (w/v).

Non-specific binding of a labeled target nucleic acid to compounds can be further minimized by treating the binding reaction with one or more blocking agents. Non-specific binding of a unlabeled target nucleic acid to labeled compounds can be further minimized by treating the binding reaction with one or more blocking agents. In one embodiment, the binding reactions are treated with a blocking agent, e.g., bovine serum albumin ("BSA"), before contacting with to the labeled target nucleic acid. In another embodiment, the binding reactions are treated sequentially with at least two different blocking agents. This blocking step is preferably performed at room temperature for from about 0.5 to about 3 hours. In a subsequent step, the reaction mixture is further treated with unlabeled RNA having a mutation at the binding site. This blocking step is preferably performed at about 4° C. for from about 12 hours to about 36 hours before addition of the dye-labeled target RNA. Preferably, the solution used in the one or more blocking steps is substantially similar to the aqueous solution used to screen the library with the dye-labeled target RNA, e.g., in pH and salt concentration.

Once contacted, the mixture of labeled target nucleic acid and the compound is preferably maintained at 4° C. for from about 1 day to about 5 days, preferably from about 2 days to about 3 days with constant agitation. To identify the reactions in which binding to the labeled target nucleic acid occurred, after the incubation period, bound from free compounds are determined using any of the methods disclosed in Section 5.5 infra. In a specific embodiment, the complexed target nucleic acid does not need to be separated from the free target nucleic acid if a technique (i.e., spectrometry) that diferentiates between bound and unbound target nucleic acids is used.

In another embodiment, once contacted, the mixture of target nucleic acid and the labeled compound is preferably maintained at 4° C. for from about 1 day to about 5 days, preferably from about 2 days to about 3 days with constant agitation. To identify the reactions in which binding to the target nucleic acid occurred, after the incubation period, bound from free compounds are determined using any of the methods disclosed in Section 5.5 infra. In a specific embodiment, the complexed target nucleic acid does not need to be separated from the free target nucleic acid if a technique (i.e., spectrometry) that diferentiates between bound and unbound target nucleic acids is used.

The methods for identifying small molecules bound to labeled nucleic acid will vary with the type of label on the target nucleic acid. For example, if a target RNA is labeled with a visible of fluorescent dye, the target RNA complexes are preferably identified using a chromatographic technique that separates bound from free target by an electrophoretic or size differential technique using individual reactions. The reactions corresponding to changes in the migration of the complexed RNA can be cross-referenced to the small molecule compound(s) added to said reaction. Alternatively, complexed target RNA can be screened en masse and then separated from free target RNA using an electrophoretic or size differential technique, the resultant complexed target is then analyzed using a mass spectrometric technique. In this fashion the bound small molecule can be identified on the basis of its molecular weight. In this reaction a priori knowledge of the exact molecular weights of all compounds within the library is known. In another embodiment, the compounds bound to the target nucleic acid may not require separation from the unbound target nucleic acid if a technique such as, but not limited to, spectrometry is used.

The methods for identifying labeled small molecules bound to unlabeled nucleic acid will vary with the type of label on the compound. For example, if compound is labeled with a visible of fluorescent dye, the target RNA complexes are preferably identified using a chromatographic technique that separates bound from free target by an electrophoretic or size differential technique using individual reactions. The reactions corresponding to changes in the migration of the complexed RNA can be cross-referenced to the small molecule compound(s) added to said reaction. Alternatively, complexed target RNA can be screened en masse and then separated from free target RNA using an electrophoretic or size differential technique, the resultant complexed target is then analyzed using a mass spectrometric technique. In this fashion the bound small molecule can be identified on the basis of its molecular weight. In this reaction a priori knowledge of the exact molecular weights of all compounds within the library is known. In another embodiment, the compounds bound to the target nucleic acid may not require separation from the unbound target nucleic acid if a technique such as, but not limited to, spectrometry is used.

5.6 Separation Methods for Screening Compounds

Any method that detects an altered physical property of a target nucleic acid complexed to a compound from the unbound target nucleic acid may be used for separation of the complexed and non-complexed target nucleic acids. Methods that can be utilized for the physical separation of complexed target RNA from unbound target RNA include, but are not limited to, electrophoresis, fluorescence spectroscopy, surface plasmon resonance, mass spectrometry, scintillation, proximity assay, structure-activity relationships ("SAR") by NMR spectroscopy, size exclusion chromatography, affinity chromatography, nanoparticle aggregation, flow cytometry, manual batch, and suspension of beads in electric fields.

In embodiments that use solid support based methods, after the labeled target RNA is contacted with the library of compounds immobilized on a solid support (e.g., beads) or the target RNA conjugated or attached to the solid support is contacted with the library of detectably labeled compounds, the solid support (e.g., beads) must then be separated from the unbound target RNA or unbound compounds, respectively, in the liquid phase. This can be accomplished by any number of physical means; e.g., sedimentation, centrifugation. Thereafter, a number of methods can be used to separate the solid support-based library that is complexed with the labeled target RNA from uncomplexed beads in order to isolate the compound on the bead. Alternatively, mass spectroscopy and NMR spectroscopy can be used to simultaneously identify and separate beads complexed to the labeled target RNA from uncomplexed beads.

5.6.1 Electrophoresis

Methods for separation of the complex of a target RNA bound to a compound from the unbound RNA comprises any method of electrophoretic separation, including but not limited to, denaturing and non-denaturing polyacrylamide gel electrophoresis, urea gel electrophoresis, gel filtration, pulsed field gel electrophoresis, two dimensional gel electrophoresis, continuous flow electrophoresis, zone electrophoresis, agarose gel electrophoresis, and capillary electrophoresis.

In a preferred embodiment, an automated electrophoretic system comprising a capillary cartridge having a plurality of capillary tubes is used for high-throughput screening of compounds bound to target RNA. Such an apparatus for performing automated capillary gel electrophoresis is disclosed in U.S. Pat. Nos. 5,885,430; 5,916,428; 6,027,627; and 6,063,251, the disclosures of which are incorporated by reference in their entireties.

The device disclosed in U.S. Pat. No. 5,885,430, which is incorporated by reference in its entirety, allows one to simultaneously introduce samples into a plurality of capillary tubes directly from microtiter trays having a standard size. U.S. Pat. No. 5,885,430 discloses a disposable capillary cartridge which can be cleaned between electrophoresis runs, the cartridge having a plurality of capillary tubes. A first end of each capillary tube is retained in a mounting plate, the first ends collectively forming an array in the mounting plate. The spacing between the first ends corresponds to the spacing between the centers of the wells of a microtiter tray having a standard size. Thus, the first ends of the capillary tubes can simultaneously be dipped into the samples present in the tray's wells. The cartridge is provided with a second mounting plate in which the second ends of the capillary tubes are retained. The second ends of the capillary tubes are arranged in an array which corresponds to the wells in the microtiter tray, which allows for each capillary tube to be isolated from its neighbors and therefore free from cross-contamination, as each end is dipped into an individual well.

Plate holes may be provided in each mounting plate and the capillary tubes inserted through these plate holes. In such a case, the plate holes are sealed airtight so that the side of the mounting plate having the exposed capillary ends can be pressurized. Application of a positive pressure in the vicinity of the capillary openings in this mounting plate allows for the introduction of air and fluids during electrophoretic operations and also can be used to force out gel and other materials from the capillary tubes during reconditioning. The capillary tubes may be protected from damage using a needle comprising a cannula and/or plastic tubes, and the like when they are placed in these plate holes. When metallic cannula or the like are used, they can serve as electrical contacts for current flow during electrophoresis. In the presence of a second mounting plate, the second mounting plate is provided with plate holes through which the second ends of the capillary tubes project. In this instance, the second mounting plate serves as a pressure containment member of a pressure cell and the second ends of the capillary tubes communicate with an internal cavity of the pressure cell. The pressure cell is also formed with an inlet and an outlet. Gels, buffer solutions, cleaning agents, and the like may be introduced into the internal cavity through the inlet, and each of these can simultaneously enter the second ends of the capillaries.

In another preferred embodiment, the automated electrophoretic system can comprise a chip system consisting of complex designs of interconnected channels that perform and analyze enzyme reactions using part of a channel design as a tiny, continuously operating electrophoresis material, where reactions with one sample are going on in one area of the chip while electrophoretic separation of the products of another sample is taking place in a different part of the chip. Such a system is disclosed in U.S. Pat. Nos. 5,699,157; 5,842,787; 5,869,004; 5,876,675; 5,942,443; 5,948,227; 6,042,709; 6,042,710; 6,046,056; 6,048,498; 6,086,740; 6,132,685; 6,150,119; 6,150,180; 6,153,073; 6,167,910; 6,171,850; and 6,186,660, the disclosures of which are incorporated by reference in their entireties.

The system disclosed in U.S. Pat. No. 5,699,157, which is hereby incorporated by reference in its entirety, provides for a microfluidic system for high-speed electrophoretic analysis of subject materials for applications in the fields of chemistry, biochemistry, biotechnology, molecular biology and numerous other areas. The system has a channel in a substrate, a light source and a photoreceptor. The channel holds subject materials in solution in an electric field so that the materials move through the channel and separate into bands according to species. The light source excites fluorescent light in the species bands and the photoreceptor is arranged to receive the fluorescent light from the bands. The system further has a means for masking the channel so that the photoreceptor can receive the fluorescent light only at periodically spaced regions along the channel. The system also has an unit connected to analyze the modulation frequencies of light intensity received by the photoreceptor so that velocities of the bands along the channel are determined, which allows the materials to be analyzed.

The system disclosed in U.S. Pat. No. 5,699,157 also provides for a method of performing high-speed electrophoretic analysis of subject materials, which comprises the steps of holding the subject materials in solution in a channel of a microfluidic system; subjecting the materials to an electric field so that the subject materials move through the channel and separate into species bands; directing light toward the channel; receiving light from periodically spaced regions along the channel simultaneously, and analyzing the frequencies of light intensity of the received light so that velocities of the bands along the channel can be determined for analysis of said materials. The determination of the velocity of a species band determines the electrophoretic mobility of the species and its identification.

U.S. Pat. No. 5,842,787, which is hereby incorporated by reference in its entirety, is generally directed to devices and systems employ channels having, at least in part, depths that are varied over those which have been previously described (such as the device disclosed in U.S. Pat. No. 5,699,157), wherein said channel depths provide numerous beneficial and unexpected results such as but not limited to, a reduction in sample perturbation, reduced non-specific sample mixture by diffusion, and increased resolution.

In another embodiment, the electrophoretic method of separation comprises polyacrylamide gel electrophoresis. In a preferred embodiment, the polyacrylamide gel electrophoresis is non-denaturing, so as to differentiate the mobilities of the target RNA bound to a compound from free target RNA. If the polyacrylamide gel electrophoresis is denaturing, then the target RNA:compound complex must be cross-linked prior to electrophoresis to prevent the disassociation of the target RNA from the compound during electrophoresis. Such techniques are well known to one of skill in the art.

In one embodiment of the method, the binding of compounds to target nucleic acid can be detected, preferably in an automated fashion, by gel electrophoretic analysis of interference footprinting. RNA can be degraded at specific base sites by enzymatic methods such as ribonucleases A, $U_2$, $CL_3$, $T_1$, Phy M, and *B. cereus* or chemical methods such as diethylpyrocarbonate, sodium hydroxide, hydrazine, piperidine formate, dimethyl sulfate, [2,12-dimethyl-3,7,11,17-tetraazacyclo[11.3.1]heptadeca-1(17),2,11,13,15-pentaenato] nickel(II) (NiCR), cobalt(II)chloride, or iron(II) ethylenediaminetetraacetate (Fe-EDTA) as described for example in Zheng et al., 1999, Biochem. 37:2207-2214; Latham & Cech, 1989, Science 245:276-282; and Sambrook et al., 2001, in Molecular Cloning: A Laboratory Manual, pp 12.61-12.73, Cold Spring Harbor Laboratory Press, and the references cited therein, which are hereby incorporated by reference in their entireties.

The specific pattern of cleavage sites is determined by the accessibility of particular bases to the reagent employed to initiate cleavage and, as such, is therefore is determined by the three-dimensional structure of the RNA. The interaction of small molecules with a target nucleic acid can change the accessibility of bases to these cleavage reagents both by causing conformational changes in the target nucleic acid or by covering a base at the binding interface. When a compound binds to the nucleic acid and changes the accessibility of bases to cleavage reagents, the observed cleavage pattern will change. This method can be used to identify and characterize the binding of small molecules to RNA as described, for example, by Prudent et al., 1995, J. Am. Chem. Soc. 117: 10145-10146 and Mei et al., 1998, Biochem. 37:14204-14212.

In the preferred embodiment of this technique, the detectably labeled target nucleic acid is incubated with an individual compound and then subjected to treatment with a cleavage reagent, either enzymatic or chemical. The reaction mixture can be preferably be examined directly, or treated further to isolate and concentrate the nucleic acid. The fragments produced are separated by electrophoresis and the pattern of cleavage can be compared to a cleavage reaction performed in the absence of compound. A change in the cleavage pattern directly indicates that the compound binds to the target nucleic acid. Multiple compounds can be examined both in parallel and serially.

Other embodiments of electrophoretic separation include, but are not limited to urea gel electrophoresis, gel filtration, pulsed field gel electrophoresis, two dimensional gel electrophoresis, continuous flow electrophoresis, zone electrophoresis, and agarose gel electrophoresis.

5.6.2 Fluorescence Spectroscopy

In a preferred embodiment, fluorescence polarization spectroscopy, an optical detection method that can differentiate the proportion of a fluorescent molecule that is either bound or unbound in solution (e.g., the labeled target nucleic acid of the present invention), can be used to read reaction results without electrophoretic separation of the samples. Fluorescence polarization spectroscopy can be used to read the reaction results in the chip system disclosed in U.S. Pat. Nos. 5,699,157; 5,842,787; 5,869,004; 5,876,675; 5,942,443; 5,948,227; 6,042,709; 6,042,710; 6,046,056; 6,048,498; 6,086,740; 6,132,685; 6,150,119; 6,150,180; 6,153,073; 6,167,910; 6,171,850; and 6,186,660, the disclosures of which are incorporated by reference in their entireties. The application of fluorescence polarization spectroscopy to the chip system disclosed in the U.S. Patents listed supra is fast, efficient, and well-adapted for high-throughput screening.

In another embodiment, a compound that has an affinity for the target nucleic acid of interest can be labeled with a fluorophore to screen for compounds that bind to the target nucleic acid. For example, a pyrene-containing aminoglycoside analog was used to accurately monitor antagonist binding to a prokaryotic 16S rRNA A site (which comprises the natural target for aminoglycoside antibiotics) in a screen using a fluorescence quenching technique in a 96-well plate format (Hamasaki & Rando, 1998, Anal. Biochem. 261(2): 183-90).

In another embodiment, fluorescence resonance energy transfer (FRET) can be used to screen for compounds that bind to the target nucleic acid. FRET, a characteristic change in fluorescence, occurs when two fluorophores with overlapping emission and excitation wavelength bands are held together in close proximity, such as by a binding event. In the preferred embodiment, the fluorophore on the target nucleic acid and the fluorophore on the compounds will have overlapping excitation and emission spectra such that one fluorophore (the donor) transfers its emission energy to excite the other fluorophore (the acceptor). The acceptor preferably emits light of a different wavelength upon relaxing to the ground state, or relaxes non-radiatively to quench fluorescence. FRET is very sensitive to the distance between the two fluorophores, and allows measurement of molecular distances less than 10 nm. For example, U.S. Pat. NO. 6,337,183 to Arenas et al., which is incorporated by reference in its entirety, describes a screen for compounds that bind RNA that uses FRET to measure the effect of compounds on the stability of a target RNA molecule where the target RNA is labeled with both fluorescent acceptor and donor molecules and the distance between the two fluorophores as determined by FRET provides a measure of the folded structure of the RNA. Matsumoto et al. (2000, Bioorg. Med. Chem. Lett. 10:1857-1861) describe a system where a peptide that binds to HIV-1 TAR RNA is labeled on one end with a fluorescein fluorophore and a tetramethylrhodamine on the other end. The conformational change of the peptide upon binding to the RNA provided a FRET signal to screen for compounds that bound to the TAR RNA.

In the preferred embodiment, both the target nucleic acid and a compound that has an affinity for the target nucleic acid of interest are labeled with fluorophores with overlapping emission and excitation spectra (donor and acceptor), including but not limited to fluorescein and derivatives, rhodamine and derivatives, cyanine dyes and derivatives, bora-3a,4a-diaza-s-indacene (BODIPY®) and derivatives, pyrene, nanoparticles, or non-fluorescent quenching molecules. Binding of a labeled compound to the target nucleic acid can be identified by the change in observable fluorescence as a result of FRET.

If the target nucleic acid is labeled with the donor fluorophore, then the compounds are labeled with the acceptor fluorophore. Conversely, if the target nucleic acid is labeled with the acceptor fluorophore, then the compounds are labeled with the donor fluorophore. A wide variety of labels may be used, with the choice of label depending on sensitivity required, ease of conjugation with the compound, stability requirements, available instrumentation, and disposal provisions. The fluorophore on the target nucleic acid must be in close proximity to the binding site of the compounds, but should not be incorporated into a target nucleic acid at the specific binding site at which compounds are likely to bind, since the presence of a covalently attached label might interfere sterically or chemically with the binding of the compounds at this site.

In yet another embodiment, homogeneous time-resolved fluorescence ("HTRF") techniques based on time-resolved energy transfer from lanthanide ion complexes to a suitable acceptor species can be adapted for high-throughput screening for inhibitors of RNA-protein complexes (Hemmilä, 1999, J. Biomol. Screening 4:303-307; Mathis, 1999, J. Biomol. Screening 4:309-313). HTRF is similar to fluorescence resonance energy transfer using conventional organic dye pairs, but has several advantages, such as increased sensitivity and efficiency, and background elimination (Xavier et al., 2000, Trends Biotechnol. 18(8):349-356).

It is also contemplated that the target RNA may be labeled with a fluorophore and the compounds in the library labeled with a quencher of the fluorophore, or alternatively, the target RNA labeled with a quencher of the fluorophore and the compounds in the library labeled with a fluorophore, so that when a compound and target RNA bind, the fluorescent signal of the fluorophore is quenched.

Fluorescence spectroscopy has traditionally been used to characterize DNA-protein and protein-protein interactions, but fluorescence spectroscopy has not been widely used to characterize RNA-protein interactions because of an interfering absorption of RNA nucleotides with the intrinsic tryptophan fluorescence of proteins (Xavier et al., 2000, Trends Biotechnol. 18(8):349-356.). However, fluorescence spectroscopy has been used in studying the single tryptophan residue within the arginine-rich RNA-binding domain of Rev protein and its interaction with the RRE in a time-resolved fluorescence study (Kwon & Carson, 1998, Anal. Biochem. 264:133-140). Thus, in this invention, fluorescence spectroscopy is less preferred if the compounds or peptides or proteins possess intrinsic tryptophan fluorescence. However, fluorescence spectroscopy can be used for compounds that do not possess intrinsic fluorescence.

5.6.3 Surface Plasmon Resonance ("SPR")

Surface plasmon resonance (SPR) can be used for determining kinetic rate constants and equilibrium constants for macromolecular interactions by following the association project in "real time" (Schuck, 1997, Annu. Rev. Biophys. Biomol. Struct. 26:541-566).

The principle of SPR is summarized by Xavier et al. (Trends Biotechnol., 2000, 18(8):349-356) as follows. Total internal reflection occurs at the boundary between two substances of different refractive index. The incident light's electromagnetic field penetrates beyond the interface as an evanescent wave, which extends a few hundred nanometers beyond the surface into the medium. Insertion of a thin gold foil at the interace produced SPR owing to the absorption of the energy from the evanescent wave by free electron clouds of the metal (plasmons). As a result of this absorbance, there is a drop in the intensity of the reflected light at a particular angle of incidence. The evanescent wave profile depends exquisitely on the refractive index of the medium it probes. Thus, the angle at which absorption occurs is very sensitive to the refractive changes in the external medium. All proteins and nucleic acids are known to change the refractive index of water by a similar amount per unit mass, irrespective of their amino acid or nucleotide composition (the refractive index change is different for proteins and nucleic acids). When the protein or nucleic acid content of the layer at the sensor changes, the refractive index also changes. Typically, one member of a complex is immobilized in a dextran layer and then the other member is introduced into the solution, either in a flow cell (Biacore AB, Uppsala, Sweden) or a stirred cuvette (Affinity Sensors, Santa Fe, N. Mex.). It has been determined that there is a linear correlation between the surface concentration of protein or nucleic acid and the shift in resonance angle, which can be used to quantitate kinetic rate constants and/or the equilibrium constants.

In the present invention, the target RNA may be immobilized to the sensor surface through a streptavidin-biotin linkage, the linkage of which is disclosed by Crouch et al. (Methods Mol. Biol., 1999, 118:143-160). The RNA is biotinylated either during synthesis or post-synthetically via the conversion of the 3' terminal ribonucleoside of the RNA into a reactive free amino group or using a T7 polymerase incorporated guanosine monophosphorothioate at the 5' end. SPR has been used to determine the stoichiometry and affinity of the interaction between the HIV Rev protein and the RRE (Van Ryk & Venkatesan, 1999, J. Biol. Chem. 274:17452-17463) and the aminoglycoside antibiotics with RRE and a model RNA derived from the 16S ribosomal A site, respectively (Hendrix et al., 1997, J. Am. Chem. Soc. 119:3641-3648; Wong et al., 1998, Chem. Biol. 5:397-406).

In one embodiment of the present invention, the target nucleic acid can be immobilized to a sensor surface (e.g., by a streptavidin-biotin linkage) and SPR can be used to (a) determine whether the target RNA binds a compound and (b) further characterize the binding of the target nucleic acids of the present invention to a compound.

5.6.4 Mass Spectrometry

An automated method for analyzing mass spectrometer data which can analyze complex mixtures containing many thousands of components and can correct for background noise, multiply charged peaks and atomic isotope peaks is described in U.S. Pat. No. 6,147,344, which is hereby incorporated by reference in its entirety. The system disclosed in U.S. Pat. No. 6,147,344 is a method for analyzing mass spectrometer data in which a control sample measurement is performed providing a background noise check The peak height and width values at each m/z ratio as a function of time are stored in a memory. A mass spectrometer operation on a material to be analyzed is performed and the peak height and width values at each m/z ratio versus time are stored in a second memory location. The mass spectrometer operation on the material to be analyzed is repeated a fixed number of times and the stored control sample values at each m/z ratio level at each time increment are subtracted from each corresponding one from the operational runs, thus producing a difference value at each mass ratio for each of the multiple runs at each time increment. If the MS value minus the background noise does not exceed a preset value, the m/z ratio data point is not recorded, thus eliminating background noise, chemical noise and false positive peaks from the mass spectrometer data. The stored data for each of the multiple runs is then compared to a predetermined value at each m/z ratio and the resultant series of peaks, which are now determined to be above the background, is stored in the m/z points in which the peaks are of significance.

One possibility for the utilization of mass spectrometry in high throughput screening is the integration of SPR with mass spectrometry. Approaches that have been tried are direct analysis of the analyte retained on the sensor chip and mass spectrometry with the eluted analyte (Sonksen et al., 1998, Anal. Chem. 70:2731-2736; Nelson & Krone, 1999, J. Mol. Recog. 12:77-93). Further developments, especially in the interfacing of the sensor chip with the mass spectrometer and in reusing the sensor chip, are required to make SPR combined with mass spectroscopy a high-throughput method for biomolecular interaction analysis and the screening of targets for small molecule inhibitors (Xavier et al., 2000, Trends Biotechnol. 18(8):349-356).

In one embodiment of the present invention, the target nucleic acid complexed to a compound can be determined by any of the mass spectrometry processed described supra. Furthermore, mass spectrometry can also be used to elucidate the structure of the compound.

5.6.5 Scintillation Proximity Assay ("SPA")

Scintillation proximity assay ("SPA") is a method that can be used for screening small molecules that bind to the target RNAs. SPA would involve radiolabeling either the target RNA or the compound and then quantitating its binding to the other member to a bead or a surface impregnated with a scintillant (Cook, 1996, Drug Discov. Today 1:287-294). Currently, fluorescence-based techniques are preferred for high-throughput screening (Pope et al., 1999, Drug Discov. Today 4:350-362).

Screening for small molecules that inhibit Tat peptide:TAR RNA interaction has been performed with SPA, and inhibitors of the interaction were isolated and characterized (Mei et al., 1997, Bioorg. Med. Chem. 5:1173-1184; Mei et al., 1998, Biochemistry 37:14204-14212). A similar approach can be used to identify small molecules that directly bind to a pre-selected target RNA element in accordance with the invention can be utilized.

SPA can be adapted to high throughput screening by the availability of microplates, wherein the scintillant is directly incorporated into the plastic of the microtiter wells (Nakayama et al., 1998, J. Biomol. Screening 3:43-48). Thus, one embodiment of the present invention comprises (a) labeling of the target nucleic acid with a radioactive or fluorescent label; (b) contacted the labeled nucleic acid with compounds, wherein each compound is in a microtiter well coated with scintillant and is tethered to the microtiter well; and (c) identifying and quantifying the compounds bound to the target nucleic acid with SPA, wherein the compound is identified by virtue of its location in the microplate.

5.6.6 Structure-Activity Relationships ("SAR") by NMR Spectroscopy

NMR spectroscopy is a valuable technique for identifying complexed target nucleic acids by qualitatively determining changes in chemical shift, specifically from distances measured using relaxation effects, and NMR-based approaches have been used in the identification of small molecule binders of protein drug targets (Xavier et al., 2000, Trends Biotechnol. 18(8):349-356). The determination of structure-activity relationships ("SAR") by NMR is the first method for NMR described in which small molecules that bind adjacent sub-sites are identified by two-dimentional $^1$H-$^{15}$N spectra of the target protein (Shuker et al., 1996, Science 274:1531-1534). The signal from the bound molecule is monitored by employing line broadening, transferred NOEs and pulsed field gradient diffusion measurements (Moore, 1999, Curr. Opin. Biotechnol. 10:54-58). A strategy for lead generation by NMR using a library of small molecules has been recently described (Fejzo et al., 1999, Chem. Biol. 6:755-769).

In one embodiment of the present invention, the target nucleic acid complexed to a compound can be determined by SAR by NMR. Furthermore, SAR by NMR can also be used to elucidate the structure of the compound.

5.6.7 Size Exclusion Chromatography

In another embodiment of the present invention, size-exclusion chromatography is used to purify compounds that are bound to a target nucleic from a complex mixture of compounds. Size-exclusion chromatography separates molecules based on their size and uses gel-based media comprised of beads with specific size distributions. When applied to a column, this media settles into a tightly packed matrix and forms a complex array of pores. Separation is accomplished by the inclusion or exclusion of molecules by these pores based on molecular size. Small molecules are included into the pores and, consequently, their migration through the matrix is retarded due to the added distance they must travel before elution. Large molecules are excluded from the pores and migrate with the void volume when applied to the matrix. In the present invention, a target nucleic acid is incubated with a mixture of compounds while free in solution and allowed to reach equilibrium. When applied to a size exclusion column, compounds free in solution are retained by the column, and compounds bound to the target nucleic acid are passed through the column. In a preferred embodiment, spin columns commonly used for "desalting" of nucleic acids will be employed to separate bound from unbound compounds (e.g., Bio-Spin columns manufactured by BIO-RAD). In another embodiment, the size exclusion matrix is packed into multi-well plates to allow high throughput separation of mixtures (e.g., PLASMID 96-well SEC plates manufactured by Millipore).

5.6.8 Affinity Chromatography

In one embodiment of the present invention, affinity capture is used to purify compounds that are bound to a target nucleic acid labeled with an affinity tag from a complex mixture of compounds. To accomplish this, a target nucleic acid labeled with an affinity tag is incubated with a mixture of compounds while free in solution and then captured to a solid support once equilibrium has been established; alternatively, target nucleic acids labeled with an affinity tag can be captured to a solid support first and then allowed to reach equilibrium with a mixture of compounds.

The solid support is typically comprised of, but not limited to, cross-linked agarose beads that are coupled with a ligand for the affinity tag. Alternatively, the solid support may be a glass, silicon, metal, or carbon, plastic (polystyrene, polypropylene) surface with or without a self-assembled monolayer (SAM) either with a covalently attached ligand for the affinity tag, or with inherent affinity for the tag on the target nucleic acid.

Once the complex between the target nucleic acid and compound has reached equilibrium and has been captured, one skilled in the art will appreciate that the retention of bound compounds and removal of unbound compounds is facilitated by washing the solid support with large excesses of binding reaction buffer. Furthermore, retention of high affinity compounds and removal of low affinity compounds can be accomplished by a number of means that increase the stringency of washing; these means include, but are not limited to, increasing the number and duration of washes, raising the salt concentration of the wash buffer, addition of detergent or surfactant to the wash buffer, and addition of non-specific competitor to the wash buffer.

In one embodiment, the compounds themselves are detectably labeled with fluorescent dyes, radioactive isotopes, or nanoparticles. When the compounds are applied to the captured target nucleic acid in a spatially addressed fashion (e.g. in separate wells of a 96-well microplate), binding between the compounds and the target nucleic acid can be determined by the presence of the detectable label on the compound using fluorescence.

Following the removal of unbound compounds, bound compounds with high affinity for the target nucleic acid can be eluted from the immobilized target nucleic acids and analyzed. The elution of compounds can be accomplished by any means that break the non-covalent interactions between the target nucleic acid and compound. Means for elution include, but are not limited to, changing the pH, changing the salt concentration, the application of organic solvents, and the application of molecules that compete with the bound ligand. In a preferred embodiment, the means employed for elution will release the compound from the target RNA, but will not effect the interaction between the affinity tag and the solid support, thereby achieving selective elution of compound. Moreover, a preferred embodiment will employ an elution buffer that is volatile to allow for subsequent concentration by lyophilization of the eluted compound (e.g., 0 M to 5 M ammonium acetate).

In another embodiment of the invention, the target RNA can be labeled with biotin, an antigen, or a ligand. Library beads complexed to the target RNA can be separated from uncomplexed beads using affinity techniques designed to capture the labeled moiety on the target RNA. For example, a solid support, such as but not limited to, a column or a well in a microwell plate coated with avidin/streptavidin, an antibody to the antigen, or a receptor for the ligand can be used to capture or immobilize the labeled beads. Complexed RNA may or may not be irreversibly bound to the bead by a further transformation between the bound RNA and an additional moiety on the surface of the bead. Such linking methods include, but are not limited to: photochemical crosslinking between RNA and bead-bound molecules such as psoralen, thymidine or uridine derivates either present as monomers, oligomers, or as a partially complementary sequence; or chemical ligation by disulfide exchange, nitrogen mustards, bond formation between an electrophile and a nucleophile, or alkylating reagents. See, e.g., International Patent Publication WO/0146461, the contents of which are hereby incorporated by reference. The unbound library beads can be removed after the binding reaction by washing the solid phase. If the RNA is irreversibly bound to the bead, compounds can be isolated from the bead following destruction of the bound RNA by preferably, but not limited to, enzymatic or chemical (e.g., alkaline hydrolysis) degradation. The library beads bound to the solid phase can then be eluted with any solution that disrupts the binding between the labeled target RNA and the solid phase. Such solutions include high salt solutions, low pH solutions, detergents, and chaotropic denaturants, and are well known to one of skill in the art. In another embodiment, the compounds can be eluted from the solid phase by heat.

In one embodiment, the library of compounds can be prepared on magnetic beads, such as Dynabeads Streptavidin (Dynal Biotech, Oslo, Norway). The magnetic bead library can then be mixed with the labeled target RNA under conditions that allow binding to occur. The separation of the beads from unbound target RNA in the liquid phase can be accomplished using a magnet. After removal of the magnetic field, the bead complexed to the labeled RNA may be separated from uncomplexed library beads via the label used on the target RNA; e.g., biotinylated target RNA can be captured by avidin/streptavidin; target RNA labeled with antigen can be captured by the appropriate antibody; target RNA labeled with ligand can be captured using the appropriate immobilized receptor. The captured library bead can then be eluted with any solution that disrupts the binding between the labeled target RNA and the immobilized surface. Such solutions include high salt solutions, low pH solutions, detergents, and chaotropic denaturants, and are well known to one of skill in the art. Complexed RNA may or may not be irreversibly bound to the bead by a further transformation between the bound RNA and an additional moiety on the surface of the bead. Such linking methods include, but are not limited to: photochemical crosslinking between RNA and bead-bound molecules such as psoralen, thymidine or uridine derivates either present as monomers, oligomers, or as a partially complementary sequence; or chemical ligation by disulfide exchange, nitrogen mustards, bond formation between an electrophile and a nucleophile, or alkylating reagents. See, e.g., International Patent Publication WO/0146461, the contents of which are hereby incorporated by reference. If the RNA is irreversibly bound to the bead, compounds can be isolated from the bead following destruction of the bound RNA by enzymatic degradation including, but not limited to, ribonucleases A, $U_2$, $CL_3$, $T_1$, Phy M, *B. cereus* or chemical degradation including, but not limited to, piperidine-promoted backbone cleavage of abasic sites (following treatment with sodium hydroxide, hydrazine, piperidine formate, or dimethyl sulfate), or metal-assisted (e.g. nickel(II), cobalt(II), or iron(II)) oxidative cleavage.

In another embodiment, the preselected target RNA can be labeled with a heavy metal tag and incubated with the library beads to allow binding of the compounds to the target RNA. The separation of the labeled beads from unlabeled beads can be accomplished using a magnetic field. After removal of the magnetic field, the compound can be eluted with any solution that disrupts the binding between the preselected target RNA and the compound. Such solutions include high salt solutions, low pH solutions, detergents, and chaotropic denaturants, and are well known to one of skill in the art. In another embodiment, the compounds can be eluted from the solid phase by heat.

5.6.9 Nanoparticle Aggregation

In one embodiment of the present invention, both the target nucleic acid and the compounds are labeled with nanoparticles. A nanoparticle is a cluster of ions with controlled size from 0.1 to 1000 nm comprised of metals, metal oxides, or semiconductors including, but not limited to $Ag_2S$, ZnS, CdS, CdTe, Au, or $TiO_2$. Methods for the attachment of nucleic acids and small molecules to nanoparticles are well know to one of skill in the art (reviewed in Niemeyer, 2001, Angew. Chem. Int. Ed. 40:4129-4158. The references cited therein are hereby incorporated by reference in their entireties). In particular, if multiple copies of the target nucleic acid are attached to a single nanoparticle and multiple copies of a compound are attached to another nanoparticle, then interaction between the compound and target nucleic acid will induce aggregation of nanoparticles as described, for example, by Mitchel et al. 1999, J. Am. Chem. Soc. 121: 8122-8123. The aggregate can be detected by changes in absorbance or fluorescence spectra and physically separated from the unbound components through filtration or centrifugation.

5.6.10 Flow Cytometry

In a preferred embodiment, the complexed and non-complexed target nucleic acids are separated by flow cytometry methods. Flow cytometers for sorting and examining biological cells are well known in the art; this technology can be applied to separate the labeled library beads from unlabeled beads. Known flow cytometers are described, for example, in U.S. Pat. Nos. 4,347,935; 5,464,581; 5,483,469; 5,602,039; 5,643,796; and 6,211,477; the entire contents of which are incorporated by reference herein. Other known flow cytometers are the FACS Vantage™ system manufactured by Becton Dickinson and Company, and the COPAS™ system manufactured by Union Biometrica.

A flow cytometer typically includes a sample reservoir for receiving a biological sample. The biological sample contains particles (hereinafter referred to as "beads") that are to be analyzed and sorted by the flow cytometer. Beads are transported from the sample reservoir at high speed (>100 beads/second) to a flow cell in a stream of liquid "sheath" fluid. High-frequency vibrations of a nozzle that directs the stream to the flow cell causes the stream to partition and form ordered droplets, with each droplet containing a single bead. Physical properties of beads can be measured as they intersect a laser beam within the cytometer flow cell. As beads move one by one through the interrogation point, they cause the laser light to scatter and fluorescent molecules on the labeled beads (i.e., beads complexed with labeled target RNA) become excited. Alternatively, if the target nucleic acid is labeled with an inorganic nanoparticle, the beads complexed with bound target nucleic acid can be distinguished not only by unique fluorescent properties but also on the basis of spectrometric properties (e.g. including but not limited to increased optical density due to the reduction of $Ag^+$ ions in the presence of gold nanoparticles (see, e.g., Taton et al. Science 2000, 289: 1757-1760)).

5.6.11 Manual Batch

In one embodiment, a for separating complexed beads. To explore a bead-based library within a reasonable time period, the primary screens should be operated with sufficient throughput. To do this, the target nucleic acid is labeled with a dye and then incubated with the combinatorial library. An advantage of such an assay is the fast identification of active library beads by color change. In the lower concentrations of the dye-labeled target molecule, only those library beads that bind the target molecules most tightly are detected because of higher local concentration of the dye. When washed and plated into a liquid monolayer, colored beads are easily separated from non-colored beads with the aid of a dissecting microscope. One of the problems associated with this method could be the interaction between the red dye and library substrates. Control experiments using the dye alone and dye attached to mutant RNA sequences with the libraries are performed to eliminate this possibility.

5.6.12 Suspension of Beads in Electric Fields

In another embodiment of the invention, library beads bound to the target RNA can be separated from unbound beads on the basis of the altered charge properties due to RNA binding. In a preferred embodiment of this technique, beads are separated from unbound nucleic acid and suspended, preferably but not only, in the presence of an electric field where the bound RNA causes the beads bound to the target RNA to migrate toward the anode, or positive, end of the field.

Beads can be preferentially suspended in solution as a colloidal suspension with the aid of detergents or surfactants. Typical detergents useful in the methods of the present invention include, but are not limited to, anionic detergents, such as salts of deoxycholic acid, 1-heptanesulfonic acid, N-laurylsarcosine, lauryl sulfate, 1-octane sulfonic acid, carboxymethylcellulose, carrageenan, and taurocholic acid; cationic detergents such as benzalkonium chloride, cetylpyridinium, methylbenzethonium chloride, and decamethonium bromide; zwitterionic detergents such as CHAPS, CHAPSO, alkyl betaines, alky amidoalkyl betaines, N-dodecyl-N,N-dimethyl-3-ammonio-1-propanesulfonate, and phosphatidylcholine; and non-ionic detergents such as n-decyl a-D-glucopyranoside, n-decyl-D-maltopyranoside, n-dodecyl -D-maltoside, n-octyl -D-glucopyranoside, sorbitan esters, n-tetradecyl-D-maltoside and tritons. Preferably, the detergent, if present, is a nonionic detergent. Typical surfactants useful in the methods of the present invention include, but are not limited to, ammonium lauryl sulfate, polyethylene glycols, butyl glucoside, decyl glucoside, Polysorbate 80, lauric acid, myristic acid, palmitic acid, potassium palmitate, undecanoic acid, lauryl betaine, and lauryl alcohol.

Complexed RNA may or may not be irreversibly bound to the bead by a further transformation between the bound RNA and an additional moiety on the surface of the bead. Such linking methods include, but are not limited to: photochemical crosslinking between RNA and bead-bound molecules such as psoralen, thymidine or uridine derivates either present as monomers, oligomers, or as a partially complementary sequence; or chemical ligation by disulfide exchange, nitrogen mustards, bond formation between an electrophile and a nucleophile, or alkylating reagents.

If the RNA is irreversibly bound to the bead, compounds can be isolated from the bead following destruction of the bound RNA by enzymatic degradation including, but not limited to, ribonucleases A, $U_2$, $CL_3$, $T_1$, Phy M, *B. cereus* or chemical degradation including, but not limited to, piperidine-promoted backbone cleavage of abasic sites (following treatment with sodium hydroxide, hydrazine, piperidine formate, or dimethyl sulfate), or metal-assisted (e.g. nickel(II), cobalt(II), or iron(II)) oxidative cleavage.

5.6.13 Microwave Spectroscopy

In another embodiment, the complexed beads are separated from uncomplexed beads by microwave spectroscopy. For example, as described in U.S. Pat. Nos. 6,395,480; 6,376,258; 6,368,795; 6,340,568; 6,338,968; 6,287,874; and 6,287,776 to Hefti, the disclosures of which are hereby incorporated by reference, the unique dielectric properties of molecules and binding complexes, such as hybridization complexes formed between a nucleic acid probe and a nucleic acid target, molecular binding events, and protein/ligand complexes, result in varying microwave spectra which can be measured. The molecule's dielectric properties can be observed by coupling a test signal to the molecule and observing the resulting signal. When the test signal excites the molecule at a frequency within the molecule's dispersion regime, especially at a resonant frequency, the molecule will interact strongly with the signal, and the resulting signal will exhibit dramatic variations in its measured amplitude and phase, thereby generating a unique signal response. This response can be used to detect and identify the bound molecular structure. In addition, because most molecules will exhibit different dispersion properties over the same or different frequency bands, each generates a unique signal response which can be used to identify the molecular structure.

5.7 Methods for Identifying or Characterizing the Compounds Bound to the Target Nucleic Acids If the library comprises arrays or microarrays of compounds, wherein each compound has an address or identifier, the compound can be deconvoluted, e.g., by cross-referencing the positive sample to original compound list that was applied to the individual test assays.

If the library is a peptide or nucleic acid library, the sequence of the compound can be determined by direct sequencing of the peptide or nucleic acid. Such methods are well known to one of skill in the art.

A number of physico-chemical techniques can be used for the de novo characterization of compounds bound to the target.

5.7.1 Mass Spectrometry

Mass spectrometry (e.g., electrospray ionization ("ESI") and matrix-assisted laser desorption-ionization ("MALDI"), Fourier-transform ion cyclotron resonance ("FT-ICR") an be used both for high-throughput screening of compounds that bind to a target RNA and elucidating the structure of the compound. Thus, one example of mass spectroscopy is that separation of a bound and unbound complex and compound structure elucidation can be carried out in a single step.

MALDI uses a pulsed laser for desorption of the ions and a time-of-flight analyzer, and has been used for the detection of noncovalent tRNA:amino-acyl-tRNA synthetase complexes (Gruic-Sovulj et al., 1997, J. Biol. Chem. 272:32084-32091). However, covalent cross-linking between the target nucleic acid and the compound is required for detection, since a non-covalently bound complex may dissociate during the MALDI process.

ESI mass spectrometry ("ESI-MS") has been of greater utility for studying non-covalent molecular interactions because, unlike the MALDI process, ESI-MS generates molecular ions with little to no fragmentation (Xavier et al., 2000, Trends Biotechnol. 18(8):349-356). ESI-MS has been used to study the complexes formed by HIV Tat peptide and protein with the TAR RNA (Sannes-Lowery et al., 1997, Anal. Chem. 69:5130-5135).

Fourier-transform ion cyclotron resonance ("FT-ICR") mass spectrometry provides high-resolution spectra, isotope-resolved precursor ion selection, and accurate mass assignments (Xavier et al., 2000, Trends Biotechnol. 18(8):349-356). FT-ICR has been used to study the interaction of aminoglycoside antibiotics with cognate and non-cognate RNAs (Hofstadler et al., 1999, Anal. Chem. 71:3436-3440; Griffey et al., 1999, Proc. Natl. Acad. Sci. USA 96:10129-10133). As true for all of the mass spectrometry methods discussed herein, FT-ICR does not require labeling of the target RNA or a compound.

An advantage of mass spectroscopy is not only the elucidation of the structure of the compound, but also the determination of the structure of the compound bound to the preselected target RNA. Such information can enable the discovery of a consensus structure of a compound that specifically binds to a preselected target RNA.

In a specific embodiment, the structure of the compound is determined by time of flight mass spectroscopy ("TOF-MS"). In time of flight methods of mass spectrometry, charged (ionized) molecules are produced in a vacuum and accelerated by an electric field into a time of flight tube or drift tube. The velocity to which the molecules may be accelerated is proportional to the accelerating potential, proportional to the charge of the molecule, and inversely proportional to the square of the mass of the molecule. The charged molecules travel, i.e., "drift" down the TOF tube to a detector. The time taken for the molecules to travel down the tube may be interpreted as a measure of their molecular weight. Time-of-flight mass spectrometers have been developed for all of the major ionization techniques such as, but limited to, electron impact ("EI"), infrared laser desorption ("IRLD"), plasma desorption ("PD"), fast atom bombardment ("FAB"), secondary ion mass spectrometry ("SIMS"), matrix-assisted laser desorption/ionization ("MALDI"), and electrospray ionization ("ESI").

5.7.2 Edman Degradation

In an embodiment wherein the library is a peptide library or a derivative thereof, Edman degradation can be used to determine the structure of the compound. In one embodiment, a modified Edman degradation process is used to obtain compositional tags for proteins, which is described in U.S. Pat. No. 6,277,644 to Farnsworth et al., which is hereby incorporated by reference in its entirety. The Edman degradation chemistry is separated from amino acid analysis, circumventing the serial requirement of the conventional Edman process. Multiple cycles of coupling and cleavage are performed prior to extraction and compositional analysis of amino acids. The amino acid composition information is then used to search a database of known protein or DNA sequences to identify the sample protein. An apparatus for performing this method comprises a sample holder for holding the sample, a coupling agent supplier for supplying at least one coupling agent, a cleavage agent supplier for supplying a cleavage agent, a controller for directing the sequential supply of the coupling agents, cleavage agents, and other reagents necessary for performing the modified Edman degradation reactions, and an analyzer for analyzing amino acids.

In another embodiment, the method can be automated as described in U.S. Pat. No. 5,565,171 to Dovichi et al., which is hereby incorporated by reference in its entirety. The apparatus includes a continuous capillary connected between two valves that control fluid flow in the capillary. One part of the capillary forms a reaction chamber where the sample may be immobilized for subsequent reaction with reagents supplied through the valves. Another part of the capillary passes through or terminates in the detector portion of an analyzer such as an electrophoresis apparatus, liquid chromatographic apparatus or mass spectrometer. The apparatus may form a peptide or protein sequencer for carrying out the Edman degradation reaction and analyzing the reaction product produced by the reaction. The protein or peptide sequencer includes a reaction chamber for carrying out coupling and cleavage on a peptide or protein to produce derivatized amino acid residue, a conversion chamber for carrying out conversion and producing a converted amino acid residue and an analyzer for identifying the converted amino acid residue. The reaction chamber may be contained within one arm of a capillary and the conversion chamber is located in another arm of the capillary. An electrophoresis length of capillary is directly capillary coupled to the conversion chamber to allow electrophoresis separation of the converted amino acid residue as it leaves the conversion chamber. Identification of the converted amino acid residue takes place at one end of the electrophoresis length of the capillary.

5.7.3 NMR Spectroscopy

As described above, NMR spectroscopy is a technique for identifying binding sites in target nucleic acids by qualitatively determining changes in chemical shift, specifically from distances measured using relaxation effects. Examples of NMR that can be used for the invention include, but are not limited to, one-dimentional NMR, two-dimentional NMR, correlation spectroscopy ("COSY"), and nuclear Overhauser effect ("NOE") spectroscopy. Such methods of structure determination of compounds are well known to one of skill in the art.

Similar to mass spectroscopy, an advantage of NMR is the not only the elucidation of the structure of the compound, but also the determination of the structure of the compound bound to the preselected target RNA. Such information can enable the discovery of a consensus structure of a compound that specifically binds to a preselected target RNA.

5.7.4 Vibrational Spectroscopy

Vibrational spectroscopy (e.g. infrared (IR) spectroscopy or Raman spectroscopy) can be used for elucidating the structure of the compound on the isolated bead.

Infrared spectroscopy measures the frequencies of infrared light (wavelengths from 100 to 10,000 nm) absorbed by the compound as a result of excitation of vibrational modes according to quantum mechanical selection rules which require that absorption of light cause a change in the electric dipole moment of the molecule. The infrared spectrum of any molecule is a unique pattern of absorption wavelengths of varying intensity that can be considered as a molecular fingerprint to identify any compound.

Infrared spectra can be measured in a scanning mode by measuring the absorption of individual frequencies of light, produced by a grating which separates frequencies from a mixed-frequency infrared light source, by the compound relative to a standard intensity (double-beam instrument) or pre-measured ('blank') intensity (single-beam instrument). In a preferred embodiment, infrared spectra are measured in a pulsed mode (FT-IR) where a mixed beam, produced by an interferometer, of all infrared light frequencies is passed through or reflected off the compound. The resulting interferogram, which may or may not be added with the resulting interferograms from subsequent pulses to increase the signal strength while averaging random noise in the electronic signal, is mathematically transformed into a spectrum using Fourier Transform or Fast Fourier Transform algorithms.

Raman spectroscopy measures the difference in frequency due to absorption of infrared frequencies of scattered visible or ultraviolet light relative to the incident beam. The incident monochromatic light beam, usually a single laser frequency, is not truly absorbed by the compound but interacts with the electric field transiently. Most of the light scattered off the sample with be unchanged (Rayleigh scattering) but a portion of the scatter light will have frequencies that are the sum or difference of the incident and molecular vibrational frequencies. The selection rules for Raman (inelastic) scattering require a change in polarizability of the molecule. While some vibrational transitions are observable in both infrared and Raman spectrometry, must are observable only with one or the other technique. The Raman spectrum of any molecule is a unique pattern of absorption wavelengths of varying intensity that can be considered as a molecular fingerprint to identify any compound.

Raman spectra are measured by submitting monochromatic light to the sample, either passed through or preferably reflected off, filtering the Rayleigh scattered light, and detecting the frequency of the Raman scattered light. An improved Raman spectrometer is described in U.S. Pat. No. 5,786,893 to Fink et al., which is hereby incorporated by reference.

Vibrational microscopy can be measured in a spatially resolved fashion to address single beads by integration of a visible microscope and spectrometer. A microscopic infrared spectrometer is described in U.S. Pat. No. 5,581,085 to Reffner et al., which is hereby incorporated by reference in its entirety. An instrument that simultaneously performs a microscopic infrared and microscopic Raman analysis on a sample is described in U.S. Pat. No. 5,841,139 to Sostek et al., which is hereby incorporated by reference in its entirety.

In one embodiment of the method, compounds are synthesized on polystyrene beads doped with chemically modified styrene monomers such that each resulting bead has a characteristic pattern of absorption lines in the vibrational (IR or Raman) spectrum, by methods including but not limited to those described by Fenniri et al., 2000, J. Am. Chem. Soc. 123:8151-8152. Using methods of split-pool synthesis familiar to one of skill in the art, the library of compounds is prepared so that the spectroscopic pattern of the bead identifies one of the components of the compound on the bead. Beads that have been separated according to their ability to bind target RNA can be identified by their vibrational spectrum. In one embodiment of the method, appropriate sorting and binning of the beads during synthesis then allows identification of one or more further components of the compound on any one bead. In another embodiment of the method, partial identification of the compound on a bead is possible through use of the spectroscopic pattern of the bead with or without the aid of further sorting during synthesis, followed by partial resynthesis of the possible compounds aided by doped beads and appropriate sorting during synthesis.

In another embodiment, the IR or Raman spectra of compounds are examined while the compound is still on a bead, preferably, or after cleavage from bead, using methods including but not limited to photochemical, acid, or heat treatment. The compound can be identified by comparison of the IR or Raman spectral pattern to spectra previously acquired for each compound in the combinatorial library.

In a specific embodiment, compounds can be identified by matching the IR or Raman spectra of a compound to a dataset of vibrational (IR or Raman) spectra previously acquired for each compound in the combinatorial library. By this method, the spectra of compounds with known structure are recorded so that comparison with these spectra can identify compounds again when isolated from RNA binding experiments.

5.7.5 Microwave Spectroscopy

In another embodiment, the microwave spectra of a compound can be used to elucidate the structure of the compound. For example, as described in U.S. Pat. Nos. 6,395,480; 6,376,258; 6,368,795; 6,340,568; 6,338,968; 6,287,874; and 6,287,776 to Hefti, the disclosures of which are hereby incorporated by reference, the unique dielectric properties of molecules and binding complexes, such as hybridization complexes formed between a nucleic acid probe and a nucleic acid target, molecular binding events, and protein/ligand complexes, result in varying microwave spectra which can be measured. The molecule's dielectric properties can be observed by coupling a test signal to the molecule and observing the resulting signal. When the test signal excites the molecule at a frequency within the molecule's dispersion regime, especially at a resonant frequency, the molecule will interact strongly with the signal, and the resulting signal will exhibit dramatic variations in its measured amplitude and phase, thereby generating a unique signal response. This response can be used to detect and identify the bound molecular structure. In addition, because most molecules will exhibit different dispersion properties over the same or different frequency bands, each generates a unique signal response which can be used to identify the molecular structure.

5.7.6 X-Ray Crystallography

X-ray crystallography can be used to elucidate the structure of a compound. For a review of x-ray crystallography see, e.g., Blundell et al. 2002, Nat Rev Drug Discov 1(1):45-54. The first step in x-ray crystallography is the formation of crystals. The formation of crystals begins with the preparation of highly purified and soluble samples. The conditions for crystallization is then determined by optimizing several solution variables known to induce nucleation, such as pH, ionic strength, temperature, and specific concentrations of organic additives, salts and detergent. Techniques for automating the crystallization process have been developed to automate the production of high-quality protein crystals. Once crystals have been formed, the crystals are harvested and prepared for data collection. The crystals are then analyzed by diffraction (such as multi-circle diffractometers, high-speed CCD detectors, and detector off-set). Generally, multiple crystals must be screened for structure determinations.

A number of methods can be used to acquire a diffraction patter so that a compound can be characterized. In one embodiment, an X-ray source is provided, for example, by a rotating anode generator producing an X-ray beam of a characteristic wavelength. There are a number of sources of X-ray radiation that may be used in the methods of the invention, including low and high intensity radiation. In one example, the tunable X-ray radiation is produced by a Synchrotron. In another embodiment, the primary X-ray beam is monochromated by either crystal monochromators or focusing mirrors and the beam is passed through a helium flushed collimator. In a preferred embodiment, the crystal is mounted on a pin on a goniometer head, that is mounted to a goniometer which allows to position the crystal in different orientations in the beam. The diffracted X-rays can be recorded using a number of techniques, including, but not limited to image plates, multiwire detectors or CCD cameras. In other embodiments, flash cooling, for example, of protein crystals, to cryogenic temperatures (~100 K) offers many advantages, the most significant of which is the elimination of radiation damage.

5.8 Naturally Occurring Genes with Premature Stop Codons: Examples of Disorders and Diseases The invention provides for naturally occurring genes with premature stop codons to ascertain the effects of compounds on premature translation termination and/or nonsense-mediated mRNA decay. In general, the expression of the gene product, in particular, a full-length gene product, is indicative of the effect of the compounds on premature translation termination and/or nonsense-mediated mRNA decay.

In a preferred embodiment, the naturally occurring genes with premature stop codons are genes that cause diseases which are due, in part, to the lack of expression of the gene resulting from the premature stop codon. Such diseases include, but are not limited to, cystic fibrosis, muscular dystrophy, heart disease (e.g., familial hypercholesterolemia), p53-associated cancers (e.g., lung, breast, colon, pancreatic, non-Hodgkin's lymphoma, ovarian, and esophageal cancer), colorectal carcinomas, neurofibromatosis, retinoblastoma, Wilm's tumor, retinitis pigmentosa, collagen disorders (e.g., osteogenesis imperfecta and cirrhosis), Tay Sachs disease, blood disorders (e.g., hemophilia, von Willebrand disease, b-Thalassemia), kidney stones, ataxia-telangiectasia, lysosomal storage diseases, and tuberous sclerosis. Genes involved in the etiology of these diseases are discussed below.

The recognition of translation termination signals is not necessarily limited to a simple trinucleotide stop codon, but is instead recognized by the sequences surrounding the stop codon in addition to the stop codon itself (see, e.g., Manuvakhova et al., 2000, RNA 6(7):1044-1055, which is hereby incorporated by reference in its entirety). Thus, any genes containing particular tetranucleotide sequences at the stop codon, such as, but not limited to, UGAC, UAGU, UAGC, UAGG, UAAC, UAAU, UAAG, and UAAA, are candidates of naturally occurring genes with premature stop codons that are useful in the present invention. Human disease genes that contain these particular sequence motifs are sorted by chromosome is presented as an Example in Section 8.

5.8.1 Cystic Fibrosis

Cystic fibrosis is caused by mutations in the cystic fibrosis conductance regulator ("CFTR") gene. Such mutations vary between populations and depend on a multitude of factors such as, but not limited to, ethnic background and geographic location. Nonsense mutations in the CFTR gene are expected to produce little or not CFTR chloride channels. Several nonsense mutations in the CFTR gene have been identified (see, e.g., Tzetis et al., 2001, Hum Genet. 109(6):592-601. Strandvik et al., 2001, Genet Test. 5(3):235-42; Feldmann et al., 2001, Hum Mutat. 17(4):356; Wilschanski et al., 2000, Am J Respir Crit Care Med. 161(3 Pt 1):860-5; Castaldo et al., 1999, Hum Mutat. 14(3):272; Mittre et al., 1999, Hum Mutat. 14(2):182; Mickle et al., 1998, Hum Mol Genet. 7(4): 729-35; Casals et al., 1997, Hum Genet. 101(3):365-70; Mittre et al., 1996, Hum Mutat. 8(4):392-3; Bonizzato et al., 1995, Hum Genet. April 1995 ;95(4):397-402; Greil et al., 1995, Wien Klin Wochenschr. 107(15):464-9; Zielenski et al., 1995, Hum Mutat. 5(1):43-7; Dork et al., 1994, Hum Genet. 94(5):533-42; Balassopoulou et al., 1994, Hum Mol Genet. 3(10):1887-8; Ghanem et al., 1994, 21(2):434-6; Will et al., J Clin Invest. 1994; Apr;93(4):1852-9; Hull et al., 1994, Genomics. 1994 January 15;19(2):362-4; Dork et al., 1994, Hum Genet. 93(1):67-73; Rolfini & Cabrini, 1993, J Clin Invest. 92(6):2683-7; Will et al., 1993, J Med Genet. 30(10): 833-7; Bienvenu et al., 1993, J Med Genet. 30(7):621-2; Cheadle et al., 1993, Hum Mol Genet. 2(7):1067-8; Casals et al., 1993, Hum Genet. 91(1):66-70; Reiss et al., 1993, Hum Genet. 91(1):78-9; Chevalier-Porst et al., 1992, Hum Mol Genet. 1(8)-647-8; Hamosh et al., 1992, Hum Mol Genet. 1(7):542-4; Gasparini et al., 1992, J Med Genet. 29(8):558-62; Fanen et al., 1992, Genomics. 13(3):770-6; Jones et al., 1992, Hum Mol Genet. 1(1):11-7; Ronchetto et al., 1992, Genomics. 12(2):417-8.; Macek et al., 1992, Hum Mutat. 1(6):501-2; Shoshani et al., 1992, Am J Hum Genet. 50(1): 222-8; Schloesser et al., 1991, J Med Genet. 28(12):878-80; Hamosh et al., 1991, J Clin Invest. 88(6):1880-5; Bal et al., 1991, J Med Genet. 28(10):715-7; Dork et al., 1991, Hum Genet. 87(4):441-6; Beaudet et al., 1991, Am J Hum Genet. 48(6):1213; Gasparini et al., 1991, Genomics. 10(1):193-200; Cutting et al., 1990, N Engl J Med. 1990, 323(24):1685-9; and Kerem et al., 1990, Proc Natl Acad Sci USA. 87(21): 8447-51, the disclosures of which are hereby incorporated by reference in their entireties). Any CFTR gene encoding a premature translation codon including, but not limited to, the nonsense mutations described in the references cited above, can be used in the present invention to identify compounds that mediate premature translation termination and/or nonsense-mediated mRNA decay.

5.8.2 Muscular Dystrophy

Muscular dystrophy is a genetic disease characterized by severe, progressive muscle wasting and weakness. Duchenne muscular dystrophy and Becker muscular dystrophy are generally caused by nonsense mutations of the dystrophin gene (see, e.g., Kerr et al., 2001, Hum Genet. 109(4):402-7 and Wagner et al., 2001, Ann Neurol. 49(6):706-11). Nonsense mutations in other genes have also been implicated in other types of muscular dystrophy, such as, but not limited to, collagen genes in Ullrich congenital muscular dystrophy (see, e.g., Demir et al., 2002, Am J Hum Genet. 70(6):1446-58), the emerin gene and lamins genes in Emery-Dreifuss muscular dystrophy (see, e.g., Holt et al., 2001, Biochem Biophys Res Commun. 287(5):1129-33; Becane et al., 2000, Pacing Clin Electrophysiol. 23(11 Pt 1): 1661-6; and Bonne et al., 2000, Ann Neurol. 48(2):170-80.), the dysferlin gene in Miyoshi myopathy (see, e.g., Nakagawa et al., 2001, J Neurol Sci. 184(1):15-9), the plectin gene in late onset muscular dystrophy (see, e.g., Bauer et al., 2001, Am J Pathol. 158(2): 617-25), the delta-sarcoglycan gene in recessive limb-girdle muscular dystrophy (see, e.g., Duggan et al., 1997, Neurogenetics. 1(1):49-58), the laminina2-chain gene in congenital muscular dystrophy (see, e.g., Mendell et al., 1998, Hum Mutat. 12(2):135), the plectin gene in late-onset muscular dystrophy (see, e.g., Rouan et al., 2000, J Invest Dermatol. 114(2):381-7 and Kunz et al., 2000, J Invest Dermatol. 114(2):376-80), the myophosphorylase gene in McArdle's disease (see, e.g., Bruno et al., 1999, Neuromuscul Disord. 9(1): 34-7), and the collagen VI in Bethlem myopathy (see, e.g., Lamande et al., 1998, Hum Mol Genet. June 1998 ;7(6):981-9).

Several nonsense mutations in the dystrophin gene have been identified (see, e.g., Kerr et al., 2001, Hum Genet. 109 (4):402-7; Mendell et al., 2001, Neurology 57(4):645-50; Fajkusova et al., 2001, Neuromuscul Disord. 11(2):133-8; Ginjaar et al., 2000, Eur J Hum Genet. 8(10):793-6; Lu et al., 2000, J Cell Biol. 148(5):985-96; Tuffery-Giraud et al., 1999, Hum Mutat. 14(5):359-68; Fajkusova et al., 1998, J Neurogenet. 12(3):183-9; Tuffery et al., 1998, Hum Genet. 102(3): 334-42; Shiga et al., 1997, J Clin Invest. 100(9):2204-10; Winnard et al., 1995, Am J Hum Genet. 56(1):158-66; Prior et al., 1994, Am J Med Genet. 50(1):68-73; Prior et al., 1993, Hum Mol Genet. 2(3):311-3; Prior et al., 1993, Hum Mutat. 2(3):192-5; Nigro et al., 1992, Hum Mol Genet. 1(7):517-20; Worton, 1992, J Inherit Metab Dis. 15(4):539-50; and Bulman et al., 1991, Genomics. 10(2):457-60; the disclosures of which are hereby incorporated by reference in their entireties). Any gene encoding a premature translation codon implicated in muscular dystrophy including, but not limited to, the nonsense mutations described in the references cited above, can be used in the present invention to identify compounds that mediate premature translation termination and/or nonsense-mediated mRNA decay.

5.8.3 Familial Hypercholesterolemia

Hypercholesterolemia, or high blood cholesterol, results from either the overproduction or the underutilization of low density lipoprotein ("LDL"). Hypercholesterolemia is caused by either the genetic disease familial hypercholesterolemia or the consumption of a high cholesterol diet. Nonsense mutations in the LDL receptor gene have been implicated in familial hypercholesterolemia Several nonsense mutations in the LDL receptor gene have been identified (see, e.g., Lind et al., 2002, Atherosclerosis 163(2):399-407; Salazar et al., 2002, Hum Mutat. 19(4):462-3; Kuhrova et al., 2002, Hum Mutat. 19(1):80; Zakharova et al., 2001, Bioorg Khim. 27(5):393-6; Kuhrova et al., 2001, Hum Mutat. 18(3):253; Genschel et al., 2001, Hum Mutat. 17(4):354; Weiss et al., 2000, J Inherit Metab Dis. 23(8):778-90; Mozas et al., 2000, Hum Mutat. 15(5):483-4; Shin et al., 2000, Clin Genet. 57(3):225-9; Graham et al., 1999, Atherosclerosis 147(2):309-16; Hattori et al., 1999, Hum Mutat. 14(1):87; Cenarro et al., 1998, Hum Mutat. 11(5):413; Rodningen et al., 1999, Hum Mutat. 13(3): 186-96; Hirayama et al., 1998, J Hum Genet. 43(4):250-4; Lind et al., 1998, J Intern Med. 244(1):19-25; Thiart et al., 1997, Mol Cell Probes 11(6):457-8; Maruyama et al., 1995, Arterioscler Thromb Vasc Biol. 15(10):1713-8; Koivisto et al., 1995, Am J Hum Genet. 57(4):789-97; Lombardi et al., 1995, J Lipid Res. 36(4):860-7; Leren et al., 1993, Hum Genet. 92(1):6-10; Landsberger et al., 1992, Am J Hum Genet. 50(2):427-33; Loux et al., 1992, Hum Mutat. 1992;1 (4):325-32; Motulsky, 1989, Arteriosclerosis. 9(1 Suppl):I3-7; Lehrman et al., 1987, J Biol Chem. 262(1):401-10; and Lehrman et al., 1985, Cell 41(3):735-43; the disclosures of which are hereby incorporated by reference in their entireties). Any LDL receptor gene encoding a premature translation codon including, but not limited to, the nonsense mutations described in the references cited above, can be used in the present invention to identify compounds that mediate premature translation termination and/or nonsense-mediated mRNA decay.

5.8.4 p53-associated Cancers

Mutant forms of the p53 protein, which is thought to act as a negative regulator of cell proliferation, transformation, and tumorigenesis, have been implicated as a common genetic change characteristic of human cancer (see, e.g., Levine et al., 1991, Nature 351:453-456 and Hollstein et al., 1991, Science 253:49-53). p53 mutations have been implicated in cancers such as, but not limited to, lung cancer, breast cancer, colon cancer, pancreatic cancer, non-Hodgkin's lymphoma, ovarian cancer, and esophageal cancer.

Nonsense mutations have been identified in the p53 gene and have been implicated in cancer. Several nonsense mutations in the p53 gene have been identified (see, e.g., Masuda et al., 2000, Tokai J Exp Clin Med. 25(2):69-77; Oh et al., 2000, Mol Cells 10(3):275-80; Li et al., 2000, Lab Invest. 80(4):493-9; Yang et al., 1999, Zhonghua Zhong Liu Za Zhi 21(2):114-8; Finkelstein et al., 1998, Mol Diagn. 3(1):37-41; Kajiyama et al., 1998, Dis Esophagus. 11(4):279-83; Kawamura et al., 1999, Leuk Res. 23(2):115-26; Radig et al., 1998, Hum Pathol. 29(11):1310-6; Schuyer et al., 1998, Int J Cancer 76(3):299-303; Wang-Gohrke et al., 1998, Oncol Rep. 5(1): 65-8; Fulop et al., 1998, J Reprod Med. 43(2):119-27; Ninomiya et al., 1997, J Dermatol Sci. 14(3):173-8; Hsieh et al., 1996, Cancer Lett. 100(1-2):107-13; Rall et al., 1996, Pancreas. 12(1):10-7; Fukutomi et al., 1995, Nippon Rinsho. 53(11):2764-8; Frebourg et al., 1995, Am J Hum Genet. 56(3):608-15; Dove et al., 1995, Cancer Surv. 25:335-55; Adamson et al., 1995, Br J Haematol. 89(1):61-6; Grayson et al., 1994, Am J Pediatr Hematol Oncol. 16(4):341-7; Lepelley et al., 1994, Leukemia. 8(8):1342-9; McIntyre et al., 1994, J Clin Oncol. 12(5):925-30; Horio et al., 1994, Oncogene. 9(4):1231-5; Nakamura et al., 1992, Jpn J Cancer Res. 83(12):1293-8; Davidoff et al., 1992, Oncogene. 7(1):127-33; and Ishioka et al., 1991, Biochem Biophys Res Commun. 177(3):901-6; the disclosures of which are hereby incorporated by reference in their entireties). Any p53 gene encoding a premature translation codon including, but not limited to, the nonsense mutations described in the references cited above, can be used in the present invention to identify compounds that mediate premature translation termination and/or nonsense-mediated mRNA decay.

5.8.5 Colorectal Carcinomas

Molecular genetic abnormalities resulting in colorectal carcinoma involve tumor-suppressor genes that undergo inactivation (such as, but not limited to, apc, mcc, dcc, p53, and possibly genes on chromosomes 8p, 1p, and 22q) and dominant-acting oncogenes (such, but not limited to, ras, src, and myc) (see, e.g., Hamilton, 1992, Cancer 70(5 Suppl):1216-21). Nonsense mutations in the adenomatous polyposis coli ("APC") gene and mismatch repair genes (such as, but not limited to, mlh1 and msh-2) have also been described. Nonsense mutations have been implicated in colorectal carcinomas (see, e.g., Viel et al., 1997, Genes Chromosomes Cancer. 18(1):8-18; Akiyama et al., 1996, Cancer 78(12):2478-84; Itoh & Imai, 1996, Hokkaido Igaku Zasshi 71(1):9-14; Kolodner et al., 1994, Genomics. 24(3):516-26; Ohue et al., 1994, Cancer Res. 54(17):4798-804; and Yin et al., 1993, Gastroenterology. 104(6):1633-9; the disclosures of which are hereby incorporated by reference in their entireties). Any gene encoding a premature translation codon implicated in colorectal carcinoma including, but not limited to, the nonsense mutations described in the references cited above, can be used in the present invention to identify compounds that mediate premature translation termination and/or nonsense-mediated mRNA decay.

5.8.6 Neurofibromatosis

Neurofibromatosis is an inherited disorder, which is commonly caused caused by mutations in the NF1 and NF2 tumor suppressor genes. It is characterized by multiple intracranial tumors including schwannomas, meningiomas, and ependymomas. Nonsense mutations in the NF1 and NF2 genes have been described. Nonsense mutations have been implicated in neurofibromatosis (see, e.g., Lamszus et al., 2001, Int J Cancer 91(6):803-8; Sestini et al., 2000, Hum Genet. 107(4):366-71; Fukasawa et al., 2000, J Cancer Res. 91(12):1241-9; Park et al., 2000, J Hum Genet. 45(2):84-5; Ueki et al., 1999, Cancer Res. 59(23):5995-8;, 1999, Hokkaido Igaku Zasshi. 74(5):377-86; Buske et al., 1999, Am J Med Genet. 86(4): 328-30; Harada et al., 1999, Surg Neurol. 51(5):528-35; Krkljus et al., 1998, Hum Mutat. 11(5):411; Klose et al., 1999, Am J Med Genet. 83(1):6-12; Park & Pivnick, 1998, J Med Genet. 35(10):813-20; Bahuau et al., 1998, Am J Med Genet. 75(3):265-72; Bijlsma et al., 1997, J Med Genet. 34(11):934-6; MacCollin et al., 1996, Ann Neurol. 40(3): 440-5; Upadhyaya et al., 1996, Am J Med Genet. 67(4):421-3; Robinson et al., 1995, Hum Genet. 96(1):95-8.; Legius et al., 1995, J Med Genet. 32(4):316-9; von Deimling et al., 1995, Brain Pathol. 5(1):11-4; Dublin et al., 1995, Hum Mutat. 5(1):81-5; Legius et al., 1994, Genes Chromosomes Cancer. 10(4):250-5; Purandare et al., 1994, Hum Mol Genet. 3(7):1109-15; Shen & Upadhyaya, 1993, Hum Genet. 92(4): 410-2; and Estivill et al., 1991, Hum Genet. 88(2):185-8; the disclosures of which are hereby incorporated by reference in their entireties). Any gene encoding a premature translation codon implicated in neurofibromatosis including, but not limited to, the nonsense mutations described in the references cited above, can be used in the present invention to identify compounds that mediate premature translation termination and/or nonsense-mediated mRNA decay.

5.8.7 Retinoblastoma

The retinoblastoma gene plays important roles in the genesis of human cancers. Several pieces of evidence have shown that the retinoblastoma protein has dual roles in gating cell cycle progression and promoting cellular differentiation (see, e.g., Lee & Lee, 1997, Gan To Kagaku Ryoho 24(11):1368-80 for a review). Nonsense mutations in the RB1 gene have been described. Nonsense mutations have been implicated in retinoblastoma (see, e.g., Klutz et al., 2002, Am J Hum Genet. 71(1):174-9; Alonso et al., 2001, Hum Mutat. 17(5):412-22; Wong et al., 2000, Cancer Res. 60(21):6171-7; Harbour, 1998, Ophthalmology 105(8):1442-7; Fulop et al., 1998, J Reprod Med. 43(2):119-27; Onadim et al., 1997, Br J Cancer 76(11):1405-9; Lohmann et al., 1997, Ophthalmologe 94(4): 263-7; Cowell & Cragg, 1996, Eur J Cancer. 32A(10):1749-52; Lohmann et al., 1996, Am J Hum Genet. 58(5):940-9; Shapiro et al., 1995, Cancer Res. 55(24):6200-9; Huang et al., 1993, Cancer Res. 53(8):1889-94; and Cheng & Haas, 1990, Mol Cell Biol. 10(10):5502-9; the disclosures of which are hereby incorporated by reference in their entireties). Any gene encoding a premature translation codon implicated in retinoblastoma including, but not limited to, the nonsense mutations described in the references cited above, can be used in the present invention to identify compounds that mediate premature translation termination and/or nonsense-mediated mRNA decay.

5.8.8 Wilm's Tumor

Wilm's tumor, or nephroblastoma, is an embryonal malignancy of the kidney that affects children. Nonsense mutations in the WT1 gene have been implicated in Wilm's tumor. Several nonsense mutations in the WT1 have been identified (see, e.g., Nakadate et al., 1999, Genes Chromosomes Cancer 25(1):26-32; Diller et al., 1998, J Clin Oncol. 16(11):3634-40; Schumacher et al., 1997, Proc Natl Acad Sci U S A. 94(8):3972-7; Coppes et al., 1993, Proc Natl Acad Sci USA. 90(4):1416-9; and Little et al., 1992, Proc Natl Acad Sci USA. 89(11):4791-5; the disclosures of which are hereby incorporated by reference in their entireties). Any WT1 gene encoding a premature translation codon including, but not limited to, the nonsense mutations described in the references cited above, can be used in the present invention to identify compounds that mediate premature translation termination and/or nonsense-mediated mRNA decay.

5.8.9 Retinitis Pigmentosa

Retinitis pigmentosa is a genetic disease in which affected individuals develop progressive degeneration of the rod and cone photoreceptors. Retinitis pigmentosa cannot be explained by a single genetic defect but instead the hereditary aberration responsible for triggering the onset of the disease is localized in different genes and at different sites within these genes (reviewed in, e.g., Kohler et al., 1997, Klin Monatsbl Augenheilkd 211(2):84-93). Nonsense mutations have been implicated in retinitis pigmentosa (see, e.g., Ching et al., 2002, Neurology 58(11):1673-4; Zhang et al., 2002, Zhonghua Yi Xue Yi Chuan Xue Za Zhi. 19(3):194-7; Zhang et al., 2002, Hum Mol Genet. 1;11(9):993-1003; Dietrich et al., 2002, Br J Ophthalmol. 86(3):328-32; Grayson et al., 2002, J Med Genet 39(1):62-7; Liu et al., 2001, Zhonghua Yi Xue Za Zhi 81(2):71-2; Damji et al., 2001, Can J Ophthalmol. 36(5):252-9; Berson et al., 2001, Invest Ophthalmol Vis Sci. 42(10):2217-24; Chan et al., 2001, Br J Ophthalmol. 85(9): 1046-8; Baum et al., 2001, Hum Mutat. 17(5):436; Mashima et al., 2001, Ophthalmic Genet. 22(1):43-7; Zwaenepoel et al., 2001, Hum Mutat. 2001;17(1):34-41; Bork et al., 2001, Am J Hum Genet. 68(1):26-37; Sharon et al., 2000, Invest Ophthalmol Vis Sci. 41(9):2712-21; Dreyer et al., 2000, Eur J Hum Genet. 8(7):500-6; Liu et al., 2000, Hum Mutat. 15(6): 584; Wang et al., 1999, Exp Eye Res. 69(4):; Bowne et al., 1999, Hum Mol Genet. 8(11):2121-8; Guillonneau et al., 1999, Hum Mol Genet. 8(8):1541-6; Dryja et al., 1999, Invest Ophthalmol Vis Sci. 40(8):1859-65; Sullivan et al., 1999, Nat Genet. 22(3):255-9; Pierce et al., 1999, Nat Genet. 22(3):248-54; Janecke et al., 1999, Hum Mutat. 13(2):133-40; Cuevas et al., 1998, Mol Cell Probes 12(6):417-20; Schwahn et al., , 1998, Nat Genet. 19(4):327-32; Buraczynska et al., 1997, Am J Hum Genet. 61(6):1287-92; Meindl et al., 1996, Nat Genet. 13(1):35-42; Keen et al., 1996, Hum Mutat. 8(4):297-303; Dryja et al., 1995, Proc Natl Acad Sci USA. 92(22):10177-81; Apfelstedt-Sylla et al., 1995, Br J Ophthalmol. 79(1):28-34; Bayes et al., 1995, Hum Mutat. 5(3):228-34; Shastry, 1994, Am J Med Genet. 52(4):467-74; Gal et al., 1994, Nat Genet. 7(1):64-8; Sargan et al., 1994, Gene Ther. 1 Suppl 1:S89; McLaughlin et al., 1993, Nat Genet. 4(2):130-4; Rosenfeld et al., 1992, Nat Genet. 1(3):209-13; the disclosures of which are hereby incorporated by reference in their entireties). Any gene encoding a premature translation codon implicated in retinitis pigmentosa including, but not limited to, the nonsense mutations described in the references cited above, can be used in the present invention to identify compounds that mediate premature translation termination and/or nonsense-mediated mRNA decay.

5.8.10 Osteogenesis Imperfecta

Osteogenesis imperfecta is a heterogeneous disorder of type I collagen resulting in varying degrees of severity and results from mutations the genes that encode the proalpha chains of type I collagen. Nonsense mutations have been implicated in the genes that encode the proalpha chains of type I collagen ("COLA1" genes) (see, e.g. Slayton et al., 2000, Matrix Biol. 19(1):1-9; Bateman et al., 1999, Hum Mutat. 13(4):311-7; and Willing et al., 1996, Am J Hum Genet. 59(4):799-809; the disclosures of which are hereby incorporated by reference in their entireties). Any COLA1 gene encoding a premature translation codon including, but not limited to, the nonsense mutations described in the references cited above, can be used in the present invention to identify compounds that mediate premature translation termination and/or nonsense-mediated mRNA decay.

5.8.11 Cirrhosis

Cirrhosis generally refers to a chronic liver disease that is marked by replacement of normal tissue with fibrous tissue. The multidrug resistance 3 gene has been implicated in cirrhosis, and nonsense mutations have been identified in this gene (see, e.g.,
Jacquemin et al., 2001, Gastroenterology. 2001 May;120 (6):1448-58; the disclosure of which is hereby incorporated by reference in its entirety). Any gene involved in cirrhosis encoding a premature translation codon including, but not limited to, the nonsense mutations described in the reference cited above, can be used in the present invention to identify compounds that mediate premature translation termination and/or nonsense-mediated mRNA decay.

5.8.12 Tay Sachs Disease

Tay Sachs disease is an autosomal recessive disorder affecting the central nervous system. The disorder results from mutations in the gene encoding the alpha-subunit of beta-hexosaminidase A, a lysosomal enzyme composed of alpha and beta polypeptides. Several nonsense mutations have been implicated in Tay Sachs disease (see, e.g., Rajavel & Neufeld, 2001, Mol Cell Biol. 21(16):5512-9; Myerowitz, 1997, Hum Mutat. 9(3):195-208; Akli et al., 1993, Hum Genet. 90(6):614-20; Mules et al., 1992, Am J Hum Genet. 50(4):834-41; and Akli et al., 1991, Genomics.

11(1):124-34; the disclosures of which are hereby incorporated by reference in their entireties). Any hexosaminidase gene encoding a premature translation codon including, but not limited to, the nonsense mutations described in the references cited above, can be used in the present invention to identify compounds that mediate premature translation termination and/or nonsense-mediated mRNA decay.

5.8.13 Blood Disorders

Hemophilia is caused by a deficiency in blood coagulation factors. Affected individuals are at risk for spontaneous bleeding into organs and treatment usually consists of administration of clotting factors. Hemophilia A is caused by a deficiency of blood coagulation factor VIII and hemophilia B is caused by a deficiency in blood coagulation factor IX. Nonsense mutations in the genes encoding coagulation factors have been implicated in hemophilia (see, e.g., Dansako et al., 2001, Ann Hematol. 80(5):292-4; Moller-Morlang et al., 1999, Hum Mutat. 13(6):504; Kamiya et al., 1998, Rinsho Ketsueki 39(5):402-4; Freson et al., 1998, Hum Mutat. 11(6): 470-9; Kamiya et al., 1995, Int J Hematol. 62(3):175-81; Walter et al., 1994, Thromb Haemost. 72(1):74-7; Figueiredo, 1993, Braz J Med Biol Res. 26(9):919-31; Reiner & Thompson, 1992, Hum Genet. 89(1):88-94; Koeberl et al., 1990, Hum Genet. 84(5):387-90; Driscoll et al., 1989, Blood. 74(2):737-42; Chen et al., 1989, Am J Hum Genet. 44(4):567-9; Mikami et al., 1988, Jinrui Idengaku Zasshi. 33(4):409-15; Gitschier et al., 1988, Blood 72(3): 1022-8; and Sommer et al., 1987, Mayo Clin Proc. 62(5):387-404; the disclosures of which are hereby incorporated by reference in their entireties). Any gene encoding a premature translation codon implicated in hemophilia including, but not limited to, the nonsense mutations described in the references cited above, can be used in the present invention to identify compounds that mediate premature translation termination and/or nonsense-mediated mRNA decay.

Von Willebrand disease is a single-locus disorder resulting from a deficiency of von Willebrand factor: a multimeric multifunctional protein involved in platelet adhesion and platelet-to-platelet cohesion in high shear stress vessels, and in protecting from proteolysis and directing circulating factor VIII to the site of injury (reviewed in Rodeghiero, 2002, Haemophilia. 8(3):292-300). Nonsense mutations have implicated in von Willehbrand disease (see, e.g., Rodeghiero, 2002, Haemophilia. 8(3):292-300; Enayat et al., 2001, Blood 98(3):674-80; Surdhar et al., 2001, Blood 98(1):248-50; Casana et al., 2000, Br J Haematol. 111(2):552-5; Baronciani et al., 2000, Thromb Haemost. 84(4):536-40; Fellowes et al., 2000, Blood 96(2):773-5; Waseem et al., 1999, Thromb Haemost. 81(6):900-5; Mohlke et al., 1999, Int J Clin Lab Res. 29(1):1-7; Rieger et al., 1998, Thromb Haemost. 80(2):332-7; Kenny et al., 1998, Blood 92(1):175-83; Mazurier et al., 1998, Ann Genet. 41(1):34-43; Hagiwara et al., 1996, Thromb Haemost. 76(2):253-7; Mazurier & Meyer, 1996, Baillieres Clin Haematol. 9(2):229-41; Schneppenheim et al., 1994, Hum Genet. 94(6):640-52; Zhang et al., 1994, Genomics 21(1):188-93; Ginsburg & Sadler, 1993, Thromb Haemost. 69(2):177-84; Eikenboom et al., 1992, Thromb Haemost. 68(4):448-54; Zhang et al., 1992, Am J Hum Genet. 51(4):850-8; Zhang et al., 1992, Hum Mol Genet. 1(1):61-2; and Mancuso et al., 1991, Biochemistry 30(1):253-69; the disclosures of which are hereby incorporated by reference in their entireties). Any gene encoding a premature translation codon implicated in von Willebrand disease including, but not limited to, the nonsense mutations described in the references cited above, can be used in the present invention to identify compounds that mediate premature translation termination and/or nonsense-mediated mRNA decay.

β thalassemia is caused by a deficiency in beta globin polypeptides which in turn causes a deficiency in hemoglobin production. Nonsense mutations have been implicated in b thalassemia (see, e.g., El-Latif et al., 2002, Hemoglobin 26(1):33-40; Sanguansermsri et al., 2001, Hemoglobin 25(1): 19-27; Romao 2000, Blood 96(8):2895-901; Perea et al., 1999, Hemoglobin 23(3):231-7; Rhodes et al., 1999, Am J Med Sci. 317(5):341-5; Fonseca et al., 1998, Hemoglobin 22(3):197-207; Gasperini et al., 1998, Am J Hematol. January 1998 ;57(1):43-7; Galanello et al., 1997, Br J Haematol. 99(2):433-6; Pistidda et al., 1997, Eur J Haematol. 58(5):320-5; Oner et al., 1997, Br J Haematol. 96(2):229-34; Yasunaga et al., 1995, Intern Med. 34(12):1198-200; Molina et al., 1994, Sangre (Barc) 39(4):253-6; Chang et al., 1994, Int J Hematol. 59(4):267-72; Gilman et al., 1994, Am J Hematol. 45(3):265-7; Chan et al., 1993, Prenat Diagn. 13(10):977-82; George et al., 1993, Med J Malaysia 48(3):325-9; Divoky et al., 1993, Br J Haematol. 83(3):523-4; Fioretti et al., 1993, Hemoglobin 17(1):9-17; Rosatelli et al., 1992, Am J Hum Genet. 50(2):422-6; Moi et al., 1992, Blood 79(2):512-6; Loudianos et al., 1992, Hemoglobin 16(6):503-9; Fukurnaki, 1991, Rinsho Ketsueki 32(6):587-91; Cao et al., 1991, Am J Pediatr Hematol Oncol. 13(2):179-88; Galanello et al., 1990, Clin Genet. 38(5):327-31; Liu, 1990, Zhongguo Yi Xue Ke Xue Yuan Xue Bao 12(2):90-5; Aulehla-Scholz et al., 1990, Hum Genet. 84(2):195-7; Cao et al., 1990, Ann N Y Acad Sci. 612:215-25; Sanguansermsri et al., 1990, Hemoglobin 14(2): 157-68; Galanello et al., 1989, Blood 74(2):823-7; Rosatelli et al., 1989, Blood 73(2):601-5; Galanello et al., 1989, Prog Clin Biol Res. 316B:113-21; Galanello et al., 1988, Am J Hematol. 29(2):63-6; Chan et al., 1988, Blood 72(4):1420-3; Atweh et al., 1988, J Clin Invest. 82(2):557-61; Masala et al., 1988, Hemoglobin 12(5-6):661-71; Pirastu et al., 1987, Proc Natl Acad Sci U S A 84(9):2882-5; Kazazian et al., 1986, Am J Hum Genet. 38(6):860-7; Cao et al., 1986, Prenat Diagn. 6(3): 159-67; Cao et al., 1985, Ann N Y Acad Sci. 1985;445: 380-92; Pirastu et al., 1984, Science 223(4639):929-30; Pirastu et al., 1983, N Engl J Med. 309(5):284-7; Trecartin et al., 1981, J Clin Invest. 68(4):1012-7; and Liebhaber et al., 1981, Trans Assoc Am Physicians 94:88-96; the disclosures of which are hereby incorporated by reference in their entireties). Any gene encoding a premature translation codon implicated in b thalassemia including, but not limited to, the nonsense mutations described in the references cited above, can be used in the present invention to identify compounds that mediate premature translation termination and/or nonsense-mediated mRNA decay.

5.8.14 Kidney Stones

Kidney stones (nephrolithiasis), which affect 12% of males and 5% of females in the western world, are familial in 45% of patients and are most commonly associated with hypercalciuria (see, e.g., Lloyd et al., Nature 1996 February 1;379 (6564):445-9). Mutations of the renal-specific chloride channel gene are associated with hypercalciuric nephrolithiasis (Kidney stones). Nonsense mutations have been implicated in kidney stones (see, e.g., Hoopes et al., 1998, Kidney Int. 54(3):698-705; Lloyd et al., 1997, Hum Mol Genet. 6(8): 1233-9; Lloyd et al., 1996, Nature 379(6564):445-9; and Pras et al., 1995, Am J Hum Genet. 56(6):1297-303; the disclosures of which are hereby incorporated by reference in their entireties). Any gene encoding a premature translation codon implicated in kidney stones including, but not limited to, the nonsense mutations described in the references cited above, can be used in the present invention to identify compounds that mediate premature translation termination and/or nonsense-mediated mRNA decay.

5.8.15 Ataxia-Telangiectasia

Ataxia-telangiectasia is characterized by increased sensitivity to ionizing radiation, increased incidence of cancer, and neurodegeneration and is generally caused by mutations in the ataxia-telangiectasia gene (see, e.g., Barlow et al., 1999, Proc Natl Acad Sci USA 96(17):9915-9). Nonsense mutations have been implicated in ataxia-telangiectasia (see, e.g., Camacho et al., 2002, Blood 99(1):238-44; Pitts et al., 2001, Hum Mol Genet. 10(11):1155-62; Laake et al., 2000, Hum Mutat. 16(3):232-46; Li & Swift, 2000, Am J Med Genet. 92(3):170-7; Teraoka et al., 1999, Am J Hum Genet. 64(6):1617-31; and Stoppa-Lyonnet et al., 1998, Blood 91(10):3920-6; the disclosures of which are hereby incorporated by reference in their entireties). Any gene encoding a premature translation codon implicated in ataxia-telangiectasia including, but not limited to, the nonsense mutations described in the references cited above, can be used in the present invention to identify compounds that mediate premature translation termination and/or nonsense-mediated mRNA decay.

5.8.16 Lysosomal Storage Diseases

There are more than 40 individually recognized lysosomal storage disorders. Each disorder results from a deficiency in the activity of a specific enzyme, which impedes the lysosome from carrying out its normal degradative role. These include but are not limited to the diseases listed subsequently. Aspartylglucosaminuria is caused by a deficiency of N-aspartyl-beta-glucosaminidase (Fisher et al., 1990, FEBS Left. 269:440-444); cholesterol ester storage disease (Wolman disease) is caused by mutations in the LIPA gene (Fujiyama et al., 1996, Hum. Mutat. 8:377-380); mutations in the CTNS gene are associated with cystinosis (Town et al., 1998, Nature Genet 18:319-324); mutations in a-galactosidase A are associated with Fabry disease (Eng et al.,1993, Pediat. Res. 33:128A; Sakuraba et al., 1990, Am. J. Hum. Genet. 47:784-789; Davies et al., 1993, Hum. Molec. Genet. 2:1051-1053; Miyamura et al., 1996, J. Clin. Invest. 98:1809-1817); fucosidosis is caused by mutations in the FUCA1 gene(Kretz et al., 1989, J. Molec. Neurosci. 1:177-180; Yang et al., 1992, Biochem. Biophys. Res. Commun. 189:1063-1068; Seo et al., 1993, Hum. Molec. Genet. 2:1205-1208); mucolipidosis type I results from mutations in the NEU1 gene (Bonten et al., 1996, Genes Dev. 10:3156-3169); mucolipidosis type IV results from mutations in the MCOLN1 gene (Bargal et al., 2000, Nature Genet. 26:120-123; Sun et al., 2000,Hum. Molec. Genet. 9:2471-2478); Mucopolysaccharidosis type I (Hurler syndrome) is caused by mutations in the IDUA gene (Scott et al., 1992, Genomics 13:1311-1313; Bach et al., 1993, Am. J. Hum. Genet. 53:330-338); Mucopolysaccharidosis type II (Hunter syndrome) is caused by mutations in the IDS gene (Sukegawa et al., 1992, Biochem. Biophys. Res. Commun. 183:809-813; Bunge et al., 1992 Hum. Molec. Genet. 1:335-339; Flomen et al., 1992, Genomics 13:543-550); mucopolysaccharidosis type 25IIIB (Sanfilippo syndrome type A) is caused by mutations in the SGSH gene (Yogalingam et al., 2001, Hum. Mutat. 18:264-281); mucopolysaccharidosis type IIIB (Sanfilippo syndrome) is caused by mutations in the NAGLU gene (Zhao et al., 1996, Proc. Nat. Acad. Sci. 93:6101-6105; Zhao et al., 1995, Am. J. Hum. Genet. 57:A185); mucopolysaccharidosis type IIID is caused by mutations in the glucosamine-6-sulfatase (G6S) gene (Robertson et al., 1988, Hum. Genet. 79:175-178); mucopolysaccharidosis type IVA (Morquio syndrome) is caused by mutations in the GALNS gene (Tomatsu et al., 1995, Am. J. Hum. Genet. 57:556-563; Tomatsu et al.,1995, Hum. Mutat. 6:195-196); mucopolysaccharidosis type VI (Maroteaux-Lamysyndrome) is caused by mutations in the ARSB gene (Litjens et al., 1992, Hum. Mutat. 1:397-402; Isbrandt et al., 1996, Hum. Mutat. 7:361-363); mucopolysaccharidosis type VII (Sly syndrome) is caused by mutations in the beta-glucuronidase (GUSB) gene(Yamada et al., 1995, Hum. Molec. Genet. 4:651-655); mutations in CLN1 (PPT1) cause infantile neuronal ceroid lipofuscinosis (Das et al., 1998 J. Clin. Invest. 102:361-370; Mitchison et al., 1998, Hum. Molec. Genet. 7:291-297); late infantile type ceroid lipofuscinosis is caused by mutations in the CLN2 gene (Sleat et al., 1997, Science 277:1802-1805); juvenile neuronal ceroid lipofuscinosis (Batten disease) is caused bymutations in the CLN3 gene (Mole et al., 1999, Hum. Mutat. 14: 199-215); late infantileneuronal ceroid lipofuscinosis, Finnish variant, is caused by mutations in the CLN5 gene(Savukoski et al., 1998, Nature Genet. 19:286-288); late-infantile form of neuronal ceroid lipofuscinosis is caused by mutations in the CLN6 gene (Gao et al., 2002, Am. J. Hum. Genet. 70:324-335); Niemann-Pick disease is caused by mutations in the ASM gene (Takahashi et al., 1992, J. Biol. Chem. 267:12552-12558; types A and B) and the NPC1 gene (Millat et al., 2001, Am. J. Hum. Genet. 68:1373-1385; type C); Kanzaki disease is caused by mutations in the NAGA gene (Keulemans et et al., 1996, J. Med. Genet. 33:458-464); Gaucher disease is caused by mutations in the GBA gene (Stone, et al., 1999, Europ. J. Hum. Genet. 7:505-509); Glycogen storage disease II is the prototypic lysosomal storage disease and is caused by mutations in the GAA gene(Becker et al., 1998, Am. J. Hum. Genet. 62:991-994); Krabbe disease is caused by mutations in the GALC gene (Sakai et al., 1994, Biochem. Biophys. Res. Commun. 198:485-491); Tay-Sachs disease is caused by mutations in the HEXA gene (Akli et al., 1991, Genomics 11:124-134; Mules et al., 1992, Am. J. Hum. Genet. 50: 834-841; Triggs-Raine et al., 1991, Am. J. Hum. Genet. 49:1041-1054; Drucker et al., 1993, Hum. Mutat. 2:415-417; Shore et al., 1992, Hum. Mutat. 1:486-490); mutations in the GM2Agene causes Tay-Sachs variant AB (Schepers et al., 1996, Am. J. Hum. Genet. 59:1048-1056; Chen et al., 1999, Am. J. Hum. Genet. 65:77-87); mutations in the HEXB gene cause Sandhoff disease (Zhang et al., 1994, Hum Mol Genet 3:139-145); alphamannosidosis type II is caused by mutations in the MAN2B1 gene (Gotoda et al., 1998, Am. J. Hum. Genet. 63:1015-1024; Autio et al., 1973, Acta Paediat. Scand. 62:555-565); metachromatic leukodystrophy is caused by mutations in the ARSA gene(Gieselmann et al., 1994, Hum. Mutat. 4:233-242). Any gene containing a premature translation codon implicated in lysosomal storage disease disorders including, but not limited to, the nonsense mutations and genes described in the references cited above, can be used in the present invention to identify compounds that mediate premature translation termination and/or nonsense-mediated mRNA decay.

5.8.17 Tuberous Sclerosis

Tuberous sclerosis complex (TSC) is a dominantly inherited disease characterized by the presence of hamartomata in multiple organ systems. The disease is caused bymutations in TSC1 (van Slegtenhorst et al., 1997 Science 277:805-808; Sato et al., 2002, J. Hum. Genet. 47:20-28) and/or TSC2 (Vrtel et al., 1996, J. Med. Genet. 33:47-51; Wilson et al., 1996, Hum. Molec. Genet. 5:249-256; Au et al., 1998, Am. J.

Hum. Genet. 62:286-294; Verhoef et al., 1999, Europ. J. Pediat. 158:284-287; Carsillo et al., 2000, Proc. Nat. Acad. Sci. 97:6085-6090). Any gene containing a premature translation codon implicated in tuberous sclerosis including, but not limited to, the nonsense mutations described in the references cited above, can be used in the present invention to identify compounds that mediate premature translation termination and/or nonsense-mediated mRNA decay.

5.9 Secondary Biological Screens

5.9.1 In Vitro Assays

The compounds identified in the nonsense suppression assay (for convenience referred to herein as a "lead" compound) can be tested for biological activity using host cells containing or engineered to contain the target RNA element coupled to a functional readout system.

5.9.1.1 Reporter Gene Assays

The lead compound can be tested in a host cell engineered to contain the RNA with a premature translation termination codon controlling the expression of a reporter gene. In this example, the lead compounds are assayed in the presence or absence of the RNA with the premature translation termination codon. Compounds that modulate premature translation termination and/or nonsense-mediated mRNA decay will result in increased expression of the full-length gene, i.e., past the premature termination codon. Alternatively, a phenotypic or physiological readout can be used to assess activity of the target RNA with the premature translation termination codon in the presence and absence of the lead compound. In another embodiment of the invention, the compounds identified in the nonsense suppression assay (for convenience referred to herein as a "lead" compound) can also be tested for biological activity using an in vitro transcribed RNA from the gene with a premature translation termination codon and subsequent in vitro translation of that RNA in a cell-free translation extract. The activity of the lead compound in the in vitro translation mixture can be determined by any method that measures increased expression of the fill-length gene, i.e., past the premature termination codon. For example, expression of a functional protein from the full-length gene (e.g., a reporter gene) can be measured to determine the effect of the lead compound on premature translation termination and/or nonsense-mediated mRNA decay in an in vitro system. Both the in vitro and in vivo nonsense suppression assays described in International Patent Publication No. WO 01/44516 and International Patent Application No. PCT/US03/19760, each of which is incorporated by reference in its entirety.

5.9.1.1.1 Reporter Gene Constructs, Transfected Cells and Cell-Free Extracts The invention provides for reporter genes to ascertain the effects of a compound on premature translation termination and/or nonsense-mediated mRNA decay. In general, the level of expression and/or activity of a reporter gene product is indicative of the effect of the compound on premature translation termination and/or nonsense-mediated mRNA decay.

The invention provides for specific vectors comprising a reporter gene operably linked to one or more regulatory elements and host cells transfected with the vectors. The invention also provides for the in vitro translation of a reporter gene flanked by one or more regulatory elements. A reporter gene may or may not contain a premature stop codon depending on the assay conducted. Techniques for practicing this specific aspect of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); Oligonucleotide Synthesis (Gait, Ed. 1984); Nucleic Acid Hybridization (Hames & Higgins, Eds. 1984); Transcription and Translation (Hames & Higgins, Eds. 1984); Animal Cell Culture (Freshney, Ed. 1986); Immobilized Cells and Enzymes (IRL Press, 1986); Perbal, A Practical Guide to Molecular Cloning (1984); Gene Transfer Vectors for Mammalian Cells (Miller & Calos, Eds. 1987, Cold Spring Harbor Laboratory); Methods in Enzymology, Volumes 154 and 155 (Wu & Grossman, and Wu, Eds., respectively), (Mayer & Walker, Eds., 1987); Immunochemical Methods in Cell and Molecular Biology (Academic Press, London, Scopes, 1987), Expression of Proteins in Mammalian Cells Using Vaccinia Viral Vectors in Current Protocols in Molecular Biology, Volume 2 (Ausubel et al., Eds., 1991).

# 5.9.1.1.1.1 Reporter Genes

Any reporter gene well-known to one of skill in the art may be used in reporter gene constructs to ascertain the effect of a compound on premature translation termination. Reporter genes refer to a nucleotide sequence encoding a protein, polypeptide or peptide that is readily detectable either by its presence or activity. Reporter genes may be obtained and the nucleotide sequence of the elements determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesized or obtained from a suitable source (e.g. a cDNA library, or a cDNA library generated from, or nucleic acid, preferably poly A+RNA, isolated from, any tissue or cells expressing the reporter gene) by PCR amplification. Once the nucleotide sequence of a reporter gene is determined, the nucleotide sequence of the reporter gene may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate reporter genes having a different amino acid sequence, for example to create amino acid substitutions, deletions, and/or insertions.

In a specific embodiment, a reporter gene is any naturally-occurring gene with a premature stop codon. Genes with premature stop codons that are useful in the present invention include, but are not limited to, the genes described below. In an alternative embodiment, a reporter gene is any gene that is not known in nature to contain a premature stop codon. Examples of reporter genes include, but are not limited to, luciferase (e.g., firefly luciferase, renilla luciferase, and click beetle luciferase), green fluorescent protein ("GFP") (e.g., green fluorescent protein, yellow fluorescent protein, red fluorescent protein, cyan fluorescent protein, and blue fluorescent protein), beta-galactosidase ("beta-gal"), beta-glucoronidase, beta-lactamase, chloramphenicol acetyltransferase ("CAT"), and alkaline phosphatase ("AP"). Alternatively, a reporter gene can also be a protein tag, such as, but not limited to, myc, His, FLAG, or GST, so that nonsense suppression will produce the peptide and the protein can be monitored by an ELISA, a western blot, or any other immunoassay to detect the protein tag. Such methods are well known to one of skill in the art. In a preferred embodiment, the reporter gene is easily assayed and has an activity which is not normally found in the gene of interest. Table 27 below lists various reporter genes and the properties of the products of the reporter genes that can be assayed. In a preferred embodiment, a reporter gene utilized in the reporter constructs is easily assayed and has an activity which is not normally found in the cell or organism of interest.

TABLE 27

Reporter Genes and the Properties of the Reporter Gene Products

| Reporter Gene | Protein Activity & Measurement |
| --- | --- |
| CAT (chloramphenicol acetyltransferase) | Transfers radioactive acetyl groups to chloramphenicol or detection by thin layer chromatography and autoradiography |
| GAL (beta-galactosidase) | Hydrolyzes colorless galactosides to yield colored products. |
| GUS (beta-glucuronidase) | Hydrolyzes colorless glucuronides to yield colored products. |
| LUC (luciferase) | Oxidizes luciferin, emitting photons |
| GFP (green fluorescent protein) | Fluorescent protein without substrate |
| SEAP (secreted alkaline phosphatase) | Luminescence reaction with suitable substrates or with substrates that generate chromophores |
| HRP (horseradish peroxidase) | In the presence of hydrogen oxide, oxidation of 3,3',5,5'-tetramethylbenzidine to form a colored complex |
| AP (alkaline phosphatase) | Luminescence reaction with suitable substrates or with substrates that generate chromophores |

Described hereinbelow in further detailed are specific reporter genes and characteristics of those reporter genes.

Luciferase

Luciferases are enzymes that emit light in the presence of oxygen and a substrate (luciferin) and which have been used for real-time, low-light imaging of gene expression in cell cultures, individual cells, whole organisms, and transgenic organisms (reviewed by Greer & Szalay, 2002, Luminescence 17(1):43-74).

As used herein, the term "luciferase" is intended to embrace all luciferases, or recombinant enzymes derived from luciferases which have luciferase activity. The luciferase genes from fireflies have been well characterized, for example, from the *Photinus* and *Luciola* species (see, e.g., International Patent Publication No. WO 95/25798 for *Photinus pyralis*, European Patent Application No. EP 0 524 448 for *Luciola cruciata* and *Luciola lateralis*, and Devine et al., 1993, Biochim. Biophys. Acta 1173(2):121-132 for *Luciola mingrelica*). Other eucaryotic luciferase genes include, but are not limited to, the click beetle (*Photinus plagiophthalamus*, see, e.g., Wood et al., 1989, Science 244:700-702), the sea panzy (*Reinilla reniformis*, see, e.g., Lorenz et al., 1991, Proc Natl Acad Sci USA 88(10):4438-4442), and the glow worm (*Lampyris noctiluca*, see e.g., Sula-Newby et al., 1996, Biochem J. 313:761-767). The click beetle is unusual in that different members of the species emit bioluminescence of different colors, which emit light at 546 nm (green), 560 nm (yellow-green), 578 nm (yellow) and 593 nm (orange) (see, e.g, U.S. Pat. Nos. 6,475,719; 6,342,379; and 6,217,847, the disclosures of which are incorporated by reference in their entireties). Bacterial luciferin-luciferase systems include, but are not limited to, the bacterial lux genes of terrestrial *Photorhabdus luminescens* (see, e.g., Manukhov et al., 2000, Genetika 36(3):322-30) and marine bacteria *Vibrio fischeri* and *Vibrio harveyi* (see, e.g., Miyamoto et al., 1988, J Biol Chem. 263(26):13393-9, and Cohn et al., 1983, Proc Natl Acad Sci USA., 80(1):120-3, respectively). The luciferases encompassed by the present invention also includes the mutant luciferases described in U.S. Pat. No. 6,265,177 to Squirrell et al., which is hereby incorporated by reference in its entirety.

In a specific embodiment, the luciferase is a firefly luciferase, a renilla luciferase, or a click beetle luciferase, as described in any one of the references listed supra, the disclosures of which are incorporated by reference in their entireties.

Green Fluorescent Protein

Green fluorescent protein ("GFP") is a 238 amino acid protein with amino acid residues 65 to 67 involved in the formation of the chromophore which does not require additional substrates or cofactors to fluoresce (see, e.g., Prasher et al., 1992, Gene 111:229-233; Yang et al., 1996, Nature Biotechnol. 14:1252-1256; and Cody et al., 1993, Biochemistry 32:1212-1218).

As used herein, the term "green fluorescent protein" or "GFP" is intended to embrace all GFPs (including the various forms of GFPs which exhibit colors other than green), or recombinant enzymes derived from GFPs which have GFP activity. In a preferred embodiment, GFP includes green fluorescent protein, yellow fluorescent protein, red fluorescent protein, cyan fluorescent protein, and blue fluorescent protein. The native gene for GFP was cloned from the bioluminescent jellyfish *Aequorea Victoria* (see, e.g., Morin et al., 1972, J. Cell Physiol. 77:313-318). Wild type GFP has a major excitation peak at 395 nm and a minor excitation peak at 470 nm. The absorption peak at 470 nm allows the monitoring of GFP levels using standard fluorescein isothiocyanate (FITC) filter sets. Mutants of the GFP gene have been found useful to enhance expression and to modify excitation and fluorescence. For example, mutant GFPs with alanine, glycine, isoleucine, or threonine substituted for serine at position 65 result in mutant GFPs with shifts in excitation maxima and greater fluorescence than wild type protein when excited at 488 nm (see, e.g., Heim et al., 1995, Nature 373:663-664; U.S. Pat. No. 5,625,048; Delagrave et al., 1995, Biotechnology 13:151-154; Cormack et al., 1996, Gene 173:33-38; and Cramer et al., 1996, Nature Biotechnol. 14:315-319). The ability to excite GFP at 488 nm permits the use of GFP with standard fluorescence activated cell sorting ("FACS") equipment. In another embodiment, GFPs are isolated from organisms other than the jellyfish, such as, but not limited to, the sea pansy, *Reniilla reniformis*.

Techniques for labeling cells with GFP in general are described in U.S. Pat. Nos. 5,491,084 and 5,804,387, which are incorporated by reference in their entireties; Chalfie et al., 1994, Science 263:802-805; Heim et al., 1994, Proc. Natl. Acad. Sci. USA 91:12501-12504; Morise et al., 1974, Biochemistry 13:2656-2662; Ward et al., 1980, Photochem. Photobiol. 31:611-615; Rizzuto et al., 1995, Curr. Biology 5:635-642; and Kaether & Gerdes, 1995, FEBS Lett 369:267-271. The expression of GFPs in *E. coli* and *C. elegans* are described in U.S. Pat. No. 6,251,384 to Tan et al., which is incorporated by reference in its entirety. The expression of GFP in plant cells is discussed in Hu & Cheng, 1995, FEBS Lett 369:331-33, and GFP expression in *Drosophila* is described in Davis et al., 1995, Dev. Biology 170:726-729.

Beta Galactosidase

Beta galactosidase ("beta-gal") is an enzyme that catalyzes the hydrolysis of beta-galactosides, including lactose, and the galactoside analogs o-nitrophenyl-beta-D-galactopyranoside ("ONPG") and chlorophenol red-beta-D-galactopyranoside ("CPRG") (see, e.g., Nielsen et al., 1983 Proc Natl Acad Sci USA 80(17):5198-5202; Eustice et al., 1991, Biotechniques 11:739-742; and Henderson et al., 1986, Clin. Chem. 32:1637-1641). The beta-gal gene functions well as a reporter gene because the protein product is extremely stable, resistant to proteolytic degradation in cellular lysates, and easily assayed. When ONPG is used as the substrate, beta-gal activity can be quantitated with a spectrophotometer or microplate reader.

As used herein, the term "beta galactosidase" or "beta-gal" is intended to embrace all beta-gals, including lacZ gene products, or recombinant enzymes derived from beta-gals which have beta-gal activity. The beta-gal gene functions well as a reporter gene because the protein product is extremely stable, resistant to proteolytic degradation in cellular lysates, and easily assayed. In an embodiment where ONPG is the substrate, beta-gal activity can be quantitated with a spectrophotometer or microplate reader to determine the amount of ONPG converted at 420 nm. In an embodiment when CPRG is the substrate, beta-gal activity can be quantitated with a spectrophotometer or microplate reader to determine the amount of CPRG converted at 570 to 595 nm. In yet another embodiment, the beta-gal activity can be visually ascertained by plating bacterial cells transformed with a beta-gal construct onto plates containing Xgal and IPTG. Bacterial colonies that are dark blue indicate the presence of high beta-gal activity and colonies that are varying shades of blue indicate varying levels of beta-gal activity.

Beta-Glucuronidase

Beta-glucuronidase ("GUS") catalyzes the hydrolysis of a very wide variety of beta-glucuronides, and, with much lower efficiency, hydrolyzes some beta-galacturonides. GUS is very stable, will tolerate many detergents and widely varying ionic conditions, has no cofactors, nor any ionic requirements, can be assayed at any physiological pH, with an optimum between 5.0 and 7.8, and is reasonably resistant to thermal inactivation (see, e.g., U.S. Pat. No. 5,268,463, which is incorporated by reference in its entirety).

In one embodiment, the GUS is derived from the *Esherichia coli* beta-glucuronidase gene. In alternate embodiments of the invention, the beta-glucuronidase encoding nucleic acid is homologous to the *E. coli* beta-glucuronidase gene and/or may be derived from another organism or species.

GUS activity can be assayed either by fluorescence or spectrometry, or any other method described in U.S. Pat. No. 5,268,463, the disclosure of which is incorporated by reference in its entirety. For a fluorescent assay, 4-trifluoromethylumbelliferyl beta-D-glucuronide is a very sensitive substrate for GUS. The fluorescence maximum is close to 500 nm—bluish green, where very few plant compounds fluoresce or absorb. 4-trifluoromethylumbelliferyl beta-D-glucuronide also fluoresces much more strongly near neutral pH, allowing continuous assays to be performed more readily than with MUG. 4-trifluoromethylumbelliferyl beta-D-glucuronide can be used as a fluorescent indicator in vivo. The spectrophotometric assay is very straightforward and moderately sensitive (Jefferson et al., 1986, Proc. Natl. Acad. Sci. USA 86:8447-8451). A preferred substrate for spectrophotometric measurement is p-nitrophenyl beta-D-glucuronide, which when cleaved by GUS releases the chromophore p-nitrophenol. At a pH greater than its $pK_a$ (around 7.15) the ionized chromophore absorbs light at 400-420 nm, giving a yellow color.

Beta-Lactamases

Beta-lactamases are nearly optimal enzymes in respect to their almost diffusion-controlled catalysis of beta-lactam hydrolysis, making them suited to the task of an intracellular reporter enzyme (see, e.g., Christensen et al., 1990, Biochem. J. 266: 853-861). They cleave the beta-lactam ring of beta-lactam antibiotics, such as penicillins and cephalosporins, generating new charged moieties in the process (see, e.g. O'Callaghan et al., 1968, Antimicrob. Agents. Chemother. 8: 57-63 and Stratton, 1988, J. Antimicrob. Chemother. 22, Suppl. A: 23-35). A large number of beta-lactamases have been isolated and characterized, all of which would be suitable for use in accordance with the present invention (see, e.g., Richmond & Sykes, 1978, Adv. Microb. Physiol. 9:31-88 and Ambler, 1980, Phil. Trans. R. Soc. Lond. [Ser.B.] 289: 321-331, the disclosures of which are incorporated by reference in their entireties).

The coding region of an exemplary beta-lactamase employed has been described in U.S. Pat. No. 6,472,205, Kadonaga et al., 1984, J. Biol. Chem. 259: 2149-2154, and Sutcliffe, 1978, Proc. Natl. Acad. Sci. USA 75: 3737-3741, the disclosures of which re incorporated by reference in their entireties. As would be readily apparent to those skilled in the field, this and other comparable sequences for peptides having beta-lactamase activity would be equally suitable for use in accordance with the present invention. The combination of a fluorogenic substrate described in U.S. Pat. Nos. 6,472,205, 5,955,604, and 5,741,657, the disclosures of which are incorporated by reference in their entireties, and a suitable beta-lactamase can be employed in a wide variety of different assay systems, such as are described in U.S. Pat. No. 4,740,459, which is hereby incorporated by reference in its entirety.

Chloramphenicol Acetyltransferase

Chloramphenicol acetyl transferase ("CAT") is commonly used as a reporter gene in mammalian cell systems because mammalian cells do not have detectable levels of CAT activity. The assay for CAT involves incubating cellular extracts with radiolabeled chloramphenicol and appropriate co-factors, separating the starting materials from the product by, for example, thin layer chromatography ("TLC"), followed by scintillation counting (see, e.g., U.S. Pat. No. 5,726,041, which is hereby incorporated by reference in its entirety).

As used herein, the term "chloramphenicol acetyltransferase" or "CAT" is intended to embrace all CATs, or recombinant enzymes derived from CAT which have CAT activity. While it is preferable that a reporter system which does not require cell processing, radioisotopes, and chromatographic separations would be more amenable to high through-put screening, CAT as a reporter gene may be preferable in situations when stability of the reporter gene is important. For example, the CAT reporter protein has an in vivo half life of about 50 hours, which is advantageous when an accumulative versus a dynamic change type of result is desired.

Secreted Alkaline Phosphatase

The secreted alkaline phosphatase ("SEAP") enzyme is a truncated form of alkaline phosphatase, in which the cleavage of the transmembrane domain of the protein allows it to be secreted from the cells into the surrounding media. In a preferred embodiment, the alkaline phosphatase is isolated from human placenta.

As used herein, the term "secreted alkaline phosphatase" or "SEAP" is intended to embrace all SEAP or recombinant enzymes derived from SEAP which have alkaline phosphatase activity. SEAP activity can be detected by a variety of methods including, but not limited to, measurement of catalysis of a fluorescent substrate, immunoprecipitation, HPLC, and radiometric detection. The luminescent method is preferred due to its increased sensitivity over calorimetric detection methods. The advantages of using SEAP is that a cell lysis step is not required since the SEAP protein is secreted out of the cell, which facilitates the automation of sampling and assay procedures. A cell-based assay using SEAP for use in cell-based assessment of inhibitors of the Hepatitis C virus protease is described in U.S. Pat. No. 6,280,940 to Potts et al. which is hereby incorporated by reference in its entirety.

5.9.1.1.1.2 Stop Codons

The present invention provides for methods for screening and identifying compounds that modulate premature translation termination and/or nonsense-mediated mRNA decay. A reporter gene may be engineered to contain a premature stop codon or may naturally contain a premature stop codon. Alternatively, a protein, polypeptide or peptide that regulates (directly or indirectly) the expression of a reporter gene may be engineered to contain or may naturally contain a premature stop codon. The premature stop codon may any one of the stop codons known in the art including UAG, UAA and UGA.

In a specific embodiment, a reporter gene contains or is engineered to contain the premature stop codon UAG. In another embodiment, a reporter gene contains or is engineered to contain the premature stop codon UGA.

In a particular embodiment, a reporter gene contains or is engineered to contain two or more stop codons. In accordance with this embodiment, the stop codons are preferably at least 10 nucleotides, at least 15 nucleotides, at least 20 nucleotides, at least 25 nucleotides, at least 30 nucleotides, at least 35 nucleotides, at least 40 nucleotides, at least 45 nucleotides, at least 50 nucleotides, at least 75 nucleotides or at least 100 nucleotides apart from each other. Further, in accordance with this embodiment, at least one of the stop codons is preferably UAG or UGA.

In a specific embodiment, a reporter gene contains or is engineered to contain a premature stop -codon at least 15 nucleotides, preferably at least 20 nucleotides, at least 25 nucleotides, at least 30 nucleotides, at least 35 nucleotides, at least 40 nucleotides, at least 45 nucleotides, at least 50 nucleotides or at least 75 nucleotides from the start codon in the coding sequence. In another embodiment, a reporter gene contains or is engineered to contain a premature stop codon at least 15 nucleotides, preferably at least 25 nucleotides, at least 50 nucleotides, at least 75 nucleotides, at least 100 nucleotides, at least 125 nucleotides, at least 150, at least 175 nucleotides or at least 200 nucleotides from the native stop codon in the coding sequence of the full-length reporter gene product or protein, polypeptide or peptide. In another embodiment, a reporter gene contains or is engineered to contain a premature stop codon at least 15 nucleotides (preferably at least 20 nucleotides, at least 25 nucleotides, at least 30 nucleotides, at least 35 nucleotides, at least 40 nucleotides, at least 45 nucleotides, at least 50 nucleotides or at least 75 nucleotides) from the start codon in the coding sequence and at least 15 nucleotides (preferably at least 25 nucleotides, at least 50 nucleotides, at least 75 nucleotides, at least 100 nucleotides, at least 125 nucleotides, at least 150, at least 175 nucleotides or at least 200 nucleotides) from the native stop codon in the coding sequence of the full-length reporter gene product or protein, polypeptide or peptide. In accordance with these embodiments, the premature stop codon is preferably UAG or UGA.

The premature translation stop codon can be produced by in vitro mutagenesis techniques such as, but not limited to, polymerase chain reaction ("PCR"), linker insertion, oligonucleotide-mediated mutagenesis, and random chemical mutagenesis.

5.9.1.1.1.3 Vectors

The nucleotide sequence encoding for a protein, polypeptide or peptide (e.g., a reporter gene), can be inserted into an appropriate expression vector, i.e., a vector which contains the necessary elements for the transcription and translation of the inserted protein-coding sequence. The necessary transcriptional and translational elements can also be supplied by the protein, polypeptide or peptide. The regulatory regions and enhancer elements can be of a variety of origins, both natural and synthetic. In a specific embodiment, a reporter gene is operably linked to regulatory element that is responsive to a regulatory protein whose expression is dependent upon the suppression of a premature stop codon.

A variety of host-vector systems may be utilized to express a protein, polypeptide or peptide. These include, but are not limited to, mammalian cell systems infected with virus (e.g., vaccinia virus, adenovinis, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a'selectable marker. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric nucleic acid consisting of appropriate transcriptional/translational control signals and the protein coding sequences. These methods may include in vitro recombinant DNA and synthetic techniques and in vivo recombinants (genetic recombination). Expression of a first nucleic acid sequence encoding a protein, polypeptide or peptide, such as a reporter gene, may be regulated by a second nucleic acid sequence so that the first nucleic acid sequence is expressed in a host transformed with the second nucleic acid sequence. For example, expression of a nucleic acid sequence encoding a protein, polypeptide or peptide, such as a reporter gene, may be controlled by any promoter/enhancer element known in the art, such as a constitutive promoter, a tissue-specific promoter, or an inducible promoter. Specific examples of promoters which may be used to control gene expression include, but are not limited to, the SV40 early promoter region (Bernoist & Chambon, 1981, Nature 290:304-310), the promoter contained in the 3' long terminal repeat of Rous sarcoma virus (Yamamoto et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42); prokaryotic expression vectors such as the β-lactamase promoter (Villa-Kamaroff et al., 1978, Proc. Natl. Acad. Sci. U.S.A. 75:3727-3731), or the tac promoter (DeBoer et al., 1983, Proc. Natl. Acad. Sci. U.S.A. 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, a vector is used that comprises a promoter operably linked to a reporter gene, one or more origins of replication, and, optionally, one or more selectable markers (e.g., an antibiotic resistance gene). In a preferred embodiment, the vectors are CMV vectors, T7 vectors, lac vectors, pCEP4 vectors, 5.0/F vectors, or vectors with a tetracycline-regulated promoter (e.g., pcDNA™5/FRT/TO from Invitrogen). Some vectors may be obtained commercially. Non-limiting examples of useful vectors are described in Appendix 5 of Current Protocols in Molecular Biology, 1988, ed. Ausubel et al., Greene Publish. Assoc. & Wiley Interscience, which is incorporated herein by reference; and the catalogs of commercial suppliers such as Clontech Laboratories, Stratagene Inc., and Invitrogen, Inc.

Expression vectors containing a construct of the present invention can be identified by the following general approaches: (a) nucleic acid hybridization, (b) presence or absence of "marker" nucleic acid functions, (c) expression of inserted sequences, and (d) sequencing. In the first approach, the presence of a particular nucleic acid sequence inserted in an expression vector can be detected by nucleic acid hybridization using probes comprising sequences that are homologous to the inserted nucleic acid sequence. In the second approach, the recombinant vector/host system can be identified and selected based upon the presence or absence of certain "marker" nucleic acid functions (e.g., thymidine kinase activity, resistance to antibiotics, transformation phenotype, occlusion body formation in baculovirus, etc.) caused by the insertion of the nucleic acid sequence of interest in the vector. For example, if the nucleic acid sequence of interest is inserted within the marker nucleic acid sequence of the vector, recombinants containing the insert can be identified by the absence of the marker nucleic acid function. In the third approach, recombinant expression vectors can be identified by assaying the product expressed by the recombinant. Such assays can be based, for example, on the physical or functional properties of the particular nucleic acid sequence.

In a preferred embodiment, nucleic acid sequences encoding proteins, polypeptides or peptides are cloned into stable cell line expression vectors. In a preferred embodiment, the stable cell line expression vector contains a site specific genomic integration site. In another preferred embodiment, the reporter gene construct is cloned into an episomal mammalian expression vector.

5.9.1.1.1.4 Transfection

Once a vector encoding the appropriate gene has been synthesized, a host cell is transformed or transfected with the vector of interest. The use of stable transformants is preferred. In a preferred embodiment, the host cell is a mammalian cell. In a more preferred embodiment, the host cell is a human cell. In another embodiment, the host cells are primary cells isolated from a tissue or other biological sample of interest. Host cells that can be used in the methods of the present invention include, but are not limited to, hybridomas, pre-B cells, 293 cells, 293T cells, HeLa cells, HepG2 cells, K562 cells, 3T3 cells. In another preferred embodiment, the host cells are derived from tissue specific to the nucleic acid sequence encoding a protein, polypeptide or peptide. In another preferred embodiment, the host cells are immortalized cell lines derived from a source, e.g., a tissue. Other host cells that can be used in the present invention include, but are not limited to, bacterial cells, yeast cells, virally-infected cells, or plant cells.

Preferred mammalian host cells include but are not limited to those derived from humans, monkeys and rodents, (see, for example, Kriegler M. in "Gene Transfer and Expression: A Laboratory Manual", New York, Freeman & Co. 1990), such as monkey kidney cell line transformed by SV40 (COS-7, ATCC Accession No. CRL 1651); human embryonic kidney cell lines (293, 293-EBNA, or 293 cells subcloned for growth in suspension culture, Graham et al., J. Gen. Virol., 36:59, 1977; baby hamster kidney cells (BHK, ATCC Accession No. CCL 10); chinese hamster ovary-cells-DHFR (CHO, Urlaub and Chasin. Proc. Natl. Acad. Sci. 77; 4216, 1980); mouse sertoli cells (Mather, Biol. Reprod. 23:243-251, 1980); mouse fibroblast cells (NIH-3T3), monkey kidney cells (CVI ATCC Accession No. CCL 70); african green monkey kidney cells (VERO76, ATCC Accession No. CRL-1587); human cervical carcinoma cells (HELA, ATCC Accession No. CCL 2); canine kidney cells (MDCK, ATCC Accession No. CCL 34); buffalo rat liver cells (BRL 3A, ATCC Accession No. CRL 1442); human lung cells (W138, ATCC Accession No. CCL 75); human liver cells (Hep G2, HB 8065); and mouse mammary tumor cells (MMT 060562, ATCC Accession No. CCL51).

Other useful eukaryotic host-vector system may include yeast and insect systems. In yeast, a number of vectors containing constitutive or inducible promoters may be used with *Saccharomyces cerevisiae* (baker's yeast), *Schizosaccharomyces pombe* (fission yeast), *Pichia pastoris*, and *Hansenula polymorpha* (methylotropic yeasts). For a review see, Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces*, 1982, Eds. Strathern et al., Cold Spring Harbor Press, Vols. I and II.

Standard methods of introducing a nucleic acid sequence of interest into host cells can be used. Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. Mammalian transformations (i.e., transfections) by direct uptake may be conducted using the calcium phosphate precipitation method of Graham & Van der Eb, 1978, Virol. 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei. Such methods are well-known to one of skill in the art.

In a preferred embodiment, stable cell lines containing the constructs of interest are generated for high throughput screening. Such stable cells lines may be generated by introducing a construct comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt-cells, respectively. Also, anti-metabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

5.9.1.1.1.5 Cell-Free Extracts

The invention provides for the translation of a nucleic acid sequence encoding a protein, polypeptide or peptide (with or without a premature translation stop codon) in a cell-free system. Techniques for practicing the specific aspect of this invention will employ, unless otherwise indicated, conventional techniques of molecular biology, microbiology, and recombinant DNA manipulation and production, which are routinely practiced by one of skill in the art. See, e.g., Sambrook, 1989, Molecular Cloning, A Laboratory Manual, Second Edition; DNA Cloning, Volumes I and II (Glover, Ed. 1985); and Transcription and Translation (Hames & Higgins, Eds. 1984).

Any technique well-known to one of skill in the art may be used to generate cell-free extracts for translation. For example, the cell-free extracts can be generated by centrifuging cells and clarifying the supernatant. In one embodiment, the cells are incubated on ice during the preparation of the cell-free extract. In another embodiment, the cells are incubated on ice at least 12 hours, at least 24 hours, at least two days, at least five days, at least one week, at least longer than one week. In a more specific embodiment, the cells are incubated on ice at least long enough so as to improve the translation activity of the cell extract in comparison to cell extracts that are not incubated on ice. In yet another embodiment, the cells are incubated at a temperature between about 0° C. and 10° C. In a preferred embodiment, the cells are incubated at about 4° C.

In another preferred embodiment, the cells are centrifuged at a low speed to isolate the cell-free extract for in vitro translation reactions. In a preferred embodiment, the cell extract is the supernatant from cells that are centrifuged at about 2×g to 20,000×g. In a more preferred embodiment, the cell extract is the supernatant from cells that are centrifuged at about 5×g to 15,000×g. In an even more preferred embodiment, the cell extract is the supernatant from cells that are centrifuged at about 10,000×g. Alternatively, in a preferred embodiment, the cell-free extract is about the S1 to S50 extract. In a more preferred embodiment, the cell extract is about the S5 to S25 extract. In an even more preferred embodiment, the cell extract is about the S10 extract.

The cell-free translation extract may be isolated from cells of any species origin. In another embodiment, the cell-free translation extract is isolated from yeast, cultured mouse or rat cells, Chinese hamster ovary (CHO) cells, *Xenopus oocytes*, reticulocytes, wheat germ, or rye embryo (see, e.g., Krieg & Melton, 1984, Nature 308:203 and Dignam et al., 1990 Methods Enzymol. 182:194-203). Alternatively, the cell-free translation extract, e.g., rabbit reticulocyte lysates and wheat germ extract, can be purchased from, e.g., Promega, (Madison, Wis.). In another embodiment, the cell-free translation extract is prepared as described in International Patent Publication No. WO 01/44516 and U.S. Pat. No. 4,668,625 to Roberts, the disclosures of which are incorporated by reference in their entireties. In a preferred embodiment, the cell-free extract is an extract isolated from human cells. In a more preferred embodiment, the human cells are HeLa cells. It is preferred that the endogenous expression of the genes with the premature translation codons is minimal, and preferably absent, in the cells from which the cell-free translation extract is prepared.

Systems for the in vitro transcription of RNAs with the gene of interest cloned in an expression vectors using promoters such as, but not limited to, Sp6, T3, or T7 promoters (see, e.g., expression vectors from Invitrogen, Carlesbad, Calif.; Promega, Madison, Wis.; and Stratagene, La Jolla, Calif.), and the subsequent transcription of the gene with the appropriate polymerase are well-known to one of skill in the art (see, e.g., Contreras et al., 1982, Nucl. Acids. Res. 10:6353). In another embodiment, the gene encoding the premature stop codon can be PCR-amplified with the appropriate primers, with the sequence of a promoter, such as but not limited to, Sp6, T3, or T7 promoters, incorporated into the upstream primer, so that the resulting amplified PCR product can be in vitro transcribed with the appropriate polymerase.

Alternatively, a coupled transcription-translation system can be used for the expression of a gene encoding a premature stop codon in a cell free extract, such as the TnT® Coupled Transcription/Translation System (Promega, Madison, Wis.) or the system described in U.S. Pat. No. 5,895,753 to Mierendorf et al., which is incorporated by reference in its entirety.

5.9.1.1.2 Assays

Various in vitro assays can be used to identify and verify the ability of a compound to modulate premature translation termination and/or nonsense-mediated mRNA decay. Multiple in vitro assays can be performed simultaneously or sequentially to assess the affect of a compound on premature translation termination and/or nonsense-mediated mRNA decay. In a preferred embodiment, the in vitro assays described herein are performed in a high throughput format (e.g., in microtiter plates).

In a specific embodiment, the invention provides a method for identifying a compound that modulates premature translation termination and/or nonsense-mediated mRNA decay, said method comprising: (a) contacting a member of a library of compounds with a cell containing a nucleic acid sequence comprising a reporter gene, wherein the reporter gene comprises a premature stop codon; and (b) detecting the expression of said reporter gene, wherein a compound that modulates premature translation termination and/or nonsense-mediated mRNA decay is identified if the expression of said reporter gene in the presence of a compound is altered relative to a previously determined reference range, or the expression of said reporter gene in the absence of said compound or the presence of an appropriate control (e.g., a negative control).

In another embodiment, the invention provides a method for identifying a compound that modulates premature translation termination and/or nonsense-mediated mRNA decay, said method comprising: (a) contacting a member of a library of compounds with a cell-free extract and a nucleic acid sequence comprising a reporter gene, wherein the reporter gene comprises a premature stop codon; and (b) detecting the expression of said reporter gene, wherein a compound that modulates premature translation termination and/or nonsense-mediated mRNA decay is identified if the expression of said reporter gene in the presence of a compound is altered relative to a previously determined reference range, or the expression of said reporter gene in the absence of said compound or the presence of an appropriate control (e.g., a negative control). In accordance with this embodiment, the cell-extract is preferably isolated from cells that have been incubated at about 0° C. to about 10° C. and/or an S10 to S30 cell-free extract.

The alteration in reporter gene expression and/or activity in the reporter gene assays relative to a previously determined reference range, or to the expression or activity of the reporter gene in the absence of the compound or the presence of an appropriate control (e.g., a negative control such as phosphate buffered saline) indicates that a particular compound modulates premature translation termination and/or nonsense-mediated mRNA decay. In particular, an increase in reporter gene expression or activity relative to a previously determined reference range, or to the expression in the absence of the compound or the presence of an appropriate control (e.g., a negative control) may, depending upon the parameters of the reporter gene assay, indicate that a particular compound reduces or suppresses premature translation termination and/or nonsense-mediated mRNA decay. In contrast, a decrease in reporter gene expression or activity relative to a previously determined reference range, or to the expression in the absence of the compound or the presence of an appropriate control (e.g., a negative control) may, depending upon the parameters of the reporter gene-based assay, indicate that a particular compound enhances premature translation termination and/or nonsense-mediated mRNA decay.

The step of contacting a compound or a member of a library of compounds with cell in the reporter gene-based assays described herein is preferably conducted under physiologic conditions. In specific embodiment, a compound or a member of a library of compounds is added to the cells in the presence of an aqueous solution. In accordance with this embodiment, the aqueous solution may comprise a buffer and a combination of salts, preferably approximating or mimicking physiologic conditions. Alternatively, the aqueous solution may comprise a buffer, a combination of salts, and a detergent or a surfactant. Examples of salts which may be used in the aqueous solution include, but not limited to, KCl, NaCl, and/or $MgCl_2$. The optimal concentration of each salt used in the aqueous solution is dependent on the cells and compounds used and can be determined using routine experimentation. The step of contacting a compound or a member of a library of compounds with a cell containing a reporter gene construct and in some circumstances, a nucleic acid sequence encoding a regulatory protein, may be performed for at least 0.2 hours, 0.25 hours, 0.5 hours, 1 hour, 2 hours, 3 hours, 4 hours, 5 hours, 6 hours, 8 hours, 10 hours, 12 hours, 18 hours, at least 1 day, at least 2 days or at least 3 days.

The expression of a reporter gene and/or activity of the protein encoded by the reporter gene in the reporter-gene assays may be detected by any technique well-known to one of skill in the art. The expression of a reporter gene can be readily detected, e.g. by quantifying the protein and/or RNA encoded by said gene. Compounds that modulate premature translation termination and/or nonsense-mediated mRNA decay may be identified by changes in the gene encoding the premature translation stop codon, i.e., there is readthrough of the premature translation stop codon and a longer gene product is detected. If a gene encoding a naturally-occurring premature translation stop codon is used, a longer gene product in the presence of a compound that modulates premature translation termination and/or nonsense-mediated mRNA decay can be detected by any method in the art that permits the detection of the longer polypeptide, such as, but not limited to, immunological methods.

Many methods standard in the art can be thus employed, including, but not limited to, immunoassays to detect and/or visualize gene expression (e.g., Western blot, immunoprecipitation followed by sodium dodecyl sulfate polyacrylamide gel electrophoresis (SDS-PAGE), immunocytochemistry, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, or an epitope tag using an antibody that is specific to the polypeptide encoded by the gene of interest) and/or hybridization assays to detect gene expression by detecting and/or visualizing respectively mRNA encoding a gene (e.g., Northern assays, dot blots, in situ hybridization, etc), etc. Preferably, the antibody is specific to the C-terminal portion of the polypeptide used in an immunoassay. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody which recognizes the antigen to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody which recognizes the antigen) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding a primary antibody (which recognizes the antigen) conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the primary antibody) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

Methods for detecting the activity of a protein encoded by a reporter gene will vary with the reporter gene used. Assays for the various reporter genes are well-known to one of skill in the art. For example, as described in Section 5.1.1., luciferase, beta-galactosidase ("beta-gal"), beta-glucoronidase ("GUS"), beta-lactamase, chloramphenicol acetyltransferase ("CAT"), and alkaline phosphatase ("AP") are enzymes that can be analyzed in the presence of a substrate and could be amenable to high throughput screening. For example, the reaction products of luciferase, beta-galactosidase ("beta-gal"), and alkaline phosphatase ("AP") are assayed by changes in light imaging (e.g., luciferase), spectrophotometric absorbance (e.g., beta-gal), or fluorescence (e.g. AP). Assays for changes in light output, absorbance, and/or fluorescence are easily adapted for high throughput screening. For example, beta-gal activity can be measured with a microplate reader. Green fluorescent protein ("GFP") activity can be measured by changes in fluorescence. For example, in the case of mutant GFPs that fluoresce at 488 nm, standard fluorescence activated cell sorting ("FACS") equipment can be used to separate cells based upon GFP activity.

Changes in mRNA stability of the gene encoding the premature translation stop codon can be measured. As discussed above, nonsense-mediated mRNA decay alters the stability of an mRNA with a premature translation stop codon so that such mRNA is targeted for rapid decay instead of translation. In the presence of a compound that modulates premature translation termination and/or nonsense-mediated mRNA decay, the stability of the mRNA with the premature translation stop codon is likely altered, i.e., stabilized. Methods of measuring changes in steady state levels of mRNA are well-known to one of skill in the art. Such methods include, but are not limited to, Northern blots, dot blots, solution hybridization, RNase protection assays, and S1 nuclease protection assays, wherein the steady state levels of the mRNA of interest are measured with an appropriately labeled nucleic acid probe. Alternatively, methods such as semi-quantitative polymerase chain reaction ("PCR") can be used to measure changes in steady state levels of the mRNA of interest using the appropriate primers for amplification.

Alterations in the expression of a reporter gene may be determined by comparing the level of expression and/or activity of the reporter gene to a negative control (e.g., PBS or another agent that is known to have no effect on the expression of the reporter gene) and optionally, a positive control (e.g., an agent that is known to have an effect on the expression of the reporter gene, preferably an agent that effects premature translation termination and/or nonsense-mediated mRNA decay). Alternatively, alterations in the expression and/or activity of a reporter gene may be determined by comparing the level of expression and/or activity of the reporter gene to a previously determined reference range.

5.9.1.2 Other In Vitro Assays

Where the gene product of interest is involved in cell growth or viability, the in vivo effect of the lead compound can be assayed by measuring the cell growth or viability of the target cell. Such assays can be carried out with representative cells of cell types involved in a particular disease or disorder (e.g., leukocytes such as T cells, B cells, natural killer cells, macrophages, neutrophils and eosinophils). A lower level of proliferation or survival of the contacted cells indicates that the lead compound is effective to treat a condition in the patient characterized by uncontrolled cell growth. Alternatively, instead of culturing cells from a patient, a lead compound may be screened using cells of a tumor or malignant cell line or an endothelial cell line. Specific examples of cell culture models include, but are not limited to, for lung cancer, primary rat lung tumor cells (see, e.g., Swafford et al., 1997, Mol. Cell. Biol., 17:1366-1374) and large-cell undifferentiated cancer cell lines (see, e.g., Mabry et al., 1991, Cancer Cells, 3:53-58); colorectal cell lines for colon cancer (see, e.g., Park & Gazdar, 1996, J. Cell Biochem. Suppl. 24:131-141); multiple established cell lines for breast cancer (see, e.g., Hambly et al., 1997, Breast Cancer Res. Treat. 43:247-258; Gierthy et al., 1997, Chemosphere 34:1495-1505; and Prasad & Church, 1997, Biochem. Biophys. Res. Commun. 232:14-19); a number of well-characterized cell models for prostate cancer (see, e.g., Webber et al., 1996, Prostate, Part 1, 29:386-394; Part 2, 30:58-64; and Part 3, 30:136-142 and Boulikas, 1997, Anticancer Res. 17:1471-1505); for genitourinary cancers, continuous human bladder cancer cell lines (see, e.g., Ribeiro et al., 1997, Int. J. Radiat. Biol. 72:11-20); organ cultures of transitional cell carcinomas (see, e.g., Booth et al., 1997, Lab Invest. 76:843-857) and rat progression models (see, e.g., Vet et al., 1997, Biochim. Biophys Acta 1360:39-44); and established cell lines for leukemias and lymphomas (see, e.g., Drexler, 1994, Leuk. Res. 18:919-927 and Tohyama, 1997, Int. J. Hematol. 65:309-317).

Many assays well-known in the art can be used to assess the survival and/or growth of a patient cell or cell line following exposure to a lead compound; for example, cell proliferation can be assayed by measuring bromodeoxyuridine (BrdU) incorporation (see, e.g., Hoshino et al., 1986, Int. J. Cancer 38:369 and Campana et al., 1988, J. Immunol. Meth. 107:79) or (3H)-thymidine incorporation (see, e.g., Chen, 1996, Oncogene 13:1395-403 and Jeoung, 1995, J. Biol. Chem. 270:18367-73), by direct cell count, by detecting changes in transcription, translation or activity of known genes such as proto-oncogenes (e.g., fos, myc) or cell cycle markers (Rb, cdc2, cyclin A, D1, D2, D3, E, etc.). The levels of such protein and mRNA and activity can be determined by any method well known in the art. For example, protein can be quantitated by known immunodiagnostic methods such as western blotting or immunoprecipitation using commercially available antibodies. mRNA can be quantitated using methods that are well known and routine in the art, for example, using northern analysis, RNase protection, the polymerase chain reaction in connection with reverse transcription ("RT-PCR"). Cell viability can be assessed by using trypan-blue staining or other cell death or viability markers known in the art. In a specific embodiment, the level of cellular ATP is measured to determined cell viability. Differentiation can be assessed, for example, visually based on changes in morphology.

The lead compound can also be assessed for its ability to inhibit cell transformation (or progression to malignant phenotype) in vitro. In this embodiment, cells with a transformed cell phenotype are contacted with a lead compound, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see, e.g., Luria et al., 1978, General Virology, 3d Ed., John Wiley & Sons, New York, pp. 436-446).

Loss of invasiveness or decreased adhesion can also be assessed to demonstrate the anti-cancer effects of a lead compound. For example, an aspect of the formation of a metastatic cancer is the ability of a precancerous or cancerous cell to detach from primary site of disease and establish a novel colony of growth at a secondary site. The ability of a cell to invade peripheral sites reflects its potential for a cancerous state. Loss of invasiveness can be measured by a variety of techniques known in the art including, for example, induction of E-cadherin-mediated cell-cell adhesion. Such E-cadherin-mediated adhesion can result in phenotypic reversion and loss of invasiveness (see, e.g., Hordijk et al., 1997, Science 278: 1464-66).

Loss of invasiveness can further be examined by inhibition of cell migration. A variety of 2-dimensional and 3-dimensional cellular matrices are commercially available (Calbiochem-Novabiochem Corp. San Diego, Calif.). Cell migration across or into a matrix can be examined using microscopy, time-lapsed photography or videography, or by any method in the art allowing measurement of cellular migration. In a related embodiment, loss of invasiveness is examined by response to hepatocyte growth factor ("HGF"). HGF-induced cell scattering is correlated with invasiveness of cells such as Madin-Darby canine kidney ("MDCK") cells. This assay identifies a cell population that has lost cell scattering activity in response to HGF (see, e.g., Hordijk et al., 1997, Science 278:1464-66).

Alternatively, loss of invasiveness can be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated can then be correlated with invasiveness (see e.g., Ohnishi, 1993, Biochem. Biophys. Res. Commun. 193:518-25).

A lead compound can also be assessed for its ability to alter the expression of a secondary protein (as determined, e.g. by western blot analysis) or RNA, whose expression and/or activation is regulated directly or indirectly by the gene product of a gene of interest containing a premature stop codon or a nonsense mutation (as determined, e.g., by RT-PCR or northern blot analysis) in cultured cells in vitro using methods which are well known in the art. Further, chemical footprinting analysis can be conducted and is well-known in the art.

In another embodiment of the invention, the lead compound can be tested in a host cell. In such an embodiment, the host cell can enode a nucleic acid with a premature translation termination sequence or stop codon. Such nucleic acids can be encoded by a number of vehicles, including, but not limited to, recombinant or chimeric vectors, viruses or the genome of the host cell. In another embodiment of the invention, the presence of the gene, containing a premature stop codon or translation termination sequence, causes a detectable phenotype in the host cell. Moreover, the effect of lead compounds on the phenotype of the cell can be examined in order to determine suitable candidates that modulate premature translation termination from a pool of compounds. In one embodiment, a host cell containing a gene encoding a premature translation termination sequence or stop codon, exhibits an abnormal phenotype relative to the wild type cell that does not encode a gene with a premature stop codon. In such an embodiment, the effect of a compound on the host cell phenotype can be examined in order to determine the effect of a lead compound on premature translation termination or nonsense mediate mRNA decay. By way of example and not meant to limit the possible models, host cells, expressing mutations in a gene that controls cell cycle or proliferation, e.g., p53, can be exposed to various lead compounds in order to determine their effect on cell proliferation. Any lead compound that affects the proliferative activity of the host cell is identified as a compound that modulates premature translation termination or nonsense mediated mRNA decay.

5.9.2 Animal Models

Animal model systems can be used to demonstrate the safety and efficacy of the lead compounds identified in the nonsense suppression assays described above. The lead compounds identified in the nonsense suppression assay can then be tested for biological activity using animal models for a disease, condition, or syndrome of interest. These include animals engineered to contain the target RNA element coupled to a functional readout system, such as a transgenic mouse.

There are a number of methods that can be used to conduct animal model studies. Briefly, a compound identified in accordance with the methods of the invention is introduced into an animal model so that the effect of the compound on the manifestation of disease can be determined. The prevention or reduction in the severity, duration or onset of a symptom associated with the disease or disorder of the animal model that is associated with, characterized by or caused by premature translation termination and/or nonsense mediated mRNA decay would indicate that the compound adminstered to the animal model had a prophylactic or therapeutic effect. Any method can be used to introduce the compound into the animal model, including, but not limited to, injection, intravenous infusion, oral ingestion, or inhalation. In a preferred embodiment, transgenic hosts are constructed so that the animal genome encodes a gene of interest with a premature translation termination sequence or stop codon. In such an embodiment, the gene, containg a premature translation termination sequence or stop codon, would not encode a full length peptide from a transcribed mRNA. The adminsitration of a compound to the animal model, and the expression of a full length protein, polypeptide or peptide, for example, corresponding to the gene containing a premature stop codon would indicate that the compound modulates premature translation termination. Any method known in the art, or described herein, can be used to determine if the stop codon was modulated by the compound. In another embodiment, the animal host genome encodes a native gene containing a premature stop codon. In another embodiment of the invention, the animal host is a natural mutant, i.e., natively encoding a gene with a premature stop codon. For example, the animal can be a model for cystic fibrosis wherein the animal genome contains a natural mutation that incorporates a premature stop codon or translation termination sequence.

Examples of animal models for cystic fibrosis include, but are not limited to, cftr(−/−) mice (see, e.g., Freedman et al., 2001, Gastroenterology 121(4):950-7), cftr(tm1HGU/tm1HGU) mice (see, e.g., Bernhard et al., 2001, Exp Lung Res 27(4):349-66), CFTR-deficient mice with defective cAMP-mediated Cl(−) conductance (see, e.g., Stotland et al., 2000, Pediatr Pulmonol 30(5):413-24), and C57BL/6-Cftr (m1UNC)/Cftr(m1UNC) knockout mice (see, e.g., Stotland et al., 2000, Pediatr Pulmonol 30(5):413-24).

Examples of animal models for muscular dystrophy include, but are not limited to, mouse, hamster, cat, dog, and C. elegans. Examples of mouse models for muscular dystrophy include, but are not limited to, the dy−/− mouse (see, e.g., Connolly et al., 2002, J Neuroimmunol 127(1-2):80-7), a muscular dystrophy with myositis (mdm) mouse mutation (see, e.g., Garvey et al., 2002, Genomics 79(2):146-9), the mdx mouse (see, e.g., Nakamura et al., 2001, Neuromuscul Disord 11(3):251-9), the utrophin-dystrophin knockout (dko) mouse (see, e.g., Nakamura et al., 2001, Neuromuscul Disord 11(3):251-9), the dy/dy mouse (see, e.g., Dubowitz et al., 2000, Neuromuscul Disord 10(4-5):292-8), the mdx(Cv3) mouse model (see, e.g., Pillers et al., 1999, Laryngoscope 109(8):1310-2), and the myotonic ADR-MDX mutant mice (see, e.g. Kramer et al., 1998, Neuromuscul Disord 8(8):542-50). Examples of hamster models for muscular dystrophy include, but are not limited to, sarcoglycan-deficient hamsters (see, e.g., Nakamura et al., 2001, Am J Physiol Cell Physiol 281(2):C690-9) and the BIO 14.6 dystrophic hamster (see, e.g., Schlenker & Burbach, 1991, J Appl Physiol 71(5):1655-62). An example of a feline model for muscular dystrophy includes, but is not limited to, the hypertrophic feline muscular dystrophy model (see, e.g., Gaschen & Burgunder, 2001, Acta Neuropathol (Berl) 101(6):591-600). Canine models for muscular dystrophy include, but are not limited to, golden retriever muscular dystrophy (see, e.g., Fletcher et al., 2001, Neuromuscul Disord 11(3):239-43) and canine X-linked muscular dystrophy (see, e.g., Valentine et al., 1992, Am J Med Genet 42(3):352-6). Examples of C. elegans models for muscular dystrophy are described in Chamberlain & Benian, 2000, Curr Biol 10(21):R795-7 and Culette & Sattelle, 2000, Hum Mol Genet 9(6):869-77.

Examples of animal models for familial hypercholesterolemia include, but are not limited to, mice lacking functional LDL receptor genes (see, e.g., Aji et al., 1997, Circulation 95(2):430-7), Yoshida rats (see, e.g., Fantappie et al., 1992, Life Sci 50(24):1913-24), the JCR:LA-cp rat (see, e.g., Richardson et al., 1998, Atherosclerosis 138(1):135-46), swine (see, e.g., Hasler-Rapacz et al., 1998, Am J Med Genet 76(5): 379-86), and the Watanabe heritable hyperlipidaemic rabbit (see, e.g., Tsutsumi et al., 2000, Arzneimittelforschung 50(2): 118-21; Harsch et al., 1998, Br J Pharmacol 124(2):227-82; and Tanaka et al., 1995, Atherosclerosis 114(1):73-82).

An example of an animal model for human cancer in general includes, but is not limited to, spontaneously occurring tumors of companion animals (see, e.g., Vail & MacEwen, 2000, Cancer Invest 18(8):781-92). Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCRbeta and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3):1873-81). Examples of animal models for colorectal carcinomas include, but are not limited to, Apc mouse models (see, e.g. Fodde & Smits, 2001, Trends Mol Med 7(8):369-73 and Kuraguchi et al., 2000, Oncogene 19(50):5755-63). An example of an animal model for neurofibromatosis includes, but is not limited to, mutant NF1 mice (see, e.g., Cichowski et al., 1996, Semin Cancer Biol 7(5):291-8). Examples of animal models for retinoblastoma include, but are not limited to, transgenic mice that expression the simian virus 40 T antigen in the retina (see, e.g., Howes et al., 1994, Invest Ophthalmol Vis Sci 35(2):342-51 and Windle et al, 1990, Nature 343 (6259):665-9) and inbred rats (see, e.g., Nishida et al., 1981, Curr Eye Res 1(1):53-5 and Kobayashi et al., 1982, Acta Neuropathol (Berl) 57(2-3):203-8). Examples of animal models for Wilm's tumor include, but are not limited to, a WT1 knockout mice (see, e.g., Scharnhorst et al., 1997, Cell Growth Differ 8(2):133-43), a rat subline with a high incidence of neuphroblastoma (see, e.g., Mesfin & Breech, 1996, Lab Anim Sci 46(3):321-6), and a Wistar/Furth rat with Wilms' tumor (see, e.g., Murphy et al., 1987, Anticancer Res 7(4B):717-9).

Examples of animal models for retinitis pigmentosa include, but are not limited to, the Royal College of Surgeons ("RCS") rat (see, e.g., Vollrath et al., 2001, Proc Natl Acad Sci USA 98(22);12584-9 and Hanitzsch et al., 1998, Acta Anat (Basel) 162(2-3):119-26), a rhodopsin knockout mouse (see, e.g., Jaissle et al., 2001, Invest Ophthalmol Vis Sci 42(2):506-13), and Wag/Rij rats (see, e.g., Lai et al., 1980, Am J Pathol 98(1):281-4).

Examples of animal models for cirrhosis include, but are not limited to, $CCl_4$-exposed rats (see, e.g., Kloehn et al., 2001, Horm Metab Res 33(7):394-401) and rodent models instigated by bacterial cell components or colitis (see, e.g., Vierling, 2001, Best Pract Res Clin Gastroenterol 15(4):591-610).

Examples of animal models for hemophilia include, but are not limited to, rodent models for hemophilia A (see, e.g., Reipert et al., 2000, Thromb Haemost 84(5):826-32; Jarvis et al., 1996, Thromb Haemost 75(2):318-25; and Bi et al., 1995, Nat Genet 10(1):119-21), canine models for hemophilia A (see, e.g., Gallo-Penn et al., 1999, Hum Gene Ther 10(11):1791-802 and Connelly et al, 1998, Blood 91(9);3273-81), murine models for hemophilia B (see, e.g., Snyder et al., 1999, Nat Med 5(1):64-70; Wang et al., 1997, Proc Natl Acad Sci USA 94(21):11563-6; and Fang et al., 1996, Gene Ther 3(3):217-22), canine models for hemophilia B (see, e.g., Mount et al., 2002, Blood 99(8):2670-6; Snyder et al., 1999, Nat Med 5(1):64-70; Fang et al., 1996, Gene Ther 3(3):217-22); and Kay et al., 1994, Proc Natl Acad Sci USA 91(6):2353-7), and a rhesus macaque model for hemophilia B (see, e.g., Lozier et al., 1999, Blood 93(6):1875-81).

Examples of animal models for von Willebrand disease include, but are not limited to, an inbred mouse strain RIIIS/J (see, e.g., Nichols et al., 1994, 83(11):3225-31 and Sweeney et al., 1990, 76(11):2258-65), rats injected with botrocetin (see, e.g., Sanders et al., 1988, Lab Invest 59(4):443-52), and porcine models for von Willebrand disease (see, e.g., Nichols et al., 1995, Proc Natl Acad Sci USA 92(7):2455-9; Johnson & Bowie, 1992, J Lab Clin Med 120(4):553-8; and Brinkhous et al., 1991, Mayo Clin Proc 66(7):733-42).

Examples of animal models for β-thalassemia include, but are not limited to, murine models with mutations in globin genes (see, e.g., Lewis et al., 1998, Blood 91(6):2152-6; Raja et al., 1994, Br J Haematol 86(1):156-62; Popp et al., 1985, 445:432-44; and Skow et al., 1983, Cell 34(3):1043-52).

Examples of animal models for kidney stones include, but are not limited to, genetic hypercalciuric rats (see, e.g., Bushinsky et al., 1999, Kidney Int 55(1):234-43 and Bushinsky et al., 1995, Kidney Int 48(6):1705-13), chemically treated rats (see, e.g., Grases et al., 1998, Scand J Urol Nephrol 32(4): 261-5; Burgess et al., 1995, Urol Res 23(4):239-42; Kumar et al., 1991, J Urol 146(5):1384-9; Okada et al., 1985, Hinyokika Kiyo 31(4):565-77; and Bluestone et al., 1975, Lab Invest 33(3):273-9), hyperoxaluric rats (see, e.g., Jones et al., 1991, J Urol 145(4):868-74), pigs with unilateral retrograde flexible nephroscopy (see, e.g., Seifmah et al., 2001, 57(4):832-6), and rabbits with an obstructed upper urinary tract (see, e.g., Itatani et al., 1979, Invest Urol 17(3):234-40).

Examples of animal models for ataxia-telangiectasia include, but are not limited to, murine models of ataxia-telangiectasia (see, e.g., Barlow et al., 1999, Proc Natl Acad Sci USA 96(17):9915-9 and Inoue et al., 1986, Cancer Res 46(8):3979-82). A mouse model was generated for ataxia-telangiectasia using gene targeting to generate mice that did not express the Atm protein (see, e.g., Elson et al., 1996, Proc. Nat. Acad. Sci. 93: 13084-13089).

Examples of animal models for lysosomal storage diseases include, but are not limited to, mouse models for mucopolysaccharidosis type VII (see, e.g., Brooks et al., 2002, Proc Natl Acad Sci USA. 99(9):6216-21; Monroy et al., 2002, Bone 30(2):352-9; Vogler et al., 2001, Pediatr Dev Pathol. 4(5):421-33; Vogler et al., 2001, Pediatr Res. 49(3):342-8; and Wolfe et al., 2000, Mol Ther. 2(6):552-6), a mouse model for metachromatic leukodystrophy (see, e.g., Matzner et al., 2002, Gene Ther. 9(1):53-63), a mouse model of Sandhoff disease (see, e.g., Sango et al., 2002, Neuropathol Appl Neurobiol. 28(1):23-34), mouse models for mucopolysaccharidosis type III A (see, e.g., Bhattacharyya et al., 2001, Glycobiology 11(1):99-10 and Bhaumik et al., 1999, Glycobiology 9(12):1389-96.), arylsulfatase A (ASA)-deficient mice (see, e.g., D'Hooge et al., 1999, Brain Res. 847(2):352-6 and D'Hooge et al, 1999, Neurosci Lett. 273(2):93-6); mice with an aspartylglucosaminuria mutation (see, e.g., Jalanko et al., 1998, Hum Mol Genet. 7(2):265-72); feline models of mucopolysaccharidosis type VI (see, e.g. Crawley et al., 1998, J Clin Invest. 101(1):109-19 and Norrdin et al., 1995, Bone 17(5):485-9); a feline model of Niemann-Pick disease type C (see, e.g., March et al., 1997, Acta Neuropathol (Berl). 94(2):164-72); acid sphingomyelinase-deficient mice (see, e.g., Otterbach & Stoffel, 1995, Cell 81(7):1053-6), and bovine mannosidosis (see, e.g., Jolly et al., 1975, Birth Defects Orig Artic Ser. 11(6):273-8).

Examples of animal models for tuberous sclerosis ("TSC") include, but are not limited to, a mouse model of TSC1 (see, e.g., Kwiatkowski et al., 2002, Hum Mol Genet. 11(5):525-34), a Tsc1 (TSC1 homologue) knockout mouse (see, e.g., Kobayashi et al., 2001, Proc Natl Acad Sci USA. Jul. 17, 2001;98(15):8762-7), a TSC2 gene mutant(Eker) rat model (see, e.g., Hino 2000, Nippon Rinsho 58(6):1255-61; Mizuguchi et al., 2000, J Neuropathol Exp Neurol. 59(3):188-9; and Hino et al., 1999, Prog Exp Tumor Res. 35:95-108); and Tsc2(+/−) mice (see, e.g., Onda et al., 1999, J Clin Invest. 104(6):687-95).

5.9.3 Toxicity

The toxicity and/or efficacy of a compound identified in accordance with the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). Cells and cell lines that can be used to assess the cytotoxicity of a compound identified in accordance with the invention include, but are not limited to, peripheral blood mononuclear cells (PBMCs), Caco-2 cells, and Huh7 cells. The dose ratio between toxic and therapeutic effects is the therapeutic index and it can be expressed as the ratio $LD_{50}/ED_{50}$. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the compound that achieves a half-maximal inhibition of symptoms) as determined in cell culture. Such information can be used to more accurately determine useful doses in humans. Levels in plasma may be measured, for example, by high performance liquid chromatography.

5.10 Design of Congeners or Analogs

The compounds which display the desired biological activity can be used as lead compounds for the development or design of congeners or analogs having useful pharmacological activity. For example, once a lead compound is identified, molecular modeling techniques can be used to design variants of the compound that can be more effective. Examples of molecular modeling systems are the CHARM and QUANTA programs (Polygen Corporation, Waltham, Mass.). CHARM performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical Fennica 97:159-166; Ripka, 1998, New Scientist 54-57; McKinaly & Rossmann, 1989, Annu. Rev. Pharmacol. Toxiciol. 29:111-122; Perry & Davies, OSAR: Quantitative Structure-Activity Relationships in Drug Design pp. 189-193 (Alan R. Liss, Inc. 1989); Lewis & Dean, 1989, Proc. R. Soc. Lond. 236:125-140 and 141-162; Askew et al., 1989, J. Am. Chem. Soc. 111:1082-1090. Other computer programs that screen and graphically depict chemicals are available from companies such as BioDesign, Inc. (Pasadena, Calif.), Allelix, Inc. (Missisauga, Ontario, Canada), and Hypercube, Inc. (Cambridge, Ontario). Although these are primarily designed for application to drugs specific to particular proteins, they can be adapted to design of drugs specific to any identified region. The analogs and congeners can be tested for binding to translational machinery using assays well-known in the art or described herein for biologic activity. Alternatively, lead compounds with little or no biologic activity, as ascertained in the screen, can also be used to design analogs and congeners of the compound that have biologic activity.

5.11 Uses of Compounds to Prevent/Treat a Disorder

The present invention provides methods of preventing, treating, managing or ameliorating a disorder or one or more symptoms thereof, said methods comprising administering to a subject in need thereof one or more compounds identified in accordance with the methods of the invention or a pharmaceutically acceptable salt thereof. In particular, the present invention provides methods of preventing, treating, managing or ameliorating a disorder associated with premature translation termination and/or nonsense-mediated mRNA decay, or one or more symptoms thereof, said methods comprising administering to a subject in need thereof one or more compounds identified in accordance with the methods of the invention or a pharmaceutically acceptable salt thereof. Examples of diseases associated with, characterized by or caused by associated with premature translation termination and/or nonsense-mediated mRNA decay include, but are not limited to, cystic fibrosis, muscular dystrophy, heart disease, lung cancer, breast cancer, colon cancer, pancreatic cancer, non-Hodgkin's lymphoma, ovarian cancer, esophageal cancer, colorectal carcinomas, neurofibromatosis, retinoblastoma, Wilm's tumor, retinitis pigmentosa, collagen disorders, cirrhosis, Tay-Sachs disease, blood disorders, kidney stones, ataxia-telangiectasia, lysosomal storage diseases, and tuberous sclerosis. See Sections 5.8 and 6.5 for additional non-limiting examples of diseases and genetic disorders which can be prevented, treated, managed or ameliorated by administering one or more of the compounds identified in accordance with the methods of the invention or a pharmaceutically acceptable salt thereof. Genes that contain one or more nonsense mutations that are potentially involved in causing disease are presented in table form according to chromosome location in Example 6.5 infra.

In a preferred embodiment, it is first determined that the patient is suffering from a disease associated with premature translation termination and/or nonsense-mediated mRNA decay before administering a compound identified in accordance with the invention or a combination therapy described herein. In a preferred embodiment, the DNA of the patient can be sequenced or subject to Southern Blot, polymerase chain reaction (PCR), use of the Short Tandem Repeat (STR), or polymorphic length restriction fragments (RFLP) analysis to determine if a nonsense mutation is present in the DNA of the patient. Alternatively, it can be determined if altered levels of the protein with the nonsense mutation are expressed in the patient by western blot or other immunoassays. Such methods are well known to one of skill in the art.

In one embodiment, the invention provides a method of preventing, treating, managing or ameliorating a disorder or one or more symptoms thereof, said method comprising administering to a subject in need thereof a dose of a prophylactically or therapeutically effective amount of one or more compounds identified in accordance with the methods of the invention. In another embodiment, a compound identified in accordance with the methods of the invention is not administered to prevent, treat, or ameliorate a disorder or one or more symptoms thereof, if such compound has been used previously to prevent, treat, manage or ameliorate said disorder. In a more specific embodiment of the invention, disorders that can be prevented, managed and/or treated with the compounds of the invention, include, but are not limited to, disorders that are associated with, characterized by or caused by premature translation termination and/or nonsense mediated mRNA decay.

The invention provides methods of preventing, treating, managing or ameliorating a disorder or one or more symptoms thereof, said methods comprising administering to a subject in need thereof one or more of the compounds identified utilizing the screening methods described herein or a pharmaceutically acceptable salt thereof and one or more other therapies (e.g., prophylactic or therapeutic agents). In particular, the invention provides methods of preventing, treating, managing or ameliorating a disorder associated with, characterized by or caused by premature translation termination and/or nonsense mediate mRNA decay, or one or more symptoms thereof, said methods comprising administering to a subject in need thereof one or more of the compounds identified utilizing the screening methods described herein or a pharmaceutically acceptable salt thereof, and one or more other therapies (e.g., prophylactic or therapeutic agents). Preferably, the other therapies are currently being used, have been used or are known to be useful in the prevention, treatment, management or amelioration of said disorder or a symptom thereof. Non-limiting examples of such therapies are in Section 5.11.1 infra.

The therapies (e.g., prophylactic or therapeutic agents) or the combination therapies of the invention can be administered sequentially or concurrently. In a specific embodiment, the combination therapies of the invention comprise a compound identified in accordance with the invention and at least one other therapy that has the same mechanism of action as said compound. In another specific embodiment, the combination therapies of the invention comprise a compound identified in accordance with the methods of the invention and at least one other therapy (e.g. prophylactic or therapeutic agent) which has a different mechanism of action than said compound. The combination therapies of the present invention improve the prophylactic or therapeutic effect of a compound of the invention by functioning together with the compound to have an additive or synergistic effect. The combination therapies of the present invention reduce the side effects associated with the therapies (e.g., prophylactic or therapeutic agents).

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In a specific embodiment, a pharmaceutical composition comprising one or more compounds identified in a screening assay described herein is administered to a subject, preferably a human, to prevent, treat, manage or ameliorate a disorder (in particular, a disorder associated with, characterized by or caused by premature translation termination and/or nonsense mediated mRNA decay) or one or more symptoms thereof. In accordance with the invention, the pharmaceutical composition may also comprise one or more other prophylactic or therapeutic agents. Preferably, such prophylactic or theapeutic agents are currently being used, have been used or are known to be useful in the prevention, treatment, management or amelioration of a disorder (in particular, a disorder associated with, characterized by, or caused by premature translation termination or nonsense-mediated mRNA decay) or one or more symptoms thereof.

A compound identified in accordance with the methods of the invention may be used as a first, second, third, fourth or fifth line of therapy for a disorder (in particular, a disorder associated with, characterized by or caused by premature translation termination and/or nonsense-mediated mRNA decay). The invention provides methods for treating, managing or ameliorating a disorder (in particular, a disorder associated with, characterized by or caused by premature translation termination and/or nonsense-mediated mRNA decay) or one or more symptoms thereof in a subject refractory to conventional therapies for such disorder, said methods comprising administering to said subject a dose of a prophylactically or therapeutically effective amount of a compound identified in accordance with the methods of the invention. In particular, a disorder may be determined to be refractory to a therapy when at least some significant portion of the disorder is not resolved in response to the therapy. Such a determination can be made either in vivo or in vitro by any method known in the art for assaying the effectiveness of a therapy on a subject, using the art-accepted meanings of "refractory" in such a context. In a specific embodiment, a disorder is refractory where the number of symptoms of the disorder has not been significantly reduced, or has increased.

The invention provides methods for treating, managing or ameliorating one or more symptoms of a disorder (in particular, a disorder associated with, characterized by or caused by premature translation termination and/or nonsense-mediated mRNA decay) in a subject refractory to existing single agent therapies for such disorder, said methods comprising administering to said subject a dose of a prophylactically or therapeutically effective amount of a compound identified in accordance with the methods of the invention and a dose of a prophylactically or therapeutically effective amount of one or more other therapies (e.g., prophylactic or therapeutic agents). The invention also provides methods for treating or managing a disorder (in particular, a disorder associated with, characterized by or caused by premature translation termination and/or nonsense-mediated mRNA decay) by administering a compound identified in accordance with the methods of the invention in combination with any other therapy (e.g., radiation therapy, chemotherapy or surgery) to patients who have proven refractory to other therapies but are no longer on these therapies. The invention also provides methods for the treatment or management of a patient having disorder (in particular, a disorder associated with, characterized by or caused by premature translation termination and/or nonsense-mediated mRNA decay) and said patient is immunosuppressed or immunocompromised by reason of having previously undergone other therapies. Further, the invention provides methods for preventing the recurrence of a disorder (in particular, a disorder associated with, characterized by or caused by premature translation termination and/or nonsense-mediated mRNA decay) such as, e.g., cancer in patients that have been undergone therapy and have no disease activity by administering a compound identified in accordance with the methods of the invention.

In addition to the use of the compounds identified in accordance with the invention for the prevention, treatment, management or amelioration of a disorder or a symptom thereof, the compounds may be used in vitro to modulate the expression of particular genes of interest, for example, the compounds may be used to increase or decrease the expression of a particular gene of interest when conducting in vitro studies.

5.11.1 Other Therapies

The present invention provides methods of preventing, treating, managing or ameliorating a disorder (in particular, a disorder associated with, characterized by or caused by premature translation termination and/or nonsense-mediated mRNA decay), or one or more symptoms thereof, said methods comprising administering to a subject in need thereof one or more compounds identified in accordance with the methods of the invention or a pharmaceutically acceptable salt thereof, and one or more other therapies (e.g., prophylactic or therapeutic agents). Any therapy (e.g., chemotherapies, radiation therapies, hormonal therapies, and/or biological therapies/immunotherapies) which is known to be useful, or which has been used or is currently being used for the prevention, treatment, management or amelioration of a disorder (in particular, a disorder associated with, characterized by or caused by premature translation termination and/or nonsense-mediated mRNA decay) or one or more symptoms thereof can be used in combination with a compound identified in accordance with the methods of the invention. Examples of therapeutic or prophylactic agents which can be used in combination with a compound identified in accordance with the invention include, but are not limited to, peptides, polypeptides, fusion proteins, nucleic acid molecules, small molecules, mimetic agents, synthetic drugs, inorganic molecules, and organic molecules.

Proliferative disorders associated with, characterized by or caused by premature translation termination and/or nonsense-mediated mRNA decay can be prevented, treated, managed or ameliorated by administering to a subject in need thereof one or more of the compounds identified in accordance with the methods of the invention, and one or more other therapies for prevention, treatment, management or amelioration of said disorders or a symptom thereof. Examples of such therapies include, but are not limited to, angiogenesis inhibitors, topoisomerase inhibitors, immunomodulatory agents (such as chemotherapeutic agents) and radiation therapy. Angiogenesis inhibitors (i.e., antiangiogenic agents) include, but are not limited to, angiostatin (plasminogen fragment); antiangiogenic antithrombin III; angiozyme; ABT-627; Bay 12-9566; Benefin; Bevacizumab; BMS-275291; cartilage-derived inhibitor (CDI); CAI; CD59 complement fragment; CEP-7055; Col 3; combretastatin A-4; endostatin (collagen XVIII fragment); fibronectin fragment; Gro-beta; Halofuginone; Heparinases; Heparin hexasaccharide fragment; HMV833; human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-methoxyestradiol; MMI 270 (CGS 27023A); MoAb IMC-1C11; Neovastat; NM-3; Panzem; PI-88; Placental ribonuclease inhibitor; plasminogen activator inhibitor; platelet factor-4 (PF4); Prinomastat; Prolactin 16 kD fragment; Proliferin-related protein (PRP); PTK 787/ZK 222594; retinoids; solimastat; squalamine; SS 3304; SU 5416; SU6668; SU11248; tetrahydrocortisol-S; tetrathiomolybdate; thalidomide; thrombospondin-1 (TSP-1); TNP-470; transforming growth factor-beta; vasculostatin; vasostatin (calreticulin fragment); ZD6126; ZD 6474; farnesyl transferase inhibitors (FTI); and bisphosphonates. In a specific embodiment, anti-angiogenic agents do not include antibodies or fragments thereof that immunospecifically bind to integrin $\alpha_v\beta_3$.

Specific examples of propylactic or therapeutic agents which can be used in accordance with the methods of the invention to prevent, treat, manage or ameliorate a proliferative disorder associated with, characterized by or caused by premature translation termination and/or nonsense-mediated mRNA decay, or a symptom thereof include, but not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer, carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur, talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor, carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor, leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor, platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor, urokinase receptor antagonists; vapreotide; variolin B; vector system, erythrocyte gene therapy; thalidomide; velaresol; veramine; verdins; verteporfin; vinorelbine; vinxaltine; vorozole; zanoterone; zeniplatin; zilascorb; and zinostatin stimalamer.

Specific examples of propylactic or therapeutic agents which can be used in accordance with the methods of the invention to prevent, treat, manage and/or ameliorate a central nervous system disorders associated with, characterized by or caused by premature translation termination and/or nonsense-mediated mRNA decay, or a symptom thereof include, but are not limited to: Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, or Symmetrel.

Specific examples of propylactic or therapeutic agents which can be used in accordance with the methods of the invention to prevent, treat, manage and/or ameliorate a metabolic disorders associated with, characterized by or caused by premature translation termination and/or nonsense-mediated mRNA decay, or a symptom thereof include, but are not limited to: a monoamine oxidase inhibitor (MAO), for example, but not limited to, iproniazid, clorgyline, phenelzine and isocarboxazid; an acetylcholinesterase inhibitor, for example, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; an antiemetic agent, for example, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and mixtures thereof.

5.12 Compounds and Methods of Administering Compounds

Biologically active compounds identified using the methods of the invention or a pharmaceutically acceptable salt thereof can be administered to a patient, preferably a mammal, more preferably a human, suffering from a disorder (in particular, a disorder associated with, characterized by or caused by premature translation termination and/or nonsense mediated mRNA decay). In a specific embodiment, a compound or a pharmaceutically acceptable salt thereof is administered to a patient, preferably a mammal, more preferably a human, as a preventative measure against a disorder (in particular, a disorder associated with, characterized by or caused by premature translation termination and/or nonsense mediated mRNA decay).

In one embodiment, the compound or a pharmaceutically acceptable salt thereof is administered as a preventative measure to a patient. According to this embodiment, the patient can have a genetic predisposition to a disease, such as a family history of the disease, or a non-genetic predisposition to the disease. Accordingly, the compound and pharmaceutically acceptable salts thereof can be used for the treatment of one manifestation of a disease and prevention of another.

A compound identified in accordance with the invention, or a pharmaceutically acceptable salt thereof, may be a component of a composition optionally comprising a carrier, diluent or excipient. When administered to a patient, the compound or a pharmaceutically acceptable salt thereof is preferably administered as component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the compound and pharmaceutically acceptable salts thereof.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of the compound or a pharmaceutically acceptable salt thereof into the bloodstream.

In specific embodiments, it may be desirable to administer the compound or a pharmaceutically acceptable salt thereof locally. This may be achieved, for example, and not by way of limitation, by local infusion during surgery, topical application, e.g. in conjunction with a wound dressing after surgery, by injection, by means of a catheter, by means of a suppository, or by means of an implant, said implant being of a porous, non-porous, or gelatinous material, including membranes, such as sialastic membranes, or fibers.

In certain embodiments, it may be desirable to introduce the compound or a pharmaceutically acceptable salt thereof into the central nervous system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound and pharmaceutically acceptable salts thereof can be formulated as a suppository, with traditional binders and vehicles such as triglycerides.

In another embodiment, the compound and pharmaceutically acceptable salts thereof can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compound and pharmaceutically acceptable salts thereof can be delivered in a controlled release system (see, e.g., Goodson, in Medical Applications of Controlled Release, supra, vol. 2, pp. 115-138 (1984)). Other controlled-release systems discussed in the review by Langer, 1990, Science 249:1527-1533 may be used. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of a target RNA of the compound or a pharmaceutically acceptable salt thereof, thus requiring only a fraction of the systemic dose.

Compositions comprising the compound or a pharmaceutically acceptable salt thereof ("compound compositions")

can additionally comprise a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, mammals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Compound compositions, if desired, can also contain minor amounts of wetting or emulsifying agents, or pH buffering agents.

Compound compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., U.S. Pat. No. 5,698,155). Other examples of suitable pharmaceutical vehicles are described in Remington's Pharmaceutical Sciences, Alfonso R. Gennaro, ed., Mack Publishing Co. Easton, Pa., 19th ed., 1995, pp. 1447 to 1676, incorporated herein by reference.

In a preferred embodiment, the compound or a pharmaceutically acceptable salt thereof is formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, and the like. Such vehicles are preferably of pharmaceutical grade. Typically, compositions for intravenous administration comprise sterile isotonic aqueous buffer. Where necessary, the compositions may also include a solubilizing agent.

In another embodiment, the compound or a pharmaceutically acceptable salt thereof can be formulated for intravenous administration. Compositions for intravenous administration may optionally include a local anesthetic such as lignocaine to lessen pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the compound or a pharmaceutically acceptable salt thereof is to be administered by infusion, it can be dispensed, for example, with an infusion bottle containing sterile pharmaceutical grade water or saline. Where the compound or a pharmaceutically acceptable salt thereof is administered by injection, an ampoule of sterile water for injection or saline can be provided so that the ingredients may be mixed prior to administration.

The amount of a compound or a pharmaceutically acceptable salt thereof that will be effective in the treatment of a particular disease will depend on the nature of the disease, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of the practitioner and each patient's circumstances. However, suitable dosage ranges for oral administration are generally about 0.001 milligram to about 500 milligrams of a compound or a pharmaceutically acceptable salt thereof per kilogram body weight per day. In specific preferred embodiments of the invention, the oral dose is about 0.01 milligram to about 100 milligrams per kilogram body weight per day, more preferably about 0.1 milligram to about 75 milligrams per kilogram body weight per day, more preferably about 0.5 milligram to 5 milligrams per kilogram body weight per day. The dosage amounts described herein refer to total amounts administered; that is, if more than one compound is administered, or if a compound is administered with a therapeutic agent, then the preferred dosages correspond to the total amount administered. Oral compositions preferably contain about 10% to about 95% active ingredient by weight.

Suitable dosage ranges for intravenous (i.v.) administration are about 0.01 milligram to about 100 milligrams per kilogram body weight per day, about 0.1 milligram to about 35 milligrams per kilogram body weight per day, and about 1 milligram to about 10 milligrams per kilogram body weight per day. Suitable dosage ranges for intranasal administration are generally about 0.01 pg/kg body weight per day to about 1 mg/kg body weight per day. Suppositories generally contain about 0.01 milligram to about 50 milligrams of a compound of the invention per kilogram body weight per day and comprise active ingredient in the range of about 0.5% to about 10% by weight.

Recommended dosages for intradermal, intramuscular, intraperitoneal, subcutaneous, epidural, sublingual, intracerebral, intravaginal, transdermal administration or administration by inhalation are in the range of about 0.001 milligram to about 200 milligrams per kilogram of body weight per day. Suitable doses for topical administration are in the range of about 0.001 milligram to about 1 milligram, depending on the area of administration. Effective doses may be extrapolated from dose-response curves derived from in vitro or animal model test systems. Such animal models and systems are well known in the art.

The compound and pharmaceutically acceptable salts thereof are preferably assayed in vitro and in vivo, for the desired therapeutic or prophylactic activity, prior to use in humans. For example, in vitro assays can be used to determine whether it is preferable to administer the compound, a pharmaceutically acceptable salt thereof, and/or another therapeutic agent. Animal model systems can be used to demonstrate safety and efficacy.

6. EXAMPLES

6.1 Example

Identification of a Dye-Labeled Target RNA Bound to Small Molecular Weight Compounds The results presented in this Example indicate that gel mobility shift assays can be used to detect the binding of small molecules, such as the Tat peptide and gentamicin, to their respective target RNAs.

Materials and Methods

Buffers

Tris-potassium chloride (TK) buffer is composed of 50 mM Tris-HCl pH 7.4, 20 mM KCl, 0.1% Triton X-100, and 0.5 mM MgCl$_2$. Tris-borate-EDTA (TBE) buffer is composed of 45 mM Tris-borate pH 8.0, and 1 mM EDTA. Tris-Potassium chloride-magnesium (TKM) buffer is composed of 50 mM Tris-HCl pH 7.4, 20 mM KCl, 0.1% Triton X-100 and 5 mM MgCl$_2$.

Gel Retardation Analysis

RNA oligonucleotides were purchased from Dharmacon, Inc, Lafayette, Colo.). 500 pmole of either a 5' fluorescein labeled oligonucleotide corresponding to the 16S rRNA A site (5'-GGCGUCACACCUUCGGGUGAAGUCGCC-3' (SEQ ID NO:1); Moazed & Noller, 1987, Nature 327:389-394; Woodcock et al., 1991, EMBO J. 10:3099-3103; Yoshizawa et al., 1998, EMBO J. 17:6437-6448) or a 5' fluorescein labeled oligonucleotide corresponding to the HIV-1 TAR element TAR RNA (5'-GGCAGAUCUGAGCCUGG-GAGCUCUCUGCC-3' (SEQ ID NO: 2); Huq et al., 1999, Nucleic Acids Research. 27:1084-1093; Hwang et al., 1999, Proc. Natl. Acad. Sci. USA 96:12997-13002) was 3' labeled with 5'-$^{32}$P cytidine 3',5'-bis(phosphate) (NEN) and T4 RNA ligase (NEBiolabs) in 10% DMSO as per manufacturer's instructions. The labeled oligonucleotides were purified using G-25 Sephadex columns (Boehringer Mannheim). For Tat-TAR gel retardation reactions the method of Huq et al. (Nucleic Acids Research, 1999, 27:1084-1093) was utilized with TK buffer containing 0.5 mM MgCl$_2$ and a 12-mer Tat peptide (YGRKKRRQRRRP (SEQ ID NO: 3; single letter amino acid code). For 16S rRNA-gentamicin reactions, the method of Huq et al was used with TKM buffer. In 20 μl reaction volumes 50 pmoles of $^{32}$P cytidine-labeled oligonucleotide and either gentamicin sulfate (Sigma) or the short Tat peptide (Tat$_{47-58}$) in TK or TKM buffer were heated at 90° C. for 2 minutes and allow to cool to room temperature (approximately 24° C.) over 2 hours. Then 10 μl of 30% glycerol was added to each reaction tube and the entire sample was loaded onto a TBE non-denaturing polyacrylamide gel and electrophoresed at 1200-1600 volt-hours at 4° C. The gel was exposed to an intensifying screen and radioactivity was quantitated using a Typhoon phosporimager molecular Dynamics).

Background

One method used to demonstrate small molecule interactions with natural occurring RNA structures such as ribosomes is by a method called chemical footprinting or toe printing (Moazed & Noller, 1987, Nature 327:389-394; Woodcock et al., 1991, EMBO J. 10:3099-3103; Yoshizawa et al., 1998, EMBO J. 17:6437-6448). Here the use of gel mobility shift assays to monitor RNA-small molecule interactions are described. This approach allows for rapid visualization of small molecule-RNA interactions based on the difference between mobility of RNA alone versus RNA in a complex with a small molecule. To validate this approach, an RNA oligonucleotide corresponding to the well-characterized gentamicin binding site on the 16S rRNA (Moazed & Noller, 1987, Nature 327:389-394) and the equally well-characterized HIV-1 TAT protein binding site on the HIV-1 TAR element (Huq et al., 1999, Nucleic Acids Res. 27: 1084-1093) were chosen. The purpose of these experiments is to lay the groundwork for the use of chromatographic techniques in a high throughput fashion, such as microcapillary electrophoresis, for drug discovery.

Results

A gel retardation assay was performed using the Tat$_{47-58}$ peptide and the TAR RNA oligonucleotide. As shown in FIG. 2, in the presence of the Tat peptide, a clear shift is visible when the products are separated on a 12% non-denaturing polyacrylamide gel. In the reaction that lacks peptide, only the free RNA is visible. These observations confirm previous reports made using other Tat peptides (Hamy et al., 1997, Proc. Natl. Acad. Sci. USA 94:3548-3553; Huq et al., 1999, Nucleic Acids Res. 27: 1084-1093).

Based on the results of FIG. 2, it was hypothesized that RNA interactions with small organic molecules could also be visualized using this method. As shown in FIG. 3, the addition of varying concentrations of gentamicin to an RNA oligonucleotide corresponding to the 16S rRNA A site produces a mobility shift. These results demonstrate that the binding of the small molecule gentamicin to an RNA oligonucleotide having a defined structure in solution can be monitored using this approach. In addition, as shown in FIG. 3, a concentration as low as 10 ng/ml gentamicin produces the mobility shift.

To determine whether lower concentrations of gentamicin would be sufficient to produce a gel shift, a similar experiment was performed, as shown in FIG. 3, except that the concentrations of gentamicin ranged from 100 ng/ml to 10 pg/ml. As shown in FIG. 4, gel mobility shifts are produced when the gentamicin concentration is as low as 10 pg/ml. Further, the results shown in FIG. 4 demonstrate that the shift is specific to the 16S rRNA oligonucleotide as the use of an unrelated oligonucleotide, corresponding to the HIV TAR RNA element, does not result in a gel mobility shift when incubated with 10 mg/ml gentamicin. In addition, if a concentration as low as 10 pg/ml gentamicin produces a gel mobility shift then it should be possible to detect changes to RNA structural motifs when small amounts of compound from a library of diverse compounds is screened in this fashion.

Further analysis of the gentamicin-RNA interaction indicates that the interaction is Mg— and temperature dependent. As shown in FIG. 5, when $MgCl_2$ is not present (TK buffer), 1 mg/ml of gentamicin must be added to the reaction to produce a gel shift. Similarly, the temperature of the reaction when gentamicin is added is also important. When gentamicin is present in the reaction during the entire denaturation/renaturation cycle, that is, when gentamicin is added at 90C° C. or 85° C., a gel shift is visualized (data not shown). In contrast, when gentamicin is added after the renaturation step has proceeded to 75° C., a mobility shift is not produced. These results are consistent with the notion that gentamicin may recognize and interact with an RNA structure formed early in the renaturation process.

6.2 Example

Identification of a Dye-Labeled Target RNA Bound to Small Molecular Weight Compounds by Capillary Electrophoresis The results presented in this Example indicate that interactions between a peptide and its target RNA, such as the Tat peptide and TAR RNA, can be monitored by gel retardation assays in an automated capillary electrophoresis system.

Materials and Methods

Buffers

Tris-potassium chloride (TK) buffer is composed of 50 mM Tris-HCl pH 7.4, 20 mM KCl, 0.1% Triton X-100, and 0.5 mM $MgC_2$. Tris-borate-EDTA (IBE) buffer is composed of 45 mM Tris-borate pH 8.0, and 1 mM EDTA. Tris-Potassium chloride-magnesium (TKM) buffer is composed of 50 mM Tris-HCl pH 7.4, 20 mM KCl, 0.1% Triton X-100 and 5 mM $MgCl_2$.

Gel Retardation Analysis Using Capillary Electrophoresis

RNA oligonucleotides were purchased from Dharmacon, Inc, Lafayette, Colo.). 500 pmole of a 5' fluorescein labeled oligonucleotide corresponding to the HIV-1 TAR element TAR RNA (5'-GGCAGAUCUGAGCCUGGGAGCUCU-CUGCC-3' (SEQ ID NO: 2); Huq et al., 1999, Nucleic Acids Research. 27:1084-1093; Hwang et al., 1999, Proc. Natl. Acad. Sci. USA 96:12997-13002) was used. For Tat-TAR gel retardation reactions the method of Huq et al. (Nucleic Acids Research, 1999, 27:1084-1093) was utilized with TK buffer containing 0.5 mM $MgCl_2$ and a 12-mer Tat peptide (YGRKKRRQRRRP (SEQ ID NO: 3); single letter amino acid code). In 20 µl reaction volumes 50 pmoles of labeled oligonucleotide and the short Tat peptide ($Tat_{47-58}$) in TK or TKM buffer were heated at 90° C. for 2 minutes and allow to cool to room temperature (approximately 24° C.) over 2 hours. The reactions were loaded onto a SCE9610 automated capillary electrophoresis apparatus (SpectruMedix; State College, Pennsylvania).

Results

As presented in the previous sections of the Example 6.1, interactions between a peptide and RNA can be monitored by gel retardation assays. It was hypothesized that interactions between a peptide and RNA could be monitored by gel retardation assays by an automated capillary electrophoresis system. To test this hypothesis, a gel retardation assay by an automated capillary electrophoresis system was performed using the $Tat_{47-58}$ peptide and the TAR RNA oligonucleotide. As shown in FIG. 6 using the capillary electrophoresis system, in the presence of the Tat peptide, a clear shift is visible upon the addition of increasing concentrations of Tat peptide. In the reaction that lacks peptide, only a peak corresponding to the free RNA is observed. These observations confirm previous reports made using other Tat peptides (Hamy et al., 1997, Proc. Natl. Acad. Sci. USA 94:3548-3553; Huq et al., 1999, Nucleic Acids Res. 27: 1084-1093).

6.3 Example

Compounds that Modulate Translation Termination Bind Specific Regions of 28S RRNA Data is presented in this Example that demonstrates that specific regions of the 28S rRNA are involved in modulating translation termination in mammalian cells. Compounds that interact in these regions or modulate local changes within these regions of the ribosome (e.g., alter base pairing interactions, base modification or modulate binding of trans-acting factors that bind to these regions) have the potential to modulate translation termination. These regions are conserved from prokaryotes to eukaryotes, but the role of these regions in modulating translation termination has not been realized in eukaryotes. In bacteria, when a short RNA fragment, complementary to the *E. coli* 23S rRNA segment comprising nucleotides 735 to 766 (in domain II), is expressed in vivo, suppression of UGA nonsense mutations, but not UAA of UAG, results (Chernyaeva et al., 1999, J Bacteriol 181: 5257-5262). Other regions of the 23S rRNA in *E. coli* have been implicated in nonsense suppression including the GTPase center in domain II (nt 1034-1120; Jemiolo et al, 1995, Proc. Nat. Acad. Sci. 92:12309-12313).

Materials and Methods

Small Molecules Involved in Modulating Translation Termination

Small molecules involved in modulating translation termination, i.e., nonsense suppression, were used in the footprinting experiments presented in FIGS. 2 to 6 and are listed as Compound A (molecular formula $C_{19}H_{21}NO_4$), Compound B (molecular formula $C_{19}H_{21}N_2O_5$), Compound C (molecular formula $C_{12}H_{15}N_5O$), Compound D (molecular formula $C_{23}H_{15}O_3Br$), Compound E (molecular formula $C_{19}H_{21}NO_4$), Compound F, Compound G (molecular formula $C_{12}H_{15}N_5O$), Compound H (molecular formula $C_{23}H_{15}NO_5$), Compound I (molecular formula $C_{23}H_{15}NO_5$), Compound J, and Compound K.

Preparation of a Translation Extract from HeLa Cells

HeLa S3 cells were grown to a density of $10^6$ cells/ml in DMEM; 5% $CO_2$, 10% FBS, 1×P/S in a spinner flask. Cells were harvested by spinning at 1000×g. Cells were washed twice with phosphate buffered saline. The cell pellet was on ice for 12-24 hours before proceeding. By letting the cells sit on ice, the activity of the extract is increased up to twentyfold. The length of time on ice can range from 0 hours to 1 week. The cells were resuspended in 1.5 volumes (packed cell volume) of hypotonic buffer (10 mM HEPES (KOH) pH 7.4; 15 mM KCl; 1.5 mM Mg(OAc) 2; 0.5 mM Pefabloc (Roche); 2 mM DTT). The cells were allowed to swell for 5 minutes on ice, dounce homogenized with 10 to 100 strokes using a tight-fitting pestle, and spun for 10 minutes at 12000×g at 4° C. in a Sorvall SS-34 rotor. The supernatant was collected with a Pasteur pipet without disturbing the lipid layer, transferred into Eppendorf tubes (50 to 200 ml aliquots), and immediately frozen in liquid nitrogen.

Footprinting

Ribosomes prepared from HeLa cells were incubated with the small molecules (at a concentration of 100 µM), followed by treatment with chemical modifying agents (dimethyl sulfate [DMS] and kethoxal [KE]). Following chemical modification, rRNA was phenol-chloroform extracted, ethanol precipitated, analyzed in primer extension reactions using end-labeled oligonucleotides hybridizing to different regions of the rRNAs and resolved on 6% polyacrylamide gels. The probes used for primer extension cover the entire 18S (7 oligonucleotide primers), 28S (24 oligonucleotide primers), and 5S (one primer) rRNAs are presented in Table 1 (also see, e.g., Gonzalez et al., 1985 Proc Natl Acad Sci USA. 82(22): 7666-70 and McCallum & Maden, 1985, Biochem. J. 232 (3): 725-733). Controls in these experiments include DMSO (a control for changes in rRNA accessibility induced by DMSO), paromomycin (a marker for 18S rRNA binding), and anisomycin (a marker for 28S rRNA binding).

TABLE 1

18S, 28S, and 5S rRNA primers

| 5S#1 | AAAGCCTACAGCACCC | SEQ ID NO.: 4 |
|---|---|---|
| 28S#1 | TACTGAGGGAATCCTGG | SEQ ID NO.: 5 |
| 28S#2 | TTACCACCCGCTTTGGG | SEQ ID NO.: 6 |
| 28S#3 | GGGGGCGGGAAAGATCC | SEQ ID NO.: 7 |
| 28S#4 | CCCCGAGCCACCTTCCC | SEQ ID NO.: 8 |
| 28S#5 | GGCCCCGGGATTCGGCG | SEQ ID NO.: 9 |
| 28S#6 | CACTGGGGACAGTCCGC | SEQ ID NO.: 10 |
| 28S#7 | CGCGGCGGGCGAGACGGG | SEQ ID NO.: 11 |
| 28S#8 | GAGGGAAACTTCGGAGGG | SEQ ID NO.: 12 |
| 28S#9 | CATCGGGCGCCTTAACCC | SEQ ID NO.: 13 |
| 28S#10 | CGACGCACACCACACGC | SEQ ID NO.: 14 |
| 28S#11 | CCAAGATCTGCACCTGC | SEQ ID NO.: 15 |
| 28S#12 | TTACCGCACTGGACGCG | SEQ ID NO.: 16 |
| 28S#13 | GCCAGAGGCTGTTCACC | SEQ ID NO.: 17 |
| 28S#14 | TGGGGAGGGAGCGAGCGGCG | SEQ ID NO.: 18 |
| 28S#15 | AAGGGCCCGGCTCGCGTCC | SEQ ID NO.: 19 |
| 28S#16 | AGGGCGGGGGACGAACCGC | SEQ ID NO.: 20 |
| 28S#17 | TTAAACAGTCGGATTCCCCTGG | SEQ ID NO.: 21 |
| 28S#18 | TTCATCCATTCATGCGCG | SEQ ID NO.: 22 |
| 28S#19 | AGTAGTGGTATTTCACCGG | SEQ ID NO.: 23 |
| 28S#20 | ACGGGAGGTTTCTGTCC | SEQ ID NO.: 24 |
| 28S#21 | ACAATGATAGGAAGAGCCG | SEQ ID NO.: 25 |

TABLE 1-continued 18S, 28S, and 5S rRNA primers

| 28S#22 | AGGCGTTCAGTCATAATCCC | SEQ ID NO.: 26 |
|---|---|---|
| 28S#23 | TCCGCACCGGACCCCGGTCC | SEQ ID NO.: 27 |
| 28S#24 | GGGCTAGTTGATTCGGCAGGTGAGTTG | SEQ ID NO.: 28 |
| 18S#1 | TCTCCGGAATCGAACCCT | SEQ ID NO.: 29 |
| 18S#2 | ATT ACC GCGGCTGCTGGC | SEQ ID NO.: 30 |
| 18S#3 | TTGGCAAATGCTTTCGC | SEQ ID NO.: 31 |
| 18S#4 | CCGTCAATTCCTTTAAGTTTC | SEQ ID NO.: 32 |
| 18S#5 | AGGGCATCACAGACCTGTTAT | SEQ ID NO.: 33 |
| 18S#6 | CGACGGGCGGTGTGTAC | SEQ ID NO.: 34 |
| 18S#7 | CCGCAGGTTCACCTACGG | SEQ ID NO.: 35 |

Results

The results of these foot-printing experiments (see, e.g., FIGS. 7 to 11) indicated that the small molecules involved in modulating translation termination alter the accessibility of the chemical modifying agents to specific nucleotides in the 28S rRNA. More specifically, the regions protected by the small molecules include a conserved region in the vicinity of the peptidyl transferase center (domain V, see, e.g., FIGS. 7 and 8) implicated in peptide bond formation and a conserved region in domain II (see, e.g. FIGS. 9, 10, and 11) that may interact with the peptidyl transferase center based on binding of vernamycin B to both these areas (Vannuffel et al., 1994, Nucleic Acids Res. 22(21):4449-53).

6.4 Example

High Throughput Identification of Compounds Using Arrays

To identify molecules of the invention, high throughput assays that enable each compound to be screened against many different nucleic acids in a parallel manner are used. In brief, synthesis beads, with compounds of the invention attached, are distributed into micro titer plates at a density of one bead per well. Compounds of the invention that are attached to the beads are then released from the beads and dissolved in a small amount of solvent in each microtiter well. A high precision technique, such as a robotic arrayer, is then used to transfer small volumes of solution containing dissolved compounds of the invention from each microtiter well, delivering the compounds to defined locations on glass slides. The glass slides are derivatized so that the compounds of the invention are immobilized on the surface of the slide. Each compound contains a functional group that allows for its immobilization on the glass slide. Each slide is then probed with a labeled RNA and binding events are detected by, e.g., a fluorescence-linked assay that is able to detect the label.

6.5 Example

Human Disease Genes Sorted by Chromosome

TABLE 2

| Genes, Locations and Genetic Disorders on Chromosome 1 | | |
|---|---|---|
| Gene | GDB Accession ID | OMIM Link |
| ABCA4 | GDB: 370748 | MACULAR DEGENERATION, SENILE STARGARDT DISEASE 1; STGD1 ATP BINDING CASSETTE TRANSPORTER; ABCR RETINITIS PIGMENTOSA-19; RP19 |
| ABCD3 | GDB: 131485 | PEROXISOMAL MEMBRANE PROTEIN 1; PXMP1 |
| ACADM | GDB: 118958 | ACYL-CoA DEHYDROGENASE, MEDIUM-CHAIN; ACADM |
| AGL | GDB: 132644 | GLYCOGEN STORAGE DISEASE III |
| AGT | GDB: 118750 | ANGIOTENSIN I; AGT |
| ALDH4A1 | GDB: 9958827 | HYPERPROLINEMIA, TYPE II |
| ALPL | GDB: 118730 | PHOSPHATASE, LIVER ALKALINE; ALPL HYPOPHOSPHATASIA, INFANTILE |
| AMPD1 | GDB: 119677 | ADENOSINE MONOPHOSPHATE DEAMINASE-1; AMPD1 |
| APOA2 | GDB: 119685 | APOLIPOPROTEIN A-II; APOA2 |
| AVSD1 | GDB: 265302 | ATRIOVENTRICULAR SEPTAL DEFECT; AVSD |
| BRCD2 | GDB: 9955322 | BREAST CANCER, DUCTAL, 2; BRCD2 |
| C1QA | GDB: 119042 | COMPLEMENT COMPONENT 1, q SUBCOMPONENT, ALPHA POLYPEPTIDE; C1QA |
| C1QB | GDB: 119043 | COMPLEMENT COMPONENT 1, q SUBCOMPONENT, BETA POLYPEPTIDE; C1QB |
| C1QG | GDB: 128132 | COMPLEMENT COMPONENT 1, q SUBCOMPONENT, GAMMA POLYPEPTIDE; C1QG |
| C8A | GDB: 119735 | COMPLEMENT COMPONENT-8, DEFICIENCY OF |
| C8B | GDB: 119736 | COMPLEMENT COMPONENT-8, DEFICIENCY OF, TYPE II |
| CACNA1S | GDB: 126431 | CALCIUM CHANNEL, VOLTAGE-DEPENDENT, L TYPE, ALPHA 1S SUBUNIT; CAGNA1S PERIODIC PARALYSIS I MALIGNANT HYPERTHERMIA SUSCEPTIBILITY-5; MHS5 |
| CCV | GDB: 1336655 | CATARACT, CONGENITAL, VOLKMANN TYPE; CCV |
| CD3Z | GDB: 119766 | CD3Z ANTIGEN, ZETA POLYPEPTIDE; CD3Z |
| CDC2L1 | GDB: 127827 | PROTEIN KINASE p58; PK58 |
| CHML | GDB: 135222 | CHOROIDEREMIA-LIKE; CHML |
| CHS1 | GDB: 4568202 | CHEDIAK-HIGASHI SYNDROME; CHS1 |
| CIAS1 | GDB: 9957338 | COLD HYPERSENSITIVITY URTICARIA, DEAFNESS, AND AMYLOIDOSIS |
| CLCNKB | GDB: 698472 | CHLORIDE CHANNEL, KIDNEY, B; CLCNKB |
| CMD1A | GDB: 434478 | CARDIOMYOPATHY, DILATED 1A; CMD1A |
| CMH2 | GDB: 137324 | CARDIOMYOPATHY, FAMILIAL HYPERTROPHIC, 2; CMH2 |
| CMM | GDB: 119059 | MELANOMA, MALIGNANT |
| COL11A1 | GDB: 120595 | COLLAGEN, TYPE XI, ALPHA-1; COL11A1 |
| COL9A2 | GDB: 138310 | COLLAGEN, TYPE IX, ALPHA-2 CHAIN; COL9A2 EPIPHYSEAL DYSPLASIA, MULTIPLE, 2; EDM2 |
| CPT2 | GDB: 127272 | MYOPATHY WITH DEFICIENCY OF CARNITINE PALMITOYLTRANSFERASE II HYPOGLYCEMIA, HYPOKETOTIC, WITH DEFICIENCY OF CARNITINE PALMITOYLTRANSFERASE CARNITINE PALMITOYLTRANSFERASE II; CPT2 |

TABLE 2-continued

Genes, Locations and Genetic Disorders on Chromosome 1

| Gene | GDB Accession ID | OMIM Link |
| --- | --- | --- |
| CRB1 | GDB: 333930 | RETINITIS PIGMENTOSA-12; RP12 |
| CSE | GDB: 596182 | CHOREOATHETOSIS/SPASTICITY, EPISODIC; CSE |
| CSF3R | GDB: 126430 | COLONY STIMULATING FACTOR 3 RECEPTOR, GRANULOCYTE; CSF3R |
| CTPA | GDB: 9863168 | CATARACT, POSTERIOR POLAR |
| CTSK | GDB: 453910 | PYCNODYSOSTOSIS CATHEPSIN K; CTSK |
| DBT | GDB: 118784 | MAPLE SYRUP URINE DISEASE, TYPE 2 |
| DIO1 | GDB: 136449 | THYROXINE DEIODINASE TYPE I; TXDI1 |
| DISC1 | GDB: 9992707 | DISORDER-2; SCZD2 |
| DPYD | GDB: 364102 | DIHYDROPYRIMIDINE DEHYDROGENASE; DPYD |
| EKV | GDB: 119106 | ERYTHROKERATODERMIA VARIABILIS; EKV |
| ENO1 | GDB: 119871 | PHOSPHOPYRUVATE HYDRATASE; PPH |
| ENO1P | GDB: 135006 | PHOSPHOPYRUVATE HYDRATASE; PPH |
| EPB41 | GDB: 119865 | ERYTHROCYTE MEMBRANE PROTEIN BAND 4.1; EPB41 HEREDITARY HEMOLYTIC |
| EPHX1 | GDB: 119876 | EPOXIDE HYDROLASE 1, MICROSOMAL; EPHX1 |
| F13B | GDB: 119893 | FACTOR XIII, B SUBUNIT; F13B |
| F5 | GDB: 119896 | FACTOR V DEFICIENCY |
| FCGR2A | GDB: 119903 | Fc FRAGMENT OF IgG, LOW AFFINITY IIa, RECEPTOR FOR; FCGR2A |
| FCGR2B | GDB: 128183 | Fc FRAGMENT OF IgG, LOW AFFINITY IIa, RECEPTOR FOR; FCGR2A |
| FCGR3A | GDB: 119904 | Fc FRAGMENT OF IgG, LOW AFFINITY IIIa, RECEPTOR FOR; FCGR3A |
| FCHL | GDB: 9837503 | HYPERLIPIDEMIA, COMBINED |
| FH | GDB: 119133 | FUMARATE HYDRATASE; FH LEIOMYOMATA, HEREDITARY MULTIPLE, OF SKIN |
| FMO3 | GDB: 135136 | FLAVIN-CONTAINING MONOOXYGENASE 3; FMO3 TRIMETHYLAMINURIA |
| FMO4 | GDB: 127981 | FLAVIN-CONTAINING MONOOXYGENASE 2; FMO2 |
| FUCA1 | GDB: 119237 | FUCOSIDOSIS |
| FY | GDB: 119242 | BLOOD GROUP - DUFFY SYSTEM; Fy |
| GALE | GDB: 119245 | GALACTOSE EPIMERASE DEFICIENCY |
| GBA | GDB: 119262 | GAUCHER DISEASE, TYPE I; GD I |
| GFND | GDB: 9958222 | GLOMERULAR NEPHRITIS, FAMILIAL, WITH FIBRONECTIN DEPOSITS |
| GJA8 | GDB: 696369 | CATARACT, ZONULAR PULVERULENT 1; CZP1 GAP JUNCTION PROTEIN, ALPHA-8, 50-KD; GJA8 |
| GJB3 | GDB: 127820 | ERYTHROKERATODERMIA VARIABILIS; EKV DEAFNESS, AUTOSOMAL DOMINANT NONSYNDROMIC SENSORINEURAL, 2; DFNA2 |
| GLC3B | GDB: 3801939 | GLAUCOMA 3, PRIMARY INFANTILE, B; GLC3B |
| HF1 | GDB: 120041 | H FACTOR 1; HF1 |
| HMGCL | GDB: 138445 | HYDROXYMETHYLGLUTARICACIDURIA; HMGCL |
| HPC1 | GDB: 5215209 | PROSTATE CANCER; PRCA1 PROSTATE CANCER, HEREDITARY 1 |
| HRD | GDB: 9862254 | HYPOPARATHYROIDISM WITH SHORT STATURE, MENTAL RETARDATION, AND SEIZURES |
| HRPT2 | GDB: 125253 | HYPERPARATHYROIDISM, FAMILIAL PRIMARY, WITH MULTIPLE OSSIFYING JAW |

TABLE 2-continued

Genes, Locations and Genetic Disorders on Chromosome 1

| Gene | GDB Accession ID | OMIM Link |
|---|---|---|
| HSD3B2 | GDB: 134044 | ADRENAL HYPERPLASIA II |
| HSPG2 | GDB: 126372 | HEPARAN SULFATE PROTEOGLYCAN OF BASEMENT MEMBRANE; HSPG2 MYOTONIC MYOPATHY, DWARFISM, CHONDRODYSTROPHY, AND OCULAR AND FACIAL |
| KCNQ4 | GDB: 439046 | DEAFNESS, AUTOSOMAL DOMINANT NONSYNDROMIC SENSORINEURAL, 2; DFNA2 |
| KCS | GDB: 9848740 | KENNY-CAFFEY SYNDROME, RECESSIVE FORM |
| KIF1B | GDB: 128645 | CHARCOT-MARIE-TOOTH DISEASE, NEURONAL TYPE, A; CMT2A |
| LAMB3 | GDB: 251820 | LAMININ, BETA 3; LAMB3 |
| LAMC2 | GDB: 136225 | LAMININ, GAMMA 2; LAMC2 EPIDERMOLYSIS BULLOSA LETALIS |
| LGMD1B | GDB: 231606 | MUSCULAR DYSTROPHY, LIMB-GIRDLE, TYPE 1B; LGMD1B |
| LMNA | GDB: 132146 | LAMIN A/C; LMNA LIPODYSTROPHY, FAMILIAL PARTIAL, DUNNIGAN TYPE; LDP1 |
| LOR | GDB: 132049 | LORICRIN; LOR |
| MCKD1 | GDB: 9859381 | POLYCYSTIC KIDNEYS, MEDULLARY TYPE |
| MCL1 | GDB: 139137 | MYELOID CELL LEUKEMIA 1; MCL1 |
| MPZ | GDB: 125266 | HYPERTROPHIC NEUROPATHY OF DEJERINE-SOTTAS MYELIN PROTEIN ZERO; MPZ |
| MTHFR | GDB: 370882 | 5,10-@METHYLENETETRAHYDROFOLATE REDUCTASE; MTHFR |
| MTR | GDB: 119440 | METHYLTETRAHYDROFOLATE:L-HOMOCYSTEINE S-METHYLTRANSFERASE; MTR |
| MUTYH | GDB: 9315115 | ADENOMATOUS POLYPOSIS OF THE COLON; APC |
| MYOC | GDB: 5584221 | GLAUCOMA 1, OPEN ANGLE; GLC1A MYOCILIN; MYOC |
| NB | GDB: 9958705 | NEUROBLASTOMA; NB |
| NCF2 | GDB: 120223 | GRANULOMATOUS DISEASE, CHRONIC, AUTOSOMAL CYTOCHROME-b-POSITIVE FORM |
| NEM1 | GDB: 127387 | NEMALINE MYOPATHY 1, AUTOSOMAL DOMINANT; NEM1 |
| NPHS2 | GDB: 9955617 | ARRHYTHMOGENIC RIGHT VENTRICULAR DYSPLASIA, FAMILIAL, 2; ARVD2 |
| NPPA | GDB: 118727 | NATRIURETIC PEPTIDE PRECURSOR A; NPPA |
| NRAS | GDB: 119457 | ONCOGENE NRAS; NRAS; NRAS1 |
| NTRK1 | GDB: 127897 | ONCOGENE TRK NEUROTROPHIC TYROSINE KINASE, RECEPTOR, TYPE 1; NTRK1 NEUROPATHY, CONGENITAL SENSORY, WITH ANHIDROSIS |
| OPTA2 | GDB: 9955577 | OSTEOPETROSIS, AUTOSOMAL DOMINANT, TYPE II; OPA2 |
| PBX1 | GDB: 125351 | PRE-B-CELL LEUKEMIA TRANSCRIPTION FACTOR-1; PBX1 |
| PCHC | GDB: 9955586 | PHEOCHROMOCYTOMA |
| PGD | GDB: 119486 | 6-@PHOSPHOGLUCONATE DEHYDROGENASE, ERYTHROCYTE |
| PHA2A | GDB: 9955628 | PSEUDOHYPOALDOSTERONISM, TYPE II; PHA2 |
| PHGDH | GDB: 9958261 | 3-@PHOSPHOGLYCERATE DEHYDROGENASE DEFICIENCY |
| PKLR | GDB: 120294 | PYRUVATE KINASE DEFICIENCY OF ERYTHROCYTE |
| PKP1 | GDB: 4249598 | PLAKOPHILIN 1; PKP1 |
| PLA2G2A | GDB: 120296 | PHOSPHOLIPASE A2, GROUP IIA; PLA2G2A |
| PLOD | GDB: 127821 | PROCOLLAGEN-LYSINE, 2-OXOGLUTARATE 5-DIOXYGENASE; PLOD EHLERS-DANLOS SYNDROME, TYPE VI; E-D VI; EDS VI |

TABLE 2-continued

Genes, Locations and Genetic Disorders on Chromosome 1

| Gene | GDB Accession ID | OMIM Link |
| --- | --- | --- |
| PPOX | GDB: 118852 | PROTOPORPHYRINOGEN OXIDASE; PPOX |
| PPT | GDB: 125227 | CEROID-LIPOFUSCINOSIS, NEURONAL 1, INFANTILE; CLN1 PALMITOYL-PROTEIN THIOESTERASE; PPT |
| PRCC | GDB: 3888215 | PAPILLARY RENAL CELL CARCINOMA; PRCC |
| PRG4 | GDB: 9955719 | ARTHROPATHY-CAMPTODACTYLY SYNDROME |
| PSEN2 | GDB: 633044 | ALZHEIMER DISEASE, FAMILIAL, TYPE 4; AD4 |
| PTOS1 | GDB: 6279920 | PTOSIS, HEREDITARY CONGENITAL 1; PTOS1 |
| REN | GDB: 120345 | RENIN; REN |
| RFX5 | GDB: 6288464 | REGULATORY FACTOR 5; RFX5 |
| RHD | GDB: 119551 | RHESUS BLOOD GROUP, D ANTIGEN; RHD |
| RMD1 | GDB: 448902 | RIPPLING MUSCLE DISEASE-1; RMD1 |
| RPE65 | GDB: 226519 | RETINAL PIGMENT EPITHELIUM-SPECIFIC PROTEIN, 65-KD; RPE65 AMAUROSIS CONGENITA OF LEBER II |
| SCCD | GDB: 9955558 | CORNEAL DYSTROPHY, CRYSTALLINE, OF SCHNYDER |
| SERPINC1 | GDB: 119024 | ANTITHROMBIN III DEFICIENCY |
| SJS1 | GDB: 1381631 | MYOTONIC MYOPATHY, DWARFISM, CHONDRODYSTROPHY, AND OCULAR AND FACIAL |
| SLC19A2 | GDB: 9837779 | THIAMINE-RESPONSIVE MEGALOBLASTIC ANEMIA SYNDROME |
| SLC2A1 | GDB: 120627 | SOLUTE CARRIER FAMILY 2, MEMBER 1; SLC2A1 |
| SPTA1 | GDB: 119601 | ELLIPTOCYTOSIS, RHESUS-UNLINKED TYPE HEREDITARY HEMOLYTIC SPECTRIN, ALPHA, ERYTHROCYTIC 1; SPTA1 |
| TAL1 | GDB: 120759 | T-CELL ACUTE LYMPHOCYTIC LEUKEMIA 1; TAL1 |
| TNFSF6 | GDB: 422178 | APOPTOSIS ANTIGEN LIGAND 1; APT1LG1 |
| TNNT2 | GDB: 221879 | TROPONIN-T2, CARDIAC; TNNT2 |
| TPM3 | GDB: 127872 | ONCOGENE TRK TROPOMYOSIN 3; TPM3 |
| TSHB | GDB: 120467 | THYROID-STIMULATING HORMONE, BETA CHAIN; TSHB |
| UMPK | GDB: 120481 | URIDINE MONOPHOSPHATE KINASE; UMPK |
| UOX | GDB: 127539 | URATE OXIDASE; UOX |
| UROD | GDB: 119628 | PORPHYRIA CUTANEA TARDA; PCT |
| USH2A | GDB: 120483 | USHER SYNDROME, TYPE II; USH2 |
| VMGLOM | GDB: 9958134 | GLOMUS TUMORS, MULTIPLE |
| VWS | GDB: 120532 | CLEFT LIP AND/OR PALATE WITH MUCOUS CYSTS OF LOWER LIP |
| WS2B | GDB: 407579 | WAARDENBURG SYNDROME, TYPE 2B; WS2B |

TABLE 3

Genes, Locations and Genetic Disorders on Chromosome 2

| Gene | GDB Accession ID | Location | OMIM Link |
| --- | --- | --- | --- |
| ABCB11 | GDB: 9864786 | 2q24-2q24 2q24.3-2q24.3 | CHOLESTASIS, PROGRESSIVE FAMILIAL INTRAHEPATIC 2; PFIC2 |
| ABCG5 | GDB: 10450298 | 2p21-2p21 | PHYTOSTEROLEMIA |
| ABCG8 | GDB: 10450300 | 2p21-2p21 | PHYTOSTEROLEMIA |

TABLE 3-continued

Genes, Locations and Genetic Disorders on Chromosome 2

| Gene | GDB Accession ID | Location | OMIM Link |
|---|---|---|---|
| ACADL | GDB: 118745 | 2q34-2q35 | ACYL-CoA DEHYDROGENASE, LONG-CHAIN, DEFICIENCY OF |
| ACP1 | GDB: 118962 | 2p25-2p25 | PHOSPHATASE, ACID, OF ERYTHROCYTE; ACP1 |
| AGXT | GDB: 127113 | 2q37.3-2q37.3 | OXALOSIS I |
| AHHR | GDB: 118984 | 2pter-2q31 | CYTOCHROME P450, SUBFAMILY I, POLYPEPTIDE 1; CYP1A1 |
| ALMS1 | GDB: 9865539 | 2p13-2p12 2p14-2p13 2p13.1-2p13.1 | ALSTROM SYNDROME |
| ALPP | GDB: 119672 | 2q37.1-2q37.1 | ALKALINE PHOSPHATASE, PLACENTAL; ALPP |
| ALS2 | GDB: 135696 | 2q33-2q35 | AMYOTROPHIC LATERAL SCLEROSIS 2, JUVENILE; ALS2 |
| APOB | GDB: 119686 | 2p24-2p23 2p24-2p24 | APOLIPOPROTEIN B; APOB |
| BDE | GDB: 9955730 | 2q37-2q37 | BRACHYDACTYLY, TYPE E; BDE |
| BDMR | GDB: 533064 | 2q37-2q37 | BRACHYDACTYLY-MENTAL RETARDATION SYNDROME; BDMR |
| BJS | GDB: 9955717 | 2q34-2q36 | TORTI AND NERVE DEAFNESS |
| BMPR2 | GDB: 642243 | 2q33-2q33 2q33-2q34 | PULMONARY HYPERTENSION, PRIMARY; PPH1 BONE MORPHOGENETIC RECEPTOR TYPE II; BMPR2 |
| CHRNA1 | GDB: 120586 | 2q24-2q32 | CHOLINERGIC RECEPTOR, NICOTINIC, ALPHA POLYPEPTIDE 1; CHRNA1 |
| CMCWTD | GDB: 11498919 | 2p22.3-2p21 | FAMILIAL CHRONIC MUCOCUTANEOUS, DOMINANT TYPE |
| CNGA3 | GDB: 434398 | 2q11.2-2q11.2 | COLORBLINDNESS, TOTAL CYCLIC NUCLEOTIDE GATED CHANNEL, OLFACTORY, 3; CNG3 |
| COL3A1 | GDB: 118729 | 2q31-2q32.3 2q32.2-2q32.2 | COLLAGEN, TYPE III; COL3A1 EHLERS-DANLOS SYNDROME, TYPE IV, AUTOSOMAL DOMINANT |
| COL4A3 | GDB: 128351 | 2q36-2q37 | COLLAGEN, TYPE IV, ALPHA-3 CHAIN; COL4A3 |
| COL4A4 | GDB: 132673 | 2q35-2q37 | COLLAGEN, TYPE IV, ALPHA-4 CHAIN; COL4A4 |
| COL6A3 | GDB: 119066 | 2q37.3-2q37.3 | COLLAGEN, TYPE VI, ALPHA-3 CHAIN; COL6A3 MYOPATHY, BENIGN CONGENITAL, WITH CONTRACTURES |
| CPS1 | GDB: 119799 | 2q33-2q36 2q34-2q35 2q35-2q35 | HYPERAMMONEMIA DUE TO CARBAMOYLPHOSPHATE SYNTHETASE I DEFICIENCY |
| CRYGA | GDB: 119076 | 2q33-2q35 | CRYSTALLIN, GAMMA A; CRYGA |
| CRYGEP1 | GDB: 119808 | 2q33-2q35 | CRYSTALLIN, GAMMA A; CRYGA |
| CYP1B1 | GDB: 353515 | 2p21-2p21 2p22-2p21 2pter-2qter | GLAUCOMA 3, PRIMARY INFANTILE, A; GLC3A CYTOCHROME P450, SUBFAMILY I (DIOXIN-INDUCIBLE), POLYPEPTIDE 1; CYP1B1 |
| CYP27A1 | GDB: 128129 | 2q33-2qter | CEREBROTENDINOUS XANTHOMATOSIS |
| DBI | GDB: 119837 | 2q12-2q21 | DIAZEPAM BINDING INHIBITOR; DBI |
| DES | GDB: 119841 | 2q35-2q35 | DESMIN; DES |
| DYSF | GDB: 340831 | 2p-2p 2p13-2p13 2pter-2p12 | MUSCULAR DYSTROPHY, LIMB-GIRDLE, TYPE 2B; LGMD2B MUSCULAR DYSTROPHY, LATE-ONSET DISTAL |

TABLE 3-continued

Genes, Locations and Genetic Disorders on Chromosome 2

| Gene | GDB Accession ID | Location | OMIM Link |
|---|---|---|---|
| EDAR | GDB: 9837372 | 2q11-2q13 | DYSPLASIA, HYPOHIDROTIC ECTODERMAL DYSPLASIA, ANHIDROTIC |
| EFEMP1 | GDB: 1220111 | 2p16-2p16 | DOYNE HONEYCOMB DEGENERATION OF RETINA FIBRILLIN-LIKE; FBNL |
| EIF2AK3 | GDB: 9956743 | 2p12-2p12 | EPIPHYSEAL DYSPLASIA, MULTIPLE, WITH EARLY-ONSET DIABETES MELLITUS |
| ERCC3 | GDB: 119881 | 2q21-2q21 | EXCISION-REPAIR, COMPLEMENTING DEFECTIVE, IN CHINESE HAMSTER; 3; ERCC3 |
| FSHR | GDB: 127510 | 2p21-2p16 | FOLLICLE-STIMULATING HORMONE RECEPTOR; FSHR GONADAL DYSGENESIS, XX TYPE |
| GAD1 | GDB: 119244 | 2q31-2q31 | PYRIDOXINE DEPENDENCY WITH SEIZURES |
| GINGF | GDB: 9848875 | 2p21-2p21 | GINGIVAL SON OF SEVENLESS (*DROSOPHILA*) HOMOLOG 1; SOS1 |
| GLC1B | GDB: 1297553 | 2q1-2q13 | GLAUCOMA 1, OPEN ANGLE, B; GLC1B |
| GPD2 | GDB: 354558 | 2q24.1-2q24.1 | GLYCEROL-3-PHOSPHATE DEHYDROGENASE-2; GPD2 |
| GYPC | GDB: 120027 | 2q14-2q21 | BLOOD GROUP - GERBICH; Ge |
| HADHA | GDB: 434026 | 2p23-2p23 | HYDROXYACYL-CoA DEHYDROGENASE/3-KETOACYL-CoA THIOLASE/ENOYL-CoA HYDRATASE, |
| HADHB | GDB: 344953 | 2p23-2p23 | HYDROXYACYL-CoA DEHYDROGENASE/3-KETOACYL-CoA THIOLASE/ENOYL-CoA HYDRATASE, |
| HOXD13 | GDB: 127225 | 2q31-2q31 | HOMEO BOX-D13; HOXD13 SYNDACTYLY, TYPE II |
| HPE2 | GDB: 136066 | 2p21-2p21 | MIDLINE CLEFT SYNDROME |
| IGKC | GDB: 120088 | 2p12-2p12 2p11.2-2p11.2 | IMMUNOGLOBULIN KAPPA CONSTANT REGION; IGKC |
| IHH | GDB: 511203 | 2q33-2q35 2q35-2q35 2pter-2qter | BRACHYDACTYLY, TYPE A1; BDA1 INDIAN HEDGEHOG, *DROSOPHILA*, HOMOLOG OF; IHH |
| IRS1 | GDB: 133974 | 2q36-2q36 | INSULIN RECEPTOR SUBSTRATE 1; IRS1 |
| ITGA6 | GDB: 128027 | 2pter-2qter | INTEGRIN, ALPHA-6; ITGA6 |
| KHK | GDB: 391903 | 2p23.3-2p23.2 | FRUCTOSURIA |
| KYNU | GDB: 9957925 | 2q22.2-2q23.3 | |
| LCT | GDB: 120140 | 2q21-2q21 | DISACCHARIDE INTOLERANCE II |
| LHCGR | GDB: 125260 | 2p21-2p21 | LUTEINIZING HORMONE/CHORIOGONADOTROPIN RECEPTOR; LHCGR |
| LSFC | GDB: 9956219 | 2-2 2p16-2p16 | CYTOCHROME c OXIDASE DEFICIENCY, FRENCH-CANADIAN TYPE |
| MSH2 | GDB: 203983 | 2p16-2p16 2p22-2p21 | COLON CANCER, FAMILIAL, NONPOLYPOSIS TYPE 1; FCC1 |
| MSH6 | GDB: 632803 | 2p16-2p16 | G/T MISMATCH-BINDING PROTEIN; GTBP |
| NEB | GDB: 120224 | 2q24.1-2q24.2 | NEBULIN; NEB NEMALINE MYOPATHY 2, AUTOSOMAL RECESSIVE; NEM2 |
| NMTC | GDB: 11498336 | 2q21-2q21 | THYROID CARCINOMA, PAPILLARY |
| NPHP1 | GDB: 128050 | 2q13-2q13 | NEPHRONOPHTHISIS, FAMILIAL JUVENILE 1; NPHP1 |
| PAFAH1P1 | GDB: 435099 | 2p11.2-2p11.2 | PLATELET-ACTIVATING FACTOR ACETYLHYDROLASE, GAMMA SUBUNIT |

TABLE 3-continued

Genes, Locations and Genetic Disorders on Chromosome 2

| Gene | GDB Accession ID | Location | OMIM Link |
|---|---|---|---|
| PAX3 | GDB: 120495 | 2q36-2q36<br>2q35-2q35 | KLEIN-WAARDENBURG SYNDROME WAARDENBURG SYNDROME; WS1 |
| PAX8 | GDB: 136447 | 2q12-2q14 | PAIRED BOX HOMEOTIC GENE 8; PAX8 |
| PMS1 | GDB: 386403 | 2q31-2q33 | POSTMEIOTIC SEGREGATION INCREASED (*S. CEREVISIAE*)-1; PMS1 |
| PNKD | GDB: 5583973 | 2q33-2q35 | CHOREOATHETOSIS, FAMILIAL PAROXYSMAL; FPD1 |
| PPH1 | GDB: 1381541 | 2q31-2q32<br>2q33-2q33 | PULMONARY HYPERTENSION, PRIMARY; PPH1 |
| PROC | GDB: 120317 | 2q13-2q21<br>2q13-2q14 | PROTEIN C DEFICIENCY, CONGENITAL THROMBOTIC DISEASE DUE TO |
| REG1A | GDB: 132455 | 2p12-2p12 | REGENERATING ISLET-DERIVED 1-ALPHA; REG1A |
| SAG | GDB: 120365 | 2q37.1-2q37.1 | S-ANTIGEN; SAG |
| SFTPB | GDB: 120374 | 2p12-2p11.2 | SURFACTANT-ASSOCIATED PROTEIN, PULMONARY-3; SFTP3 |
| SLC11A1 | GDB: 371444 | 2q35-2q35 | CIRRHOSIS, PRIMARY; PBC NATURAL RESISTANCE-ASSOCIATED MACROPHAGE PROTEIN 1; NRAMP1 |
| SLC3A1 | GDB: 202968 | 2p16.3-2p16.3<br>2p21-2p21 | SOLUTE CARRIER FAMILY 3, MEMBER 1; SLC3A1 CYSTINURIA; CSNU |
| SOS1 | GDB: 230004 | 2p22-2p21 | GINGIVAL SON OF SEVENLESS (*DROSOPHILA*) HOMOLOG 1; SOS1 |
| SPG4 | GDB: 230127 | 2p24-2p21 | SPASTIC PARAPLEGIA-4, AUTOSOMAL DOMINANT; SPG4 |
| SRD5A2 | GDB: 127343 | 2p23-2p23 | PSEUDOVAGINAL PERINEOSCROTAL HYPOSPADIAS; PPSH |
| TCL4 | GDB: 136378 | 2q34-2q34 | T-CELL LEUKEMIA/LYMPHOMA-4; TCL4 |
| TGFA | GDB: 120435 | 2p13-2p13 | TRANSFORMING GROWTH FACTOR, ALPHA; TGFA |
| TMD | GDB: 9837196 | 2q31-2q31 | TIBIAL MUSCULAR DYSTROPHY, TARDIVE |
| TPO | GDB: 120446 | 2p25-2p25<br>2p25-2p24 | THYROID HORMONOGENESIS, GENETIC DEFECT IN, IIA |
| UGT1 | GDB: 120007 | 2q37-2q37 | UDP GLUCURONOSYLTRANSFERASE 1 FAMILY, A1; UGT1A1 |
| UV24 | GDB: 9955737 | 2pter-2qter | UV-DAMAGE, EXCISION REPAIR OF, UV-24 |
| WSS | GDB: 9955707 | 2q32-2q32 | WRINKLY SKIN SYNDROME; WSS |
| XDH | GDB: 266386 | 2p23-2p22 | XANTHINURIA |
| ZAP70 | GDB: 433738 | 2q11-2q13<br>2q12-2q12 | SYK-RELATED TYROSINE KINASE; SRK |
| ZFHX1B | GDB: 9958310 | 2q22-2q22 | DISEASE, MICROCEPHALY, AND IRIS COLOBOMA |

TABLE 4

Genes, Locations and Genetic Disorders on Chromosome 3

| Gene | GDB Accession ID | Location | OMIM Link |
|---|---|---|---|
| ACAA1 | GDB: 119643 | 3p23–3p22 | PEROXISOMAL 3-OXOACYL-COENZYME A THIOLASE DEFICIENCY |
| AGTR1 | GDB: 132359 | 3q21–3q25 | ANGIOTENSIN II RECEPTOR, VASCULAR TYPE 1; AT2R1 |
| AHSG | GDB: 118985 | 3q27–3q27 | ALPHA-2-HS-GLYCOPROTEIN; AHSG |
| AMT | GDB: 132138 | 3p21.3–3p21.2 3p21.2–3p21.1 | HYPERGLYCINEMIA, ISOLATED NONKETOTIC, TYPE II; NKH2 |
| ARP | GDB: 9959049 | 3p21.1–3p21.1 | ARGININE-RICH PROTEIN |
| BBS3 | GDB: 376501 | 3p–3p 3p12.3–3q11.1 | BARDET-BIEDL SYNDROME, TYPE 3; BBS3 |
| BCHE | GDB: 120558 | 3q26.1–3q26.2 | BUTYRYLCHOLINESTERASE; BCHE |
| BCPM | GDB: 433809 | 3q21–3q21 | BENIGN CHRONIC PEMPHIGUS; BCPM |
| BTD | GDB: 309078 | 3p25–3p25 | BIOTINIDASE; BTD |
| CASR | GDB: 134196 | 3q21–3q24 | HYPOCALCIURIC HYPERCALCEMIA, FAMILIAL; HHC1 |
| CCR2 | GDB: 337364 | 3p21–3p21 | CHEMOKINE (C—C) RECEPTOR 2; CMKBR2 |
| CCR5 | GDB: 1230510 | 3p21–3p21 | CHEMOKINE (C—C) RECEPTOR 5; CMKBR5 |
| CDL1 | GDB: 136344 | 3q26.3–3q26.3 | DE LANGE SYNDROME; CDL |
| CMT2B | GDB: 604021 | 3q13–3q22 | CHARCOT-MARIE-TOOTH DISEASE, NEURONAL TYPE, B; CMT2B |
| COL7A1 | GDB: 128750 | 3p21–3p21 3p21.3–3p21.3 | COLLAGEN, TYPE VII, ALPHA-1; COL7A1 |
| CP | GDB: 119069 | 3q23–3q25 3q21–3q24 | CERULOPLASMIN; CP |
| CRV | GDB: 11498333 | 3p21.3–3p21.1 | VASCULOPATHY, RETINAL, WITH CEREBRAL LEUKODYSTROPHY |
| CTNNB1 | GDB: 141922 | 3p22–3p22 3p21.3–3p21.3 | CATENIN, BETA 1; CTNNB1 |
| DEM | GDB: 681157 | 3p12–3q11 | DEMENTIA, FAMILIAL NONSPECIFIC; DEM |
| ETM1 | GDB: 9732523 | 3q13–3q13 | TREMOR, HEREDITARY ESSENTIAL 1; ETM1 |
| FANCD2 | GDB: 698345 | 3p25.3–3p25.3 3pter–3p24.2 | FANCONI PANCYTOPENIA, COMPLEMENTATION GROUP D |
| FIH | GDB: 9955790 | 3q13–3q13 | HYPOPARATHYROIDISM, FAMILIAL ISOLATED; FIH |
| FOXL2 | GDB: 129025 | 3q23–3q23 3q22–3q23 | BLEPHAROPHIMOSIS, EPICANTHUS INVERSUS, AND PTOSIS; BPES |
| GBE1 | GDB: 138442 | 3p12–3p12 | GLYCOGEN STORAGE DISEASE IV |
| GLB1 | GDB: 119987 | 3p22–3p21.33 3p21.33–3p21.33 | GANGLIOSIDOSIS, GENERALIZED GM1, TYPE I |
| GLC1C | GDB: 3801941 | 3q21–3q24 | GLAUCOMA 1, OPEN ANGLE, C; GLC1C |
| GNAI2 | GDB: 120516 | 3p21.3–3p21.2 | GUANINE NUCLEOTIDE-BINDING PROTEIN, ALPHA-INHIBITING, POLYPEPTIDE-2; |
| GNAT1 | GDB: 119277 | 3p21.3–3p21.2 | GUANINE NUCLEOTIDE-BINDING PROTEIN, ALPHA-TRANSDUCING, POLYPEPTIDE |
| GP9 | GDB: 126370 | 3pter–3qter | PLATELET GLYCOPROTEIN IX; GP9 |
| GPX1 | GDB: 119282 | 3q11–3q12 3p21.3–3p21.3 | GLUTATHIONE PEROXIDASE; GPX1 |
| HGD | GDB: 203935 | 3q21–3q23 | ALKAPTONURIA; AKU |
| HRG | GDB: 120055 | 3q27–3q27 | HISTIDINE-RICH GLYCOPROTEIN; HRG; HRGP |
| ITIH1 | GDB: 120107 | 3p21.2–3p21.1 | INTER-ALPHA-TRYPSIN INHIBITOR, HEAVY CHAIN-1; ITIH1; IATIH; ITIH |
| KNG | GDB: 125256 | 3q27–3q27 | FLAUJEAC FACTOR DEFICIENCY |

TABLE 4-continued

Genes, Locations and Genetic Disorders on Chromosome 3

| Gene | GDB Accession ID | Location | OMIM Link |
| --- | --- | --- | --- |
| LPP | GDB: 1391795 | 3q27–3q28 | LIM DOMAIN-CONTAINING PREFERRED TRANSLOCATION PARTNER IN LIPOMA; LPP |
| LRS1 | GDB: 682448 | 3p21.1–3p14.1 | LARSEN SYNDROME, AUTOSOMAL DOMINANT; LRS1 |
| MCCC1 | GDB: 135989 | 3q27–3q27 3q25–3q27 | BETA-METHYLCROTONYLGLYCINURIA I |
| MDS1 | GDB: 250411 | 3q26–3q26 | MYELODYSPLASIA SYNDROME 1; MDS1 |
| MHS4 | GDB: 574245 | 3q13.1–3q13.1 | HYPERTHERMIA SUSCEPTIBILITY-4; MHS4 |
| MITF | GDB: 214776 | 3p14.1–3p12 | MICROPHTHALMIA-ASSOCIATED TRANSCRIPTION FACTOR; MITF WAARDENBURG SYNDROME, TYPE II; WS2 |
| MLH1 | GDB: 249617 | 3p23–3p22 3p21.3–3p21.3 | COLON CANCER, FAMILIAL, NONPOLYPOSIS TYPE 2; FCC2 |
| MYL3 | GDB: 120218 | 3p21.3–3p21.2 | MYOSIN, LIGHT CHAIN, ALKALI, VENTRICULAR AND SKELETAL SLOW; MYL3 |
| MYMY | GDB: 11500610 | 3p26–3p24.2 | DISEASE |
| OPA1 | GDB: 118848 | 3q28–3q29 | OPTIC ATROPHY 1; OPA1 |
| PBXP1 | GDB: 125352 | 3q22–3q23 | PRE-B-CELL LEUKEMIA TRANSCRIPTION FACTOR-1; PBX1 |
| PCCB | GDB: 119474 | 3q21–3q22 | GLYCINEMIA, KETOTIC, II |
| POU1F1 | GDB: 129070 | 3p11–3p11 | POU DOMAIN, CLASS 1, TRANSCRIPTION FACTOR 1; POU1F1 |
| PPARG | GDB: 1223810 | 3p25–3p25 | CANCER OF COLON PEROXISOME PROLIFERATOR ACTIVATED RECEPTOR, GAMMA; PPARG |
| PROS1 | GDB: 120721 | 3p11–3q11 3p11.1–3q11.2 | PROTEINS, ALPHA; PROS1 |
| PTHR1 | GDB: 138128 | 3p22–3p21.1 | METAPHYSEAL CHONDRODYSPLASIA, MURK JANSEN TYPE PARATHYROID HORMONE RECEPTOR 1; PTHR1 |
| RCA1 | GDB: 230233 | 3p14.2–3p14.2 | RENAL CARCINOMA, FAMILIAL, ASSOCIATED 1; RCA1 |
| RHO | GDB: 120347 | 3q21.3–3q24 | RHODOPSIN; RHO |
| SCA7 | GDB: 454471 | 3p21.1–3p12 | SPINOCEREBELLAR ATAXIA 7; SCA7 |
| SCLC1 | GDB: 9955750 | 3p23–3p21 | SMALL-CELL CANCER OF THE LUNG; SCCL |
| SCN5A | GDB: 132152 | 3p21–3p21 | SODIUM CHANNEL, VOLTAGE-GATED, TYPE V, ALPHA POLYPEPTIDE; SCN5A |
| SI | GDB: 120377 | 3q25.2–3q26.2 | DISACCHARIDE INTOLERANCE I |
| SLC25A20 | GDB: 6503297 | 3p21.31–3p21.31 | CARNITINE-ACYLCARNITINE TRANSLOCASE; CACT |
| SLC2A2 | GDB: 119995 | 3q26.2–3q27 3q26.1–3q26.3 | SOLUTE CARRIER FAMILY 2, MEMBER 2; SLC2A2 FANCONI-BICKEL SYNDROME; FBS |
| TF | GDB: 120432 | 3q21–3q21 | TRANSFERRIN; TF |
| TGFBR2 | GDB: 224909 | 3p22–3p22 3pter–3p24.2 | TRANSFORMING GROWTH FACTOR-BETA RECEPTOR, TYPE II; TGFBR2 |
| THPO | GDB: 374007 | 3q26.3–3q27 | THROMBOPOIETIN; THPO |
| THRB | GDB: 120731 | 3p24.1–3p22 3p24.3–3p24.3 | THYROID HORMONE RECEPTOR, BETA; THRB |
| TKT | GDB: 132402 | 3p14.3–3p14.3 | WERNICKE-KORSAKOFF SYNDROME |
| TM4SF1 | GDB: 250815 | 3q21–3q25 | TUMOR-ASSOCIATED ANTIGEN L6; TAAL6 |
| TRH | GDB: 128072 | 3pter–3qter | THYROTROPIN-RELEASING HORMONE DEFICIENCY |
| UMPS | GDB: 120482 | 3q13–3q13 | OROTICACIDURIA I |
| UQCRC1 | GDB: 141850 | 3p21.3–3p21.2 3p21.3–3p21.3 | UBIQUINOL-CYTOCHROME c REDUCTASE CORE PROTEIN I; UQCRC1 |
| USH3A | GDB: 392645 | 3q21–3q25 | USHER SYNDROME, TYPE III; USH3 |

TABLE 4-continued

Genes, Locations and Genetic Disorders on Chromosome 3

| Gene | GDB Accession ID | Location | OMIM Link |
| --- | --- | --- | --- |
| VHL | GDB: 120488 | 3p26–3p25 | VON HIPPEL-LINDAU SYNDROME; VHL |
| WS2A | GDB: 128053 | 3p14.2–3p13 | MICROPHTHALMIA-ASSOCIATED TRANSCRIPTION FACTOR; MITF WAARDENBURG SYNDROME, TYPE II; WS2 |
| XPC | GDB: 134769 | 3p25.1–3p25.1 | XERODERMA PIGMENTOSUM, COMPLEMENTATION GROUP C; XPC |
| ZNF35 | GDB: 120507 | 3p21–3p21 | ZINC FINGER PROTEIN-35; ZNF35 |

TABLE 5

Genes, Locations and Genetic Disorders on Chromosome 4

| Gene | GDB Accession ID | Location | OMIM Link |
| --- | --- | --- | --- |
| ADH1B | GDB: 119651 | 4q21–4q23 4q22–4q22 | ALCOHOL DEHYDROGENASE-2; ADH2 |
| ADH1C | GDB: 119652 | 4q21–4q23 4q22–4q22 | ALCOHOL DEHYDROGENASE-3; ADH3 |
| AFP | GDB: 119660 | 4q11–4q13 | ALPHA-FETOPROTEIN; AFP |
| AGA | GDB: 118981 | 4q23–4q35 4q32–4q33 | ASPARTYLGLUCOSAMINURIA; AGU |
| AIH2 | GDB: 118751 | 4q11–4q13 4q13.3–4q21.2 | AMELOGENESIS IMPERFECTA 2, HYPOPLASTIC LOCAL, AUTOSOMAL DOMINANT; |
| ALB | GDB: 118990 | 4q11–4q13 | ALBUMIN; ALB |
| ASMD | GDB: 119705 | 4q–4q 4q28–4q31 | ANTERIOR SEGMENT OCULAR DYSGENESIS; ASOD |
| BFHD | GDB: 11498907 | 4q34.1–4q35 | DYSPLASIA, BEUKES TYPE |
| CNGA1 | GDB: 127557 | 4p14–4q13 | CYCLIC NUCLEOTIDE GATED CHANNEL, PHOTORECEPTOR, cGMP GATED, 1; CNCG1 |
| CRBM | GDB: 9958132 | 4p16.3–4p16.3 | CHERUBISM |
| DCK | GDB: 126810 | 4q13.3–4q21.1 | DEOXYCYTIDINE KINASE; DCK |
| DFNA6 | GDB: 636175 | 4p16.3–4p16.3 | DEAFNESS, AUTOSOMAL DOMINANT NONSYNDROMIC SENSORINEURAL, 6; DFNA6 |
| DSPP | GDB: 5560457 | 4pter–4qter 4q21.3–4q21.3 | DENTIN PHOSPHOPROTEIN; DPP DENTINOGENESIS IMPERFECTA; DGI1 |
| DTDP2 | GDB: 9955810 | 4q–4q | DENTIN DYSPLASIA, TYPE II |
| ELONG | GDB: 11498700 | 4q24–4q24 | |
| ENAM | GDB: 9955259 | 4q21–4q21 | AMELOGENESIS IMPERFECTA 2, HYPOPLASTIC LOCAL, AUTOSOMAL DOMINANT; AMELOGENESIS IMPERFECTA, HYPOPLASTIC TYPE |
| ETFDH | GDB: 135992 | 4q32–4q35 | GLUTARICACIDURIA IIC; GA IIC |
| EVC | GDB: 555573 | 4p16–4p16 | ELLIS-VAN CREVELD SYNDROME; EVC |
| F11 | GDB: 119891 | 4q35–4q35 | PTA DEFICIENCY |
| FABP2 | GDB: 119127 | 4q28–4q31 | FATTY ACID BINDING PROTEIN 2, INTESTINAL; FABP2 |
| FGA | GDB: 119129 | 4q28–4q28 | AMYLOIDOSIS, FAMILIAL VISCERAL FIBRINOGEN, A ALPHA POLYPEPTIDE; FGA |
| FGB | GDB: 119130 | 4q28–4q28 | FIBRINOGEN, B BETA POLYPEPTIDE; FGB |
| FGFR3 | GDB: 127526 | 4p16.3–4p16.3 | ACHONDROPLASIA; ACH BLADDER CANCER FIBROBLAST GROWTH FACTOR RECEPTOR-3; FGFR3 |
| FGG | GDB: 119132 | 4q28–4q28 | FIBRINOGEN, G GAMMA POLYPEPTIDE; FGG |
| FSHMD1A | GDB: 119914 | 4q35–4q35 | FACIOSCAPULOHUMERAL MUSCULAR DYSTROPHY 1A; FSHMD1A |

TABLE 5-continued

Genes, Locations and Genetic Disorders on Chromosome 4

| Gene | GDB Accession ID | Location | OMIM Link |
|---|---|---|---|
| GC | GDB: 119263 | 4q12–4q13<br>4q12–4q12 | GROUP-SPECIFIC COMPONENT; GC |
| GNPTA | GDB: 119280 | 4q21–4q23 | MUCOLIPIDOSIS II; ML2; ML II |
| GNRHR | GDB: 136456 | 4q13–4q13<br>4q21.2–4q21.2 | GONADOTROPIN-RELEASING HORMONE RECEPTOR; GNRHR |
| GYPA | GDB: 118890 | 4q28–4q31<br>4q28.2–4q31.1 | BLOOD GROUP - MN LOCUS; MN |
| HCA | GDB: 9954675 | 4q33–4qter | HYPERCALCIURIA, FAMILIAL IDIOPATHIC |
| HCL2 | GDB: 119305 | 4q28–4q31 4q–4q | HAIR COLOR-2; HCL2 |
| HD | GDB: 119307 | 4p16.3–4p16.3 | HUNTINGTON DISEASE; HD |
| HTN3 | GDB: 125601 | 4q12–4q21 | HISTATIN-3; HTN3 |
| HVBS6 | GDB: 120687 | 4q32–4q32 | HEPATOCELLULAR CARCINOMA-2; HCC2 |
| IDUA | GDB: 119327 | 4p16.3–4p16.3 | MUCOPOLYSACCHARIDOSIS TYPE I; MPS I |
| IF | GDB: 120077 | 4q24–4q25<br>4q25–4q25 | COMPLEMENT COMPONENT-3 INACTIVATOR, DEFICIENCY OF |
| JPD | GDB: 120113 | 4pter–4qter<br>4q12–4q13 | PERIODONTITIS, JUVENILE; JPD |
| KIT | GDB: 120117 | 4q12–4q12 | V-KIT HARDY-ZUCKERMAN 4 FELINE SARCOMA VIRAL ONCOGENE HOMOLOG; KIT |
| KLKB1 | GDB: 127575 | 4q34–4q35<br>4q35–4q35 | FLETCHER FACTOR DEFICIENCY |
| LQT4 | GDB: 682072 | 4q25–4q27 | SYNDROME WITHOUT PSYCHOMOTOR RETARDATION |
| MANBA | GDB: 125261 | 4q21–4q25 | MANNOSIDOSIS, BETA; MANB1 |
| MLLT2 | GDB: 136792 | 4q21–4q21 | MYELOID/LYMPHOID OR MIXED LINEAGE LEUKEMIA, TRANSLOCATED TO, 2; MLLT2 |
| MSX1 | GDB: 120683 | 4p16.3–4p16.1<br>4p16.1–4p16.1 | MSH, *DROSOPHILA*, HOMEO BOX, HOMOLOG OF, 1; MSX1 |
| MTP | GDB: 228961 | 4q24–4q24 | MICROSOMAL TRIGLYCERIDE TRANSFER PROTEIN, 88 KD; MTP |
| NR3C2 | GDB: 120188 | 4q31–4q31<br>4q31.1–4q31.1 | PSEUDOHYPOALDOSTERONISM, TYPE I, AUTOSOMAL RECESSIVE; PHA1 |
| PBT | GDB: 120260 | 4q12–4q21 | PIEBALD TRAIT; PBT |
| PDE6B | GDB: 125915 | 4p16.3–4p16.3 | NIGHTBLINDNESS, CONGENITAL STATIONARY; CSNB3 PHOSPHODIESTERASE 6B, cGMP-SPECIFIC, ROD, BETA; PDE6B |
| PEE1 | GDB: 7016765 | 4q31–4q34<br>4q25–4qter | 1; PEE1 |
| PITX2 | GDB: 134770 | 4q25–4q27<br>4q25–4q26<br>4q25–4q25 | IRIDOGONIODYSGENESIS, TYPE 2; IRID2 RIEGER SYNDROME, TYPE 1; RIEG1 RIEG BICOID-RELATED HOMEOBOX TRANSCRIPTION FACTOR 1; RIEG1 HOMEO BOX 2 |
| PKD2 | GDB: 118851 | 4q21–4q23 | POLYCYSTIC KIDNEY DISEASE 2; PKD2 |
| QDPR | GDB: 120331 | 4p15.3–4p15.3<br>4p15.31–4p15.31 | PHENYLKETONURIA II |
| SGCB | GDB: 702072 | 4q12–4q12 | MUSCULAR DYSTROPHY, LIMB-GIRDLE, TYPE 2E; LGMD2E |
| SLC25A4 | GDB: 119680 | 4q35–4q35 | ADENINE NUCLEOTIDE TRANSLOCATOR 1; ANT1 PROGRESSIVE EXTERNAL OPHTHALMOPLEGIA; PEO |
| SNCA | GDB: 439047 | 4q21.3–4q22<br>4q21–4q21 | SYNUCLEIN, ALPHA; SNCA PARKINSON DISEASE, FAMILIAL, TYPE 1; PARK1 |
| SOD3 | GDB: 125291 | 4p16.3–4q21 | SUPEROXIDE DISMUTASE, EXTRACELLULAR; SOD3 |
| STATH | GDB: 120391 | 4q11–4q13 | STATHERIN; STATH; STR |
| TAPVR1 | GDB: 392646 | 4p13–4q11 | ANOMALOUS PULMONARY VENOUS RETURN; APVR |

TABLE 5-continued

Genes, Locations and Genetic Disorders on Chromosome 4

| Gene | GDB Accession ID | Location | OMIM Link |
|---|---|---|---|
| TYS | GDB: 119624 | 4q–4q | SCLEROTYLOSIS; TYS |
| WBS2 | GDB: 132426 | 4q33–4q35.1 | WILLIAMS-BEUREN SYNDROME; WBS |
| WFS1 | GDB: 434294 | 4p–4p 4p16–4p16 | DIABETES MELLITUS AND INSIPIDUS WITH OPTIC ATROPHY AND DEAFNESS |
| WHCR | GDB: 125355 | 4p16.3–4p16.3 | WOLF-HIRSCHHORN SYNDROME; WHS |

TABLE 6

Genes, Locations and Genetic Disorders on Chromosome 5

| Gene | GDB Accession ID | OMIM Link |
|---|---|---|
| ADAMTS2 | GDB: 9957209 | EHLERS-DANLOS SYNDROME, TYPE VII, AUTOSOMAL RECESSIVE |
| ADRB2 | GDB: 120541 | BETA-2-ADRENERGIC RECEPTOR; ADRB2 |
| AMCN | GDB: 9836823 | ARTHROGRYPOSIS MULTIPLEX CONGENITA, NEUROGENIC TYPE |
| AP3B1 | GDB: 9955590 | HERMANSKY-PUDLAK SYNDROME; HPS |
| APC | GDB: 119682 | ADENOMATOUS POLYPOSIS OF THE COLON; APC |
| ARSB | GDB: 119008 | MUCOPOLYSACCHARIDOSIS TYPE VI; MPS VI |
| B4GALT7 | GDB: 9957653 | SYNDROME, PROGEROID FORM |
| BHR1 | GDB: 9956078 | ASTHMA |
| C6 | GDB: 119045 | COMPLEMENT COMPONENT-6, DEFICIENCY OF |
| C7 | GDB: 119046 | COMPLEMENT COMPONENT-7, DEFICIENCY OF |
| CCAL2 | GDB: 5584265 | CHONDROCALCINOSIS, FAMILIAL ARTICULAR |
| CKN1 | GDB: 128586 | COCKAYNE SYNDROME, TYPE I; CKN1 |
| CMDJ | GDB: 9595425 | CRANIOMETAPHYSEAL DYSPLASIA, JACKSON TYPE; CMDJ |
| CRHBP | GDB: 127438 | CORTICOTROPIN RELEASING HORMONE-BINDING PROTEIN; CRHBP |
| CSF1R | GDB: 120600 | COLONY-STIMULATING FACTOR-1 RECEPTOR; CSF1R |
| DHFR | GDB: 119845 | DIHYDROFOLATE REDUCTASE; DHFR |
| DIAPH1 | GDB: 9835482 | DEAFNESS, AUTOSOMAL DOMINANT NONSYNDROMIC SENSORINEURAL, 1; DFNA1 DIAPHANOUS, *DROSOPHILA*, HOMOLOG OF, 1 |
| DTR | GDB: 119853 | DIPHTHERIA TOXIN SENSITIVITY; DTS |
| EOS | GDB: 9956083 | EOSINOPHILIA, FAMILIAL |
| ERVR | GDB: 9835857 | HYALOIDEORETINAL DEGENERATION OF WAGNER |
| F12 | GDB: 119892 | HAGEMAN FACTOR DEFICIENCY |
| FBN2 | GDB: 128122 | CONTRACTURAL ARACHNODACTYLY, CONGENITAL; CCA |
| GDNF | GDB: 450609 | GLIAL CELL LINE-DERIVED NEUROTROPHIC FACTOR; GDNF |
| GHR | GDB: 119984 | GROWTH HORMONE RECEPTOR; GHR |
| GLRA1 | GDB: 118801 | GLYCINE RECEPTOR, ALPHA-1 SUBUNIT; GLRA1 KOK DISEASE |
| GM2A | GDB: 120000 | TAY-SACHS DISEASE, AB VARIANT |
| HEXB | GDB: 119308 | SANDHOFF DISEASE |
| HSD17B4 | GDB: 385059 | 17-@BETA-HYDROXYSTEROID DEHYDROGENASE IV; HSD17B4 |

TABLE 6-continued

Genes, Locations and Genetic Disorders on Chromosome 5

| Gene | GDB Accession ID | OMIM Link |
|---|---|---|
| ITGA2 | GDB: 128031 | INTEGRIN, ALPHA-2; ITGA2 |
| KFS | GDB: 9958987 | VERTEBRAL FUSION |
| LGMD1A | GDB: 118832 | MUSCULAR DYSTROPHY, LIMB-GIRDLE, TYPE 1A; LGMD1A |
| LOX | GDB: 119367 | LYSYL OXIDASE; LOX |
| LTC4S | GDB: 384080 | LEUKOTRIENE C4 SYNTHASE; LTC4S |
| MAN2A1 | GDB: 136413 | MANNOSIDASE, ALPHA, II; MANA2 DYSERYTHROPOIETIC ANEMIA, CONGENITAL, TYPE II |
| MCC | GDB: 128163 | MUTATED IN COLORECTAL CANCERS; MCC |
| MCCC2 | GDB: 135990 | II |
| MSH3 | GDB: 641986 | MutS, *E. COLI*, HOMOLOG OF, 3; MSH3 |
| MSX2 | GDB: 138766 | MSH (*DROSOPHILA*) HOMEO BOX HOMOLOG 2; MSX2 PARIETAL FORAMINA, SYMMETRIC; PFM |
| NR3C1 | GDB: 120017 | GLUCOCORTICOID RECEPTOR; GRL |
| PCSK1 | GDB: 128033 | PROPROTEIN CONVERTASE SUBTILISIN/KEXIN TYPE 1; PCSK1 |
| PDE6A | GDB: 120265 | PHOSPHODIESTERASE 6A, cGMP-SPECIFIC, ROD, ALPHA; PDE6A |
| PFBI | GDB: 9956096 | INTENSITY OF INFECTION IN |
| RASA1 | GDB: 120339 | RAS p21 PROTEIN ACTIVATOR 1; RASA1 |
| SCZD1 | GDB: 120370 | DISORDER-1; SCZD1 |
| SDHA | GDB: 378037 | SUCCINATE DEHYDROGENASE COMPLEX, SUBUNIT A, FLAVOPROTEIN; SDHA |
| SGCD | GDB: 5886421 | SARCOGLYCAN, DELTA; SGCD |
| SLC22A5 | GDB: 9863277 | CARNITINE DEFICIENCY, SYSTEMIC, DUE TO DEFECT IN RENAL REABSORPTION |
| SLC26A2 | GDB: 125421 | DIASTROPHIC DYSPLASIA; DTD EPIPHYSEAL DYSPLASIA, MULTIPLE; MED NEONATAL OSSEOUS DYSPLASIA I ACHONDROGENESIS, TYPE IB; ACG1B |
| SLC6A3 | GDB: 132445 | SOLUTE CARRIER FAMILY 6, MEMBER 3; SLC6A3 DEFICIT-HYPERACTIVITY DISORDER; ADHD |
| SM1 | GDB: 9834488 | SCHISTOSOMA MANSONI SUSCEPTIBILITY/RESISTANCE |
| SMA@ | GDB: 120378 | SPINAL MUSCULAR ATROPHY I; SMA I SURVIVAL OF MOTOR NEURON 1, TELOMERIC; SMN1 |
| SMN1 | GDB: 5215173 | SPINAL MUSCULAR ATROPHY I; SMA I SURVIVAL OF MOTOR NEURON 1, TELOMERIC; SMN1 |
| SMN2 | GDB: 5215175 | SPINAL MUSCULAR ATROPHY I; SMA I SURVIVAL OF MOTOR NEURON 2, CENTROMERIC; SMN2 |
| SPINK5 | GDB: 9956114 | NETHERTON DISEASE |
| TCOF1 | GDB: 127390 | TREACHER COLLINS-FRANCESCHETTI SYNDROME 1; TCOF1 |
| TGFBI | GDB: 597601 | CORNEAL DYSTROPHY, GRANULAR TYPE CORNEAL DYSTROPHY, LATTICE TYPE I; CDL1 TRANSFORMING GROWTH FACTOR, BETA-INDUCED, 68 KD; TGFBI |

TABLE 7

Genes, Locations and Genetic Disorders on Chromosome 6

| Gene | GDB Accession ID | OMIM Link |
|---|---|---|
| ALDH5A1 | GDB: 454767 | SUCCINIC SEMIALDEHYDE DEHYDROGENASE, NAD(+)-DEPENDENT; SSADH |
| ARG1 | GDB: 119006 | ARGININEMIA |
| AS | GDB: 135697 | ANKYLOSING SPONDYLITIS; AS |
| ASSP2 | GDB: 119017 | CITRULLINEMIA |
| BCKDHB | GDB: 118759 | MAPLE SYRUP URINE DISEASE, TYPE IB |
| BF | GDB: 119726 | GLYCINE-RICH BETA-GLYCOPROTEIN; GBG |
| C2 | GDB: 119731 | COMPLEMENT COMPONENT-2, DEFICIENCY OF |
| C4A | GDB: 119732 | COMPLEMENT COMPONENT 4A; C4A |
| CDKN1A | GDB: 266550 | CYCLIN-DEPENDENT KINASE INHIBITOR 1A CDKN1A |
| COL10A1 | GDB: 128635 | COLLAGEN, TYPE X, ALPHA 1; COL10A1 |
| COL11A2 | GDB: 119788 | COLLAGEN, TYPE XI, ALPHA-2; COL11A2 STICKLER SYNDROME, TYPE II; STL2 DEAFNESS, AUTOSOMAL DOMINANT NONSYNDROMIC SENSORINEURAL, 13; DFNA13 |
| CYP21A2 | GDB: 120605 | ADRENAL HYPERPLASIA, CONGENITAL, DUE TO 21-HYDROXYLASE DEFICIENCY |
| DYX2 | GDB: 437584 | DYSLEXIA, SPECIFIC, 2; DYX2 |
| EJM1 | GDB: 119864 | MYOCLONIC EPILEPSY, JUVENILE; EJM1 |
| ELOVL4 | GDB: 11499609 | STARGARDT DISEASE 3; STGD3 |
| EPM2A | GDB: 3763331 | EPILEPSY, PROGRESSIVE MYOCLONIC 2; EPM2 |
| ESR1 | GDB: 119120 | ESTROGEN RECEPTOR; ESR |
| EYA4 | GDB: 700062 | DEAFNESS, AUTOSOMAL DOMINANT NONSYNDROMIC SENSORINEURAL, 10; DFNA10 |
| F13A1 | GDB: 120614 | FACTOR XIII, A1 SUBUNIT; F13A1 |
| FANCE | GDB: 1220236 | FANCONI ANEMIA, COMPLEMENTATION GROUP E; FACE |
| GCLC | GDB: 132915 | GAMMA-GLUTAMYLCYSTEINE SYNTHETASE DEFICIENCY, HEMOLYTIC ANEMIA DUE |
| GJA1 | GDB: 125196 | GAP JUNCTION PROTEIN, ALPHA-1, 43 KD; GJA1 |
| GLYS1 | GDB: 136421 | GLYCOSURIA, RENAL |
| GMPR | GDB: 127058 | GUANINE MONOPHOSPHATE REDUCTASE |
| GSE | GDB: 9956235 | DISEASE; CD |
| HCR | GDB: 9993306 | PSORIASIS, SUSCEPTIBILITY TO HFEGDB: 119309 HEMOCHROMATOSIS; HFE |
| HLA-A | GDB: 119310 | HLA-A HISTOCOMPATIBILITY TYPE; HLAA HLA-DPB1GDB: 120636 LA-DP HISTOCOMPATIBILITY TYPE, BETA-1 SUBUNIT |
| HLA-DRA | GDB: 120641 | HLA-DR HISTOCOMPATIBILITY TYPE; HLA-DRA |
| HPFH | GDB: 9849006 | HETEROCELLULAR HEREDITARY PERSISTENCE OF FETAL HEMOGLOBIN |
| ICS1 | GDB: 136433 | IMMOTILE CILIA SYNDROME-1; ICS1 |
| IDDM1 | GDB: 9953173 | DIABETES MELLITUS, JUVENILE-ONSET INSULIN-DEPENDENT; IDDM |
| IFNGR1 | GDB: 120688 | INTERFERON, GAMMA, RECEPTOR-1; IFNGR1 |
| IGAD1 | GDB: 6929077 | SELECTIVE DEFICIENCY OF |
| IGF2R | GDB: 120083 | INSULIN-LIKE GROWTH FACTOR 2 RECEPTOR; IGF2R |
| ISCW | GDB: 9956158 | SUPPRESSION; IS |
| LAMA2 | GDB: 132362 | LAMININ, ALPHA 2; LAMA2 |
| LAP | GDB: 9958992 | LARYNGEAL ADDUCTOR PARALYSIS; LAP |
| LCA5 | GDB: 11498764 | AMAUROSIS CONGENITA OF LEBER I |
| LPA | GDB: 120699 | APOLIPOPROTEIN(a); LPA |

TABLE 7-continued

Genes, Locations and Genetic Disorders on Chromosome 6

| Gene | GDB Accession ID | OMIM Link |
|---|---|---|
| MCDR1 | GDB: 131406 | MACULAR DYSTROPHY, RETINAL, 1, NORTH CAROLINA TYPE; MCDR1 |
| MOCS1 | GDB: 9862235 | MOLYBDENUM COFACTOR DEFICIENCY |
| MUT | GDB: 120204 | METHYLMALONICACIDURIA DUE TO METHYLMALONIC CoA MUTASE DEFICIENCY |
| MYB | GDB: 119441 | V-MYB AVIAN MYELOBLASTOSIS VIRAL ONCOGENE HOMOLOG; MYB |
| NEU1 | GDB: 120230 | NEURAMINIDASE DEFICIENCY |
| NKS1 | GDB: 128100 | SUSCEPTIBILITY TO LYSIS BY ALLOREACTIVE NATURAL KILLER CELLS; EC1 |
| NYS2 | GDB: 9848763 | NYSTAGMUS, CONGENITAL |
| OA3 | GDB: 136429 | ALBINISM, OCULAR, AUTOSOMAL RECESSIVE; OAR |
| ODDD | GDB: 6392584 | OCULODENTODIGITAL DYSPLASIA; ODDD |
| OFC1 | GDB: 120247 | OROFACIAL CLEFT 1; OFC1 |
| PARK2 | GDB: 6802742 | PARKINSONISM, JUVENILE |
| PBCA | GDB: 9956321 | BETA CELL AGENESIS WITH NEONATAL DIABETES MELLITUS |
| PBCRA1 | GDB: 3763333 | CHORIORETINAL ATROPHY, PROGRESSIVE BIFOCAL; CRAPB |
| PDB1 | GDB: 136349 | DISEASE OF BONE; PDB |
| PEX3 | GDB: 9955507 | ZELLWEGER SYNDROME; ZS |
| PEX6 | GDB: 5592414 | ZELLWEGER SYNDROME; ZS PEROXIN-6; PEX6 |
| PEX7 | GDB: 6155803 | RHIZOMELIC CHONDRODYSPLASIA PUNCTATA; RCDP PEROXIN-7; PEX7 |
| PKHD1 | GDB: 433910 | POLYCYSTIC KIDNEY AND HEPATIC DISEASE-1; PKHD1 |
| PLA2G7 | GDB: 9958829 | PLATELET-ACTIVATING FACTOR ACETYLHYDROLASE, SUBUNIT |
| PLG | GDB: 119498 | PLASMINOGEN; PLG |
| POLH | GDB: 6963323 | PIGMENTOSUM WITH NORMAL DNA REPAIR RATES |
| PPAC | GDB: 9956248 | ARTHROPATHY, PROGRESSIVE PSEUDORHEUMATOID, OF CHILDHOOD |
| PSORS1 | GDB: 6381310 | PSORIASIS, SUSCEPTIBILITY TO |
| PUJO | GDB: 9956231 | MULTICYSTIC RENAL DYSPLASIA, BILATERAL; MRD |
| RCD1 | GDB: 333929 | RETINAL CONE DEGENERATION |
| RDS | GDB: 118863 | RETINAL DEGENERATION, SLOW; RDS |
| RHAG | GDB: 136011 | RHESUS BLOOD GROUP-ASSOCIATED GLYCOPROTEIN; RHAG RH-NULL, REGULATOR TYPE; RHN |
| RP14 | GDB: 433713 | RETINITIS PIGMENTOSA-14; RP14 TUBBY-LIKE PROTEIN 1; TULP1 |
| RUNX2 | GDB: 392082 | CLEIDOCRANIAL DYSPLASIA; CCD CORE-BINDING FACTOR, RUNT DOMAIN, ALPHA SUBUNIT 1; CBFA1 |
| RWS | GDB: 9956195 | SENSITIVITY |
| SCA1 | GDB: 119588 | SPINOCEREBELLAR ATAXIA 1; SCA1 |
| SCZD3 | GDB: 635974 | DISORDER-3; SCZD3 |
| SIASD | GDB: 433552 | SIALIC ACID STORAGE DISEASE; SIASD |
| SOD2 | GDB: 119597 | SUPEROXIDE DISMUTASE 2, MITOCHONDRIAL; SOD2 |
| ST8 | GDB: 6118456 | OVARIAN TUMOR |
| TAP1 | GDB: 132668 | TRANSPORTER 1, ABC; TAP1 |
| TAP2 | GDB: 132669 | TRANSPORTER 2, ABC; TAP2 |
| TFAP2B | GDB: 681506 | DUCTUS ARTERIOSUS; PDA TRANSCRIPTION FACTOR AP-2 BETA; TFAP2B |
| TNDM | GDB: 9956265 | DIABETES MELLITUS, TRANSIENT NEONATAL |
| TNF | GDB: 120441 | TUMOR NECROSIS FACTOR; TNF |
| TPBG | GDB: 125568 | TROPHOBLAST GLYCOPROTEIN; TPBG; M6P1 |

TABLE 7-continued

Genes, Locations and Genetic Disorders on Chromosome 6

| Gene | GDB Accession ID | OMIM Link |
|---|---|---|
| TPMT | GDB: 209025 | THIOPURINE S-METHYLTRANSFERASE; TPMT |
| TULP1 | GDB: 6199353 | TUBBY-LIKE PROTEIN 1; TULP1 |
| WISP3 | GDB: 9957361 | ARTHROPATHY, PROGRESSIVE PSEUDORHEUMATOID, OF CHILDHOOD |

TABLE 8

Genes, Locations and Genetic Disorders on Chromosome 7

| Gene | GDB Accession ID | OMIM Link |
|---|---|---|
| AASS | GDB: 11502144 | HYPERLYSINEMIA |
| ABCB1 | GDB: 120712 | P-GLYCOPROTEIN-1; PGY1 |
| ABCB4 | GDB: 120713 | P-GLYCOPROTEIN-3; PGY3 |
| ACHE | GDB: 118746 | ACETYLCHOLINESTERASE BLOOD GROUP - Yt SYSTEM; YT |
| AQP1 | GDB: 129082 | AQUAPORIN-1; AQP1 BLOOD GROUP - COLTON; CO |
| ASL | GDB: 119703 | ARGININOSUCCINICACIDURIA |
| ASNS | GDB: 119706 | ASPARAGINE SYNTHETASE; ASNS; AS |
| AUTS1 | GDB: 9864226 | DISORDER |
| BPGM | GDB: 119039 | DIPHOSPHOGLYCERATE MUTASE DEFICIENCY OF ERYTHROCYTE |
| C7orf2 | GDB: 10794644 | ACHEIROPODY |
| CACNA2D1 | GDB: 132010 | CALCIUM CHANNEL, VOLTAGE-DEPENDENT, L TYPE, ALPHA-2/DELTA SUBUNIT; MALIGNANT HYPERTHERMIA SUSCEPTIBILITY-3 |
| CCM1 | GDB: 580824 | CEREBRAL CAVERNOUS MALFORMATIONS 1; CCM1 |
| CD36 | GDB: 138800 | CD36 ANTIGEN; CD36 |
| CFTR | GDB: 120584 | CYSTIC FIBROSIS; CF DEFERENS, CONGENITAL BILATERAL APLASIA OF; CBAVD; CAVD |
| CHORDOMA | GDB: 11498328 | |
| CLCN1 | GDB: 134688 | CHLORIDE CHANNEL 1, SKELETAL MUSCLE; CLCN1 |
| CMH6 | GDB: 9956392 | CARDIOMYOPATHY, FAMILIAL HYPERTROPHIC, WITH WOLFF-PARKINSON-WHITE |
| CMT2D | GDB: 9953232 | CHARCOT-MARIE-TOOTH DISEASE, NEURONAL TYPE, D |
| COL1A2 | GDB: 119062 | COLLAGEN, TYPE I, ALPHA-2 POLYPEPTIDE; COL1A2 OSTEOGENESIS IMPERFECTA TYPE I OSTEOGENESIS IMPERFECTA TYPE IV; OI4 |
| CRS | GDB: 119073 | CRANIOSYNOSTOSIS, TYPE 1; CRS1 |
| CYMD | GDB: 366594 | MACULAR EDEMA, CYSTOID |
| DFNA5 | GDB: 636174 | DEAFNESS, AUTOSOMAL DOMINANT NONSYNDROMIC SENSORINEURAL, 5; DFNA5 |
| DLD | GDB: 120608 | LIPOAMIDE DEHYDROGENASE DEFICIENCY, LACTIC ACIDOSIS DUE TO |
| DYT11 | GDB: 10013754 | MYOCLONUS, HEREDITARY ESSENTIAL |
| EEC1 | GDB: 136338 | ECTRODACTYLY, ECTODERMAL DYSPLASIA, AND CLEFT LIP/PALATE; EEC |
| ELN | GDB: 119107 | ELASTIN; ELN WILLIAMS-BEUREN SYNDROME; WBS |
| ETV1 | GDB: 335229 | ETS VARIANT GENE 1; ETV1 |
| FKBP6 | GDB: 9955215 | WILLIAMS-BEUREN SYNDROME; WBS |
| GCK | GDB: 127550 | DIABETES MELLITUS, AUTOSOMAL DOMINANT, TYPE II GLUCOKINASE; GCK |
| GHRHR | GDB: 138465 | GROWTH HORMONE-RELEASING HORMONE RECEPTOR; GHRHR |
| GHS | GDB: 9956363 | MICROSOMIA WITH RADIAL DEFECTS |

TABLE 8-continued

Genes, Locations and Genetic Disorders on Chromosome 7

| Gene | GDB Accession ID | OMIM Link |
|---|---|---|
| GLI3 | GDB: 119990 | PALLISTER-HALL SYNDROME; PHS GLI-KRUPPEL FAMILY MEMBER 3; GLI3 POSTAXIAL POLYDACTYLY, TYPE A1 GREIG CEPHALOPOLYSYNDACTYLY SYNDROME; GCPS |
| GPDS1 | GDB: 9956410 | GLAUCOMA, PIGMENT-DISPERSION TYPE |
| GUSB | GDB: 120025 | MUCOPOLYSACCHARIDOSIS TYPE VII |
| HADH | GDB: 120033 | HYDROXYACYL-CoA DEHYDROGENASE/3-KETOACYL-CoA THIOLASE/ENOYL-CoA HYDRATASE, |
| HLXB9 | GDB: 136411 | HOMEO BOX GENE HB9; HLXB9 SACRAL AGENESIS, HEREDITARY, WITH PRESACRAL MASS, ANTERIOR MENINGOCELE, |
| HOXA13 | GDB: 120656 | HOMEO BOX A13; HOXA13 |
| HPFH2 | GDB: 128071 | HEREDITARY PERSISTENCE OF FETAL HEMOGLOBIN, HETEROCELLULAR, INDIAN |
| HRX | GDB: 9958999 | HRX |
| IAB | GDB: 11498909 | ANEURYSM, INTRACRANIAL BERRY |
| IMMP2L | GDB: 11499195 | GILLES DE LA TOURETTE SYNDROME; GTS |
| KCNH2 | GDB: 138126 | LONG QT SYNDROME, TYPE 2; LQT2 |
| LAMB1 | GDB: 119357 | LAMININ BETA 1; LAMB1 |
| LEP | GDB: 136420 | LEPTIN; LEP |
| MET | GDB: 120178 | MET PROTO-ONCOGENE; MET |
| NCF1 | GDB: 120222 | GRANULOMATOUS DISEASE, CHRONIC, AUTOSOMAL CYTOCHROME-b-POSITIVE FORM |
| NM | GDB: 119454 | NEUTROPHIL CHEMOTACTIC RESPONSE; NCR |
| OGDH | GDB: 118847 | ALPHA-KETOGLUTARATE DEHYDROGENASE DEFICIENCY |
| OPN1SW | GDB: 119032 | TRITANOPIA |
| PEX1 | GDB: 9787110 | ZELLWEGER SYNDROME; ZS PEROXIN-1; PEX1 |
| PGAM2 | GDB: 120280 | PHOSPHOGLYCERATE MUTASE, DEFICIENCY OF M SUBUNIT OF |
| PMS2 | GDB: 386406 | POSTMEIOTIC SEGREGATION INCREASED (*S. CEREVISIAE*)-2; PMS2 |
| PON1 | GDB: 120308 | PARAOXONASE 1; PON1 |
| PPP1R3A | GDB: 136797 | PROTEIN PHOSPHATASE 1, REGULATORY (INHIBITOR) SUBUNIT 3; PPP1R3 |
| PRSS1 | GDB: 119620 | PANCREATITIS, HEREDITARY; PCTT PROTEASE, SERINE, 1; PRSS1 |
| PTC | GDB: 118744 | PHENYLTHIOCARBAMIDE TASTING |
| PTPN12 | GDB: 136846 | PROTEIN-TYROSINE PHOSPHATASE, NONRECEPTOR TYPE, 12; PTPN12 |
| RP10 | GDB: 138786 | RETINITIS PIGMENTOSA-10; RP10 |
| RP9 | GDB: 333931 | RETINITIS PIGMENTOSA-9; RP9 |
| SERPINE1 | GDB: 120297 | PLASMINOGEN ACTIVATOR INHIBITOR, TYPE I; PAI1 |
| SGCE | GDB: 9958714 | MYOCLONUS, HEREDITARY ESSENTIAL |
| SHFM1 | GDB: 128195 | SPLIT-HAND/FOOT DEFORMITY, TYPE I; SHFD1 |
| SHH | GDB: 456309 | HOLOPROSENCEPHALY, TYPE 3; HPE3 SONIC HEDGEHOG, *DROSOPHILA*, HOMOLOG OF; SHH |
| SLC26A3 | GDB: 138165 | DOWN-REGULATED IN ADENOMA; DRA CHLORIDE DIARRHEA, FAMILIAL; CLD |
| SLC26A4 | GDB: 5584511 | PENDRED SYNDROME; PDS DEAFNESS, NEUROSENSORY, AUTOSOMAL RECESSIVE, 4; DFNB4 |
| SLOS | GDB: 385950 | SMITH-LEMLI-OPITZ SYNDROME |
| SMAD1 | GDB: 3763345 | SPINAL MUSCULAR ATROPHY, DISTAL, WITH UPPER LIMB PREDOMINANCE; SMAD1 |
| TBXAS1 | GDB: 128744 | THROMBOXANE A SYNTHASE 1; TBXAS1 |

TABLE 8-continued

Genes, Locations and Genetic Disorders on Chromosome 7

| Gene | GDB Accession ID | OMIM Link |
|---|---|---|
| TWIST | GDB: 135694 | ACROCEPHALOSYNDACTYLY TYPE III TWIST, *DROSOPHILA*, HOMOLOG OF; TWIST |
| ZWS1 | GDB: 120511 | ZELLWEGER SYNDROME; ZS |

TABLE 9

Genes, Locations and Genetic Disorders on Chromosome 8

| Gene | GDB AccessionID | OMIM Link |
|---|---|---|
| ACHM3 | GDB: 9120558 | PINGELAPESE BLINDNESS |
| ADRB3 | GDB: 203869 | BETA-3-ADRENERGIC RECEPTOR; ADRB3 |
| ANK1 | GDB: 118737 | SPHEROCYTOSIS, HEREDITARY; HS |
| CA1 | GDB: 119047 | CARBONIC ANHYDRASE I, ERYTHROCYTE, ELECTROPHORETIC VARIANTS OF; CA1 |
| CA2 | GDB: 119739 | OSTEOPETROSIS WITH RENAL TUBULAR ACIDOSIS |
| CCAL1 | GDB: 512892 | CHONDROCALCINOSIS WITH EARLY-ONSET OSTEOARTHRITIS; CCAL2 |
| CLN8 | GDB: 252118 | EPILEPSY, PROGRESSIVE, WITH MENTAL RETARDATION; EPMR |
| CMT4A | GDB: 138755 | CHARCOT-MARIE-TOOTH NEUROPATHY 4A; CMT4A |
| CNGB3 | GDB: 9993286 | PINGELAPESE BLINDNESS |
| COH1 | GDB: 252122 | COHEN SYNDROME; COH1 |
| CPP | GDB: 119798 | CERULOPLASMIN; CP |
| CRH | GDB: 119804 | CORTICOTROPIN-RELEASING HORMONE; CRH |
| CYP11B1 | GDB: 120603 | ADRENAL HYPERPLASIA, CONGENITAL, DUE TO 11-@BETA-HYDROXYLASE DEFICIENCY |
| CYP11B2 | GDB: 120514 | CYTOCHROME P450, SUBFAMILY XIB, POLYPEPTIDE 2; CYP11B2 |
| DECR1 | GDB: 453934 | 2,4-@DIENOYL-CoA REDUCTASE; DECR |
| DPYS | GDB: 5885803 | DIHYDROPYRIMIDINASE; DPYS |
| DURS1 | GDB: 9958126 | DUANE SYNDROME |
| EBS1 | GDB: 119856 | EPIDERMOLYSIS BULLOSA SIMPLEX, OGNA TYPE |
| ECA1 | GDB: 10796318 | JUVENILE ABSENCE |
| EGI | GDB: 128830 | EPILEPSY, GENERALIZED, IDIOPATHIC; EGI |
| EXT1 | GDB: 135994 | EXOSTOSES, MULTIPLE, TYPE I; EXT1 CHONDROSARCOMA |
| EYA1 | GDB: 5215167 | BRANCHIOOTORENAL DYSPLASIA EYES ABSENT 1; EYA1 |
| FGFR1 | GDB: 119913 | ACROCEPHALOSYNDACTYLY TYPE V FIBROBLAST GROWTH FACTOR RECEPTOR-1; FGFR1 |
| GNRH1 | GDB: 133746 | GONADOTROPIN-RELEASING HORMONE 1; GNRH1 FAMILIAL HYPOGONADOTROPHIC |
| GSR | GDB: 119288 | GLUTATHIONE REDUCTASE; GSR |
| Gene | GDB AccessionID | OMIM Link |
| GULOP | GDB: 128078 | SCURVY |
| HR | GDB: 595499 | ALOPECIA UNIVERSALIS ATRICHIA WITH PAPULAR LESIONS HAIRLESS, MOUSE, HOMOLOG OF |
| KCNQ3 | GDB: 9787230 | CONVULSIONS, BENIGN FAMILIAL NEONATAL, TYPE 2; BFNC2 POTASSIUM CHANNEL, VOLTAGE-GATED, SUBFAMILY Q, MEMBER 3 |
| KFM | GDB: 265291 | KLIPPEL-FEIL SYNDROME; KFS; KFM |
| KWE | GDB: 9315120 | KERATOLYTIC WINTER ERYTHEMA |
| LGCR | GDB: 120698 | LANGER-GIEDION SYNDROME; LGS |
| LPL | GDB: 120700 | HYPERLIPOPROTEINEMIA, TYPE I |
| MCPH1 | GDB: 9834525 | MICROCEPHALY; MCT |
| MOS | GDB: 119396 | TRANSFORMATION GENE: ONCOGENE MOS |
| MYC | GDB: 120208 | TRANSFORMATION GENE: ONCOGENE MYC; MYC |

TABLE 9-continued

Genes, Locations and Genetic Disorders on Chromosome 8

| Gene | GDB AccessionID | OMIM Link |
|---|---|---|
| NAT1 | GDB: 125364 | ARYLAMIDE ACETYLASE 1; AAC1 |
| NAT2 | GDB: 125365 | ISONIAZID INACTIVATION |
| NBS1 | GDB: 9598211 | NIJMEGEN BREAKAGE SYNDROME |
| PLAT | GDB: 119496 | PLASMINOGEN ACTIVATOR, TISSUE; PLAT |
| PLEC1 | GDB: 4119073 | EPIDERMOLYSIS BULLOSA SIMPLEX AND LIMB-GIRDLE MUSCULAR DYSTROPHY PLECTIN 1; PLEC1 |
| PRKDC | GDB: 234702 | SEVERE COMBINED IMMUNODEFICIENCY DISEASE-1; SCID 1 PROTEIN KINASE, DNA-ACTIVATED, CATALYTIC SUBUNIT; PRKDC |
| PXMP3 | GDB: 131487 | PEROXIN-2; PEX2 ZELLWEGER SYNDROME; ZS |
| RP1 | GDB: 120352 | RETINITIS PIGMENTOSA-1; RP1 |
| SCZD6 | GDB: 9864736 | DISORDER-2; SCZD2 |
| SFTPC | GDB: 120373 | PULMONARY SURFACTANT APOPROTEIN PSP-C |
| SGM1 | GDB: 135350 | KLIPPEL-FEIL SYNDROME; KFS; KFM |
| SPG5A | GDB: 250332 | SPASTIC PARAPLEGIA-5A, AUTOSOMAL RECESSIVE; SPG5A |
| STAR | GDB: 635457 | STEROIDOGENIC ACUTE REGULATORY PROTEIN; STAR |
| TG | GDB: 120434 | THYROGLOBULIN; TG |
| TRPS1 | GDB: 594960 | TRICHORHINOPHALANGEAL SYNDROME, TYPE I; TRPS1 |
| TTPA | GDB: 512364 | VITAMIN E, FAMILIAL ISOLATED DEFICIENCY OF; VED TOCOPHEROL (ALPHA) TRANSFER PROTEIN; TTPA |
| VMD1 | GDB: 119631 | MACULAR DYSTROPHY, ATYPICAL VITELLIFORM; VMD1 |
| WRN | GDB: 128446 | WERNER SYNDROME; WRN |

TABLE 10

Genes, Locations and Genetic Disorders on Chromosome 9

| Gene | GDB AccessionID | OMIM Link |
|---|---|---|
| ABCA1 | GDB: 305294 | ANALPHALIPOPROTEINEMIA ATP-BINDING CASSETTE 1; ABC1 |
| ABL1 | GDB: 119640 | ABELSON MURINE LEUKEMIA VIRAL ONCOGENE HOMOLOG 1; ABL1 |
| ABO | GDB: 118956 | ABO BLOOD GROUP; ABO |
| ADAMTS13 | GDB: 9956467 | THROMBOCYTOPENIC PURPURA |
| AK1 | GDB: 119664 | ADENYLATE KINASE-1; AK1 |
| ALAD | GDB: 119665 | DELTA-AMINOLEVULINATE DEHYDRATASE; ALAD |
| ALDH1A1 | GDB: 119667 | ALDEHYDE DEHYDROGENASE-1; ALDH1 |
| ALDOB | GDB: 119669 | FRUCTOSE INTOLERANCE, HEREDITARY |
| AMBP | GDB: 120696 | PROTEIN HC; HCP |
| AMCD1 | GDB: 437519 | ARTHROGRYPOSIS MULTIPLEX CONGENITA, DISTAL, TYPE 1; AMCD1 |
| ASS | GDB: 119010 | CITRULLINEMIA |
| BDMF | GDB: 9954424 | BONE DYSPLASIA WITH MEDULLARY FIBROSARCOMA |
| BSCL | GDB: 9957720 | SEIP SYNDROME |
| C5 | GDB: 119734 | COMPLEMENT COMPONENT-5, DEFICIENCY OF |
| CDKN2A | GDB: 335362 | MELANOMA, CUTANEOUS MALIGNANT, 2; CMM2 CYCLIN-DEPENDENT KINASE INHIBITOR 2A; CDKN2A |
| CHAC | GDB: 6268491 | CHOREOACANTHOCYTOSIS; CHAC |
| CHH | GDB: 138268 | CARTILAGE-HAIR HYPOPLASIA; CHH |
| CMD1B | GDB: 677147 | CARDIOMYOPATHY, DILATED 1B; CMD1B |
| COL5A1 | GDB: 131457 | COLLAGEN, TYPE V, ALPHA-1 POLYPEPTIDE; COL5A1 |
| CRAT | GDB: 359759 | CARNITINE ACETYLTRANSFERASE; CRAT |
| DBH | GDB: 119836 | DOPAMINE BETA-HYDROXYLASE, PLASMA; DBH |
| DFNB11 | GDB: 1220180 | DEAFNESS, NEUROSENSORY, AUTOSOMAL RECESSIVE, 7; DFNB7 |
| DFNB7 | GDB: 636178 | DEAFNESS, NEUROSENSORY, AUTOSOMAL RECESSIVE, 7; DFNB7 |

TABLE 10-continued

Genes, Locations and Genetic Disorders on Chromosome 9

| Gene | GDB AccessionID | OMIM Link |
|---|---|---|
| DNAI1 | GDB: 11500297 | IMMOTILE CILIA SYNDROME-1; ICS1 |
| DYS | GDB: 137085 | DYSAUTONOMIA, FAMILIAL; DYS |
| DYT1 | GDB: 119854 | DYSTONIA 1, TORSION; DYT1 |
| ENG | GDB: 137193 | ENDOGLIN; ENG |
| EPB72 | GDB: 128993 | ERYTHROCYTE SURFACE PROTEIN BAND 7.2; EPB72 STOMATOCYTOSIS I |
| FANCC | GDB: 132672 | FANCONI ANEMIA, COMPLEMENTATION GROUP C; FACC |
| FBP1 | GDB: 141539 | FRUCTOSE-1,6-BISPHOPHATASE 1; FBP1 |
| FCMD | GDB: 250412 | FUKUYAMA-TYPE CONGENITAL MUSCULAR DYSTROPHY; FCMD |
| FRDA | GDB: 119951 | FRIEDREICH ATAXIA 1; FRDA1 |
| GALT | GDB: 119971 | GALACTOSEMIA |
| GLDC | GDB: 128611 | HYPERGLYCINEMIA, ISOLATED NONKETOTIC, TYPE I; NKH1 |
| GNE | GDB: 9954891 | INCLUSION BODY MYOPATHY; IBM2 |
| GSM1 | GDB: 9784210 | GENIOSPASM 1; GSM1 |
| GSN | GDB: 120019 | AMYLOIDOSIS V GELSOLIN; GSN |
| HSD17B3 | GDB: 347487 | PSEUDOHERMAPHRODITISM, MALE, WITH GYNECOMASTIA |
| HSN1 | GDB: 3853677 | NEUROPATHY, HEREDITARY SENSORY, TYPE 1 |
| IBM2 | GDB: 3801447 | INCLUSION BODY MYOPATHY; IBM2 |
| LALL | GDB: 9954426 | LEUKEMIA, ACUTE, WITH LYMPHOMATOUS FEATURES; LALL |
| LCCS | GDB: 386141 | LETHAL CONGENITAL CONTRACTURE SYNDROME; LCCS |
| LGMD2H | GDB: 9862233 | DYSTROPHY, HUTTERITE TYPE |
| LMX1B | GDB: 9834526 | NAIL-PATELLA SYNDROME; NPS1 |
| MLLT3 | GDB: 138172 | MYELOID/LYMPHOID OR MIXED LINEAGE LEUKEMIA, TRANSLOCATED TO, 3; MLLT3 |
| MROS | GDB: 9954430 | MELKERSSON SYNDROME |
| MSSE | GDB: 128019 | EPITHELIOMA, SELF-HEALING SQUAMOUS |
| NOTCH1 | GDB: 131400 | NOTCH, *DROSOPHILA*, HOMOLOG OF, 1; NOTCH 1 |
| ORM1 | GDB: 120250 | OROSOMUCOID 1; ORM1 |
| PAPPA | GDB: 134729 | PREGNANCY-ASSOCIATED PLASMA PROTEIN A; PAPPA |
| PIP5K1B | GDB: 686238 | FRIEDREICH ATAXIA 1; FRDA1 |
| PTCH | GDB: 119447 | BASAL CELL NEVUS SYNDROME; BCNS PATCHED, *DROSOPHILA*, HOMOLOG OF; PTCH |
| PTGS1 | GDB: 128070 | PROSTAGLANDIN-ENDOPEROXIDASE SYNTHASE 1; PTGS1 |
| RLN1 | GDB: 119552 | RELAXIN; RLN1 |
| RLN2 | GDB: 119553 | RELAXIN, OVARIAN, OF PREGNANCY |
| RMRP | GDB: 120348 | MITOCHONDRIAL RNA-PROCESSING ENDORIBONUCLEASE, RNA COMPONENT OF; RMRP; CARTILAGE-HAIR HYPOPLASIA; CHH |
| ROR2 | GDB: 136454 | BRACHYDACTYLY, TYPE B; BDB ROBINOW SYNDROME, RECESSIVE FORM NEUROTROPHIC TYROSINE KINASE, RECEPTOR-RELATED 2; NTRKR2 |
| RPD1 | GDB: 9954440 | RETINITIS PIGMENTOSA-DEAFNESS SYNDROME 1, AUTOSOMAL DOMINANT |
| SARDH | GDB: 9835149 | SARCOSINEMIA |
| TDFA | GDB: 9954420 | FACTOR, AUTOSOMAL |
| TEK | GDB: 344185 | VENOUS MALFORMATIONS, MULTIPLE CUTANEOUS AND MUCOSAL; VMCM TEK TYROSINE KINASE, ENDOTHELIAL; TEK |
| TSC1 | GDB: 120735 | TUBEROUS SCLEROSIS-1; TSC1 |
| TYRP1 | GDB: 126337 | TYROSINASE-RELATED PROTEIN 1; TYRP1 ALBINISM III XANTHISM |
| XPA | GDB: 125363 | XERODERMA PIGMENTOSUM I |

TABLE 11

Genes, Locations and Genetic Disorders on Chromosome 10

| Gene | GDB Accession ID | OMIM Link |
|---|---|---|
| CACNB2 | GDB: 132014 | CALCIUM CHANNEL, VOLTAGE-DEPENDENT, BETA-2 SUBUNIT; CACNB2 |
| COL17A1 | GDB: 131396 | COLLAGEN, TYPE XVII, ALPHA-1 POLYPEPTIDE; COL17A1 |
| CUBN | GDB: 636049 | MEGALOBLASTIC ANEMIA 1; MGA1 |
| CYP17 | GDB: 119829 | ADRENAL HYPERPLASIA, CONGENITAL, DUE TO 17-ALPHA-HYDROXYLASE DEFICIENCY |
| CYP2C19 | GDB: 119831 | CYTOCHROME P450, SUBFAMILY IIC, POLYPEPTIDE 19; CYP2C19 |
| CYP2C9 | GDB: 131455 | CYTOCHROME P450, SUBFAMILY IIC, POLYPEPTIDE 9; CYP2C9 |
| EGR2 | GDB: 120611 | EARLY GROWTH RESPONSE-2; EGR2 |
| EMX2 | GDB: 277886 | EMPTY SPIRACLES, *DROSOPHILA*, 2, HOMOLOG OF; EMX2 |
| EPT | GDB: 9786112 | EPILEPSY, PARTIAL; EPT |
| ERCC6 | GDB: 119882 | EXCISION-REPAIR CROSS-COMPLEMENTING RODENT REPAIR DEFICIENCY, COMPLEMENTATION |
| FGFR2 | GDB: 127273 | ACROCEPHALOSYNDACTYLY TYPE V FIBROBLAST GROWTH FACTOR RECEPTOR-2; FGFR2 |
| HK1 | GDB: 120044 | HEXOKINASE-1; HK1 |
| HOX11 | GDB: 119607 | HOMEO BOX-11; HOX11 |
| HPS | GDB: 127359 | HERMANSKY-PUDLAK SYNDROME; HPS |
| IL2RA | GDB: 119345 | INTERLEUKIN-2 RECEPTOR, ALPHA; IL2RA |
| LGI1 | GDB: 9864936 | EPILEPSY, PARTIAL; EPT |
| LIPA | GDB: 120153 | WOLMAN DISEASE |
| MAT1A | GDB: 129077 | METHIONINE ADENOSYLTRANSFERASE DEFICIENCY |
| MBL2 | GDB: 120167 | MANNOSE-BINDING PROTEIN, SERUM; MBP1 |
| MKI67 | GDB: 120185 | PROLIFERATION-RELATED Ki-67 ANTIGEN; MKI67 |
| MXI1 | GDB: 137182 | MAX INTERACTING PROTEIN 1; MXI1 |
| OAT | GDB: 120246 | ORNITHINE AMINOTRANSFERASE DEFICIENCY |
| OATL3 | GDB: 215803 | ORNITHINE AMINOTRANSFERASE DEFICIENCY |
| PAX2 | GDB: 138771 | PAIRED BOX HOMEOTIC GENE 2; PAX2 |
| PCBD | GDB: 138478 | PTERIN-4-ALPHA-CARBINOLAMINE DEHYDRATASE; PCBD PRIMAPTERINURIA |
| PEO1 | GDB: 632784 | PROGRESSIVE EXTERNAL OPHTHALMOPLEGIA; PEO |
| PHYH | GDB: 9263423 | REFSUM DISEASE PHYTANOYL-CoA HYDROXYLASE; PHYH |
| PNLIP | GDB: 127916 | LIPASE, CONGENITAL ABSENCE OF PANCREATIC |
| PSAP | GDB: 120366 | PROSAPOSIN; PSAP |
| PTEN | GDB: 6022948 | MACROCEPHALY, MULTIPLE LIPOMAS AND HEMANGIOMATA MULTIPLE HAMARTOMA SYNDROME; MHAM POLYPOSIS, JUVENILE INTESTINAL PHOSPHATASE AND TENSIN HOMOLOG; PTEN |
| RBP4 | GDB: 120342 | RETINOL-BINDING PROTEIN, PLASMA; RBP4 |
| RDPA | GDB: 9954445 | REFSUM DISEASE WITH INCREASED PIPECOLICACIDEMIA; RDPA |
| RET | GDB: 120346 | RET PROTO-ONCOGENE; RET |
| SDF1 | GDB: 433267 | STROMAL CELL-DERIVED FACTOR 1; SDF1 |
| SFTPA1 | GDB: 119593 | PULMONARY SURFACTANT APOPROTEIN PSP-A; PSAP |
| SFTPD | GDB: 132674 | PULMONARY SURFACTANT APOPROTEIN PSP-D; PSP-D |
| SHFM3 | GDB: 386030 | SPLIT-HAND/FOOT MALFORMATION, TYPE 3; SHFM3 |
| SIAL | GDB: 6549924 | NEURAMINIDASE DEFICIENCY |
| THC2 | GDB: 10794765 | THROMBOCYTOPENIA |
| TNFRSF6 | GDB: 132671 | APOPTOSIS ANTIGEN 1; APT1 |
| UFS | GDB: 6380714 | UROFACIAL SYNDROME; UFS |
| UROS | GDB: 128112 | PORPHYRIA, CONGENITAL ERYTHROPOIETIC; CEP |

TABLE 12

Genes, Locations and Genetic Disorders on Chromosome 11

| Gene | GDB Accession ID | OMIM Link |
|---|---|---|
| AA | GDB: 568984 | ATROPHIA AREATA; AA |
| ABCC8 | GDB: 591370 | SULFONYLUREA RECEPTOR; SUR PERSISTENT HYPERINSULINEMIC HYPOGLYCEMIA OF INFANCY |
| ACAT1 | GDB: 126861 | ALPHA-METHYLACETOACETICACIDURIA |
| ALX4 | GDB: 10450304 | PARIETAL FORAMINA, SYMMETRIC; PFM |
| AMPD3 | GDB: 136013 | ADENOSINE MONOPHOSPHATE DEAMINASE-3; AMPD3 |
| ANC | GDB: 9954484 | CANAL CARCINOMA |
| APOA1 | GDB: 119684 | AMYLOIDOSIS, FAMILIAL VISCERAL APOLIPOPROTEIN A-I OF HIGH DENSITY LIPOPROTEIN; APOA1 |
| APOA4 | GDB: 119000 | APOLIPOPROTEIN A-IV; APOA4 |
| APOC3 | GDB: 119001 | APOLIPOPROTEIN C-III; APOC3 |
| ATM | GDB: 593364 | ATAXIA-TELANGIECTASIA; AT |
| BSCL2 | GDB: 9963996 | SEIP SYNDROME |
| BWS | GDB: 120567 | BECKWITH-WIEDEMANN SYNDROME; BWS |
| CALCA | GDB: 120571 | CALCITONIN/CALCITONIN-RELATED POLYPEPTIDE, ALPHA; CALCA |

TABLE 12-continued

Genes, Locations and Genetic Disorders on Chromosome 11

| Gene | GDB Accession ID | OMIM Link |
|---|---|---|
| CAT | GDB: 119049 | CATALASE; CAT |
| CCND1 | GDB: 128222 | LEUKEMIA, CHRONIC LYMPHATIC; CLL CYCLIN D1; CCND1 |
| CD3E | GDB: 119764 | CD3E ANTIGEN, EPSILON POLYPEPTIDE; CD3E |
| CD3G | GDB: 119765 | T3 T-CELL ANTIGEN, GAMMA CHAIN; T3G; CD3G |
| CD59 | GDB: 119769 | CD59 ANTIGEN P18-20; CD59 HUMAN LEUKOCYTE ANTIGEN MIC11; MIC11 |
| CDKN1C | GDB: 593296 | CYCLIN-DEPENDENT KINASE INHIBITOR 1C; CDKN1C |
| CLN2 | GDB: 125228 | CEROID-LIPOFUSCINOSIS, NEURONAL 2, LATE INFANTILE TYPE; CLN2 |
| CNTF | GDB: 125919 | CILIARY NEUROTROPHIC FACTOR; CNTF |
| CPT1A | GDB: 597642 | HYPOGLYCEMIA, HYPOKETOTIC, WITH DEFICIENCY OF CARNITINE PALMITOYLTRANSFERASE CARNITINE PALMITOYLTRANSFERASE I, LIVER; CPT1A |
| CTSC | GDB: 642234 | KERATOSIS PALMOPLANTARIS WITH PERIODONTOPATHIA KERATOSIS PALMOPLANTARIS WITH PERIODONTOPATHIA AND ONYCHOGRYPOSIS CATHEPSIN C; CTSC |
| DDB1 | GDB: 595014 | DNA DAMAGE-BINDING PROTEIN; DDB1 |
| DDB2 | GDB: 595015 | DNA DAMAGE-BINDING PROTEIN-2; DDB2 |
| DHCR7 | GDB: 9835302 | SMITH-LEMLI-OPITZ SYNDROME |
| DLAT | GDB: 118785 | CIRRHOSIS, PRIMARY; PBC |
| DRD4 | GDB: 127782 | DOPAMINE RECEPTOR D4; DRD4 |
| ECB2 | GDB: 9958955 | POLYCYTHEMIA, BENIGN FAMILIAL |
| ED4 | GDB: 9837373 | DYSPLASIA, MARGARITA TYPE |
| EVR1 | GDB: 134029 | EXUDATIVE VITREORETINOPATHY, FAMILIAL; EVR EXT2GDB: 344921EXOSTOSES, MULTIPLE, TYPE II; EXT2 CHONDROSARCOMA |
| F2 | GDB: 119894 | COAGULATION FACTOR II; F2 |
| FSHB | GDB: 119955 | FOLLICLE-STIMULATING HORMONE, BETA POLYPEPTIDE; FSHB |
| FTH1 | GDB: 120617 | FERRITIN HEAVY CHAIN 1; FTH1 |
| GIF | GDB: 118800 | PERNICIOUS ANEMIA, CONGENITAL, DUE TO DEFECT OF INTRINSIC FACTOR |
| GSD1B | GDB: 9837619 | GLYCOGEN STORAGE DISEASE Ib |
| GSD1C | GDB: 9837637 | STORAGE DISEASE Ic |
| HBB | GDB: 119297 | HEMOGLOBIN—BETA LOCUS; HBB |
| HBBP1 | GDB: 120035 | HEMOGLOBIN—BETA LOCUS; HBB |
| HBD | GDB: 119298 | HEMOGLOBIN—DELTA LOCUS; HBD |
| HBE1 | GDB: 119299 | HEMOGLOBIN—EPSILON LOCUS; HBE1 |
| HBG1 | GDB: 119300 | HEMOGLOBIN, GAMMA A; HBG1 |
| HBG2 | GDB: 119301 | HEMOGLOBIN, GAMMA G; HBG2 |
| HMBS | GDB: 120528 | PORPHYRIA, ACUTE INTERMITTENT; AIP |
| HND | GDB: 9954478 | HARTNUP DISORDER |
| HOMG2 | GDB: 9956484 | MAGNESIUM WASTING, RENAL |
| HRAS | GDB: 120684 | BLADDER CANCER V-HA-RAS HARVEY RAT SARCOMA VIRAL ONCOGENE HOMOLOG; HRAS |
| HVBS1 | GDB: 120069 | CANCER, HEPATOCELLULAR |
| IDDM2 | GDB: 128530 | DIABETES MELLITUS, INSULIN-DEPENDENT, 2 DIABETES MELLITUS, JUVENILE-ONSET INSULIN-DEPENDENT; IDDM |
| IGER | GDB: 119696 | IgE RESPONSIVENESS, ATOPIC; IGER |
| INS | GDB: 119349 | INSULIN; INS |
| JBS | GDB: 120111 | JACOBSEN SYNDROME; JBS |
| KCNJ11 | GDB: 7009893 | POTASSIUM CHANNEL, INWARDLY-RECTIFYING, SUBFAMILY J, MEMBER 11; KCNJ11 PERSISTENT HYPERINSULINEMIC HYPOGLYCEMIA OF INFANCY |
| KCNJ1 | GDB: 204206 | POTASSIUM CHANNEL, INWARDLY-RECTIFYING, SUBFAMILY J, MEMBER 1; KCNJ1 |
| KCNQ1 | GDB: 741244 | LONG QT SYNDROME, TYPE 1; LQT1 |
| LDHA | GDB: 120141 | LACTATE DEHYDROGENASE-A; LDHA |

TABLE 12-continued

Genes, Locations and Genetic Disorders on Chromosome 11

| Gene | GDB Accession ID | OMIM Link |
|---|---|---|
| LRP5 | GDB: 9836818 | OSTEOPOROSIS-PSEUDOGLIOMA SYNDROME; OPPG HIGH BONE MASS |
| MEN1 | GDB: 120173 | MULTIPLE ENDOCRINE NEOPLASIA, TYPE 1; MEN1 |
| MLL | GDB: 128819 | MYELOID/LYMPHOID OR MIXED-LINEAGE LEUKEMIA; MLL |
| MTACR1 | GDB: 125743 | MULTIPLE TUMOR ASSOCIATED CHROMOSOME REGION 1; MTACR1 |
| MYBPC3 | GDB: 579615 | CARDIOMYOPATHY, FAMILIAL HYPERTROPHIC, 4; CMH4 MYOSIN-BINDING PROTEIN C, CARDIAC; MYBPC3 |
| MYO7A | GDB: 132543 | MYOSIN VIIA; MYO7A DEAFNESS, NEUROSENSORY, AUTOSOMAL RECESSIVE, 2; DFNB2 DEAFNESS, AUTOSOMAL DOMINANT NONSYNDROMIC SENSORINEURAL, 11; DFNA11 |
| NNO1 | GDB: 10450513 | SIMPLE, AUTOSOMAL DOMINANT |
| OPPG | GDB: 3789438 | OSTEOPOROSIS-PSEUDOGLIOMA SYNDROME; OPPG |
| OPTB1 | GDB: 9954474 | OSTEOPETROSIS, AUTOSOMAL RECESSIVE |
| PAX6 | GDB: 118997 | PAIRED BOX HOMEOTIC GENE 6; PAX6 |
| PC | GDB: 119472 | PYRUVATE CARBOXYLASE DEFICIENCY |
| PDX1 | GDB: 9836634 | PYRUVATE DEHYDROGENASE COMPLEX, COMPONENT X |
| PGL2 | GDB: 511177 | PARAGANGLIOMAS, FAMILIAL NONCHROMAFFIN, 2; PGL2 |
| PGR | GDB: 119493 | PROGESTERONE RESISTANCE |
| PORC | GDB: 128610 | PORPHYRIA, CHESTER TYPE; PORC |
| PTH | GDB: 119522 | PARATHYROID HORMONE; PTH |
| PTS | GDB: 118856 | 6-@PYRUVOYLTETRAHYDROPTERIN SYNTHASE; PTS |
| PVRL1 | GDB: 583951 | ECTODERMAL DYSPLASIA, CLEFT LIP AND PALATE, HAND AND FOOT DEFORMITY, DYSPLASIA, MARGARITA TYPE POLIOVIRUS RECEPTOR RELATED; PVRR |
| PYGM | GDB: 120329 | GLYCOGEN STORAGE DISEASE V |
| RAG1 | GDB: 120334 | RECOMBINATION ACTIVATING GENE-1; RAG1 |
| RAG2 | GDB: 125186 | RECOMBINATION ACTIVATING GENE-2; RAG2 |
| ROM1 | GDB: 120350 | ROD OUTER SEGMENT PROTEIN-1; ROM1 |
| SAA1 | GDB: 120364 | SERUM AMYLOID A1; SAA1 |
| SCA5 | GDB: 378219 | SPINOCEREBELLAR ATAXIA 5; SCA5 |
| SCZD2 | GDB: 118874 | DISORDER-2; SCZD2 |
| SDHD | GDB: 132456 | PARAGANGLIOMAS, FAMILIAL NONCHROMAFFIN, 1; PGL1 |
| SERPING1 | GDB: 119041 | ANGIONEUROTIC EDEMA, HEREDITARY; HANE |
| SMPD1 | GDB: 128144 | NIEMANN-PICK DISEASE |
| TCIRG1 | GDB: 9956269 | OSTEOPETROSIS, AUTOSOMAL RECESSIVE |
| TCL2 | GDB: 9954468 | LEUKEMIA, ACUTE T-CELL; ATL |
| TECTA | GDB: 6837718 | DEAFNESS, AUTOSOMAL DOMINANT NONSYNDROMIC SENSORINEURAL, 8; DFNA8 DEAFNESS, AUTOSOMAL DOMINANT NONSYNDROMIC SENSORINEURAL, 12; DFNA12 |
| TH | GDB: 119612 | TYROSINE HYDROXYLASE; TH |
| TREH | GDB: 9958953 | TREHALASE |
| TSG101 | GDB: 1313414 | TUMOR SUSCEPTIBILITY GENE 101; TSG101 |
| TYR | GDB: 120476 | ALBINISM I |
| USH1C | GDB: 132544 | USHER SYNDROME, TYPE IC; USH1C |
| VMD2 | GDB: 133795 | VITELLIFORM MACULAR DYSTROPHY; VMD2 |
| VRNI | GDB: 135662 | VITREORETINOPATHY, NEOVASCULAR INFLAMMATORY; VRNI |
| WT1 | GDB: 120496 | FRASIER SYNDROME WILMS TUMOR; WT1 |

TABLE 12-continued

Genes, Locations and Genetic Disorders on Chromosome 11

| Gene | GDB Accession ID | OMIM Link |
|---|---|---|
| WT2 | GDB: 118886 | MULTIPLE TUMOR ASSOCIATED CHROMOSOME REGION 1; MTACR1 |
| ZNF145 | GDB: 230064 | PROMYELOCYTIC LEUKEMIA ZINC FINGER; PLZF |

TABLE 13

Genes, Locations and Genetic Disorders on Chromosome 12

| Gene | GDB Accession ID | OMIM Link |
|---|---|---|
| A2M | GDB: 119639 | ALPHA-2-MACROGLOBULIN; A2M |
| AAAS | GDB: 9954498 | GLUCOCORTICOID DEFICIENCY AND ACHALASIA |
| ACADS | GDB: 118959 | ACYL-CoA DEHYDROGENASE, SHORT-CHAIN; ACADS |
| ACLS | GDB: 136346 | ACROCALLOSAL SYNDROME; ACLS |
| ACVRL1 | GDB: 230240 | OSLER-RENDU-WEBER SYNDROME 2; ORW2 ACTIVIN A RECEPTOR, TYPE II-LIKE KINASE 1; ACVRL1 |
| ADHR | GDB: 9954488 | VITAMIN D-RESISTANT RICKETS, AUTOSOMAL DOMINANT |
| ALDH2 | GDB: 119668 | ALDEHYDE DEHYDROGENASE-2; ALDH2 |
| AMHR2 | GDB: 696210 | ANTI-MULLERIAN HORMONE TYPE II RECEPTOR; AMHR2 |
| AOM | GDB: 118998 | STICKLER SYNDROME, TYPE I; STL1 |
| AQP2 | GDB: 141853 | AQUAPORIN-2; AQP2 DIABETES INSIPIDUS, RENAL TYPE DIABETES INSIPIDUS, RENAL TYPE, AUTOSOMAL RECESSIVE |
| ATD | GDB: 696353 | ASPHYXIATING THORACIC DYSTROPHY; ATD |
| ATP2A2 | GDB: 119717 | ATPase, Ca(2+)-TRANSPORTNG, SLOW-TWITCH; ATP2A2 DARIER-WHITE DISEASE; DAR |
| BDC | GDB: 5584359 | BRACHYDACTYLY, TYPE C; BDC |
| C1R | GDB: 119729 | COMPLEMENT COMPONENT-C1r, DEFICIENCY OF |
| CD4 | GDB: 119767 | T-CELL ANTIGEN T4/LEU3; CD4 |
| CDK4 | GDB: 204022 | CYCLIN-DEPENDENT KINASE 4; CDK4 |
| CNA1 | GDB: 252119 | CORNEA PLANA 1; CNA1 |
| COL2A1 | GDB: 119063 | STICKLER SYNDROME, TYPE I; STL1 COLLAGEN, TYPE II, ALPHA-1 CHAIN; COL2A1 ACHONDROGENESIS, TYPE II; ACG2 |
| CYP27B1 | GDB: 9835730 | PSEUDOVITAMIN D DEFICIENCY RICKETS; PDDR |
| DRPLA | GDB: 270336 | DENTATORUBRAL-PALLIDOLUYSIAN ATROPHY; DRPLA |
| ENUR2 | GDB: 666422 | ENURESIS, NOCTURNAL, 2; ENUR2 |
| FEOM1 | GDB: 345037 | FIBROSIS OF EXTRAOCULAR MUSCLES, CONGENITAL; FEOM |
| FPF | GDB: 9848880 | PERIODIC FEVER, AUTOSOMAL DOMINANT |
| GNB3 | GDB: 120005 | GUANINE NUCLEOTIDE-BINDING PROTEIN, BETA POLYPEPTIDE-3; GNB3 |
| GNS | GDB: 120006 | MUCOPOLYSACCHARIDOSIS TYPE IIID |
| HAL | GDB: 120746 | HISTIDINEMIA |
| HBP1 | GDB: 701889 | BRACHYDACTYLY WITH HYPERTENSION |
| HMGIC | GDB: 362658 | HIGH MOBILITY GROUP PROTEIN ISOFORM I-C; HMGIC |
| HMN2 | GDB: 9954508 | MUSCULAR ATROPHY, ADULT SPINAL |
| HPD | GDB: 135978 | TYROSINEMIA, TYPE III |
| IGF1 | GDB: 120081 | INSULINLIKE GROWTH FACTOR 1; IGF1 |
| KCNA1 | GDB: 127903 | POTASSIUM VOLTAGE-GATED CHANNEL, SHAKER-RELATED SUBFAMILY, MEMBER |
| KERA | GDB: 252121 | CORNEA PLANA 2; CNA2 |
| KRAS2 | GDB: 120120 | V-KI-RAS2 KIRSTEN RAT SARCOMA 2 VIRAL ONCOGENE HOMOLOG; KRAS2 |
| KRT1 | GDB: 128198 | KERATIN 1; KRT1 |
| KRT2A | GDB: 407640 | ICHTHYOSIS, BULLOUS TYPE KERATIN 2A; KRT2A |
| KRT3 | GDB: 136276 | KERATIN 3; KRT3 |
| KRT4 | GDB: 120697 | KERATIN 4; KRT4 |
| KRT5 | GDB: 128110 | EPIDERMOLYSIS BULLOSA HERPETIFORMIS, DOWLING-MEARA TYPE KERATIN 5; KRT5 |
| KRT6A | GDB: 128111 | KERATIN 6A; KRT6A |
| KRT6B | GDB: 128113 | KERATIN 6B; KRT6B PACHYONYCHIA CONGENITA, JACKSON-LAWLER TYPE |
| KRTHB6 | GDB: 702078 | MONILETHRIX KERATIN, HAIR BASIC (TYPE II) 6 |
| LDHB | GDB: 120147 | LACTATE DEHYDROGENASE-B; LDHB |
| LYZ | GDB: 120160 | AMYLOIDOSIS, FAMILIAL VISCERAL LYSOZYME; LYZ |
| MGCT | GDB: 9954504 | TESTICULAR TUMORS |
| MPE | GDB: 120191 | MALIGNANT PROLIFERATION OF |
| MVK | GDB: 134189 | MEVALONICACIDURIA |
| MYL2 | GDB: 128829 | MYOSIN, LIGHT CHAIN, REGULATORY VENTRICULAR; MYL2 |
| NS1 | GDB: 439388 | NOONAN SYNDROME 1; NS1 |
| OAP | GDB: 120245 | OSTEOARTHROSIS, PRECOCIOUS; OAP |
| PAH | GDB: 119470 | PHENYLKETONURIA; PKU1 |
| PPKB | GDB: 696352 | PALMOPLANTAR KERATODERMA, BOTHNIAN TYPE; PPKB |
| PRB3 | GDB: 119513 | PAROTID SALIVARY GLYCOPROTEIN; G1 |
| PXR1 | GDB: 433739 | ZELLWEGER SYNDROME; ZS PEROXISOME RECEPTOR 1; PXR1 |
| RLS | GDB: 11501392 | ACROMELALGIA, HEREDITARY |
| RSN | GDB: 139158 | RESTIN; RSN |
| SAS | GDB: 128054 | SARCOMA AMPLIFIED SEQUENCE; SAS |
| SCA2 | GDB: 128034 | SPINOCEREBELLAR ATAXIA 2; SCA2 ATAXIN-2; ATX2 |
| SCNN1A | GDB: 366596 | SODIUM CHANNEL, NONVOLTAGE-GATED, 1; SCNN1A |
| SMAL | GDB: 9954506 | SPINAL MUSCULAR ATROPHY, CONGENITAL NONPROGRESSIVE, OF LOWER LIMBS |
| SPPM | GDB: 9954502 | SCAPULOPERONEAL MYOPATHY; SPM |
| SPSMA | GDB: 9954510 | SCAPULOPERONEAL AMYOTROPHY, NEUROGENIC, NEW ENGLAND TYPE |
| TBX3 | GDB: 681969 | ULNAR-MAMMARY SYNDROME; UMS T-BOX 3; TBX3 |

TABLE 13-continued

Genes, Locations and Genetic Disorders on Chromosome 12

| Gene | GDB Accession ID | OMIM Link |
|---|---|---|
| TBX5 | GDB: 6175917 | HOLT-ORAM SYNDROME; HOS T-BOX 5; TBX5 |
| TCF1 | GDB: 125297 | TRANSCRIPTION FACTOR 1, HEPATIC; TCF1 MATURITY-ONSET DIABETES OF THE YOUNG, TYPE III; MODY3 |
| TPI1 | GDB: 119617 | TRIOSEPHOSPHATE ISOMERASE 1; TPI1 |
| TSC3 | GDB: 127930 | SCLEROSIS-3; TSC3 |
| ULR | GDB: 594089 | UTERINE |
| VDR | GDB: 120487 | VITAMIN D-RESISTANT RICKETS WITH END-ORGAN UNRESPONSIVENESS TO 1,25-DIHYDROXYCHOLECALCIFEROL VITAMIN D RECEPTOR; VDR |
| VWF | GDB: 119125 | VON WILLEBRAND DISEASE; VWD |

TABLE 14

Genes, Locations and Genetic Disorders on Chromosome 13

| Gene | GDB Accession ID | OMIM Link |
|---|---|---|
| ATP7B | GDB: 120494 | WILSON DISEASE; WND |
| BRCA2 | GDB: 387848 | BREAST CANCER 2, EARLY-ONSET; BRCA2 |
| BRCD1 | GDB: 9954522 | BREAST CANCER, DUCTAL, 1; BRCD1 |
| CLN5 | GDB: 230991 | CEROID-LIPOFUSCNOSIS, NEURONAL 5; CLN5 |
| CPB2 | GDB: 129546 | CARBOXYPEPTIDASE B2, PLASMA; CPB2 |
| ED2 | GDB: 9834522 | ECTODERMAL DYSPLASIA, HIDROTIC; HED |
| EDNRB | GDB: 129075 | ENDOTHELIN-B RECEPTOR; EDNRB HIRSCHSPRUNG DISEASE-2; HSCR2 |
| ENUR1 | GDB: 594516 | ENURESIS, NOCTURNAL, 1; ENUR1 |
| ERCC5 | GDB: 120515 | EXCISION-REPAIR, COMPLEMENTING DEFECTIVE, IN CHINESE HAMSTER, 5; ERCC5 |
| F10 | GDB: 119890 | X, QUANTITATIVE VARIATION IN FACTOR X DEFICIENCY; F10 |
| F7 | GDB: 119897 | FACTOR VII DEFICIENCY |
| GJB2 | GDB: 125247 | GAP JUNCTION PROTEIN, BETA-2, 26 KD; GJB2 DEAFNESS, NEUROSENSORY, AUTOSOMAL RECESSIVE, 1; DFNB1 DEAFNESS, AUTOSOMAL DOMINANT NONSYNDROMIC SENSORINEURAL, 3; DFNA3 |
| GJB6 | GDB: 9958357 | ECTODERMAL DYSPLASIA, HIDROTIC; HED DEAFNESS, AUTOSOMAL DOMINANT NONSYNDROMIC SENSORINEURAL, 3; DFNA3 |
| IPF1 | GDB: 448899 | INSULIN PROMOTER FACTOR 1; IPF1 |
| MBS1 | GDB: 128365 | MOEBIUS SYNDROME; MBS |
| MCOR | GDB: 9954520 | CONGENITAL |
| PCCA | GDB: 119473 | GLYCINEMIA, KETOTIC, I |
| RB1 | GDB: 118734 | BLADDER CANCER RETINOBLASTOMA; RB1 |
| RHOK | GDB: 371598 | RHODOPSIN KINASE; RHOK |
| SCZD7 | GDB: 9864734 | DISORDER-2; SCZD2 |
| SGCG | GDB: 3763329 | MUSCULAR DYSTROPHY, LIMB GIRDLE, TYPE 2C; LGMD2C |
| SLC10A2 | GDB: 677534 | SOLUTE CARRIER FAMILY 10, MEMBER 2; SLC10A2 |
| SLC25A15 | GDB: 120042 | HYPERORNITHINEMIA-HYPERAMMONEMIA-HOMOCITRULLINURIA SYNDROME |
| STARP1 | GDB: 635459 | STEROIDOGENIC ACUTE REGULATORY PROTEIN; STAR |
| ZNF198 | GDB: 6382650 | ZINC FINGER PROTEIN-198; ZNF198 |

TABLE 15

| Genes, Locations and Genetic Disorders on Chromosome 14 | | |
|---|---|---|
| Gene | GDB Accession ID | OMIM Link |
| ACHM1 | GDB: 132458 | COLORBLINDNESS, TOTAL |
| ARVD1 | GDB: 371339 | ARRHYTHMOGENIC RIGHT VENTRICULAR DYSPLASIA, FAMILIAL, 1; ARVD1 |
| CTAA1 | GDB: 265299 | CATARACT, ANTERIOR POLAR 1; CTAA1 |
| DAD1 | GDB: 407505 | DEFENDER AGAINST CELL DEATH; DAD1 |
| DFNB5 | GDB: 636176 | DEAFNESS, NEUROSENSORY, AUTOSOMAL RECESSIVE, 5; DFNB5 |
| EML1 | GDB: 6328385 | USHER SYNDROME, TYPE IA; USH1A |
| GALC | GDB: 119970 | KRABBE DISEASE |
| GCH1 | GDB: 118798 | DYSTONIA, PROGRESSIVE, WITH DIURNAL VARIATION GTP CYCLOHYDROLASE I DEFICIENCY GTP CYCLOHYDROLASE I; GCH1 |
| HE1 | GDB: 9957680 | MALFORMATIONS, MULTIPLE, WITH LIMB ABNORMALITIES AND HYPOPITUITARISM |
| IBGC1 | GDB: 10450404 | CEREBRAL CALCIFICATION, NONARTERIOSCLEROTIC |
| IGH@ | GDB: 118731 | IgA CONSTANT HEAVY CHAIN 1; IGHA1 IMMUNOGLOBULIN: D (DIVERSITY) REGION OF HEAVY CHAIN IgA CONSTANT HEAVY CHAIN 2; IGHA2 IMMUNOGLOBULIN: J (JOINING) LOCI OF HEAVY CHAIN; IGHJ IMMUNOGLOBULIN: HEAVY Mu CHAIN; Mu1; IGHM1 IMMUNOGLOBULIN: VARIABLE REGION OF HEAVY CHAINS—Hv1; IGHV IgG HEAVY CHAIN LOCUS; IGHG1 IMMUNOGLOBULIN Gm-2; IGHG2 IMMUNOGLOBULIN Gm-3; IGHG3 IMMUNOGLOBULIN Gm-4; IGHG4 IMMUNOGLOBULIN: HEAVY DELTA CHAIN; IGHD IMMUNOGLOBULIN: HEAVY EPSILON CHAIN; IGHE |
| IGHC group | GDB: 9992632 | IgA CONSTANT HEAVY CHAIN 1; IGHA1 IgA CONSTANT HEAVY CHAIN 2; IGHA2 IMMUNOGLOBULIN: HEAVY Mu CHAIN; Mu1; IGHM1 IgG HEAVY CHAIN LOCUS; IGHG1 IMMUNOGLOBULIN Gm-2; IGHG2 IMMUNOGLOBULIN Gm-3; IGHG3 IMMUNOGLOBULIN Gm-4; IGHG4 IMMUNOGLOBULIN: HEAVY DELTA CHAIN; IGHD IMMUNOGLOBULIN: HEAVY EPSILON CHAIN; IGHE |
| IGHG1 | GDB: 120085 | IgG HEAVY CHAIN LOCUS; IGHG1 |
| IGHM | GDB: 120086 | IMMUNOGLOBULIN: HEAVY Mu CHAIN; Mu1; IGHM1 |
| IGHR | GDB: 9954529 | G1(A1) SYNDROME |
| IV | GDB: 139274 | INVERSUS VISCERUM |
| LTBP2 | GDB: 453890 | LATENT TRANSFORMING GROWTH FACTOR-BETA BINDING PROTEIN 2; LTBP2 |
| MCOP | GDB: 9954527 | MICROPHTHALMOS |
| MJD | GDB: 118840 | MACHADO-JOSEPH DISEASE; MJD |
| MNG1 | GDB: 6540062 | GOITER, MULTINODULAR 1; MNG1 |
| MPD1 | GDB: 230271 | MYOPATHY, LATE DISTAL HEREDITARY |
| MPS3C | GDB: 9954532 | MUCOPOLYSACCHARIDOSIS TYPE IIIC |
| MYH6 | GDB: 120214 | MYOSIN, HEAVY POLYPEPTIDE 6; MYH6 |
| MYH7 | GDB: 120215 | MYOSIN, CARDIAC, HEAVY CHAIN, BETA; MYH7 |
| NP | GDB: 120239 | NUCLEOSIDE PHOSPHORYLASE; NP |
| PABPN1 | GDB: 567135 | OCULOPHARYNGEAL MUSCULAR DYSTROPHY; OPMD OCULOPHARYNGEAL MUSCULAR DYSTROPHY, AUTOSOMAL RECESSIVE POLYADENYLATE-BINDING PROTEIN-2; PABP2 |
| PSEN1 | GDB: 135682 | ALZHEIMER DISEASE, FAMILIAL, TYPE 3; AD3 |
| PYGL | GDB: 120328 | GLYCOGEN STORAGE DISEASE VI |
| RPGRIP1 | GDB: 11498766 | AMAUROSIS CONGENITA OF LEBER I |
| SERPINA1 | GDB: 120289 | PROTEASE INHIBITOR 1; PI |
| SERPINA3 | GDB: 118955 | ALPHA-1-ANTICHYMOTRYPSIN; AACT |
| SERPINA6 | GDB: 127865 | CORTICOSTEROID-BINDING GLOBULIN; CBG |
| SLC7A7 | GDB: 9863033 | DIBASICAMINOACIDURIA II |
| SPG3A | GDB: 230126 | SPASTIC PARAPLEGIA-3, AUTOSOMAL DOMINANT; SPG3A |

TABLE 15-continued

Genes, Locations and Genetic Disorders on Chromosome 14

| Gene | GDB Accession ID | OMIM Link |
|---|---|---|
| SPTB | GDB: 119602 | ELLIPTOCYTOSIS, RHESUS-UNLINKED TYPE HEREDITARY HEMOLYTIC SPECTRIN, BETA, ERYTHROCYTIC; SPTB |
| TCL1A | GDB: 250785 | T-CELL LYMPHOMA OR LEUKEMIA |
| TCRAV17S1 | GDB: 642130 | T-CELL ANTIGEN RECEPTOR, ALPHA SUBUNIT; TCRA |
| TCRAV5S1 | GDB: 451966 | T-CELL ANTIGEN RECEPTOR, ALPHA SUBUNIT; TCRA |
| TGM1 | GDB: 125299 | TRANSGLUTAMINASE 1; TGM1 ICHTHYOSIS CONGENITA |
| TITF1 | GDB: 132588 | THYROID TRANSCRIPTION FACTOR 1; TITF1 |
| TMIP | GDB: 9954523 | AND ULNA, DUPLICATION OF, WITH ABSENCE OF TIBIA AND RADIUS |
| TRA@ | GDB: 120404 | T-CELL ANTIGEN RECEPTOR, ALPHA SUBUNIT; TCRA |
| TSHR | GDB: 125313 | THYROTROPIN, UNRESPONSIVENESS TO |
| USH1A | GDB: 118885 | USHER SYNDROME, TYPE IA; USH1A |
| VP | GDB: 120492 | PORPHYRIA VARIEGATA |

TABLE 16

Genes, Locations and Genetic Disorders on Chromosome 15

| Gene | GDB Accession ID | OMIM Link |
|---|---|---|
| ACCPN | GDB: 5457725 | CORPUS CALLOSUM, AGENESIS OF, WITH NEURONOPATHY |
| AHO2 | GDB: 9954535 | HEREDITARY OSTEODYSTROPHY-2; AHO2 |
| ANCR | GDB: 119678 | ANGELMAN SYNDROME |
| B2M | GDB: 119028 | BETA-2-MICROGLOBULIN; B2M |
| BBS4 | GDB: 511199 | BARDET-BIEDL SYNDROME, TYPE 4; BBS4 |
| BLM | GDB: 135698 | BLOOM SYNDROME; BLM |
| CAPN3 | GDB: 119751 | CALPAIN, LARGE POLYPEPTIDE L3; CAPN3 MUSCULAR DYSTROPHY, LIMB-GIRDLE, TYPE 2; LGMD2 |
| CDAN1 | GDB: 9823267 | DYSERYTHROPOIETIC ANEMIA, CONGENITAL, TYPE I |
| CDAN3 | GDB: 386192 | DYSERYTHROPOIETIC ANEMIA, CONGENITAL, TYPE III; CDAN3 |
| CLN6 | GDB: 4073043 | CEROID-LIPOFUSCINOSIS, NEURONAL 6, LATE INFANTILE, VARIANT; CLN6 |
| CMH3 | GDB: 138299 | CARDIOMYOPATHY, FAMILIAL HYPERTROPHIC, 3; CMH3 |
| CYP19 | GDB: 119830 | CYTOCHROME P450, SUBFAMILY XIX; CYP19 |
| CYP1A1 | GDB: 120604 | CYTOCHROME P450, SUBFAMILY I, POLYPEPTIDE 1; CYP1A1 |
| CYP1A2 | GDB: 118780 | CYTOCHROME P450, SUBFAMILY I, POLYPEPTIDE 2; CYP1A2 |
| DYX1 | GDB: 1391796 | DYSLEXIA, SPECIFIC, 1; DYX1 |
| EPB42 | GDB: 127385 | HEREDITARY HEMOLYTIC PROTEIN 4.2, ERYTHROCYTIC; EPB42 |
| ETFA | GDB: 119121 | GLUTARICACIDURIA IIA; GA IIA |
| EYCL3 | GDB: 4590306 | EYE COLOR-3; EYCL3 |
| FAH | GDB: 119901 | TYROSINEMIA, TYPE I |
| FBN1 | GDB: 127115 | FIBRILLIN-1; FBN1 MARFAN SYNDROME; MFS |
| FES | GDB: 119906 | V-FES FELINE SARCOMA VIRAL/V-FPS FUJINAMI AVIAN SARCOMA VIRAL ONCOGENE |
| HCVS | GDB: 119306 | CORONAVIRUS 229E SUSCEPTIBILITY; CVS |
| HEXA | GDB: 120040 | TAY-SACHS DISEASE; TSD |
| IVD | GDB: 119354 | ISOVALERICACIDEMIA; IVA |
| LCS1 | GDB: 11500552 | CHOLESTASIS-LYMPHEDEMA SYNDROME |
| LIPC | GDB: 119366 | LIPASE, HEPATIC; LIPC |
| MYO5A | GDB: 218824 | MYOSIN VA; MYO5A |
| OCA2 | GDB: 136820 | ALBINISM II |
| OTSC1 | GDB: 9860473 | OTOSCLEROSIS |
| PWCR | GDB: 120325 | PRADER-WILLI SYNDROME |
| RLBP1 | GDB: 127341 | RETINALDEHYDE-BINDING PROTEIN 1,; RLBP1 |
| SLC12A1 | GDB: 386121 | SOLUTE CARRIER FAMILY 12, MEMBER 1; SLC12A1 |
| SPG6 | GDB: 511201 | SPASTIC PARAPLEGIA 6, AUTOSOMAL DOMINANT; SPG6 |
| TPM1 | GDB: 127875 | TROPOMYOSIN 1; TPM1 |
| UBE3A | GDB: 228487 | ANGELMAN SYNDROME UBIQUITIN-PROTEIN LIGASE E3A; UBE3A |
| WMS | GDB: 5583902 | WEILL-MARCHESANI SYNDROME |

TABLE 17

Genes, Locations and Genetic Disorders on Chromosome 16

| Gene | GDB Accession ID | OMIM Link |
|---|---|---|
| ABCC6 | GDB: 9315106 | PSEUDOXANTHOMA ELASTICUM, AUTOSOMAL DOMINANT; PXE PSEUDOXANTHOMA ELASTICUM, AUTOSOMAL RECESSIVE; PXE |

TABLE 17-continued

Genes, Locations and Genetic Disorders on Chromosome 16

| Gene | GDB Accession ID | OMIM Link |
|---|---|---|
| ALDOA | GDB: 118993 | ALDOLASE A, FRUCTOSE-BISPHOSPHATE; ALDOA |
| APRT | GDB: 119003 | ADENINE PHOSPHORIBOSYLTRANSFERASE; APRT |
| ATP2A1 | GDB: 119716 | ATPase, Ca(2+)-TRANSPORTING, FAST-TWITCH 1; ATP2A1 BRODY MYOPATHY |
| BBS2 | GDB: 229992 | BARDET-BIEDL SYNDROME, TYPE 2; BBS2 |
| CARD15 | GDB: 11026232 | SYNOVITIS, GRANULOMATOUS, WITH UVEITIS AND CRANIAL NEUROPATHIES REGIONAL ENTERITIS |
| CATM | GDB: 701219 | MICROPHTHALMIA-CATARACT |
| CDH1 | GDB: 120484 | CADHERIN 1; CDH1 |
| CETP | GDB: 119773 | CHOLESTERYL ESTER TRANSFER PROTEIN, PLASMA; CETP |
| CHST6 | GDB: 131407 | CORNEAL DYSTROPHY, MACULAR TYPE |
| CLN3 | GDB: 120593 | CEROID-LIPOFUSCINOSIS, NEURONAL 3, JUVENILE; CLN3 |
| CREBBP | GDB: 437159 | RUBINSTEIN SYNDROME CREB-BINDING PROTEIN; CREBBP |
| CTH | GDB: 119086 | CYSTATHIONINURIA |
| CTM | GDB: 119819 | CATARACT, ZONULAR |
| CYBA | GDB: 125238 | GRANULOMATOUS DISEASE, CHRONIC, AUTOSOMAL CYTOCHROME-b-NEGATIVE FORM |
| CYLD | GDB: 701216 | EPITHELIOMA, HEREDITARY MULTIPLE BENIGN CYSTIC |
| DHS | GDB: 9958268 | XEROCYTOSIS, HEREDITARY |
| DNASE1 | GDB: 132846 | DEOXYRIBONUCLEASE I; DNASE1 |
| DPEP1 | GDB: 128059 | RENAL DIPEPTIDASE |
| ERCC4 | GDB: 119113 | EXCISION-REPAIR, COMPLEMENTING DEFECTIVE, IN CHINESE HAMSTER, 4; ERCC4 XERODERMA PIGMENTOSUM, COMPLEMENTATION GROUP F; XPF |
| FANCA | GDB: 701221 | FANCONI ANEMIA, COMPLEMENTATION GROUP A; FACA |
| GALNS | GDB: 129085 | MUCOPOLYSACCHARIDOSIS TYPE IVA |
| GAN | GDB: 9864885 | NEUROPATHY, GIANT AXONAL; GAN |
| HAGH | GDB: 119292 | HYDROXYACYL GLUTATHIONE HYDROLASE; HAGH |
| HBA1 | GDB: 119293 | HEMOGLOBIN—ALPHA LOCUS-1; HBA1 |
| HBA2 | GDB: 119294 | HEMOGLOBIN—ALPHA LOCUS-2; HBA2 |
| HBHR | GDB: 9954541 | HEMOGLOBIN H-RELATED MENTAL RETARDATION |
| HBQ1 | GDB: 120036 | HEMOGLOBIN—THETA-1 LOCUS; HBQ1 |
| HBZ | GDB: 119302 | HEMOGLOBIN—ZETA LOCUS; HBZ |
| HBZP | GDB: 120037 | HEMOGLOBIN—ZETA LOCUS; HBZ |
| HP | GDB: 119314 | HAPTOGLOBIN; HP |
| HSD11B2 | GDB: 409951 | CORTISOL 11-BETA-KETOREDUCTASE DEFICIENCY |
| IL4R | GDB: 118823 | INTERLEUKIN-4 RECEPTOR; IL4R |
| LIPB | GDB: 119365 | LIPASE B, LYSOSOMAL ACID; LIPB |
| MC1R | GDB: 135162 | MELANOCORTIN-1 RECEPTOR; MC1R |
| MEFV | GDB: 125263 | MEDITERRANEAN FEVER, FAMILIAL; MEFV |
| MHC2TA | GDB: 6268475 | MHC CLASS II TRANSACTIVATOR; MHC2TA |
| MLYCD | GDB: 11500940 | MALONYL CoA DECARBOXYLASE DEFICIENCY |
| PHKB | GDB: 120286 | PHOSPHORYLASE KINASE, BETA SUBUNIT; PHKB |
| PHKG2 | GDB: 140316 | PHOSPHORYLASE KINASE, TESTIS/LIVER, GAMMA 2; PHKG2 |
| PKD1 | GDB: 120293 | POLYCYSTIC KIDNEYS POLYCYSTIC KIDNEY DISEASE 1; PKD1 |
| PKDTS | GDB: 9954545 | POLYCYSTIC KIDNEY DISEASE, INFANTILE SEVERE, WITH TUBEROUS SCLEROSIS; |
| PMM2 | GDB: 438697 | CARBOHYDRATE-DEFICIENT GLYCOPROTEIN SYNDROME, TYPE I; CDG1 PHOSPHOMANNOMUTASE 2; PMM2 |
| PXE | GDB: 6053895 | PSEUDOXANTHOMA ELASTICUM, AUTOSOMAL DOMINANT; PXE PSEUDOXANTHOMA ELASTICUM, AUTOSOMAL RECESSIVE; PXE |

TABLE 17-continued

Genes, Locations and Genetic Disorders on Chromosome 16

| Gene | GDB Accession ID | OMIM Link |
|---|---|---|
| SALL1 | GDB: 4216161 | TOWNES-BROCKS SYNDROME; TBS SAL-LIKE 1; SALL1 |
| SCA4 | GDB: 250364 | SPINOCEREBELLAR ATAXIA 4; SCA4 |
| SCNN1B | GDB: 434471 | SODIUM CHANNEL, NONVOLTAGE-GATED 1 BETA; SCNN1B |
| SCNN1G | GDB: 568759 | SODIUM CHANNEL, NONVOLTAGE-GATED 1 GAMMA; SCNN1G |
| TAT | GDB: 120398 | TYROSINE TRANSAMINASE DEFICIENCY |
| TSC2 | GDB: 120466 | TUBEROUS SCLEROSIS-2; TSC2 |
| VDI | GDB: 119629 | DEFECTIVE INTERFERING PARTICLE INDUCTION, CONTROL OF |
| WT3 | GDB: 9958957 | WILMS TUMOR, TYPE III; WT3 |

TABLE 18

Genes, Locations and Genetic Disorders on Chromosome 17

| Gene | GDB Accession ID | OMIM Link |
|---|---|---|
| ABR | GDB: 119642 | ACTIVE BCR-RELATED GENE; ABR |
| ACACA | GDB: 120534 | ACETYL-CoA CARBOXYLASE DEFICIENCY |
| ACADVL | GDB: 1248185 | ACYL-CoA DEHYDROGENASE, VERY-LONG-CHAIN, DEFICIENCY OF |
| ACE | GDB: 119840 | DIPEPTIDYL CARBOXYPEPTIDASE-1; DCP1 |
| ALDH3A2 | GDB: 1316855 | SJOGREN-LARSSON SYNDROME; SLS |
| APOH | GDB: 118887 | APOLIPOPROTEIN H; APOH |
| ASPA | GDB: 231014 | SPONGY DEGENERATION OF CENTRAL NERVOUS SYSTEM |
| AXIN2 | GDB: 9864782 | CANCER OF COLON |
| BCL5 | GDB: 125178 | LEUKEMIA/LYMPHOMA, CHRONIC B-CELL, 5; BCL5 |
| BHD | GDB: 11498904 | WITH TRICHODISCOMAS AND ACROCHORDONS |
| BLMH | GDB: 3801467 | BLEOMYCIN HYDROLASE |
| BRCA1 | GDB: 126611 | BREAST CANCER, TYPE 1; BRCA1 |
| CACD | GDB: 5885801 | CHOROIDAL DYSTROPHY, CENTRAL AREOLAR; CACD |
| CCA1 | GDB: 118763 | CATARACT, CONGENITAL, CERULEAN TYPE 1; CCA1 |
| CCZS | GDB: 681973 | CATARACT, CONGENITAL ZONULAR, WITH SUTURAL OPACITIES; CCZS |
| CHRNB1 | GDB: 120587 | CHOLINERGIC RECEPTOR, NICOTINIC, BETA POLYPEPTIDE 1; CHRNB1 |
| CHRNE | GDB: 132246 | CHOLINERGIC RECEPTOR, NICOTINIC, EPSILON POLYPEPTIDE; CHRNE |
| CMT1A | GDB: 119785 | CHARCOT-MARIE-TOOTH DISEASE, TYPE 1A; CMT1A NEUROPATHY, HEREDITARY, WITH LIABILITY TO PRESSURE PALSIES; HNPP |
| COL1A1 | GDB: 119061 | COLLAGEN, TYPE I, ALPHA-1 CHAIN; COL1A1 OSTEOGENESIS IMPERFECTA TYPE I OSTEOGENESIS IMPERFECTA TYPE IV; OI4 |
| CORD5 | GDB: 568473 | CONE-ROD DYSTROPHY-5; CORD5 |
| CTNS | GDB: 700761 | CYSTINOSIS, EARLY-ONSET OR INFANTILE NEPHROPATHIC TYPE |
| EPX | GDB: 377700 | EOSINOPHIL PEROXIDASE; EPX |
| ERBB2 | GDB: 120613 | V-ERB-B2 AVIAN ERYTHROBLASTIC LEUKEMIA VIRAL ONCOGENE HOMOLOG 2; ERBB2 |
| G6PC | GDB: 231927 | GLYCOGEN STORAGE DISEASE I; GSD-I |
| GAA | GDB: 119965 | GLYCOGEN STORAGE DISEASE II |
| GALK1 | GDB: 119246 | GALACTOKINASE DEFICIENCY |
| GCGR | GDB: 304516 | GLUCAGON RECEPTOR, GCGR |
| GFAP | GDB: 118799 | GLIAL FIBRILLARY ACIDIC PROTEIN; GFAP ALEXANDER DISEASE |
| GH1 | GDB: 119982 | GROWTH HORMONE 1; GH1 |
| GH2 | GDB: 119983 | GROWTH HORMONE 2; GH2 |
| GP1BA | GDB: 118806 | GIANT PLATELET SYNDROME |

TABLE 18-continued

Genes, Locations and Genetic Disorders on Chromosome 17

| Gene | GDB Accession ID | OMIM Link |
|---|---|---|
| GPSC | GDB: 9954564 | FAMILIAL PROGRESSIVE SUBCORTICAL |
| GUCY2D | GDB: 136012 | AMAUROSIS CONGENITA OF LEBER I GUANYLATE CYCLASE 2D, MEMBRANE; GUC2D CONE-ROD DYSTROPHY-6; CORD6 |
| ITGA2B | GDB: 120012 | THROMBASTHENIA OF GLANZMANN AND NAEGELI |
| ITGB3 | GDB: 120013 | INTEGRIN, BETA-3; ITGB3 |
| ITGB4 | GDB: 128028 | INTEGRIN, BETA-4; ITGB4 |
| KRT10 | GDB: 118828 | KERATIN 10; KRT10 |
| KRT12 | GDB: 5583953 | CORNEAL DYSTROPHY, JUVENILE EPITHELIAL, OF MEESMANN KERATIN 12; KRT12 |
| KRT13 | GDB: 120740 | KERATIN 13; KRT13 |
| KRT14 | GDB: 132145 | KERATIN 14; KRT14 GLUTATHIONE SYNTHETASE; GSS |
| KRT14L1 | GDB: 120121 | KERATIN 14; KRT14 |
| KRT14L2 | GDB: 120122 | KERATIN 14; KRT14 |
| KRT14L3 | GDB: 120123 | KERATIN 14; KRT14 |
| KRT16 | GDB: 136207 | KERATIN 16; KRT16 |
| KRT16L1 | GDB: 120125 | KERATIN 16; KRT16 |
| KRT16L2 | GDB: 120126 | KERATIN 16; KRT16 |
| KRT17 | GDB: 136211 | KERATIN 17; KRT17 PACHYONYCHIA CONGENITA, JACKSON-LAWLER TYPE |
| KRT9 | GDB: 303970 | HYPERKERATOSIS, LOCALIZED EPIDERMOLYTIC |
| MAPT | GDB: 119434 | MICROTUBULE-ASSOCIATED PROTEIN TAU; MAPT PALLIDOPONTONIGRAL DEGENERATION; PPND DISINHIBITION-DEMENTIA-PARKINSONISM-AMYOTROPHY COMPLEX; DDPAC |
| MDB | GDB: 9958959 | MEDULLOBLASTOMA; MDB |
| MDCR | GDB: 120525 | MILLER-DIEKER LISSENCEPHALY SYNDROME; MDLS PLATELET-ACTIVATING FACTOR ACETYLHYDROLASE, GAMMA SUBUNIT |
| MGI | GDB: 9954550 | MYASTHENIA GRAVIS, FAMILIAL INFANTILE; FIMG |
| MHS2 | GDB: 132580 | MALIGNANT HYPERTHERMIA SUSCEPTIBILITY-2; MHS2 |
| MKS1 | GDB: 681967 | MECKEL SYNDROME; MKS |
| MPO | GDB: 120192 | MYELOPEROXIDASE DEFICIENCY |
| MUL | GDB: 636050 | MULIBREY NANISM; MUL |
| MYO15A | GDB: 9838006 | DEAFNESS, NEUROSENSORY, AUTOSOMAL RECESSIVE, 3; DFNB3 |
| NAGLU | GDB: 636533 | MUCOPOLYSACCHARIDOSIS TYPE IIIB |
| NAPB | GDB: 9954572 | NEURITIS WITH BRACHIAL PREDILECTION; NAPB |
| NF1 | GDB: 120231 | NEUROFIBROMATOSIS, TYPE I; NF1 |
| NME1 | GDB: 127965 | NON-METASTATIC CELLS 1, PROTEIN EXPRESSED IN; NME1 |
| P4HB | GDB: 120708 | PROLYL-4-HYDROXYLASE, BETA POLYPEPTIDE; PHDB; PROHB |
| PAFAH1B1 | GDB: 677430 | MILLER-DIEKER LISSENCEPHALY SYNDROME; MDLS PLATELET-ACTIVATING FACTOR ACETYLHYDROLASE, GAMMA SUBUNIT |
| PECAM1 | GDB: 696372 | PLATELET-ENDOTHELIAL CELL ADHESION MOLECULE; PECAM1 |
| PEX12 | GDB: 6155804 | ZELLWEGER SYNDROME; ZS PEROXIN-12; PEX12 |
| PHB | GDB: 126600 | PROHIBITIN; PHB |
| PMP22 | GDB: 134190 | CHARCOT-MARIE-TOOTH DISEASE, TYPE 1A; CMT1A HYPERTROPHIC NEUROPATHY OF DEJERINE-SOTTAS PERIPHERAL MYELIN PROTEIN 22; PMP22 |
| PRKAR1A | GDB: 120313 | MYXOMA, SPOTTY PIGMENTATION, AND ENDOCRINE OVERACTIVITY PROTEIN KINASE, cAMP-DEPENDENT, REGULATORY, TYPE I, ALPHA; PRKAR1A |
| PRKCA | GDB: 128015 | PROTEIN KINASE C, ALPHA; PRKCA |
| PRKWNK4 | GDB: 9954566 | PSEUDOHYPOALDOSTERONISM TYPE II, LOCUS B; PHA2B |
| PRP8 | GDB: 9957697 | RETINITIS PIGMENTOSA-13; RP13 |

TABLE 18-continued

Genes, Locations and Genetic Disorders on Chromosome 17

| Gene | GDB Accession ID | OMIM Link |
| --- | --- | --- |
| PRPF8 | GDB: 392647 | RETINITIS PIGMENTOSA-13; RP13 |
| PTLAH | GDB: 9957342 | APLASIA OR HYPOPLASIA |
| RARA | GDB: 120337 | RETINOIC ACID RECEPTOR, ALPHA; RARA |
| RCV1 | GDB: 135477 | RECOVERIN; RCV1 |
| RMSA1 | GDB: 304519 | REGULATOR OF MITOTIC SPINDLE ASSEMBLY 1; RMSA1 |
| RP17 | GDB: 683199 | RETINITIS PIGMENTOSA-17; RP17 |
| RSS | GDB: 439249 | RUSSELL-SILVER SYNDROME; RSS |
| SCN4A | GDB: 125181 | PERIODIC PARALYSIS II |
| SERPINF2 | GDB: 120301 | PLASMIN INHIBITOR DEFICIENCY |
| SGCA | GDB: 384077 | ADHALIN; ADL |
| SGSH | GDB: 1319101 | MUCOPOLYSACCHARIDOSIS TYPE IIIA |
| SHBG | GDB: 125280 | SEX HORMONE BINDING GLOBULIN; SHBG |
| SLC2A4 | GDB: 119997 | SOLUTE CARRIER FAMILY 2, MEMBER 4; SLC2A4 |
| SLC4A1 | GDB: 119874 | SOLUTE CARRIER FAMILY 4, ANION EXCHANGER, MEMBER 1; SLC4A1 BLOOD GROUP-DIEGO SYSTEM; DI BLOOD GROUP-WRIGHT ANTIGEN; Wr ELLIPTOCYTOSIS, RHESUS-UNLINKED TYPE HEREDITARY HEMOLYTIC |
| SLC6A4 | GDB: 134713 | SOLUTE CARRIER FAMILY 6, MEMBER 4; SLC6A4 |
| SMCR | GDB: 120379 | SMITH-MAGENIS SYNDROME; SMS |
| SOST | GDB: 10450629 | SCLEROSTEOSIS |
| SOX9 | GDB: 134730 | DYSPLASIA |
| SSTR2 | GDB: 134186 | SOMATOSTATIN RECEPTOR-2; SSTR2 |
| SYM1 | GDB: 512174 | SYMPHALANGISM, PROXIMAL; SYM1 |
| SYNS1 | GDB: 9862343 | SYNOSTOSES, MULTIPLE, WITH BRACHYDACTYLY |
| TCF2 | GDB: 125298 | TRANSCRIPTION FACTOR-2, HEPATIC; TCF2 |
| THRA | GDB: 120730 | THYROID HORMONE RECEPTOR, ALPHA 1; THRA |
| TIMP2 | GDB: 132612 | TISSUE INHIBITOR OF METALLOPROTEINASE-2; TIMP2 |
| TOC | GDB: 451978 | TYLOSIS WITH ESOPHAGEAL CANCER; TOC |
| TOP2A | GDB: 118884 | TOPOISOMERASE (DNA) II, ALPHA; TOP2A |
| TP53 | GDB: 120445 | CANCER, HEPATOCELLULAR LI-FRAUMENI SYNDROME; LFS TUMOR PROTEIN p53; TP53 CARCINOMA |
| VBCH | GDB: 9954554 | HYPEROSTOSIS CORTICALIS GENERALISATA |

TABLE 19

Genes, Locations and Genetic Disorders on Chromosome 18

| Gene | GDB Accession ID | OMIM Link |
| --- | --- | --- |
| ATP8B1 | GDB: 453352 | CHOLESTASIS, PROGRESSIVE FAMILIAL INTRAHEPATIC 1; PFIC1 INTRAHEPATIC CHOLESTASIS FAMILIAL INTRAHEPATIC CHOLESTASIS-1; FIC1 |
| BCL2 | GDB: 119031 | B-CELL CLL/LYMPHOMA 2; BCL2 |
| CNSN | GDB: 9954580 | CARNOSINEMIA |
| CORD1 | GDB: 118773 | CONE-ROD DYSTROPHY-1; CORD1 |
| CYB5 | GDB: 125236 | METHEMOGLOBINEMIA DUE TO DEFICIENCY OF CYTOCHROME b5 |
| DCC | GDB: 119838 | DELETED IN COLORECTAL CARCINOMA; DCC |
| F5F8D | GDB: 6919858 | FACTOR V AND FACTOR VIII, COMBINED DEFICIENCY OF; F5F8D |
| FECH | GDB: 127282 | PROTOPORPHYRIA, ERYTHROPOIETIC |
| FEO | GDB: 4378120 | POLYOSTOTIC OSTEOLYTIC DYSPLASIA, HEREDITARY EXPANSILE; HEPOD |
| LAMA3 | GDB: 251818 | LAMININ, ALPHA 3; LAMA3 |
| LCFS2 | GDB: 9954578 | CANCER |

TABLE 19-continued

Genes, Locations and Genetic Disorders on Chromosome 18

| Gene | GDB Accession ID | OMIM Link |
|---|---|---|
| MADH4 | GDB: 4642788 | POLYPOSIS, JUVENILE INTESTINAL MOTHERS AGAINST DECAPENTAPLEGIC, *DROSOPHILA*, HOMOLOG OF, 4; MADH4 |
| MAFD1 | GDB: 120163 | MANIC-DEPRESSIVE PSYCHOSIS, AUTOSOMAL |
| MC2R | GDB: 135163 | ADRENAL UNRESPONSIVENESS TO ACTH |
| MCL | GDB: 9954574 | LEIOMYOMATA, HEREDITARY MULTIPLE, OF SKIN |
| MYP2 | GDB: 9862232 | MYOPIA |
| NPC1 | GDB: 138178 | NIEMANN-PICK DISEASE, TYPE C1; NPC1 |
| SPPK | GDB: 606444 | PALMOPLANTARIS STRIATA |
| TGFBRE | GDB: 250852 | TRANSFORMING GROWTH FACTOR, BETA 1 RESPONSE ELEMENT |
| TGIF | GDB: 9787150 | HOLOPROSENCEPHALY, TYPE 4; HPE4 |
| TTR | GDB: 119471 | TRANSTHYRETIN; TTR |

TABLE 20

Genes, Locations and Genetic Disorders on Chromosome 19

| Gene | GDB Accession ID | OMIM Link |
|---|---|---|
| AD2 | GDB: 118748 | ALZHEIMER DISEASE-2; AD2 |
| AMH | GDB: 118996 | PERSISTENT MULLERIAN DUCT SYNDROME, TYPES I AND II; PMDS ANTI-MULLERIAN HORMONE; AMH |
| APOC2 | GDB: 119689 | APOLIPOPROTEIN C-II DEFICIENCY, TYPE I HYPERLIPOPROTEINEMIA DUE TO |
| APOE | GDB: 119691 | APOLIPOPROTEIN E; APOE |
| ATHS | GDB: 128803 | LIPOPROTEIN PHENOTYPE; ALP |
| BAX | GDB: 228082 | BCL2-ASSOCIATED X PROTEIN; BAX |
| BCKDHA | GDB: 119723 | MAPLE SYRUP URINE DISEASE |
| BCL3 | GDB: 120561 | B-CELL LEUKEMIA/LYMPHOMA-3; BCL3 |
| BFIC | GDB: 9954584 | BENIGN FAMILIAL INFANTILE CONVULSIONS |
| C3 | GDB: 119044 | COMPLEMENT COMPONENT-3; C3 |
| CACNA1A | GDB: 126432 | ATAXIA, PERIODIC VESTIBULOCEREBELLAR HEMIPLEGIC MIGRAINE, FAMILIAL; MHP SPINOCEREBELLAR ATAXIA 6; SCA6 CALCIUM CHANNEL, VOLTAGE-DEPENDENT, P/Q TYPE, ALPHA 1A SUBUNIT; CACNA1A |
| CCO | GDB: 119755 | CENTRAL CORE DISEASE OF MUSCLE |
| CEACAM5 | GDB: 119054 | CARCINOEMBRYONIC ANTIGEN; CEA |
| COMP | GDB: 344263 | EPIPHYSEAL DYSPLASIA, MULTIPLE; MED PSEUDOACHONDROPLASTIC DYSPLASIA CARTILAGE OLIGOMERIC MATRIX PROTEIN; COMP |
| CRX | GDB: 333932 | CONE-ROD DYSTROPHY-2; CORD2 AMAUROSIS CONGENITA OF LEBER I CONE-ROD HOMEO BOX-CONTAINING GENE |
| DBA | GDB: 9600353 | ANEMIA, CONGENITAL HYPOPLASTIC, OF BLACKFAN AND DIAMOND |
| DDU | GDB: 10796026 | URTICARIA; DDU |
| DFNA4 | GDB: 606540 | DEAFNESS, AUTOSOMAL DOMINANT NONSYNDROMIC SENSORINEURAL, 4; DFNA4 |
| DLL3 | GDB: 9959026 | VERTEBRAL ANOMALIES |
| DMPK | GDB: 119097 | DYSTROPHIA MYOTONICA; DM |
| DMWD | GDB: 7178354 | DYSTROPHIA MYOTONICA; DM |
| DPD1 | GDB: 10796170 | ENGELMANN DISEASE |
| E11S | GDB: 119101 | ECHO 11 SENSITIVITY; E11S |
| ELA2 | GDB: 118792 | ELASTASE-2; ELA2 NEUTROPENIA, CYCLIC |
| EPOR | GDB: 125242 | ERYTHROPOIETIN RECEPTOR; EPOR |
| ERCC2 | GDB: 119112 | EXCISION-REPAIR, COMPLEMENTING DEFECTIVE, IN CHINESE HAMSTER, 2; ERCC2 XERODERMA PIGMENTOSUM IV; XP4 |

TABLE 20-continued

Genes, Locations and Genetic Disorders on Chromosome 19

| Gene | GDB Accession ID | OMIM Link |
|---|---|---|
| ETFB | GDB: 119887 | ELECTRON TRANSFER FLAVOPROTEIN, BETA POLYPEPTIDE; ETFB |
| EXT3 | GDB: 383780 | EXOSTOSES, MULTIPLE, TYPE III; EXT3 |
| EYCL1 | GDB: 119269 | EYE COLOR-1; EYCL1 |
| FTL | GDB: 119234 | FERRITIN LIGHT CHAIN; FTL |
| FUT1 | GDB: 120618 | FUCOSYLTRANSFERASE-1; FUT1 |
| FUT2 | GDB: 120619 | FUCOSYLTRANSFERASE-2; FUT2 |
| FUT6 | GDB: 135180 | FUCOSYLTRANSFERASE-6; FUT6 |
| GAMT | GDB: 1313736 | GUANIDINOACETATE METHYLTRANSFERASE; GAMT |
| GCDH | GDB: 136004 | GLUTARICACIDEMIA I |
| GPI | GDB: 120015 | GLUCOSEPHOSPHATE ISOMERASE; GPI |
| GUSM | GDB: 119291 | GLUCURONIDASE, MOUSE, MODIFIER OF; GUSM |
| HB1 | GDB: 9954586 | BUNDLE BRANCH BLOCK |
| HCL1 | GDB: 119304 | HAIR COLOR-1; HCL1 |
| HHC2 | GDB: 249836 | HYPOCALCIURIC HYPERCALCEMIA, FAMILIAL, TYPE II; HHC2 |
| HHC3 | GDB: 9955121 | HYPOCALCIURIC HYPERCALCEMIA, FAMILIAL, TYPE III; HHC3 |
| ICAM3 | GDB: 136236 | INTERCELLULAR ADHESION MOLECULE-3; ICAM3 |
| INSR | GDB: 119352 | INSULIN RECEPTOR; INSR |
| JAK3 | GDB: 376460 | JANUS KINASE 3 JAK3 |
| KLK3 | GDB: 119695 | ANTIGEN, PROSTATE-SPECIFIC; APS |
| LDLR | GDB: 119362 | HYPERCHOLESTEROLEMIA, FAMILIAL; FHC |
| LHB | GDB: 119364 | LUTEINIZING HORMONE, BETA POLYPEPTIDE; LHB |
| LIG1 | GDB: 127274 | LIGASE I, DNA, ATP-DEPENDENT; LIG1 |
| LOH19CR1 | GDB: 9837482 | ANEMIA, CONGENITAL HYPOPLASTIC, OF BLACKFAN AND DIAMOND |
| LYL1 | GDB: 120158 | LEUKEMIA, LYMPHOID, 1; LYL1 |
| MAN2B1 | GDB: 119376 | MANNOSIDOSIS, ALPHA B, LYSOSOMAL |
| MCOLN1 | GDB: 10013974 | MUCOLIPIDOSIS IV |
| MDRV | GDB: 6306714 | MUSCULAR DYSTROPHY, AUTOSOMAL DOMINANT, WITH RIMMED VACUOLES; MDRV |
| MLLT1 | GDB: 136791 | MYELOID/LYMPHOID OR MIXED LINEAGE LEUKEMIA, TRANSLOCATED TO, 1; MLLT1 |
| NOTCH3 | GDB: 361163 | DEMENTIA, HEREDITARY MULTI-INFARCT TYPE NOTCH, *DROSOPHILA*, HOMOLOG OF, 3; NOTCH3 |
| NPHS1 | GDB: 342105 | NEPHROSIS 1, CONGENITAL, FINNISH TYPE; NPHS1 |
| OFC3 | GDB: 128060 | OROFACIAL CLEFT-3; OFC3 |
| OPA3 | GDB: 9954590 | OPTIC ATROPHY, INFANTILE, WITH CHOREA AND SPASTIC PARAPLEGIA |
| PEPD | GDB: 120273 | PEPTIDASE D; PEPD |
| PRPF31 | GDB: 333911 | RETINITIS PIGMENTOSA 11; RP11 |
| PRTN3 | GDB: 126876 | PROTEINASE 3; PRTN3; PR3 |
| PRX | GDB: 11501256 | HYPERTROPHIC NEUROPATHY OF DEJERINE-SOTTAS |
| PSG1 | GDB: 120321 | PREGNANCY-SPECIFIC BETA-1-GLYCOPROTEIN 1; PSG1 |
| PVR | GDB: 120324 | POLIOVIRUS SUSCEPTIBILITY, OR SENSITIVITY; PVS |
| RYR1 | GDB: 120359 | CENTRAL CORE DISEASE OF MUSCLE HYPERTHERMIA OF ANESTHESIA RYANODINE RECEPTOR-1; RYR1 |
| SLC5A5 | GDB: 5892184 | SOLUTE CARRIER FAMILY 5, MEMBER 5; SLC5A5 |
| SLC7A9 | GDB: 9958852 | CYSTINURIA, TYPE III; CSNU3 |
| STK11 | GDB: 9732383 | PEUTZ-JEGHERS SYNDROME SERINE/THREONINE PROTEIN KINASE 11; STK11 |
| TBXA2R | GDB: 127517 | THROMBOXANE A2 RECEPTOR, PLATELET; TBXA2R |
| TGFB1 | GDB: 120729 | ENGELMANN DISEASE TRANSFORMING GROWTH FACTOR, BETA-1; TGFB1 |

TABLE 20-continued

Genes, Locations and Genetic Disorders on Chromosome 19

| Gene | GDB Accession ID | OMIM Link |
| --- | --- | --- |
| TNNI3 | GDB: 125309 | TROPONIN I, CARDIAC; TNNI3 |
| TYROBP | GDB: 9954457 | POLYCYSTIC LIPOMEMBRANOUS OSTEODYSPLASIA WITH SCLEROSING LEUKOENCEPHALOPATHY |

TABLE 21

Genes, Locations and Genetic Disorders on Chromosome 20

| Gene | GDB Accession ID | OMIM Link |
| --- | --- | --- |
| ADA | GDB: 119649 | ADENOSINE DEAMINASE; ADA |
| AHCY | GDB: 118983 | S-ADENOSYLHOMOCYSTEINE HYDROLASE; AHCY |
| AVP | GDB: 119009 | DIABETES INSIPIDUS, NEUROHYPOPHYSEAL TYPE ARGININE VASOPRESSIN; AVP |
| CDAN2 | GDB: 9823270 | DYSERYTHROPOIETIC ANEMIA, CONGENITAL, TYPE II |
| CDMP1 | GDB: 438940 | CHONDRODYSPLASIA, GREBE TYPE CARTILAGE-DERIVED MORPHOGENETIC PROTEIN 1 |
| CHED1 | GDB: 3837719 | CORNEAL DYSTROPHY, CONGENITAL ENDOTHELIAL; CHED |
| CHRNA4 | GDB: 128169 | CHOLINERGIC RECEPTOR, NEURONAL NICOTINIC, ALPHA POLYPEPTIDE 4; CHRNA4 EPILEPSY, BENIGN NEONATAL; EBN1 |
| CST3 | GDB: 119817 | AMYLOIDOSIS VI |
| EDN3 | GDB: 119862 | ENDOTHELIN-3; EDN3 WAARDENBURG-SHAH SYNDROME |
| EEGV1 | GDB: 127525 | ELECTROENCEPHALOGRAM, LOW-VOLTAGE |
| FTLL1 | GDB: 119235 | FERRITIN LIGHT CHAIN; FTL |
| GNAS | GDB: 120628 | GUANINE NUCLEOTIDE-BINDING PROTEIN, ALPHA-STIMULATING POLYPEPTIDE; |
| GSS | GDB: 637022 | GLUTATHIONE SYNTHETASE DEFICIENCY OF ERYTHROCYTES, HEMOLYTIC ANEMIA PYROGLUTAMICACIDURIA HNF4AGDB: 393281DIABETES MELLITUS, AUTOSOMAL DOMINANT TRANSCRIPTION FACTOR 14, HEPATIC NUCLEAR FACTOR; TCF14 |
| JAG1 | GDB: 6175920 | CHOLESTASIS WITH PERIPHERAL PULMONARY STENOSIS JAGGED 1; JAG1 |
| KCNQ2 | GDB: 9787229 | EPILEPSY, BENIGN NEONATAL; EBN1 POTASSIUM CHANNEL, VOLTAGE-GATED, SUBFAMILY Q, MEMBER 2 |
| MKKS | GDB: 9860197 | HYDROMETROCOLPOS SYNDROME |
| NBIA1 | GDB: 4252819 | HALLERVORDEN-SPATZ DISEASE |
| PCK1 | GDB: 125349 | PHOSPHOENOLPYRUVATE CARBOXYKINASE 1, SOLUBLE; PCK1 |
| PI3 | GDB: 203940 | PROTEINASE INHIBITOR 3; PI3 |
| PPGB | GDB: 119507 | NEURAMINIDASE DEFICIENCY WITH BETA-GALACTOSIDASE DEFICIENCY |
| PPMD | GDB: 702144 | CORNEAL DYSTROPHY, HEREDITARY POLYMORPHOUS POSTERIOR; PPCD |
| PRNP | GDB: 120720 | GERSTMANN-STRAUSSLER DISEASE; GSD PRION PROTEIN; PRNP |
| THBD | GDB: 119613 | THROMBOMODULIN; THBD |
| TOP1 | GDB: 120444 | TOPOISOMERASE (DNA) I; TOP1 |

TABLE 22

Genes, Locations and Genetic Disorders on Chromosome 21

| Gene | GDB Accession ID | OMIM Link |
|---|---|---|
| AIRE | GDB: 567198 | AUTOIMMUNE POLYENDOCRINOPATHY-CANDIDIASIS-ECTODERMAL DYSTROPHY; APECED |
| APP | GDB: 119692 | ALZHEIMER DISEASE; AD AMYLOID BETA A4 PRECURSOR PROTEIN; APP |
| CBS | GDB: 119754 | HOMOCYSTINURIA |
| COL6A1 | GDB: 119065 | COLLAGEN, TYPE VI, ALPHA-1 CHAIN; COL6A1 MYOPATHY, BENIGN CONGENITAL, WITH CONTRACTURES |
| COL6A2 | GDB: 119793 | COLLAGEN, TYPE VI, ALPHA-2 CHAIN; COL6A2 MYOPATHY, BENIGN CONGENITAL, WITH CONTRACTURES |
| CSTB | GDB: 5215249 | MYOCLONUS EPILEPSY OF UNVERRICHT AND LUNDBORG CYSTATIN B; CSTB |
| DCR | GDB: 125354 | TRISOMY 21 |
| DSCR1 | GDB: 731000 | TRISOMY 21 |
| FPDMM | GDB: 9954610 | CORE-BINDING FACTOR, RUNT DOMAIN, ALPHA SUBUNIT 2; CBFA2 PLATELET DISORDER, FAMILIAL, WITH ASSOCIATED MYELOID MALIGNANCY |
| HLCS | GDB: 392648 | MULTIPLE CARBOXYLASE DEFICIENCY, BIOTIN-RESPONSIVE; MCD |
| HPE1 | GDB: 136065 | HOLOPROSENCEPHALY, FAMILIAL ALOBAR |
| ITGB2 | GDB: 120574 | INTEGRIN BETA-2; ITGB2 |
| KCNE1 | GDB: 127909 | POTASSIUM VOLTAGE-GATED CHANNEL, ISK-RELATED SUBFAMILY, MEMBER 1; |
| KNO | GDB: 4073044 | KNOBLOCH SYNDROME; KNO |
| PRSS7 | GDB: 384083 | ENTEROKINASE DEFICIENCY |
| RUNX1 | GDB: 128313 | CORE-BINDING FACTOR, RUNT DOMAIN, ALPHA SUBUNIT 2; CBFA2 PLATELET DISORDER, FAMILIAL, WITH ASSOCIATED MYELOID MALIGNANCY |
| SOD1 | GDB: 119596 | AMYOTROPHIC LATERAL SCLEROSIS SUPEROXIDE DISMUTASE-1; SOD1 MUSCULAR ATROPHY, PROGRESSIVE, WITH AMYOTROPHIC LATERAL SCLEROSIS |
| TAM | GDB: 9958709 | MYELOPROLIFERATIVE SYNDROME, TRANSIENT |

TABLE 23

Genes, Locations and Genetic Disorders on Chromosome 22

| Gene | GDB Accession ID | OMIM Link |
|---|---|---|
| ADSL | GDB: 119655 | ADENYLOSUCCINATE LYASE; ADSL |
| ARSA | GDB: 119007 | METACHROMATIC LEUKODYSTROPHY, LATE-INFANTILE |
| BCR | GDB: 120562 | BREAKPOINT CLUSTER REGION; BCR |
| CECR | GDB: 119772 | CAT EYE SYNDROME; CES |
| CHEK2 | GDB: 9958730 | LI-FRAUMENI SYNDROME; LFS OSTEOGENIC SARCOMA |
| COMT | GDB: 119795 | CATECHOL-O-METHYLTRANSFERASE; COMT |
| CRYBB2 | GDB: 119075 | CRYSTALLIN, BETA B2; CRYBB2 CATARACT, CONGENITAL, CERULEAN TYPE, 2; CCA2 |
| CSF2RB | GDB: 126838 | GRANULOCYTE-MACROPHAGE COLONY-STIMULATING FACTOR RECEPTOR, BETA SUBUNIT; |
| CTHM | GDB: 439247 | HEART MALFORMATIONS; CTHM |
| CYP2D6 | GDB: 132127 | CYTOCHROME P450, SUBFAMILY IID; CYP2D |
| CYP2D@ | GDB: 119832 | CYTOCHROME P450, SUBFAMILY IID; CYP2D |
| DGCR | GDB: 119843 | DIGEORGE SYNDROME; DGS |
| DIA1 | GDB: 119848 | METHEMOGLOBINEMIA DUE TO DEFICIENCY OF METHEMOGLOBIN REDUCTASE |
| EWSR1 | GDB: 135984 | EWING SARCOMA; EWS |
| GGT1 | GDB: 120623 | GLUTATHIONURIA |
| MGCR | GDB: 120180 | MENINGIOMA; MGM |
| MN1 | GDB: 580528 | MENINGIOMA; MGM |
| NAGA | GDB: 119445 | ALPHA-GALACTOSIDASE B; GALB |
| NF2 | GDB: 120232 | NEUROFIBROMATOSIS, TYPE II; NF2 |
| OGS2 | GDB: 9954619 | HYPERTELORISM WITH ESOPHAGEAL ABNORMALITY AND HYPOSPADIAS |
| PDGFB | GDB: 120709 | V-SIS PLATELET-DERIVED GROWTH FACTOR BETA POLYPEPTIDE; PDGFB |
| PPARA | GDB: 202877 | PEROXISOME PROLIFERATOR ACTIVATED RECEPTOR, ALPHA; PPARA |
| PRODH | GDB: 5215168 | HYPERPROLINEMIA, TYPE I |
| SCO2 | GDB: 9958568 | CYTOCHROME c OXIDASE DEFICIENCY |
| SCZD4 | GDB: 1387047 | SCHIZOPHRENIA DISORDER-4; SCZD4 |
| SERPIND1 | GDB: 120038 | HEPARIN COFACTOR II; HCF2 |
| SLC5A1 | GDB: 120375 | SOLUTE CARRIER FAMILY 5, MEMBER 1; SLC5A1 |
| SOX10 | GDB: 9834028 | SRY-BOX 10; SOX10 |
| TCN2 | GDB: 119608 | TRANSCOBALAMIN II DEFICIENCY |
| TIMP3 | GDB: 138175 | TISSUE INHIBITOR OF METALLOPROTEINASE-3; TIMP3 |
| VCF | GDB: 136422 | VELOCARDIOFACIAL SYNDROME |

TABLE 24

Genes, Locations and Genetic Disorders on Chromosome X

| Gene | GDB Accession ID | OMIM Link |
|---|---|---|
| ABCD1 | GDB: 118991 | ADRENOLEUKODYSTROPHY; ALD |
| ACTL1 | GDB: 119648 | ACTIN-LIKE SEQUENCE-1; ACTL1 |
| ADFN | GDB: 118977 | ALBINISM-DEAFNESS SYNDROME; ADFN; ALDS |
| AGMX2 | GDB: 119661 | AGAMMAGLOBULINEMIA, X-LINKED, TYPE 2; AGMX2; XLA2 |
| AHDS | GDB: 125899 | MENTAL RETARDATION, X-LINKED, WITH HYPOTONIA |
| AIC | GDB: 118986 | CORPUS CALLOSUM, AGENESIS OF, WITH CHORIORETINAL ABNORMALITY |

TABLE 24-continued

Genes, Locations and Genetic Disorders on Chromosome X

| Gene | GDB Accession ID | OMIM Link |
|---|---|---|
| AIED | GDB: 119663 | ALBINISM, OCULAR, TYPE 2; OA2 |
| AIH3 | GDB: 131443 | AMELOGENESIS IMPERFECTA-3, HYPOPLASTIC TYPE; AIH3 |
| ALAS2 | GDB: 119666 | ANEMIA, HYPOCHROMIC |
| AMCD | GDB: 5584286 | ARTHROGRYPOSIS MULTIPLEX CONGENITA, DISTAL |
| AMELX | GDB: 119675 | AMELOGENESIS IMPERFECTA-1, HYPOPLASTIC TYPE; AIH1 |
| ANOP1 | GDB: 128454 | CLINICAL; ANOP1 |
| AR | GDB: 120556 | ANDROGEN INSENSITIVITY SYNDROME; AIS ANDROGEN RECEPTOR; AR |
| ARAF1 | GDB: 119004 | V-RAF MURINE SARCOMA 3611 VIRAL ONCOGENE HOMOLOG 1; ARAF1 |
| ARSC2 | GDB: 119702 | ARYLSULFATASE C, f FORM; ARSC2 |
| ARSE | GDB: 555743 | CHONDRODYSPLASIA PUNCTATA 1, X-LINKED RECESSIVE; CDPX1 |
| ARTS | GDB: 9954651 | FATAL X-LINKED, WITH DEAFNESS AND LOSS OF VISION |
| ASAT | GDB: 9954649 | SIDEROBLASTIC, AND SPINOCEREBELLAR ATAXIA; ASAT |
| ASSP5 | GDB: 119019 | CITRULLINEMIA |
| ATP7A | GDB: 119395 | ATPase, Cu(2+)-TRANSPORTING, ALPHA POLYPEPTIDE; ATP7A MENKES SYNDROME |
| ATRX | GDB: 136052 | ALPHA-THALASSEMIA/MENTAL RETARDATION SYNDROME, X-LINKED; ATRX ALPHA-THALASSEMIA/MENTAL RETARDATION SYNDROME, NONDELETION TYPE |
| AVPR2 | GDB: 131475 | DIABETES INSIPIDUS, NEPHROGENIC |
| BFLS | GDB: 120566 | BORJESON SYNDROME; BORJ |
| BGN | GDB: 119727 | BIGLYCAN; BGN |
| BTK | GDB: 120542 | BRUTON AGAMMAGLOBULINEMIA TYROSINE KINASE; BTK |
| BZX | GDB: 5205912 | BAZEX SYNDROME; BZX |
| C1HR | GDB: 119040 | TATA BOX BINDING PROTEIN (TBP)-ASSOCIATED FACTOR 2A; TAF2A |
| CACNA1F | GDB: 6053864 | NIGHTBLINDNESS, CONGENITAL STATIONARY, X-LINKED, TYPE 2; CSNB2 CALCIUM CHANNEL, VOLTAGE-DEPENDENT, ALPHA 1F SUBUNIT; CACNA1F |
| CALB3 | GDB: 133780 | CALBINDIN 3; CALB3 |
| CBBM | GDB: 9958963 | COLORBLINDNESS, BLUE-MONO-CONE-MONOCHROMATIC TYPE; CBBM |
| CCT | GDB: 119756 | CATARACT, CONGENITAL TOTAL, WITH POSTERIOR SUTURAL OPACITIES IN HETEROZYGOTES; |
| CDR1 | GDB: 119053 | CEREBELLAR DEGENERATION-RELATED AUTOANTIGEN-1; CDR1; CDR34 |
| CFNS | GDB: 9579470 | CRANIOFRONTONASAL SYNDROME; CFNS |
| CGF1 | GDB: 6275867 | COGNITION |
| CHM | GDB: 120400 | CHOROIDEREMIA; CHM |
| CHR39C | GDB: 119779 | CHOLESTEROL REPRESSIBLE PROTEIN 39C; CHR39C |
| CIDX | GDB: 127736 | SEVERE COMBINED IMMUNODEFICIENCY DISEASE, X-LINKED, 2; SCIDX2 |
| CLA2 | GDB: 119782 | CEREBELLAR ATAXIA, X-LINKED; CLA2 |
| CLCN5 | GDB: 270667 | CHLORIDE CHANNEL 5; CLCN5 FANCONI SYNDROME, RENAL, WITH NEPHROCALCINOSIS AND RENAL STONES NEPHROLITHIASIS, X-LINKED RECESSIVE, WITH RENAL FAILURE; XRN |
| CLS | GDB: 119784 | RIBOSOMAL PROTEIN S6 KINASE, 90 KD, POLYPEPTIDE 3; RPS6KA3 COFFIN-LOWRY SYNDROME; CLS |
| CMTX2 | GDB: 128311 | CHARCOT-MARIE-TOOTH NEUROPATHY, X-LINKED RECESSIVE, 2; CMTX2 |
| CMTX3 | GDB: 128151 | CHARCOT-MARIE-TOOTH NEUROPATHY, X-LINKED RECESSIVE, 3; CMTX3 |
| CND | GDB: 9954627 | DERMOIDS OF CORNEA; CND |
| COD1 | GDB: 119787 | CONE DYSTROPHY, X-LINKED, 1; COD1 |
| COD2 | GDB: 6520166 | CONE DYSTROPHY, X-LINKED, 2; COD2 |

TABLE 24-continued

Genes, Locations and Genetic Disorders on Chromosome X

| Gene | GDB Accession ID | OMIM Link |
|---|---|---|
| COL4A5 | GDB: 120596 | COLLAGEN, TYPE IV, ALPHA-5 CHAIN; COL4A5 LEIOMYOMATOSIS, ESOPHAGEAL AND VULVAL, WITH NEPHROPATHY |
| COL4A6 | GDB: 222775 | COLLAGEN, TYPE IV, ALPHA-6 CHAIN; COL4A6 LEIOMYOMATOSIS, ESOPHAGEAL AND VULVAL, WITH NEPHROPATHY |
| CPX | GDB: 120598 | CLEFT PALATE, X-LINKED; CPX |
| CVD1 | GDB: 9954659 | CARDIAC VALVULAR DYSPLASIA, X-LINKED |
| CYBB | GDB: 120513 | GRANULOMATOUS DISEASE, CHRONIC; CGD |
| DCX | GDB: 9823272 | LISSENCEPHALY, X-LINKED |
| DFN2 | GDB: 119091 | DEAFNESS, X-LINKED 2, PERCEPTIVE CONGENITAL; DFN2 |
| DFN4 | GDB: 433255 | DEAFNESS, X-LINKED 4, CONGENITAL SENSORINEURAL; DFN4 |
| DFN6 | GDB: 1320698 | DEAFNESS, X-LINKED, 6, PROGRESSIVE; DFN6 |
| DHOF | GDB: 119847 | FOCAL DERMAL HYPOPLASIA; DHOF |
| DIAPH2 | GDB: 9835484 | DIAPHANOUS, *DROSOPHILA*, HOMOLOG OF, 2 DKC1GDB: 119096 DYSKERATOSIS CONGENITA; DKC |
| DMD | GDB: 119850 | MUSCULAR DYSTROPHY, PSEUDOHYPERTROPHIC PROGRESSIVE, DUCHENNE AND BECKER |
| DSS | GDB: 433750 | DOSAGE-SENSITIVE SEX REVERSAL; DSS |
| DYT3 | GDB: 118789 | TORSION DYSTONIA-3, X-LINKED TYPE; DYT3 |
| EBM | GDB: 119102 | BULLOUS DYSTROPHY, HEREDITARY MACULAR TYPE |
| EBP | GDB: 125212 | CHONDRODYSPLASIA PUNCTATA, X-LINKED DOMINANT; CDPX2; CDPXD; CPXD |
| ED1 | GDB: 119859 | ECTODERMAL DYSPLASIA, ANHIDROTIC; EDA |
| ELK1 | GDB: 119867 | ELK1, MEMBER OF ETS ONCOGENE FAMILY; ELK1 |
| EMD | GDB: 119108 | MUSCULAR DYSTROPHY, TARDIVE, DREIFUSS-EMERY TYPE, WITH CONTRACTURES |
| EVR2 | GDB: 136068 | EXUDATIVE VITREORETINOPATHY, FAMILIAL, X-LINKED RECESSIVE; EVR2 |
| F8C | GDB: 119124 | HEMOPHILIA A |
| F9 | GDB: 119900 | HEMOPHILIA B; HEMB |
| FCP1 | GDB: 347490 | F-CELL PRODUCTION, X-LINKED; FCPX |
| FDPSL5 | GDB: 119922 | SYNTHETASE-5; FPSL5 |
| FGD1 | GDB: 119131 | SYNDROME FACIOGENITAL DYSPLASIA; FGDY |
| FGS1 | GDB: 9836950 | FG SYNDROME |
| FMR1 | GDB: 129038 | FRAGILE SITE MENTAL RETARDATION-1; FMR1 |
| FMR2 | GDB: 141566 | FRAGILE SITE, FOLIC ACID TYPE, RARE, FRA(X)(q28); FRAXE |
| G6PD | GDB: 120621 | GLUCOSE-6-PHOSPHATE DEHYDROGENASE; G6PD |
| GABRA3 | GDB: 119968 | GAMMA-AMINOBUTYRIC ACID RECEPTOR, ALPHA-3; GABRA3 |
| GATA1 | GDB: 125373 | GATA-BINDING PROTEIN 1; GATA1 |
| GDI1 | GDB: 1347097 | GDP DISSOCIATION INHIBITOR 1; GDI1 MENTAL RETARDATION, X-LINKED NONSPECIFIC, TYPE 3; MRX3 |
| GDXY | GDB: 9954629 | DYSGENESIS, XY FEMALE TYPE; GDXY |
| GJB1 | GDB: 125246 | CHARCOT-MARIE-TOOTH PERONEAL MUSCULAR ATROPHY, X-LINKED; CMTX1 GAP JUNCTION PROTEIN, BETA-1, 32 KD; GJB1 |
| GK | GDB: 119271 | HYPERGLYCEROLEMIA |
| GLA | GDB: 119272 | ANGIOKERATOMA, DIFFUSE |
| GPC3 | GDB: 3770726 | GLYPICAN-3; GPC3 SIMPSON DYSMORPHIA SYNDROME; SDYS |
| GRPR | GDB: 128035 | GASTRIN-RELEASING PEPTIDE RECEPTOR; GRPR |

TABLE 24-continued

Genes, Locations and Genetic Disorders on Chromosome X

| Gene | GDB Accession ID | OMIM Link |
|---|---|---|
| GTD | GDB: 9954635 | GONADOTROPIN DEFICIENCY; GTD |
| GUST | GDB: 9954655 | MENTAL RETARDATION WITH OPTIC ATROPHY, DEAFNESS, AND SEIZURES 1; HMS1 |
| HMS1 | GDB: 251827 | |
| HPRT1 | GDB: 119317 | HYPOXANTHINE GUANINE PHOSPHORIBOSYLTRANSFERASE 1; HPRT1 |
| HPT | GDB: 119322 | HYPOPARATHYROIDISM, X-LINKED; HYPX |
| HTC2 | GDB: 700980 | HYPERTRICHOSIS, CONGENITAL GENERALIZED; CGH; HCG |
| HTR2C | GDB: 378202 | 5-@HYDROXYTRYPTAMINE RECEPTOR 2C; HTR2C |
| HYR | GDB: 9954625 | REGULATOR; HYR |
| IDS | GDB: 120521 | MUCOPOLYSACCHARIDOSIS TYPE II |
| IHG1 | GDB: 119343 | HYPOPLASIA OF, WITH GLAUCOMA; IHG |
| IL2RG | GDB: 134807 | INTERLEUKIN-2 RECEPTOR, GAMMA; IL2RG SEVERE COMBINED IMMUNODEFICIENCY DISEASE, X-LINKED, 2; SCIDX2 |
| INDX | GDB: 9954657 | IMMUNONEUROLOGIC DISORDER, X-LINKED |
| IP1 | GDB: 120105 | INCONTINENTIA PIGMENTI, TYPE I; IP1 |
| IP2 | GDB: 120106 | INCONTINENTIA PIGMENTI, TYPE II; IP2 |
| JMS | GDB: 204055 | MENTAL RETARDATION, X-LINKED, WITH GROWTH RETARDATION, DEAFNESS, AND |
| KAL1 | GDB: 120116 | KALLMANN SYNDROME 1; KAL1 |
| KFSD | GDB: 128174 | KERATOSIS FOLLICULARIS SPINULOSA DECALVANS CUM OPHIASI; KFSD |
| L1CAM | GDB: 120133 | CLASPED THUMB AND MENTAL RETARDATION L1 CELL ADHESION MOLECULE; L1CAM |
| LAMP2 | GDB: 125376 | LYSOSOME-ASSOCIATED MEMBRANE PROTEIN B; LAMP2; LAMPB |
| MAA | GDB: 119372 | MICROPHTHALMIA OR ANOPHTHALMOS, WITH ASSOCIATED ANOMALIES; MAA |
| MAFD2 | GDB: 119373 | PSYCHOSIS, X-LINKED |
| MAOA | GDB: 120164 | MONOAMINE OXIDASE A; MAOA |
| MAOB | GDB: 119377 | MONOAMINE OXIDASE B; MAOB |
| MCF2 | GDB: 120168 | MCF.2 CELL LINE DERIVED TRANSFORMING SEQUENCE; MCF2 |
| MCS | GDB: 128370 | MENTAL RETARDATION, X-LINKED, SYNDROMIC-4, WITH CONGENITAL CONTRACTURES |
| MEAX | GDB: 119383 | X-LINKED, WITH EXCESSIVE AUTOPHAGY; XMEA; MEAX |
| MECP2 | GDB: 3851454 | SYNDROME; RTT |
| MF4 | GDB: 119386 | METACARPAL 4-5 FUSION; MF4 |
| MGC1 | GDB: 120179 | MEGALOCORNEA; MGC1; MGCN |
| MIC5 | GDB: 120526 | SURFACE ANTIGEN, X-LINKED; SAX |
| MID1 | GDB: 9772232 | OPITZ SYNDROME |
| MLLT7 | GDB: 392309 | MYELOID/LYMPHOID OR MIXED-LINEAGE LEUKEMIA, TRANSLOCATED TO, 7; MLLT7 |
| MLS | GDB: 262123 | MICROPHTHALMIA WITH LINEAR SKIN DEFECTS; MLS |
| MRSD | GDB: 119398 | MENTAL RETARDATION, SKELETAL DYSPLASIA, AND ABDUCENS PALSY; MRSD |
| MRX14 | GDB: 138453 | RETARDATION, X-LINKED 14; MRX14 |
| MRX1 | GDB: 120193 | MENTAL RETARDATION, X-LINKED NONSPECIFIC, TYPE 1; MRX1 |
| MRX20 | GDB: 217050 | MENTAL RETARDATION, X-LINKED 20; MRX20 |
| MRX2 | GDB: 120194 | RETARDATION, X-LINKED NONSPECIFIC, TYPE 2; MRX2 |
| MRX3 | GDB: 128105 | GDP DISSOCIATION INHIBITOR 1; GDI1 MENTAL RETARDATION, X-LINKED NONSPECIFIC, TYPE 3; MRX3 |
| MRX40 | GDB: 700754 | MENTAL RETARDATION, X-LINKED, WITH HYPOTONIA |
| MRXA | GDB: 9954641 | MENTAL RETARDATION, X-LINKED NONSPECIFIC, WITH APHASIA; MRXA |
| MSD | GDB: 119399 | SYNDROME |
| MTM1 | GDB: 119439 | MYOTUBULAR MYOPATHY 1; MTM1 |

TABLE 24-continued

Genes, Locations and Genetic Disorders on Chromosome X

| Gene | GDB Accession ID | OMIM Link |
|---|---|---|
| MYCL2 | GDB: 120209 | MYCL-RELATED PROCESSED GENE; MYCL2 |
| MYP1 | GDB: 127783 | MYOPIA, X-LINKED; MYP1 |
| NDP | GDB: 119449 | NORRIE DISEASE; NDP |
| NHS | GDB: 120235 | CATARACT-DENTAL SYNDROME |
| NPHL1 | GDB: 433705 | NEPHROLITHIASIS, X-LINKED RECESSIVE, WITH RENAL FAILURE; XRN |
| NR0B1 | GDB: 118982 | ADRENAL HYPOPLASIA, CONGENITAL; AHC |
| NSX | GDB: 125596 | SYNDROME; NSX |
| NYS1 | GDB: 119458 | NYSTAGMUS, X-LINKED; NYS |
| NYX | GDB: 119814 | NIGHTBLINDNESS, CONGENITAL STATIONARY, WITH MYOPIA; CSNB1 |
| OA1 | GDB: 119459 | ALBINISM, OCULAR, TYPE 1; OA1 |
| OASD | GDB: 138457 | OCULAR, WITH LATE-ONSET SENSORINEURAL DEAFNESS; OASD |
| OCRL | GDB: 119461 | LOWE OCULOCEREBRORENAL SYNDROME; OCRL |
| ODT1 | GDB: 125360 | TEETH, ABSENCE OF |
| OFD1 | GDB: 120248 | OROFACIODIGITAL SYNDROME 1; OFD1 |
| OPA2 | GDB: 125358 | OPTIC ATROPHY 2; OPA2 |
| OPD1 | GDB: 120249 | OTOPALATODIGITAL SYNDROME |
| OPEM | GDB: 119467 | OPHTHALMOPLEGIA, EXTERNAL, AND MYOPIA; OPEM |
| OPN1LW | GDB: 120724 | COLORBLINDNESS, PARTIAL, PROTAN SERIES; CBP |
| OPN1MW | GDB: 120622 | COLORBLINDNESS, PARTIAL, DEUTAN SERIES; CBD; DCB |
| OTC | GDB: 119468 | ORNITHINE TRANSCARBAMYLASE DEFICIENCY, HYPERAMMONEMIA DUE TO; OTC |
| P3 | GDB: 9954667 | PROTEIN P3 |
| PDHA1 | GDB: 118895 | PYRUVATE DEHYDROGENASE COMPLEX, E1-ALPHA POLYPEPTIDE-1; PDHA1 |
| PDR | GDB: 203409 | AMYLOIDOSIS, FAMILIAL CUTANEOUS |
| PFC | GDB: 120275 | PROPERDIN DEFICIENCY, X-LINKED |
| PFKFB1 | GDB: 125375 | 6-@PHOSPHOFRUCTO-2-KINASE; PFKFB1 |
| PGK1 | GDB: 120282 | PHOSPHOGLYCERATE KINASE 1; PGK1 |
| PGK1P1 | GDB: 120283 | PHOSPHOGLYCERATE KINASE 1; PGK1 |
| PGS | GDB: 128372 | DANDY-WALKER MALFORMATION WITH MENTAL RETARDATION, BASAL GANGLIA DISEASE, |
| PHEX | GDB: 120520 | HYPOPHOSPHATEMIA, VITAMIN D-RESISTANT RICKETS; HYP |
| PHKA1 | GDB: 120285 | PHOSPHORYLASE KINASE, ALPHA 1 SUBUNIT (MUSCLE); PHKA1 |
| PHKA2 | GDB: 127279 | GLYCOGEN STORAGE DISEASE VIII |
| PHP | GDB: 119494 | PANHYPOPITUITARISM; PHP |
| PIGA | GDB: 138138 | PHOSPHATIDYLINOSITOL GLYCAN, CLASS A; PIGA |
| PLP1 | GDB: 120302 | PROTEOLIPID PROTEIN, MYELIN; PLP |
| POF1 | GDB: 120716 | PREMATURE OVARIAN FAILURE 1; POF1 |
| POLA | GDB: 120304 | POLYMERASE, DNA, ALPHA; POLA |
| POU3F4 | GDB: 351386 | DEAFNESS, CONDUCTIVE, WITH STAPES FIXATION |
| PPMX | GDB: 9954669 | RETARDATION WITH PSYCHOSIS, PYRAMIDAL SIGNS, AND MACROORCHIDISM |
| PRD | GDB: 371323 | DYSPLASIA, PRIMARY |
| PRPS1 | GDB: 120318 | PHOSPHORIBOSYLPYROPHOSPHATE SYNTHETASE-I; PRPS1 |
| PRPS2 | GDB: 120320 | PHOSPHORIBOSYLPYROPHOSPHATE SYNTHETASE-II; PRPS2 |
| PRS | GDB: 128368 | MENTAL RETARDATION, X-LINKED, SYNDROMIC-2, WITH DYSMORPHISM AND CEREBRAL |
| PRTS | GDB: 128367 | PARTINGTON X-LINKED MENTAL RETARDATION SYNDROME; PRTS |
| PSF2 | GDB: 119519 | TRANSPORTER 2, ABC; TAP2 |
| RENBP | GDB: 133792 | RENIN-BINDING PROTEIN; RENBP |
| RENS1 | GDB: 9806348 | MENTAL RETARDATION, X-LINKED, RENPENNING TYPE |
| RP2 | GDB: 120353 | RETINITIS PIGMENTOSA-2; RP2 |
| RP6 | GDB: 125381 | PIGMENTOSA-6; RP6 |

TABLE 24-continued

Genes, Locations and Genetic Disorders on Chromosome X

| Gene | GDB Accession ID | OMIM Link |
|---|---|---|
| RPGR | GDB: 118736 | RETINITIS PIGMENTOSA-3; RP3 |
| RPS4X | GDB: 128115 | RIBOSOMAL PROTEIN S4, X-LINKED; RPS4X |
| RPS6KA3 | GDB: 365648 | RIBOSOMAL PROTEIN S6 KINASE, 90 KD, POLYPEPTIDE 3; RPS6KA3 |
| RS1 | GDB: 119581 | RETINOSCHISIS; RS |
| S11 | GDB: 120361 | ANTIGEN, X-LINKED, SECOND; SAX2 |
| SDYS | GDB: 119590 | GLYPICAN-3; GPC3 SIMPSON DYSMORPHIA SYNDROME; SDYS |
| SEDL | GDB: 120372 | SPONDYLOEPIPHYSEAL DYSPLASIA, LATE; SEDL |
| SERPINA7 | GDB: 120399 | THYROXINE-BINDING GLOBULIN OF SERUM; TBG |
| SH2D1A | GDB: 120701 | IMMUNODEFICIENCY, X-LINKED PROGRESSIVE COMBINED VARIABLE |
| SHFM2 | GDB: 226635 | SPLIT-HAND/SPLIT-FOOT ANOMALY, X-LINKED |
| SHOX | GDB: 6118451 | SHORT STATURE; SS |
| SLC25A5 | GDB: 125190 | ADENINE NUCLEOTIDE TRANSLOCATOR 2; ANT2 |
| SMAX2 | GDB: 9954643 | SPINAL MUSCULAR ATROPHY, X-LINKED LETHAL INFANTILE |
| SRPX | GDB: 3811398 | RETINITIS PIGMENTOSA-3; RP3 |
| SRS | GDB: 136337 | MENTAL RETARDATION, X-LINKED, SNYDER-ROBINSON TYPE |
| STS | GDB: 120393 | ICHTHYOSIS, X-LINKED |
| SYN1 | GDB: 119606 | SYNAPSIN I; SYN1 |
| SYP | GDB: 125295 | SYNAPTOPHYSIN; SYP |
| TAF1 | GDB: 120573 | TATA BOX BINDING PROTEIN (TBP)-ASSOCIATED FACTOR 2A; TAF2A |
| TAZ | GDB: 120609 | CARDIOMYOPATHY, DILATED 3A; CMD3A ENDOCARDIAL FIBROELASTOSIS-2; EFE2 |
| TBX22 | GDB: 10796448 | CLEFT PALATE, X-LINKED; CPX |
| TDD | GDB: 119610 | MALE PSEUDOHERMAPHRODITISM: DEFICIENCY OF TESTICULAR 17, 20-DESMOLASE; |
| TFE3 | GDB: 125870 | TRANSCRIPTION FACTOR FOR IMMUNOGLOBULIN HEAVY-CHAIN ENHANCER-3; TFE3 |
| THAS | GDB: 128158 | THORACOABDOMINAL SYNDROME; TAS |
| THC | GDB: 125361 | THROMBOCYTOPENIA, X-LINKED; THC; XLT |
| TIMM8A | GDB: 119090 | DEAFNESS 1, PROGRESSIVE; DFN1 |
| TIMP1 | GDB: 119615 | TISSUE INHIBITOR OF METALLOPROTEINASE-1; TIMP1 |
| TKCR | GDB: 119616 | TORTICOLLIS, KELOIDS, CRYPTORCHIDISM, AND RENAL DYSPLASIA; TKC |
| TNFSF5 | GDB: 120632 | IMMUNODEFICIENCY WITH INCREASED IgM |
| UBE1 | GDB: 118954 | UBIQUITIN-ACTIVATING ENZYME 1; UBE1 |
| UBE2A | GDB: 131647 | UBIQUITIN-CONJUGATING ENZYME E2A; UBE2A |
| WAS | GDB: 120736 | WISKOTT-ALDRICH SYNDROME; WAS |
| WSN | GDB: 125864 | PARKINSONISM, EARLY-ONSET, WITH MENTAL RETARDATION |
| WTS | GDB: 128373 | MENTAL RETARDATION, X-LINKED, SYNDROMIC-6, WITH GYNECOMASTIA AND OBESITY; |
| WWS | GDB: 120497 | WIEACKER SYNDROME |
| XIC | GDB: 120498 | X-INACTIVATION-SPECIFIC TRANSCRIPT; XIST |
| XIST | GDB: 126428 | X-INACTIVATION-SPECIFIC TRANSCRIPT; XIST |
| XK | GDB: 120499 | Xk LOCUS |
| XM | GDB: 119634 | XM SYSTEM |
| XS | GDB: 119636 | LUTHERAN SUPPRESSOR, X-LINKED; XS; LUXS |
| ZFX | GDB: 120502 | ZINC FINGER PROTEIN, X-LINKED; ZFX |
| ZIC3 | GDB: 249141 | HETEROTAXY, X-LINKED VISCERAL; HTX1 |

TABLE 24-continued

Genes, Locations and Genetic Disorders on Chromosome X

| Gene | GDB Accession ID | OMIM Link |
|---|---|---|
| ZNF261 | GDB: 9785766 | MENTAL RETARDATION, X-LINKED; DXS6673E |
| ZNF41 | GDB: 125865 | ZINC FINGER PROTEIN-41; ZNF41 |
| ZNF6 | GDB: 120508 | ZINC FINGER PROTEIN-6; ZNF6 |

TABLE 25

Genes, Locations and Genetic Disorders on Chromosome Y

| Gene | GDB Accession ID | OMIM Link |
|---|---|---|
| AMELY | GDB: 119676 | AMELOGENIN, Y-CHROMOSOMAL; AMELY |
| ASSP6 | GDB: 119020 | CITRULLINEMIA |
| AZF1 | GDB: 119027 | AZOOSPERMIA FACTOR 1; AZF1 |
| AZF2 | GDB: 456131 | AZOOSPERMIA FACTOR 2; AZF2 |
| DAZ | GDB: 635890 | DELETED IN AZOOSPERMIA; DAZ |
| GCY | GDB: 119267 | CONTROL, Y-CHROMOSOME INFLUENCED; GCY |
| RPS4Y | GDB: 128052 | RIBOSOMAL PROTEIN S4, Y-LINKED; RPS4Y |
| SMCY | GDB: 5875390 | HISTOCOMPATIBILITY Y ANTIGEN; HY; HYA |
| SRY | GDB: 125556 | SEX-DETERMINING REGION Y; SRY |
| ZFY | GDB: 120503 | ZINC FINGER PROTEIN, Y-LINKED; ZFY |

TABLE 26

Genes, Locations and Genetic Disorders in Unknown or Multiple Locations

| Gene | GDB Accession ID | OMIM Link |
|---|---|---|
| ABAT | GDB: 581658 | GAMMA-AMINOBUTYRATE TRANSAMINASE |
| AEZ | GDB: 128360 | ACRODERMATITIS ENTEROPATHICA, ZINC-DEFICIENCY TYPE; AEZ |
| AFA | GDB: 265277 | FILIFORME ADNATUM AND CLEFT PALATE |
| AFD1 | GDB: 265292 | DYSOSTOSIS, TREACHER COLLINS TYPE, WITH LIMB ANOMALIES |
| AGS1 | GDB: 10795417 | ENCEPHALOPATHY, FAMILIAL INFANTILE, WITH CALCIFICATION OF BASAL GANGLIA |
| ASAH | GDB: 6837715 | FARBER LIPOGRANULOMATOSIS |
| ASD1 | GDB: 6276019 | ATRIAL SEPTAL DEFECT; ASD |
| ASMT | GDB: 136259 | CETYLSEROTONIN METHYLTRANSFERASE; ASMT ACETYLSEROTONIN METHYLTRANSFERASE, Y-CHROMOSOMAL; ASMTY; HIOMTY |
| BCH | GDB: 118758 | CHOREA, HEREDITARY BENIGN; BCH |
| CCAT | GDB: 118738 | CATARACT, CONGENITAL OR JUVENILE |
| CECR9 | GDB: 10796163 | CAT EYE SYNDROME; CES |
| CEPA | GDB: 581848 | CONTROL, CONGENITAL FAILURE OF |
| CHED2 | GDB: 9957389 | CORNEAL DYSTROPHY, CONGENITAL HEREDITARY |
| CLA1 | GDB: 119781 | CEREBELLOPARENCHYMAL DISORDER III |
| CLA3 | GDB: 128453 | CEREBELLOPARENCHYMAL DISORDER I; CPD I |
| CLN4 | GDB: 125229 | CEROID-LIPOFUSCINOSIS, NEURONAL 4; CLN4 |
| CPO | GDB: 119070 | COPROPORPHYRIA |
| CSF2RA | GDB: 118777 | COLONY STIMULATING FACTOR 2 RECEPTOR, ALPHA; CSF2RA GRANULOCYTE-MACROPHAGE COLONY-STIMULATING FACTOR RECEPTOR, ALPHA SUBUNIT, |
| CTS1 | GDB: 118779 | CARPAL TUNNEL SYNDROME; CTS; CTS1 |
| DF | GDB: 132645 | FACTOR D |
| DIH1 | GDB: 439243 | DIAPHRAGMATIC |
| DWS | GDB: 128371 | SYNDROME; DWS |
| DYT2 | GDB: 118788 | DYSTONIA MUSCULORUM DEFORMANS 2; DYT2 |
| DYT4 | GDB: 433751 | DYSTONIA MUSCULORUM DEFORMANS 4; DYT4 |
| EBR3 | GDB: 118739 | EPIDERMOLYSIS BULLOSA DYSTROPHICA NEUROTROPHICA |
| ECT | GDB: 128640 | CENTRALOPATHIC EPILEPSY |
| EEF1A1L14 | GDB: 1327185 | PROSTATIC CARCINOMA ONCOGENE PTI-1 |
| EYCL2 | GDB: 4642815 | EYE COLOR-3; EYCL3 |
| FA1 | GDB: 118795 | FANCONI ANEMIA, COMPLEMENTATION GROUP A; FACA |

TABLE 26-continued

Genes, Locations and Genetic Disorders
in Unknown or Multiple Locations

| Gene | GDB Accession ID | OMIM Link |
|---|---|---|
| FANCB | GDB: 9864269 | FANCONI PANCYTOPENIA, TYPE 2 |
| GCSH | GDB: 126842 | HYPERGLYCINEMIA, ISOLATED NONKETOTIC, TYPE III; NKH3 |
| GCSL | GDB: 132139 | ISOLATED NONKETOTIC, TYPE IV; NKH4 |
| GDF5 | GDB: 433948 | CARTILAGE-DERIVED MORPHOGENETIC PROTEIN 1 |
| GIP | GDB: 119985 | GASTRIC INHIBITORY POLYPEPTIDE; GIP |
| GTS | GDB: 118807 | GILLES DE LA TOURETTE SYNDROME; GTS |
| HHG | GDB: 118740 | HYPERGONADOTROPIC HYPOGONADISM; HHG |
| HMI | GDB: 265275 | OF ITO; HMI |
| HOAC | GDB: 118812 | DEAFNESS, CONGENITAL, AUTOSOMAL RECESSIVE |
| HOKPP2 | GDB: 595535 | HYPOKALEMIC PERIODIC PARALYSIS, TYPE II; HOKPP2 |
| HRPT1 | GDB: 125252 | HYPERPARATHYROIDISM, FAMILIAL PRIMARY |
| HSD3B3 | GDB: 676973 | GIANT CELL HEPATITIS, NEONATAL |
| HTC1 | GDB: 265286 | HYPERTRICHOSIS UNIVERSALIS CONGENITA, AMBRAS TYPE; HTC1 |
| HV1S | GDB: 9955009 | HERPES VIRUS SENSITIVITY; HV1S |
| ICR1 | GDB: 127785 | LAMELLAR, AUTOSOMAL DOMINANT FORM |
| ICR5 | GDB: 127789 | ICHTHYOSIS CONGENITA, HARLEQUIN FETUS TYPE |
| IL3RA | GDB: 128985 | INTERLEUKIN-3 RECEPTOR, ALPHA; IL3RA INTERLEUKIN-3 RECEPTOR, Y-CHROMOSOMAL; IL3RA |
| KAL2 | GDB: 265288 | KALLMANN SYNDROME 2; KAL2 |
| KMS | GDB: 118827 | SYNDROME; KMS |
| KRT18 | GDB: 120127 | KERATIN 18; KRT18 |
| KSS | GDB: 9957718 | KEARNS-SAYRE SYNDROME; KSS |
| LCAT | GDB: 119359 | FISH-EYE DISEASE; FED LECITHIN: CHOLESTEROL ACYLTRANSFERASE DEFICIENCY |
| LIMM | GDB: 9958161 | MYOPATHY, MITOCHONDRIAL, LETHAL INFANTILE; LIMM |
| MANBB | GDB: 125262 | MANNOSIDOSIS, BETA; MANB1 |
| MCPH2 | GDB: 9863035 | MICROCEPHALY; MCT |
| MEB | GDB: 599557 | DISEASE |
| MELAS | GDB: 9955855 | MELAS SYNDROME |
| MIC2 | GDB: 120184 | SURFACE ANTIGEN MIC2; MIC2; CD99 MIC2 SURFACE ANTIGEN, Y-CHROMOSOMAL; MIC2Y |
| MPFD | GDB: 439372 | CONGENITAL, WITH FIBER-TYPE DISPROPORTION |
| MS | GDB: 229116 | SCLEROSIS; MS |
| MSS | GDB: 118743 | MARINESCO-SJOGREN SYNDROME; MSS |
| MTATP6 | GDB: 118897 | ATP SYNTHASE 6; MTATP6 |
| MTCO1 | GDB: 118900 | COMPLEX IV, CYTOCHROME c OXIDASE SUBUNIT I; MTCO1; COI |
| MTCO3 | GDB: 118902 | CYTOCHROME c OXIDASE III; MTCO3 |
| MTCYB | GDB: 118906 | COMPLEX III, CYTOCHROME b SUBUNIT |
| MTND1 | GDB: 118911 | COMPLEX I, SUBUNIT ND1; MTND 1 |
| MTND2 | GDB: 118912 | COMPLEX I, SUBUNIT ND2; MTND2 |
| MTND4 | GDB: 118914 | COMPLEX I, SUBUNIT ND4; MTND4 |
| MTND5 | GDB: 118916 | COMPLEX I, SUBUNIT ND5; MTND5 |
| MTND6 | GDB: 118917 | COMPLEX I, SUBUNIT ND6; MTND6 |
| MTRNR1 | GDB: 118920 | RIBOSOMAL RNA, MITOCHONDRIAL, 12S; MTRNR1 |
| MTRNR2 | GDB: 118921 | RIBOSOMAL RNA, MITOCHONDRIAL, 16S; MTRNR2 |
| MTTE | GDB: 118926 | TRANSFER RNA, MITOCHONDRIAL, GLUTAMIC ACID; MTTE |
| MTTG | GDB: 118933 | TRANSFER RNA, MITOCHONDRIAL, GLYCINE; MTTG |
| MTTI | GDB: 118935 | TRANSFER RNA, MITOCHONDRIAL, ISOLEUCINE; MTTI |
| MTTK | GDB: 118936 | MERRF SYNDROME TRANSFER RNA, MITOCHONDRIAL, LYSINE; MTTK |
| MTTL1 | GDB: 118937 | MERRF SYNDROME TRANSFER RNA, MITOCHONDRIAL, LEUCINE, 1; MTTL1 |
| MTTL2 | GDB: 118938 | TRANSFER RNA, MITOCHONDRIAL, LEUCINE, 2; MTTL2 |
| MTTN | GDB: 118940 | TRANSFER RNA, MITOCHONDRIAL, ASPARAGINE; MTTN |
| MTTP | GDB: 118941 | TRANSFER RNA, MITOCHONDRIAL, PROLINE; MTTP |

TABLE 26-continued

Genes, Locations and Genetic Disorders
in Unknown or Multiple Locations

| Gene | GDB Accession ID | OMIM Link |
|---|---|---|
| MTTS1 | GDB: 118944 | TRANSFER RNA, MITOCHONDRIAL, SERINE, 1; MTTS1 |
| NAMSD | GDB: 681237 | NEUROPATHY, MOTOR-SENSORY, TYPE II, WITH DEAFNESS AND MENTAL RETARDATION |
| NODAL | GDB: 9848762 | NODAL, MOUSE, HOMOLOG OF |
| OCD1 | GDB: 118846 | DISORDER-1; OCD1 |
| OPD2 | GDB: 131394 | SYNDROME |
| PCK2 | GDB: 137198 | PHOSPHOENOLPYRUVATE CARBOXYKINASE 2, MITOCHONDRIAL; PCK2 |
| PCLD | GDB: 433949 | POLYCYSTIC LIVER DISEASE; PLD |
| PCOS1 | GDB: 1391802 | STEIN-LEVENTHAL SYNDROME |
| PFKM | GDB: 120277 | GLYCOGEN STORAGE DISEASE VII |
| PKD3 | GDB: 127866 | KIDNEY DISEASE 3, AUTOSOMAL DOMINANT; PKD3 |
| PRCA1 | GDB: 342066 | PROSTATE CANCER; PRCA1 |
| PRO1 | GDB: 128585 | |
| PROP1 | GDB: 9834318 | PROPHET OF PIT1, MOUSE, HOMOLOG OF; PROP1 |
| RBS | GDB: 118862 | ROBERTS SYNDROME; RBS |
| RFXAP | GDB: 9475355 | REGULATORY FACTOR X-ASSOCIATED PROTEIN; RFXAP |
| RP | GDB: 9958158 | RETINITIS PIGMENTOSA-8 |
| SLC25A6 | GDB: 125184 | ADENINE NUCLEOTIDE TRANSLOCATOR 3; ANT3 ADENINE NUCLEOTIDE TRANSLOCATOR 3, Y-CHROMOSOMAL; ANT3Y |
| SPG5B | GDB: 250333 | SPASTIC PARAPLEGIA-5B, AUTOSOMAL RECESSIVE; SPG5B |
| STO | GDB: 439375 | CEREBRAL GIGANTISM |
| SUOX | GDB: 5584405 | SULFOCYSTEINURIA |
| TC21 | GDB: 5573831 | ONCOGENE TC21 |
| THM | GDB: 439378 | FAMILIAL |
| TST | GDB: 134043 | RHODANESE; RDS |
| TTD | GDB: 230276 | TRICHOTHIODYSTROPHY; TTD |

Equivalents:

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

The invention can be illustrated by the following embodiments enumerated in the numbered paragraphs that follow:

1. A method for identifying a compound that modulates premature translation termination or nonsense-mediated mRNA decay, comprising the steps of (a) contacting a detectably labeled target RNA molecule with a library of compounds under conditions that permit direct binding of the labeled target RNA to a member of the library of compounds so that a detectably labeled target RNA: compound complex is formed; (b) separating the detectably labeled target RNA: compound complex formed in step (a) from uncomplexed target RNA molecules and compounds; and (c) determining a structure of the compound bound to the RNA in the RNA: compound complex.

2. A method for identifying a compound that modulates premature translation termination or nonsense-mediated mRNA decay, comprising the steps of (a) contacting a target RNA molecule with a library of detectably labeled compounds under conditions that permit direct binding of the target RNA to a member of the library of labeled compounds so that a target RNA: compound complex that is detectably labeled is formed; (b) separating the target RNA: compound complex formed in step (a) from uncomplexed target RNA molecules and compounds; and (c) determining a structure of the compound bound to the RNA in the RNA: compound complex.

3. The method of paragraph 1 in which the target RNA molecule contains regions of 28S rRNA or analogs thereof.

4. The method of paragraph 1 in which the detectably labeled RNA is labeled with a fluorescent dye, phosphorescent dye, ultraviolet dye, infrared dye, visible dye, radiolabel, enzyme, spectroscopic colorimetric label, affinity tag, or nanoparticle.

5. The method of paragraph 1 in which the compound is selected from a combinatorial library comprising peptoids; random bio-oligomers; diversomers such as hydantoins, benzodiazepines and dipeptides; vinylogous polypeptides; non-peptidal peptidomimetics; oligocarbamates; peptidyl phosphonates; peptide nucleic acid libraries; antibody libraries; carbohydrate libraries; and small organic molecule libraries, including but not limited to, libraries of benzodiazepines, isoprenoids, thiazolidinones, metathiazanones, pyrrolidines, morpholino compounds, or diazepindiones.

6. The method of paragraph 1 in which screening a library of compounds comprises contacting the compound with the target nucleic acid in the presence of an aqueous solution, the aqueous solution comprising a buffer and a combination of salts, preferably approximating or mimicking physiologic conditions.

7. The method of paragraph 6 in which the aqueous solution optionally further comprises non-specific nucleic acids comprising DNA, yeast tRNA, salmon sperm DNA, homoribopolymers, and nonspecific RNAs.

8. The method of paragraph 6 in which the aqueous solution further comprises a buffer, a combination of salts, and optionally, a detergent or a surfactant. In another embodiment, the aqueous solution further comprises a combination of salts, from about 0 mM to about 100 mM KCl, from about 0 mM to about 1 M NaCl, and from about 0 mM to about 200 mM $MgCl_2$. In a preferred embodiment, the combination of salts is about 100 mM KCl, 500 mM NaCl, and 10 mM $MgCl_2$. In another embodiment, the solution optionally comprises from about 0.01% to about 0.5% (w/v) of a detergent or a surfactant.

9. Any method that detects an altered physical property of a target nucleic acid complexed to a compound from the unbound target nucleic acid may be used for separation of the complexed and non-complexed target nucleic acids in the method of paragraph 1. In a preferred embodiment, electrophoresis is used for separation of the complexed and non-complexed target nucleic acids. In a preferred embodiment, the electrophoresis is capillary electrophoresis. In other embodiments, fluorescence spectroscopy, surface plasmon resonance, mass spectrometry, scintillation, proximity assay, structure-activity relationships ("SAR") by NMR spectroscopy, size exclusion chromatography, affinity chromatography, and nanoparticle aggregation are used for the separation of the complexed and non-complexed target nucleic acids.

10. The structure of the compound of the RNA: compound complex of paragraph 1 is determined, in part, by the type of library of compounds. In a preferred embodiment wherein the combinatorial libraries are small organic molecule libraries, mass spectroscopy, NMR, or vibration spectroscopy are used to determine the structure of the compounds.

What is claimed is:

1. A method of identifying a small molecule that modulates premature translation termination or nonsense-mediated mRNA decay, said method comprising:
   (a) contacting a region of human 28S rRNA with a library of small molecules under conditions that permit direct binding of the region of human 28S rRNA to a member of the library of small molecules and the formation of a region of human 28S rRNA:small molecule complex;
   (b) detecting the formation of a region of human 28S rRNA:small molecule comple, wherein a small molecule that binds to the region of human 28S rRNA is identified if a region of human 28S rRNA:small molecule complex is detected;
   (c) contacting the small molecule identified as binding to a region of human 28S rRNA with a cell-free extract and a nucleic acid sequence comprising a regulatory element operably linked to a reporter gene coding region, wherein the reporter gene coding region comprises a premature stop codon, and wherein the cell-free extract is isolated from cells that have been incubated on ice for at least 12 hours; and
   (d) detecting the protein expressed from the reporter gene coding region, wherein a small molecule that modulates premature translation termination or nonsense-mediated mRNA decay is identified if the protein expressed from the reporter gene coding, region in the presence of the small molecule is altered relative to the protein expressed from the reporter gene coding region in the absence of the small molecule or the presence of a negative control.

2. A method of identifying a small molecule that modulates premature translation termination or nonsense-mediated mRNA decay, said method comprising:
   (a) contacting a region of human 28S rRNA With a library of small molecules under conditions that permit direct binding of the region of human 28S rRNA to a member of the library of small molecules and the formation of a region of human 28S rRNA:small molecule complex;
   (b) detecting the formation of a region of human 28S rRNA:small molecule complex, wherein a small molecule that binds to the region of human 28S rRNA is identified if a region of human 28S rRNA:small molecule complex is detected;
   (c) contacting the small molecule identified as binding to a region of human 28S rRNA with a cell-free extract and a nucleic acid sequence comprising a regulatory element operably linked to a reporter gene coding region, wherein the reporter gene coding region comprises a premature stop codon, and wherein the cell-free extract is isolated from cells that have been incubated on ice for at least 24 hours; and (d) detecting the protein expressed from the reporter gene coding region, wherein a small molecule that modulates premature translation termination or nonsense-mediated mRNA decay is identified if the protein expressed from the reporter gene coding region in the presence of the small molecule is altered relative to the protein expressed from the reporter gene coding region in the absence of the compound or the presence of a negative control.

3. The method of claim 1 or 2 wherein the region of human 28S rRNA is detectably labeled.

4. The method of claim 1 or 2, wherein the small molecules in the library are detectably labeled.

5. The method of claim 1 or 2, wherein the cell-free extract is from human cells.

6. The method of claim 1 or 2, wherein the cell-free extract is rabbit reticulocyte lysate or wheat germ extract.

7. The method of claim 1 or 2, wherein the cell-free extract is a cell free extract from HeLa cells.

8. The method of claim 2, wherein the cell-free extract is a S10 to S30 cell-free extract.

9. The method of claim 5, wherein the cell-free extract is a S10 to S30 cell-free extract.

10. The method of claim 1, wherein the cell-free extract is a S10 to S30 cell-free extract.

11. The method of claim 2, wherein the cell-free extract is a S5 to S25 cell-free extract.

12. The method of claim 5, wherein the cell-free extract is a S5 to S25 cell-free extract.

13. The method of claim 1, wherein the cell-free extract is a S5 to S25 cell-free extract.

14. The method of claim 11, wherein the cell-free extract is a S10 cell-free extract.

15. The method of claim 12, wherein the cell-free extract is a S10 cell-free extract.

16. The method of claim 13, wherein the cell-free extract is a S10 cell-free extract.

17. The method of claim 1 or 2, wherein the region of human 28S rRNA comprises a region involved in frameshifting, nonsense mutation suppression, GTPase activity, or peptidyl transferase activity.

18. The method of claim 1, or 2, wherein each small molecule in the library is attached to a solid support.

19. The method of claim 18, wherein the solid support is a silica gel, a resin, a derivatived plastic film, a glass bead, cotton, a plastic bead, a polystyrene bead, an aluminum gel, a glass slide or a polysaccharide.

20. The method of claim 1 or 2 wherein the library of small molecules is attached to a chip.

21. The method of claim 3 wherein the detectably labeled region of human 28S rRNA is labeled with a fluorescent dye, phosphorescent dye, ultraviolet dye, infrared dye, visible dye, radiolabel, enzyme, spectroscopic colorimetric label, affinity tag, or nanoparticle.

22. The method of claim 4, wherein the detectably labeled small molecules in the library are labeled with a fluorescent dye, phosphorescent dye, ultraviolet dye, infrared dye, visible dye, radiolabel, enzyme, spectroscopic colorimetric label, affinity tag, or nanoparticle.

23. The method of claim 1 or 2 wherein the small molecule library is a library of benzodiazepines, isoprenoids, thiazolidinones, metathiazanones, pyrrolidines, morpholino compounds, or diazepindiones.

24. The method of claim 1 or 12 wherein the detectably labeled region of human 28S rRNA:small molecule complex is detected by electrophoresis, fluorescence spectroscopy, surface plasmon resonance, mass spectrometry, scintillation, proximity assay, structure-activity relationships ("SAR") by NMR spectroscopy, size exclusion chromatography, affinity chromatography, or nanoparticle aggregation.

25. The method of claim 1 or 2 wherein the method further comprises determining the structure of the small molecule.

26. The method of claim 25 wherein the structure of the small molecule is determined by mass spectroscopy, NMR, X-ray crystallography, Edman degradation or vibration spectroscopy.

27. The method of claim 1 or 2 wherein the premature stop codon is UAG, UGA or UAA.

28. The method of claim 1 or 2 wherein the premature stop codon is in the context of UAAG, UAAA, UAGG, UAGC, UAGU, UAAC, UGAC, or UAAU.

29. The method of claim 1 or 2 wherein the reporter gene coding region contains 2 or more premature stop codons.

30. The method of claim 1 or 2 wherein an increase in the amount of protein expressed in the presence of the small molecule relative to the amount of protein expressed in the absence of the small molecule or the presence of a negative control indicates that the small molecule suppresses premature translation termination or nonsense-mediated mRNA decay.

31. The method of claim 1 or 2 wherein a decrease in the amount of protein expressed in the presence of the small molecule relative to the amount of protein expressed in the absence of the small molecule or the presence of a negative control indicates that the small molecule enhances premature translation termination or nonsense-mediated mRNA decay.

32. The method of claim 1 or 2 wherein the region of human 28S rRNA comprises domains II and V.

* * * * *

SEQUENCE LISTING

```
<160> NUMBER OF SEQ ID NOS: 35

<210> SEQ ID NO 1
<211> LENGTH: 27
<212> TYPE: RNA
<213> ORGANISM: Artificial Sequence
<220> FEATURE:
<223> OTHER INFORMATION: Description of Artificial Sequence: 16s
      rRNA A site

<400> SEQUENCE: 1
ggcgucacac cuucggguga agucgcc                                          27

<210> SEQ ID NO 2
<211> LENGTH: 29
<212> TYPE: RNA
<213> ORGANISM: Artificial Sequence
<220> FEATURE:
<223> OTHER INFORMATION: Description of Artificial Sequence: 16s
      rRNA A site

<400> SEQUENCE: 2
ggcagaucug agccugggag cucucugcc                                        29

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: 16s
      rRNA A site

<400> SEQUENCE: 3

Tyr Gly Arg Lys Lys Arg Arg Gln Arg Arg Arg Pro
1               5                   10

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 4
aaagcctaca gcaccc                                                      16

<210> SEQ ID NO 5
<211> LENGTH: 17
```

```
<212> TYPE: DNA
<213> ORGANISM: Artificial Sequence
<220> FEATURE:
<223> OTHER INFORMATION: Description of Artificial Sequence: Primer

<400> SEQUENCE: 5
tactgaggga atcctgg                                                    17

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 6
ttaccacccg ctttgggggg ggcgggaaag atcc                                 34

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 7
gggggcggga aagatcc                                                    17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 8
ccccgagcca ccttccc                                                    17

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 9
ggccccggga ttcggcg                                                    17

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 10
cactggggac agtccgc                                                    17

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 11
cgcggcgggc gagacggg                                                   18
```

```
<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 12
gagggaaact tcggaggg                                                 18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 13
catcgggcgc cttaaccc                                                 18

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 14
cgacgcacac cacacgc                                                  17

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 15
ccaagatctg cacctgc                                                  17

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 16
ttaccgcact ggacgcc                                                  17

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 17
gccagaggct gttcacc                                                  17

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer
```

```
<400> SEQUENCE: 18
tggggaggga gcgagcggcg                                                  20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 19
aagggcccgg ctcgcgtcc                                                   19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
agggcggggg gacgaaccgc                                                  20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 21
ttaaacagtc ggattcccct gg                                               22

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 22
ttcatccatt catgcgcg                                                    18

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 23
agtagtggta tttcaccgg                                                   19

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 24
acgggaggtt tctgtcc                                                     17

<210> SEQ ID NO 25
<211> LENGTH: 19
```

```
<212> TYPE: DNA
<213> ORGANISM: Artificial Sequence
<220> FEATURE:
<223> OTHER INFORMATION: Description of Artificial Sequence: Primer

<400> SEQUENCE: 25
acaatgatag gaagagccg                                                    19

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 26
aggcgttcag tcataatccc                                                   20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 27
tccgcaccgg accccggtcc                                                   20

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 28
gggctagttg attcggcagg tgagttg                                           27

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 29
tctccggaat cgaaccct                                                     18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 30
attaccgcgg ctgctggc                                                     18

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 31
ttggcaaatg ctttcgc                                                      17
```

```
<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 32
ccgtcaattc ctttaagttt c                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 33
agggcatcac agacctgtta t                                              21

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 34
cgacgggcgg tgtgtac                                                   17

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 35
ccgcaggttc acctacgg                                                  18
```